(12) United States Patent
Osaka et al.

(10) Patent No.: US 9,972,790 B2
(45) Date of Patent: *May 15, 2018

(54) ANTHRACENE DERIVATIVE, AND LIGHT-EMITTING MATERIAL, LIGHT-EMITTING ELEMENT, LIGHT-EMITTING DEVICE, AND ELECTRONIC DEVICE USING THE SAME

(71) Applicant: SEMICONDUCTOR ENERGY LABORATORY CO., LTD., Atsugi-shi, Kanagawa-ken (JP)

(72) Inventors: Harue Osaka, Kanagawa (JP); Sachiko Kawakami, Kanagawa (JP); Nobuharu Ohsawa, Kanagawa (JP); Satoshi Seo, Kanagawa (JP)

(73) Assignee: Semiconductor Energy Laboratory Co., Ltd., Kanagawa-ken (JP)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/712,483

(22) Filed: May 14, 2015

(65) Prior Publication Data

US 2015/0249220 A1 Sep. 3, 2015

Related U.S. Application Data

(63) Continuation of application No. 13/893,376, filed on May 14, 2013, now Pat. No. 9,070,883, which is a (Continued)

(30) Foreign Application Priority Data

Dec. 21, 2007 (JP) .................................. 2007-330688

(51) Int. Cl.
| | |
|---|---|
| *H01L 51/00* | (2006.01) |
| *C07D 209/86* | (2006.01) |
| *C09K 11/06* | (2006.01) |
| *H05B 33/14* | (2006.01) |
| *H01L 51/50* | (2006.01) |

(52) U.S. Cl.
CPC ........ *H01L 51/0072* (2013.01); *C07D 209/86* (2013.01); *C09K 11/06* (2013.01); *H01L 51/0052* (2013.01); *H05B 33/14* (2013.01); *C09K 2211/1007* (2013.01); *C09K 2211/1011* (2013.01); *C09K 2211/1029* (2013.01); (Continued)

(58) Field of Classification Search
USPC ........................................................ 548/440
See application file for complete search history.

(56) References Cited

U.S. PATENT DOCUMENTS

| | | |
|---|---|---|
| 7,790,892 B2 | 9/2010 | Ikeda et al. |
| 7,985,491 B2 | 7/2011 | Kubota et al. |

(Continued)

FOREIGN PATENT DOCUMENTS

| | | |
|---|---|---|
| CN | 001984897 A | 6/2007 |
| CN | 101124292 A | 2/2008 |

(Continued)

OTHER PUBLICATIONS

Caruso et al., Molecules (2008) 13, 1312-1320.*
Guo-Liang Feng et al. Synlett (2006) No. 17, 2841-2845.*
Tavasli et al., Synthesis (2005), No. 10, 1619-1624.*
Shi.J et al., "Anthracene Derivatives for Stable Blue-Emitting Organic Electroluminescence Devices", Appl. Phys. Lett. (Applied Physics Letters) , Apr. 29, 2002, vol. 80, No. 17, pp. 3201-3203.
International Search Report (Application No. PCT/JP2008/072899) dated Feb. 10, 2009.

(Continued)

*Primary Examiner* — Michael Barker
(74) *Attorney, Agent, or Firm* — Nixon Peabody LLP; Jeffrey L. Costellia

(57) ABSTRACT

Novel anthracene derivatives, novel materials capable of blue light emission with high color purity, and a light-emitting element, a light-emitting device, and an electronic device using any of the novel materials. The anthracene derivative represented by general formula (1) is provided. With the anthracene derivative, a light-emitting element with high emission efficiency can be provided. With the anthracene derivative, a light-emitting element emitting blue light with high color purity can be provided.

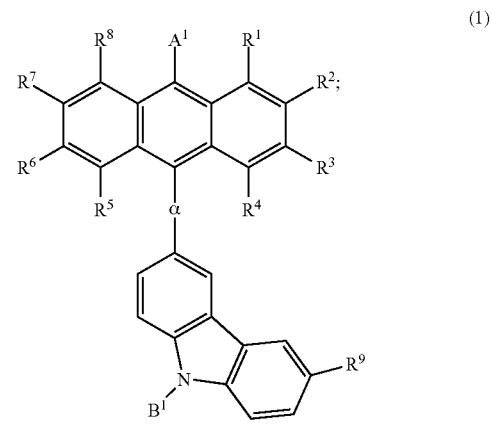

In the formula, $A^1$ represents a substituted or unsubstituted phenyl group, $B^1$ represents any of an alkyl group having 1 to 4 carbon atoms or a substituted or unsubstituted phenyl group, $\alpha$ represents any of a substituted or unsubstituted phenylene group or a substituted or unsubstituted biphenyl-4,4'-diyl group, and $R^1$ to $R^9$ individually represent any of hydrogen, an alkyl group having 1 to 4 carbon atoms, or a substituted or unsubstituted phenyl group.

10 Claims, 35 Drawing Sheets

Related U.S. Application Data continuation of application No. 12/336,234, filed on Dec. 16, 2008, now Pat. No. 8,603,644.

(52) U.S. Cl.
CPC ...... *H01L 51/0002* (2013.01); *H01L 51/0021* (2013.01); *H01L 51/5012* (2013.01)

(56) References Cited

U.S. PATENT DOCUMENTS

| | | | |
|---|---|---|---|
| 8,039,122 B2 | 10/2011 | Kawakami et al. | |
| 8,084,146 B2 | 12/2011 | Murase et al. | |
| 8,217,570 B2 | 7/2012 | Kawamura et al. | |
| 8,231,942 B2* | 7/2012 | Shitagaki | C07D 209/86 252/301.31 |
| 8,283,855 B2* | 10/2012 | Osaka | C07D 209/86 313/504 |
| 8,283,856 B2* | 10/2012 | Ushikubo | H01L 51/5072 313/506 |
| 8,298,687 B2 | 10/2012 | Kawakami et al. | |
| 8,324,615 B2* | 12/2012 | Seo | H01L 51/0059 257/40 |
| 8,518,492 B2* | 8/2013 | Shitagaki | C07D 209/86 252/301.31 |
| 8,603,644 B2* | 12/2013 | Osaka | C07D 209/86 313/504 |
| 8,603,647 B2 | 12/2013 | Kawakami et al. | |
| 8,614,334 B2* | 12/2013 | Osaka | C07D 209/86 428/917 |
| 8,669,373 B2* | 3/2014 | Suzuki | C07D 209/86 548/440 |
| 8,815,410 B2 | 8/2014 | Nakashima et al. | |
| 8,845,926 B2* | 9/2014 | Shitagaki | C07D 209/86 252/301.31 |
| 9,040,720 B2* | 5/2015 | Osaka | C07D 209/86 428/917 |
| 9,070,883 B2* | 6/2015 | Osaka | C07D 209/86 |
| 2003/0215667 A1 | 11/2003 | Xie | |
| 2005/0260442 A1 | 11/2005 | Yu et al. | |
| 2007/0075632 A1 | 4/2007 | Kawakami et al. | |
| 2007/0088185 A1* | 4/2007 | Kubota | C07C 13/567 585/407 |
| 2007/0152572 A1 | 7/2007 | Kawakami et al. | |
| 2007/0202355 A1 | 8/2007 | Kim et al. | |
| 2007/0247063 A1 | 10/2007 | Murase et al. | |
| 2007/0267969 A1 | 11/2007 | Nakashima et al. | |
| 2008/0111478 A1 | 5/2008 | Lyu et al. | |
| 2008/0268284 A1 | 10/2008 | Kawakami et al. | |
| 2011/0049482 A1 | 3/2011 | Ikeda et al. | |
| 2012/0138907 A1 | 6/2012 | Murase et al. | |
| 2013/0253206 A1 | 9/2013 | Osaka et al. | |
| 2014/0364626 A1 | 12/2014 | Nakashima et al. | |

FOREIGN PATENT DOCUMENTS

| | | |
|---|---|---|
| EP | 1496041 A | 1/2005 |
| EP | 1748045 A | 1/2007 |
| EP | 1864962 A | 12/2007 |
| EP | 2450356 A | 5/2012 |
| EP | 2479814 A | 7/2012 |
| JP | 09-310066 A | 12/1997 |
| JP | 2004-224723 A | 8/2004 |
| JP | 2006-176448 A | 7/2006 |
| JP | 2007-039431 A | 2/2007 |
| JP | 2007-055996 A | 3/2007 |
| JP | 2007-063501 A | 3/2007 |
| JP | 2007-131722 A | 5/2007 |
| JP | 2008-530086 | 8/2008 |
| JP | 2009-120582 A | 6/2009 |
| JP | 5235246 | 7/2013 |
| JP | 5716068 | 5/2015 |
| JP | 5780664 | 9/2015 |
| KR | 2007-0032658 A | 3/2007 |
| KR | 2007-0053148 A | 5/2007 |
| KR | 2007-0114760 A | 12/2007 |
| KR | 2008-0042589 A | 5/2008 |
| WO | WO-2003/087023 | 10/2003 |
| WO | WO-2005/113531 | 12/2005 |
| WO | WO-2006/070907 | 7/2006 |
| WO | WO-2006/104044 | 10/2006 |
| WO | WO-2006/104221 | 10/2006 |
| WO | WO-2007/013537 | 2/2007 |
| WO | WO-2007/058503 | 5/2007 |
| WO | WO-2009/081800 | 7/2009 |

OTHER PUBLICATIONS

Written Opinion (Application No. PCT/JP2008/072899) dated Feb. 10, 2009.

Chinese Office Action (Application No. 200880122913.3) dated Dec. 15, 2011.

European Search Report (Application No. 08864725.0) dated Nov. 14, 2011.

Korean Office Action (Application No. 2010-7015773) dated Mar. 23, 2015.

\* cited by examiner

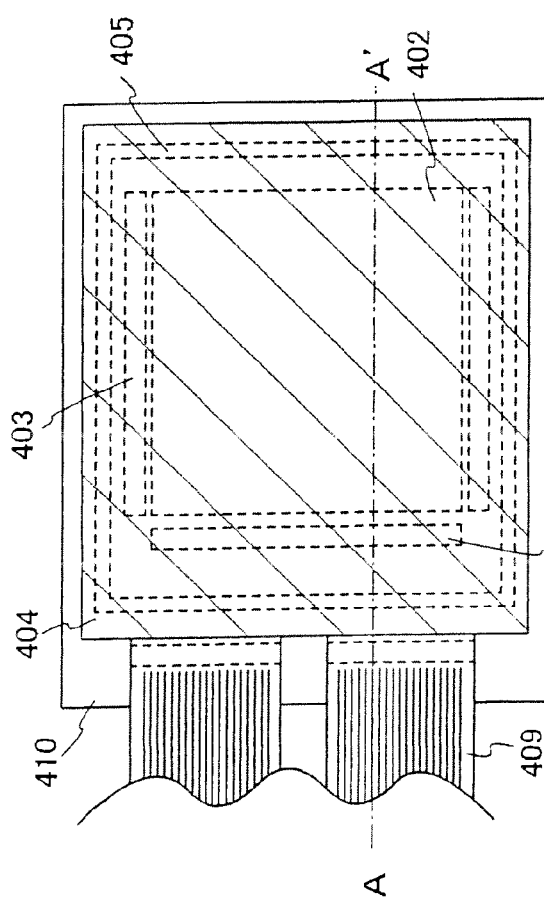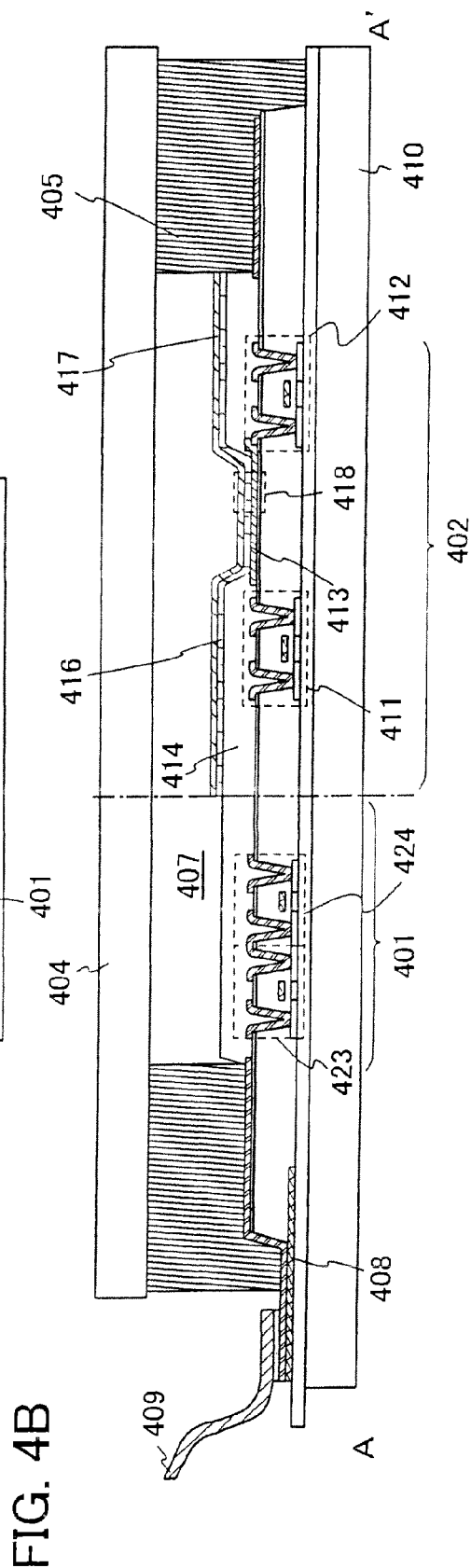
FIG. 4A
FIG. 4B

ANTHRACENE DERIVATIVE, AND LIGHT-EMITTING MATERIAL, LIGHT-EMITTING ELEMENT, LIGHT-EMITTING DEVICE, AND ELECTRONIC DEVICE USING THE SAME

TECHNICAL FIELD

The present invention relates to a light-emitting material applicable to a light-emitting element utilizing electroluminescence. Further, the present invention relates to a light-emitting element using the light-emitting material, and a light-emitting device and an electronic device each using the light-emitting element.

BACKGROUND ART

A light-emitting element using a light-emitting material features thinness, lightness in weight, and the like, and is expected to be applied to a next-generation flat panel display. Further, because of its self-luminous properties, such a light-emitting element using a light-emitting material seems to be advantageous over conventional liquid crystal displays (LCDs) in wide viewing angle and high visibility.

A light-emitting element seems to emit light by the following manner; a voltage is applied to a pair of electrodes which interpose a light-emitting layer therebetween so that holes injected from an anode and electrons injected from a cathode are recombined at luminescence centers of the light-emitting layer to excite molecules, and the excited molecules discharge energy in returning to a ground state, thereby light is emitted. Note that excited states that are generated by recombination are a singlet excited state and a triplet excited state. Light emission is considered to be possible through either state of the singlet excited state or the triplet excited state. The light emission occurring when excited molecules return from the singlet excited state to the ground state directly is called fluorescence, and the light emission occurring when excited molecules return from the triplet excited state to the ground state is called phosphorescence.

Such a light-emitting element has many problems depending on materials in order to enhance its characteristic. In order to overcome the problems, reformation of the element structure, development of the material, and the like have been conducted.

For example, an anthracene derivative emitting green light is disclosed in Patent Document 1 (: United States Published Patent Application No. 2005/0260442).

DISCLOSURE OF INVENTION

However, although the emission spectrum of the anthracene derivative is disclosed in Patent Document 1, the characteristic of the anthracene derivative being applied to a light-emitting element is not disclosed. For commercialization, development of a light-emitting element having better characteristic has been demanded.

In view of the foregoing problems, the present invention provides novel anthracene derivatives.

It is one object of the present invention to provide an anthracene derivative applicable to a light-emitting element or a light-emitting device utilizing electroluminescence and enables blue light emission. Further, it is also one object of the present invention to improve the color purity of the blue light emission.

Anthracene derivatives of the present invention can be roughly divided into compounds of two modes represented by general formula (1) and general formula (5) described below. That is, the anthracene derivatives of the present invention can be roughly divided into the mode where substitution groups α each of which is bonded to a carbazole-derivative functional group are bonded at both positions of the 9-position and the 10-position of anthracene and the mode where the substitution group α is bonded at only one position of the positions. One mode of the present invention, which is roughly divided, is the anthracene derivatives represented by the general formula (1) described below, as described above.

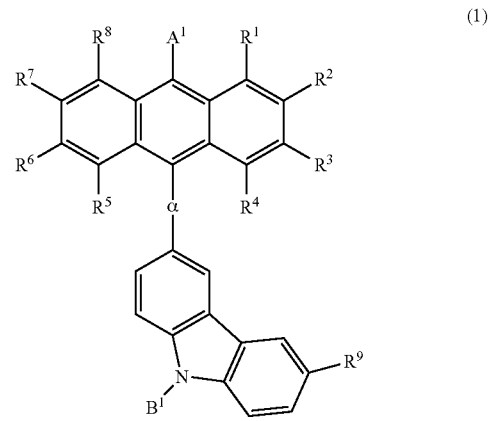

(1)

In the general formula (1), $A^1$ represents a substituted or unsubstituted phenyl group, $B^1$ represents any of an alkyl group having 1 to 4 carbon atoms or a substituted or unsubstituted phenyl group, α represents any of a substituted or unsubstituted phenylene group (preferably, a substituted or unsubstituted 1,4-phenylene group) or a substituted or unsubstituted biphenyl-4,4'-diyl group, and $R^1$ to $R^9$ individually represent any of hydrogen, an alkyl group having 1 to 4 carbon atoms, or a substituted or unsubstituted phenyl group.

Further, one aspect of the present invention is an anthracene derivative represented by general formula (2) described below.

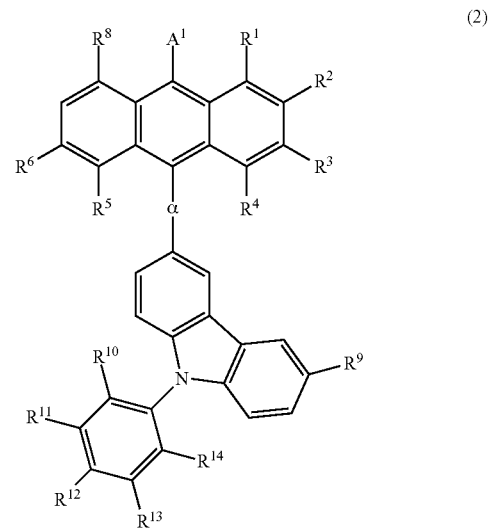

(2)

In the general formula (2), $A^1$ represents a substituted or unsubstituted phenyl group, α represents any of a substituted or unsubstituted phenylene group or a substituted or unsubstituted biphenyl-4,4'-diyl group, and $R^1$ to $R^{14}$ individually represent any of hydrogen, an alkyl group having 1 to 4 carbon atoms, or a substituted or unsubstituted phenyl group.

In the general formula (2), it is preferable that α be an unsubstituted phenylene group or biphenyl-4,4'-diyl group.

Further, one aspect of the present invention is an anthracene derivative represented by general formula (3) described below.

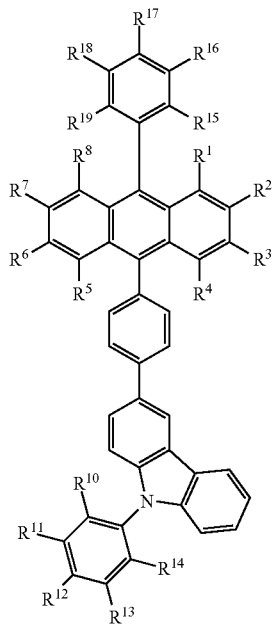

(3)

In the general formula (3), $R^1$ to $R^8$ and $R^{10}$ to $R^{19}$ individually represent any of hydrogen, an alkyl group having 1 to 4 carbon atoms, or a substituted or unsubstituted phenyl group.

Further, one aspect of the present invention is an anthracene derivative represented by general formula (4) described below,

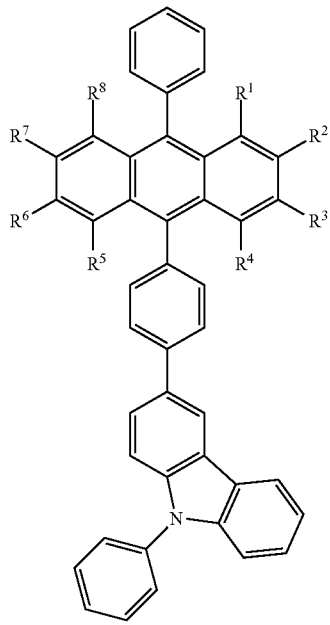

(4)

In the general formula (4), $R^1$ to $R^5$ individually represent any of hydrogen, an alkyl group having 1 to 4 carbon atoms, or a substituted or unsubstituted phenyl group.

The other mode of the present invention, which is roughly divided, is the anthracene derivatives represented by the general formula (5) described below, as described above.

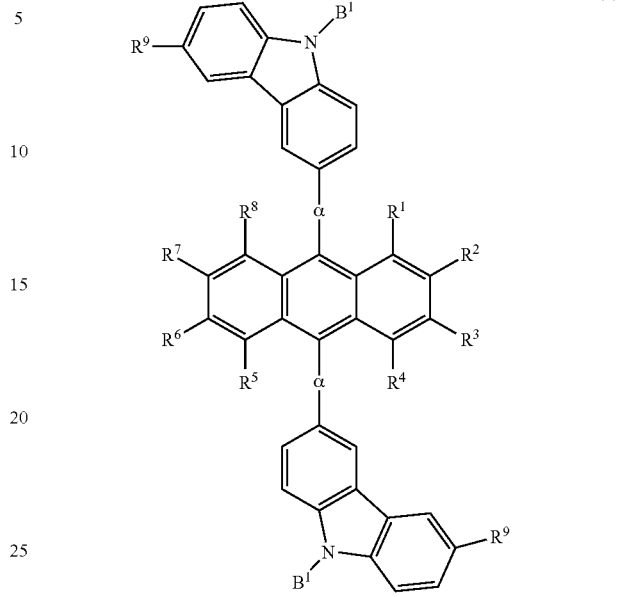

(5)

In the general formula (5), $B^1$ represents any of an alkyl group having 1 to 4 carbon atoms or a substituted or unsubstituted phenyl group, α represents any of a substituted or unsubstituted phenylene group or a substituted or unsubstituted biphenyl-4,4'-diyl group, and $R^1$ to $R^9$ individually represent any of hydrogen, an alkyl group having 1 to 4 carbon atoms, or a substituted or unsubstituted phenyl group.

Further, one aspect of the present invention is an anthracene derivative represented by general formula (6) described below.

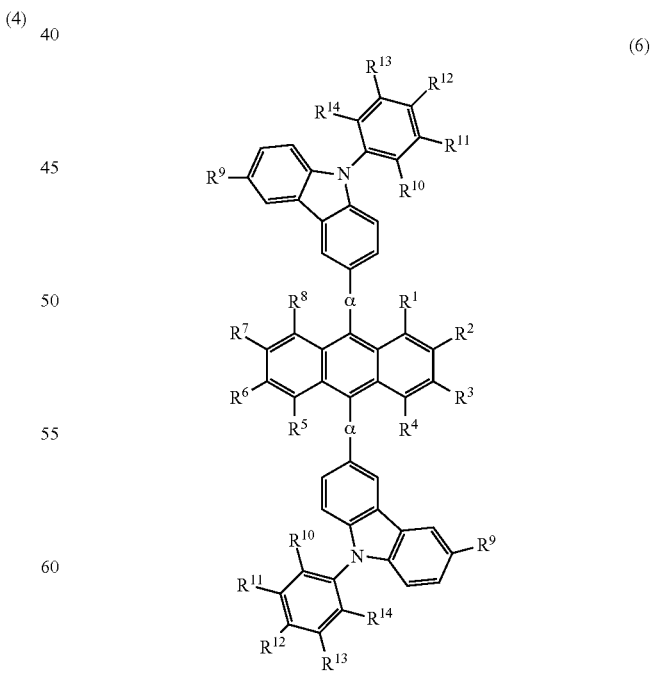

(6)

In the general formula (6), α represents any of a substituted or unsubstituted phenylene group or a substituted or unsubstituted biphenyl-4,4'-diyl group, and $R^1$ to $R^{14}$ individually represent any of hydrogen, an alkyl group having 1 to 4 carbon atoms, or a substituted or unsubstituted phenyl group.

In the general formula (6), it is preferable that a be an unsubstituted phenylene group or biphenyl-4,4'-diyl group.

Further, one aspect of the present invention is an anthracene derivative represented by general formula (7) described below.

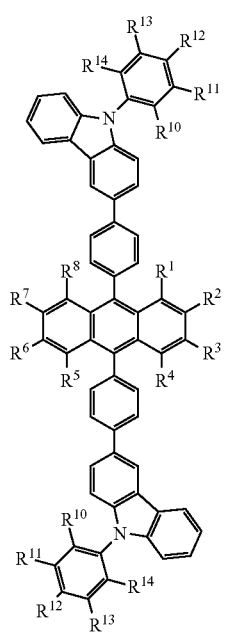

(7)

In the general formula (7), $R^1$ to $R^8$ and $R^{10}$ to $R^{14}$ individually represent any of hydrogen, an alkyl group having 1 to 4 carbon atoms, or a substituted or unsubstituted phenyl group.

Further, one aspect of the present invention is an anthracene derivative represented by general formula (8) described below.

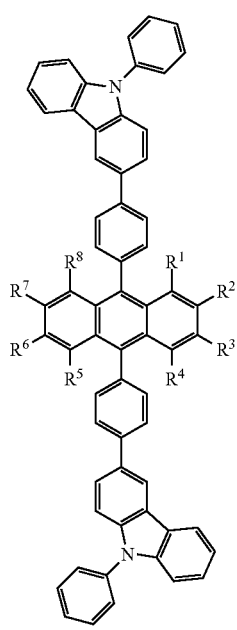

(8)

In the general formula (8), $R^1$ to $R^8$ individually represent any of hydrogen, an alkyl group having 1 to 4 carbon atoms, or a substituted or unsubstituted phenyl group.

Further, one aspect of the present invention is a light-emitting material including any of the above-described anthracene derivatives.

Further, one aspect of the present invention is a light-emitting element including any of the above-described anthracene derivatives.

Further, one aspect of the present invention is a light-emitting element including a light-emitting layer including a light-emitting material and any of the above-described anthracene derivatives.

Further, one aspect of the present invention is a light-emitting device including the above-descried light-emitting element and a control circuit which controls light emission of the light-emitting element.

Further, one aspect of the present invention is an electronic device including a display portion provided with the above-described light-emitting element and a control circuit which controls the light-emitting element.

The 'light-emitting device' of the present invention includes in its category an image display device using a light-emitting element. Moreover, the category of the 'light-emitting device' includes a module including a light-emitting element attached with a connector, such as a module attached with an anisotropic conductive film, TAB (tape automated bonding) tape, or a TCP (tape carrier package), and a module in which an IC (integrated circuit) is directly mounted on a light-emitting element by COG (chip on glass). Furthermore, a light-emitting device used in a lighting apparatus or the like is also included.

The anthracene derivatives of the present invention have an electron-transporting property and the hand gap which is extremely large, and can emit light with extremely short wavelength, and can provide blue light emission with high color purity. Therefore, the anthracene derivatives each can be preferably used in a light-emitting element.

The anthracene derivatives of the present invention are preferable as host materials of a light-emitting layer of a light-emitting element. That is, a light-emitting material having a smaller band gap than any of the anthracene derivatives of the present invention (hereinafter the light-emitting material is referred to as a dopant) is added into a layer made of the anthracene derivative of the present invention so that light emission from the dopant can be obtained. At this time, since the anthracene derivative of the present invention has an extremely large band gap, light emission from the dopant can be obtained efficiently instead of light emission from the anthracene derivative of the present invention even in the case of using a dopant emitting light of a relatively short wavelength. Specifically, a light-emitting material having light emission maximum in around 450 nm of the wavelength, which provides high blue color purity, is used as a dopant so that a light-emitting element capable of blue light emission with high color purity can be obtained.

Alternatively, any of the anthracene derivatives of the present invention is added into a layer made of a material having a larger band gap than the anthracene derivative of the present invention (hereinafter the material is referred to as a host) to manufacture a light-emitting, element so that light emission from the anthracene derivative of the present invention can be obtained. That is, the anthracene derivatives of the present invention also functions as a dopant. At this time, since the anthracene derivative of the present invention has an extremely large hand gap and provides light emission of a short wavelength, a light-emitting element capable of blue light emission with high blue color purity can be manufactured.

The anthracene derivatives of the present invention each emit light efficiently. With any of the anthracene derivatives of the present invention, a light-emitting element with high emission efficiency can be provided.

With the light-emitting element of the present invention, a light-emitting device and an electronic device each with high blue color purity can be provided. Further, a light-emitting device and an electronic device each with high emission efficiency and less power consumption can be provided.

BRIEF DESCRIPTION OF DRAWINGS

FIGS. 4A and 4B illustrate a light-emitting device according to an aspect of the present invention.

BEST MODE FOR CARRYING OUT THE INVENTION

Figure 1:
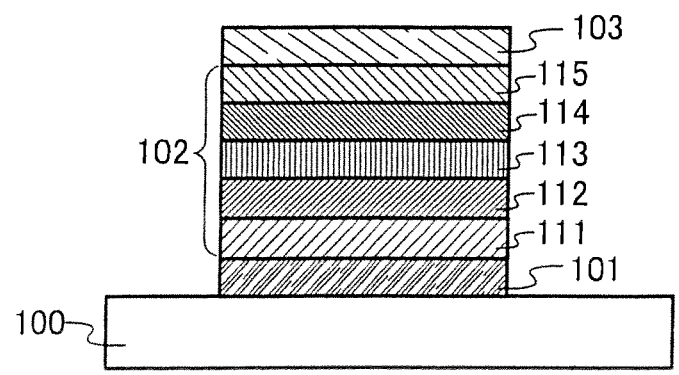
FIG. 1 illustrates a light-emitting element according to an aspect of the present invention.

Embodiment modes and examples of the present invention will be detailed with reference to the drawings. It is to be noted that the present invention is not limited to the following description, and it is easily understood by those skilled in the art that modes and details thereof can be modified in various ways without departing from the purpose and scope of the present invention. Therefore, the present invention should not be construed as being limited to the description of the following embodiment modes and examples.

Embodiment Mode 1

In this embodiment mode, the anthracene derivatives of the present invention will be described.

The anthracene derivatives of the present invention are each represented by general formula (9) described below.

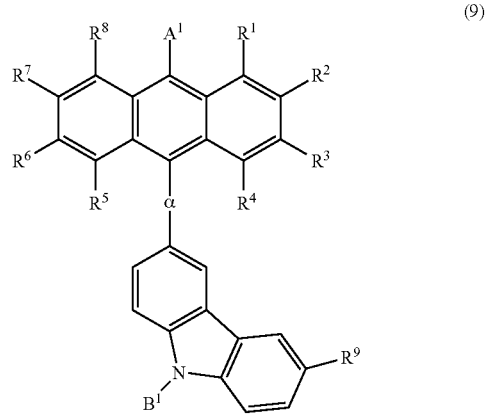

(9)

In the general formula (9), $A^1$ represents a substituted or unsubstituted phenyl group, $B^1$ represents any of an alkyl group having 1 to 4 carbon atoms or a substituted or unsubstituted phenyl group, α represents any of a substituted or unsubstituted phenylene group or a substituted or unsubstituted biphenyl-4,4'-diyl group, and $R^1$ to $R^9$ individually represent any of hydrogen, an alkyl group having 1 to 4 carbon atoms, or a substituted or unsubstituted phenyl group.

In the general formula (9), in the case where $A^1$ has a substituent, it is preferable that the substituent be an alkyl group having 1 to 4 carbon atoms, an alkoxy group having 1 to 4 carbon atoms, a phenyl group, or a biphenyl group. As examples of the alkyl group having 1 to 4 carbon atoms, a methyl group, an ethyl group, and a butyl group are given. As examples of the alkoxy group having 1 to 4 carbon atoms, a methoxy group, an ethoxy group, and a butoxy group are given. As examples of the substituent denoted by $A^1$, substituents represented by structural formulae (10-1) to (10-6) are given specifically.

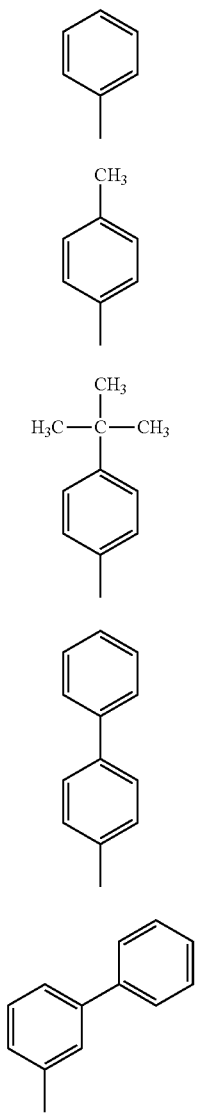

(10-1)

(10-2)

(10-3)

(10-4)

(10-5)

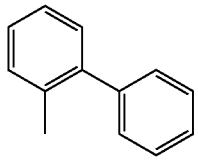

(10-6)

In the general formula (9), in the case where α has a substituent, it is preferable that the substituent be an alkyl group having 1 to 4 carbon atoms or an alkoxy group having 1 to 4 carbon atoms. As examples of the alkyl group having 1 to 4 carbon atoms, a methyl group, an ethyl group, and a butyl group are given. As examples of the alkoxy group having 1 to 4 carbon atoms, a methoxy group, an ethoxy group, and a butoxy group are given. It is preferable that the substituent denoted by a be any of substituents represented by structural formulae (11-1) to (11-5).

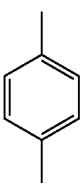

(11-1)

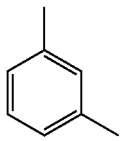

(11-2)

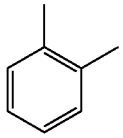

(11-3)

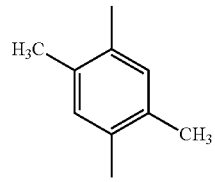

(11-4)

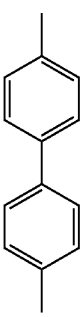

(11-5)

In the general formula (9), in the case where $B^1$ has a substituent, it is preferable that the substituent be an alkyl group having 1 to 4 carbon atoms, an alkoxy group having 1 to 4 carbon atoms, or a phenyl group. As examples of the alkyl group having 1 to 4 carbon atoms, there are a methyl group, an ethyl group, and a butyl group. As examples of the alkoxy group having 1 to 4 carbon atoms, there are a methoxy group, an ethoxy group, and a butoxy group. As examples of the substituent denoted by B¹, substituents represented by structural formulae (12-1) to (12-10) are given specifically.

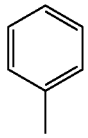
(12-1)

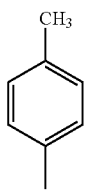
(12-2)

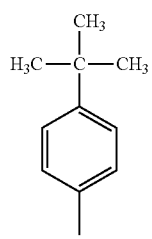
(12-3)

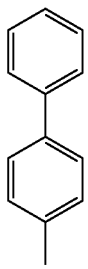
(12-4)

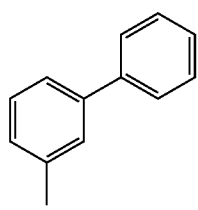
(12-5)

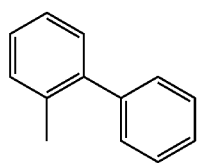
(12-6)

(12-7)

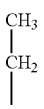
(12-8)

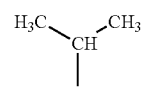
(12-9)

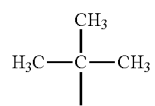
(12-10)

In the general formula (9), in the case where one or more of $R^1$ to $R^9$ have a substituent, it is preferable that the substituent be an alkyl group having 1 to 4 carbon atoms, an alkoxy group having 1 to 4 carbon atoms, or a phenyl group. As examples of the alkyl group having 1 to 4 carbon atoms, there are a methyl group, an ethyl group, and a butyl group. It is preferable that the alkoxy group having 1 to 4 carbon atoms be a methoxy group, an ethoxy group, a butoxy group, or the like.

As examples of the anthracene derivatives of the present invention, anthracene derivatives represented by structural formulae (101) to (443) can be given. However, the present invention is not limited thereto.

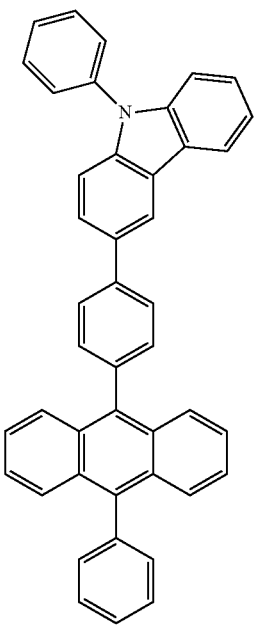
(101)

(102)
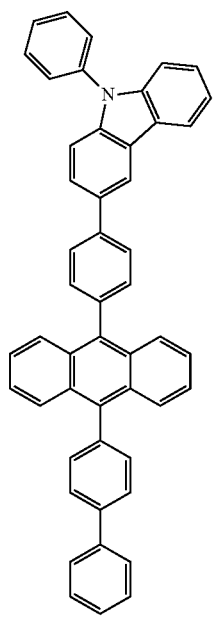
(104)
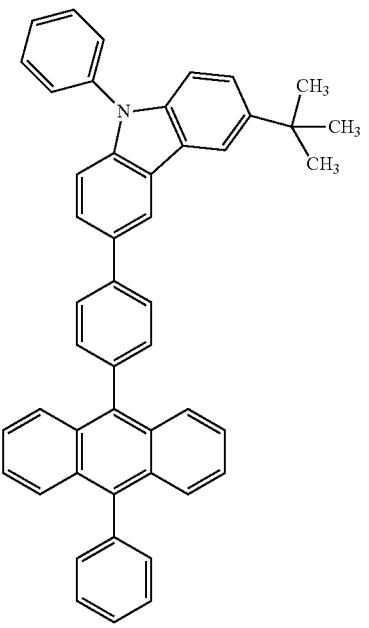
(103)
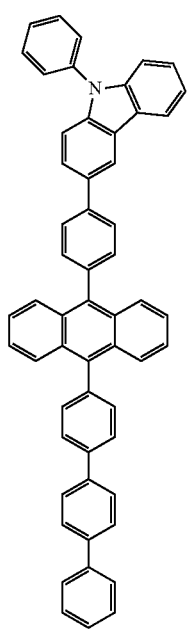
(105)
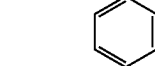

(106)
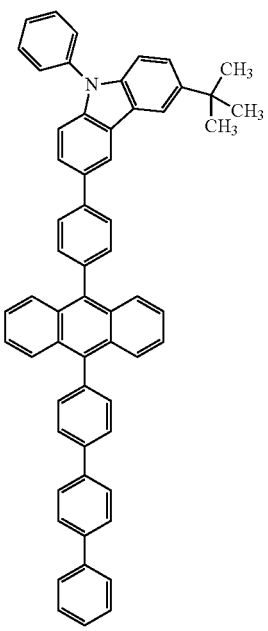
(107)
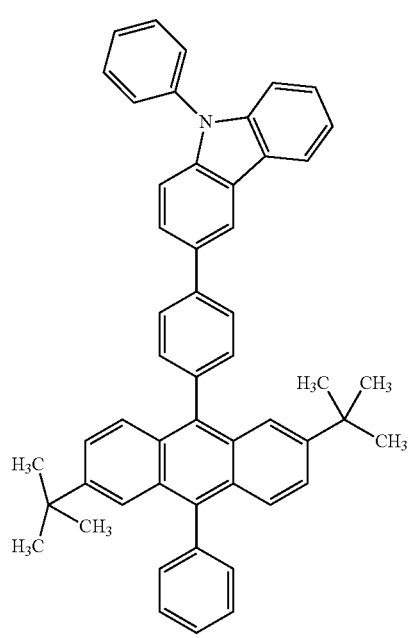
(108)
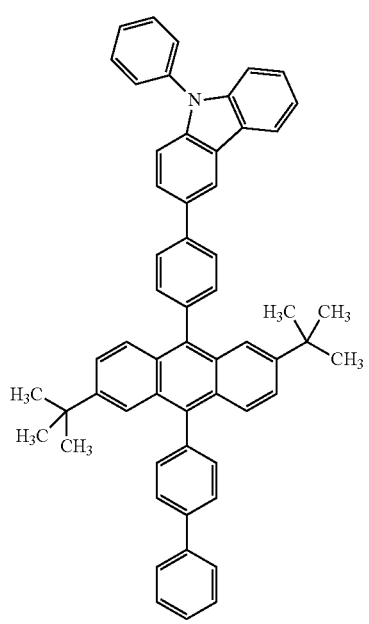
(109)
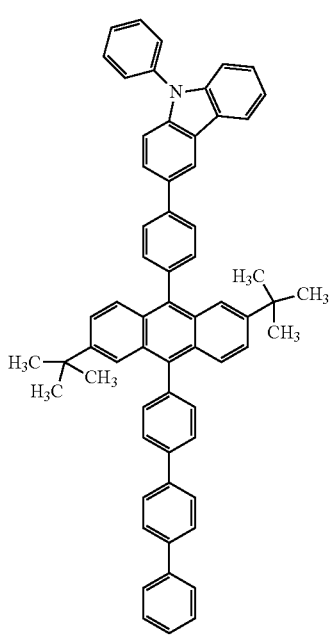

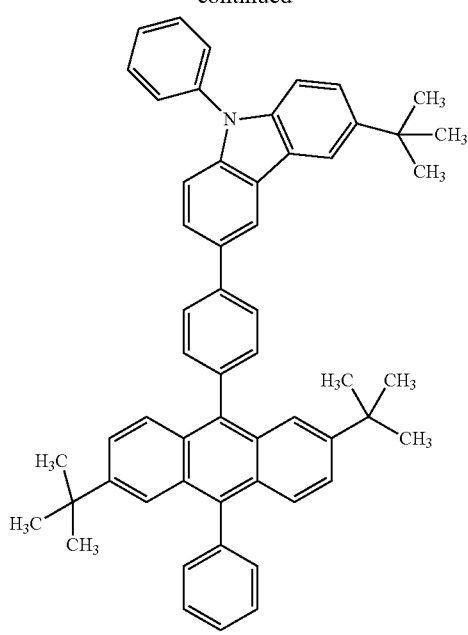
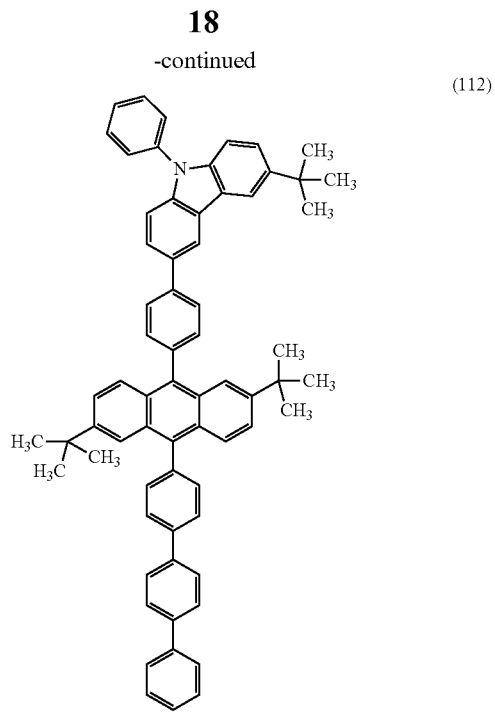
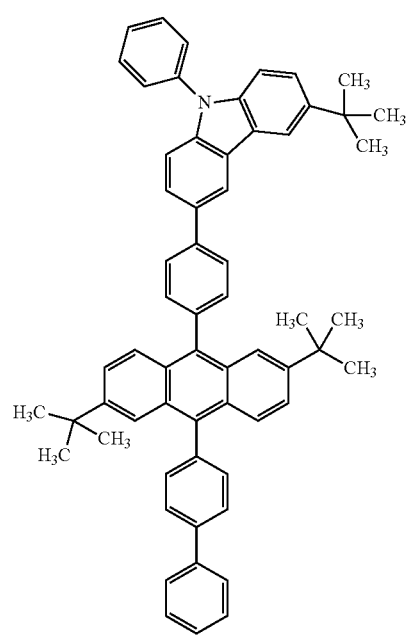
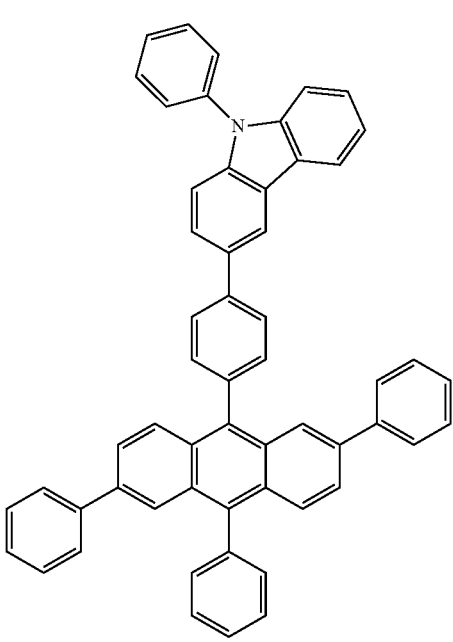

(114)
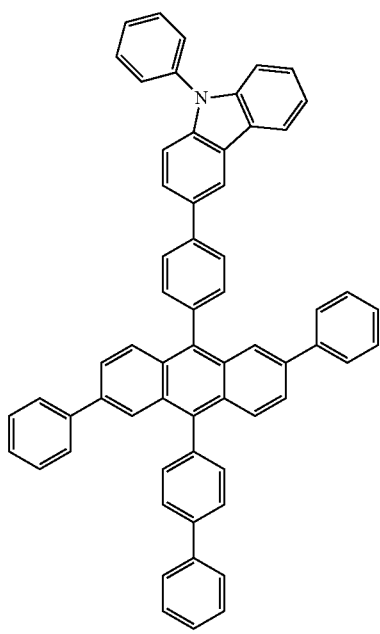
(115)
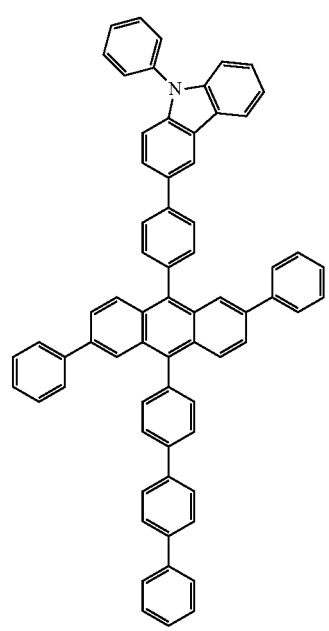
(116)
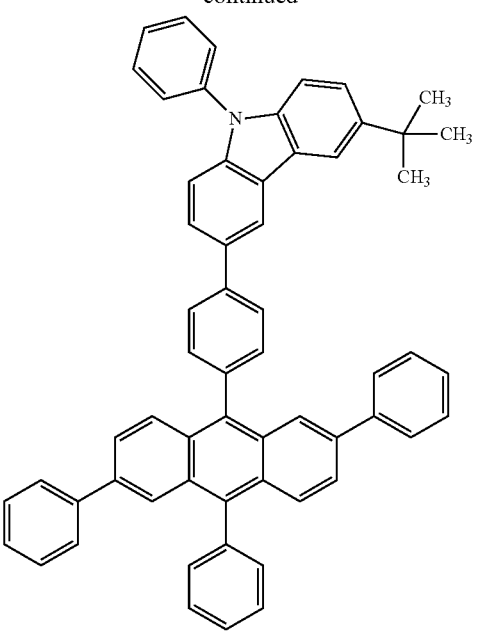
(117)
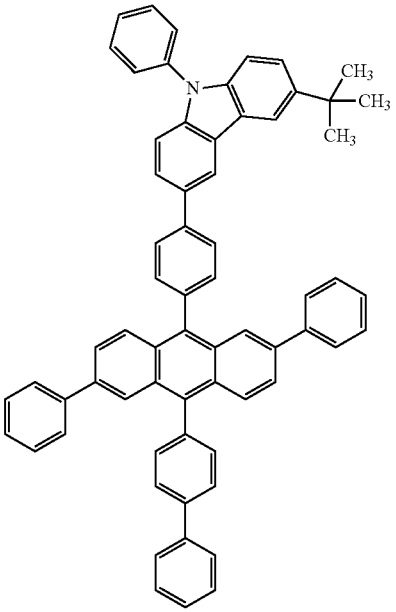

(118)
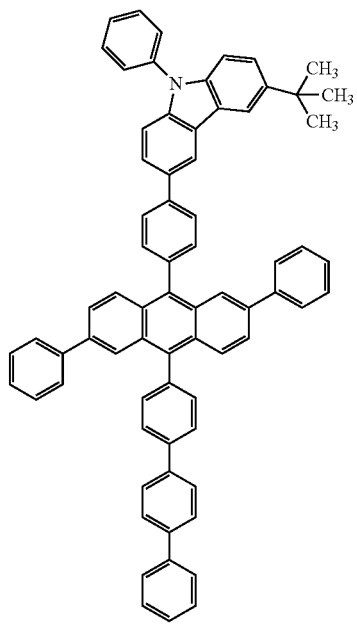
(120)
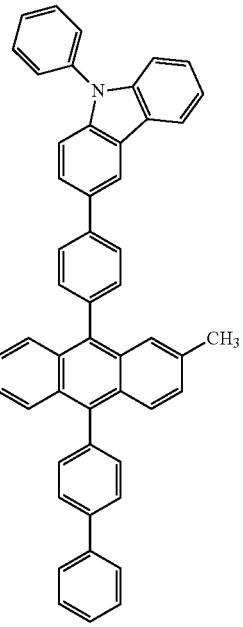
(119)
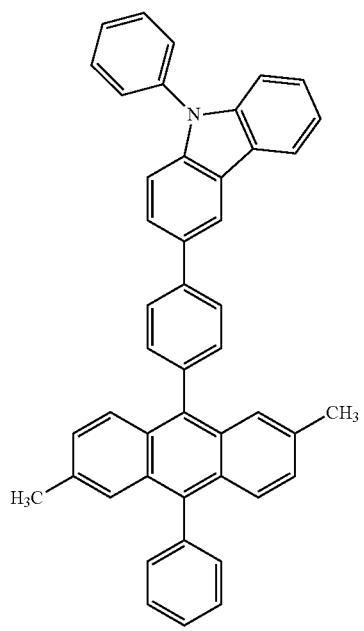
(121)
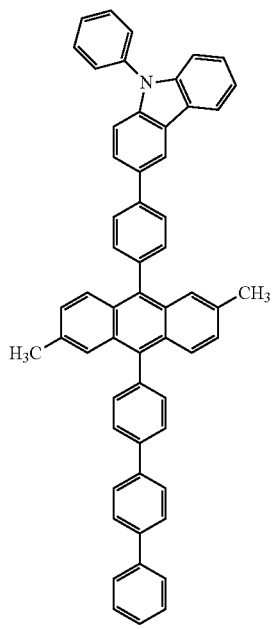

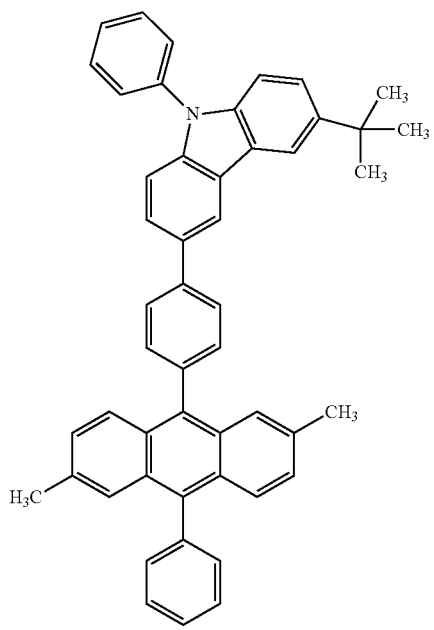
(122)
(123)
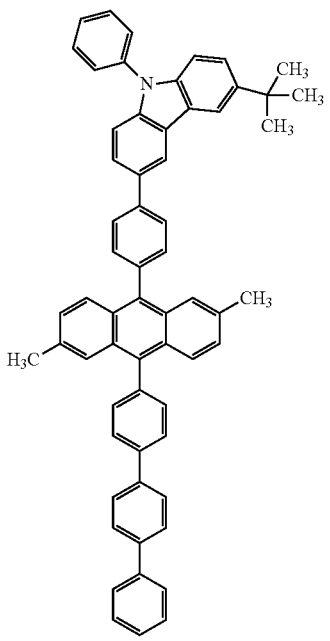
(124)
(125)

(126)
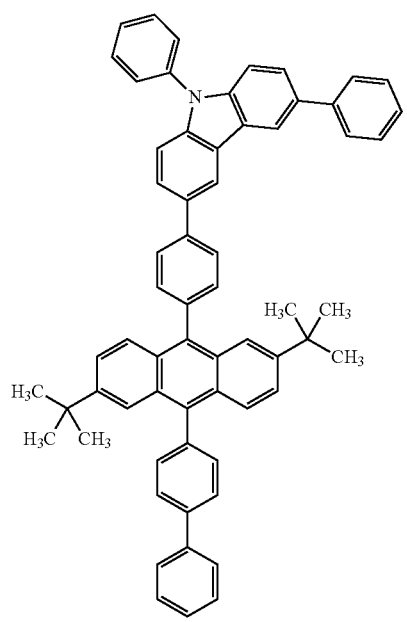
(127)
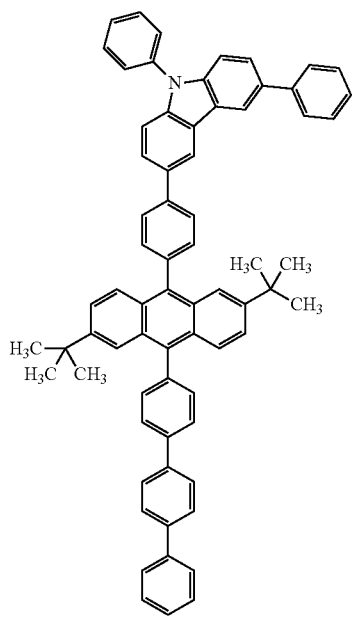
(128)
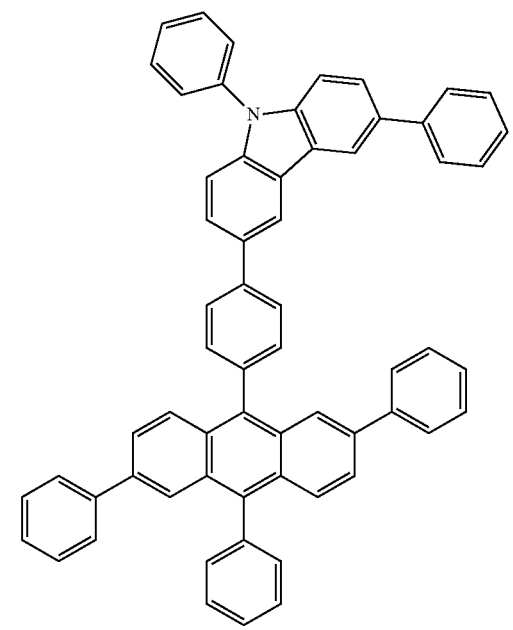
(129)
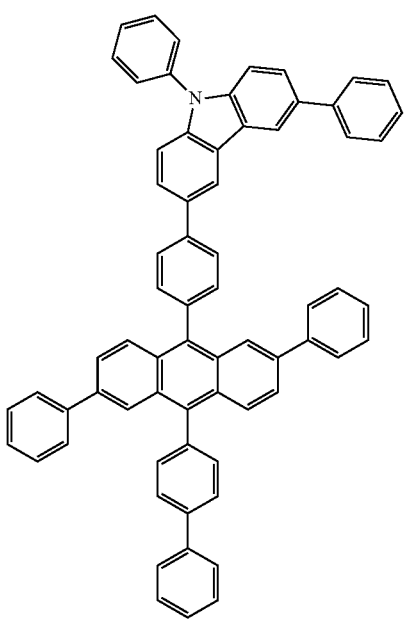

(130)
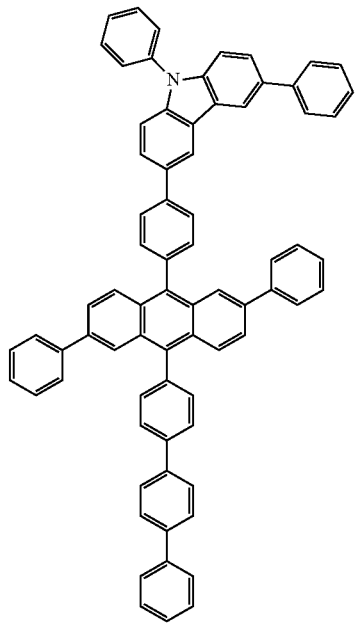
(131)
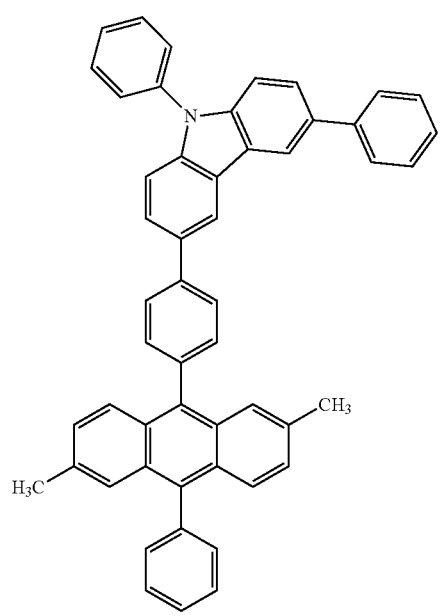
(132)
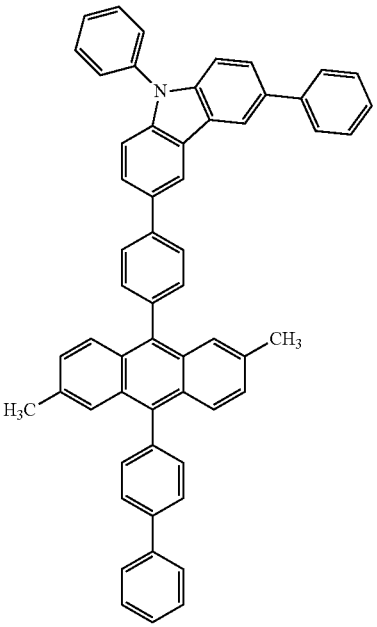
(133)
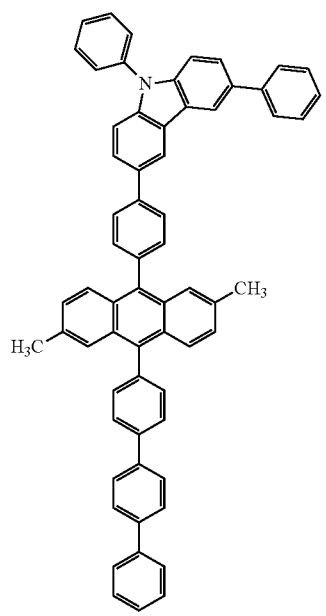

(134)
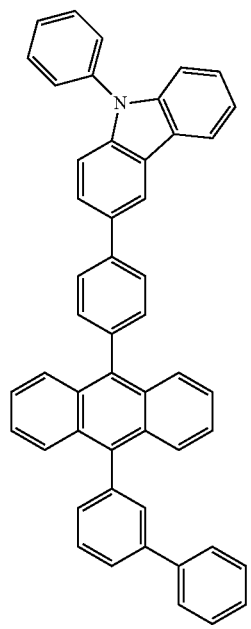
(135)
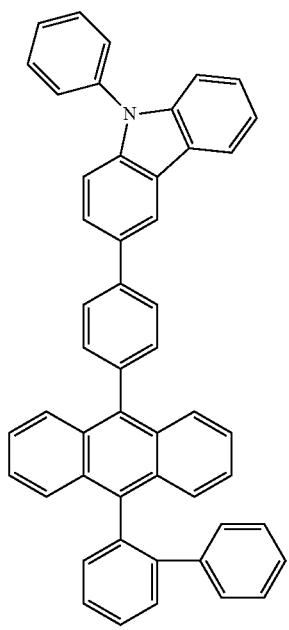
(136)
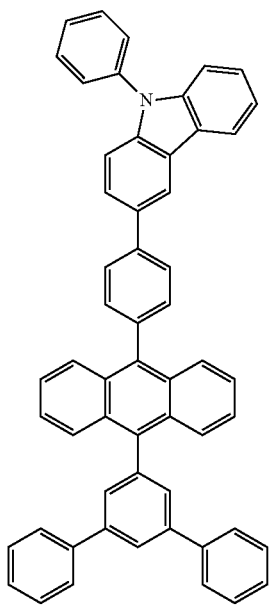
(137)
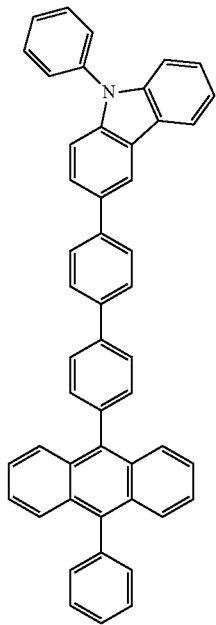

(138)
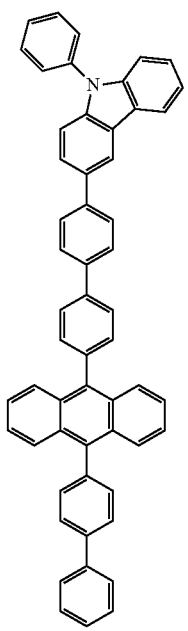
(139)
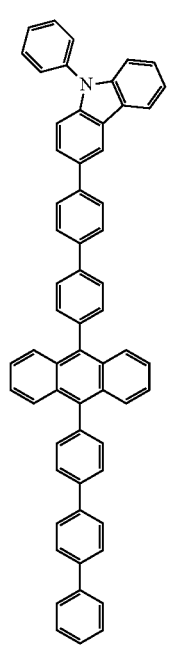
(140)
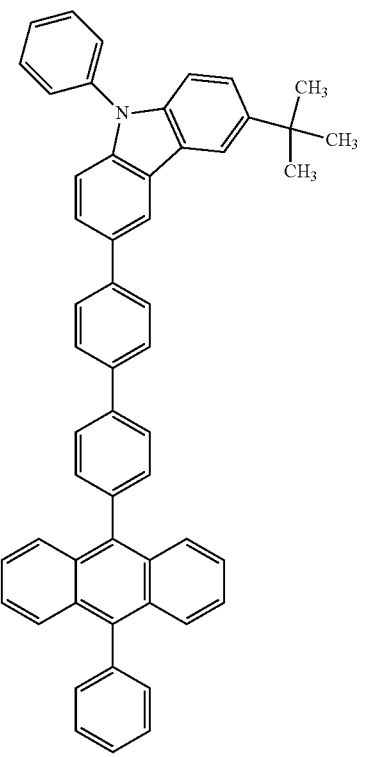
(141)
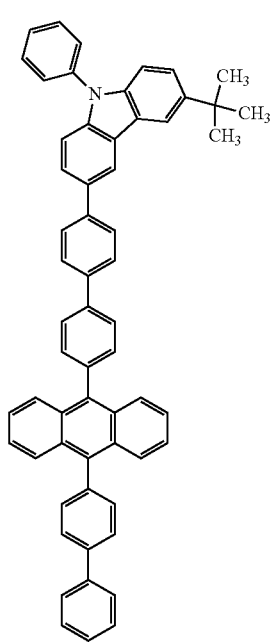

(142)
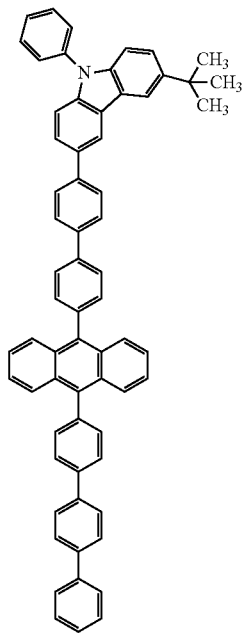
(143)
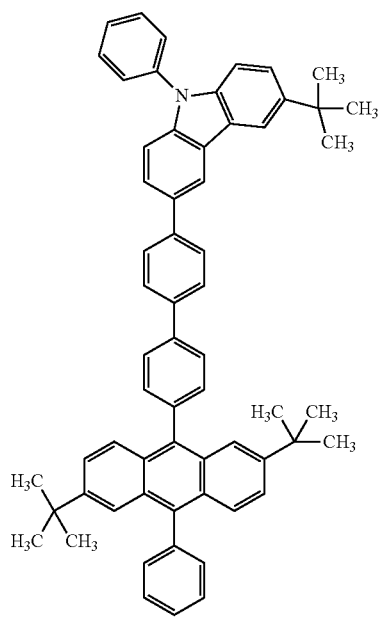
(144)
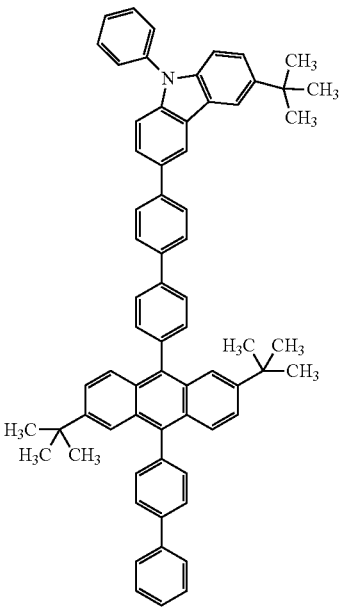
(145)
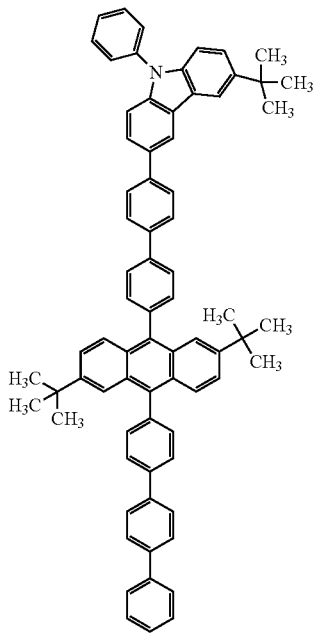

(146)
(147)
(148)
(149)

(150)
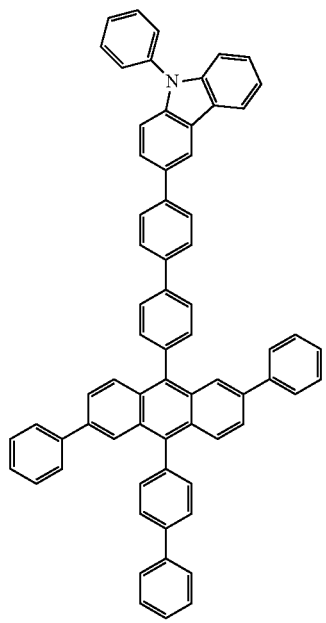
(151)
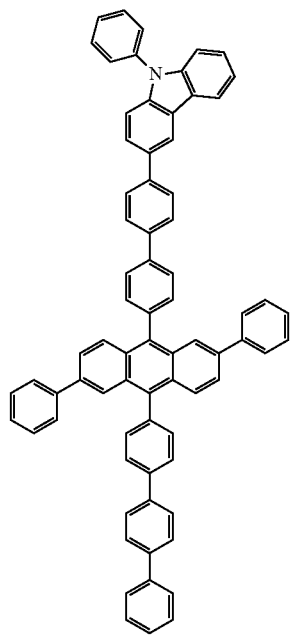
(152)
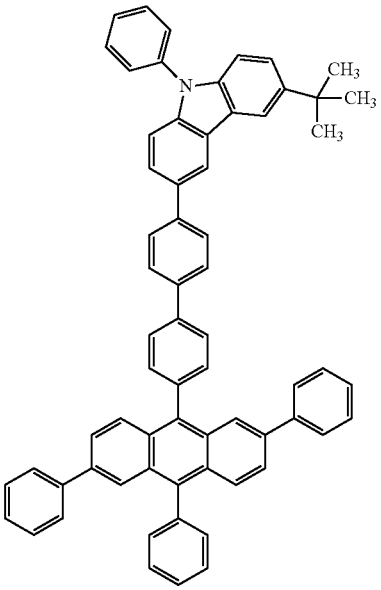
(153)
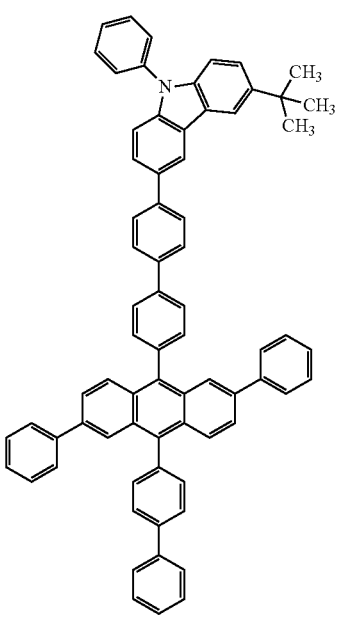

(154)
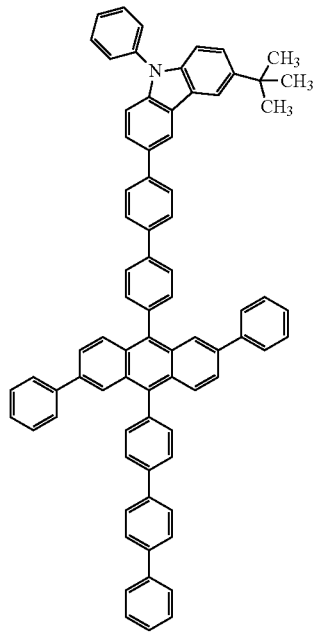
(156)
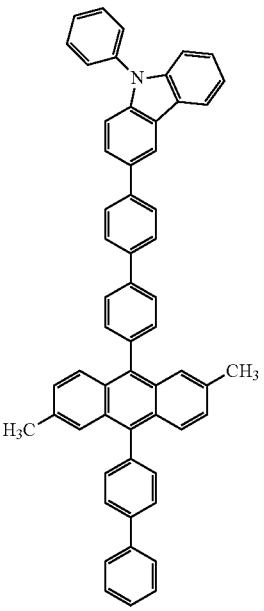
(155)
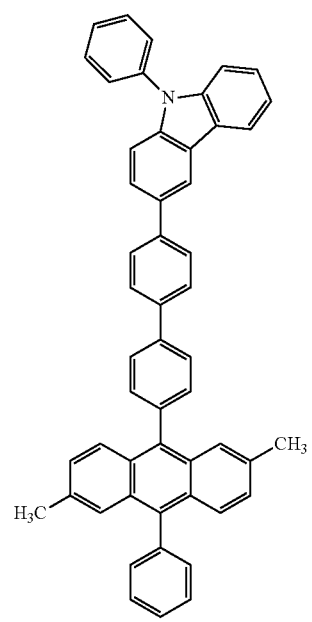
(157)
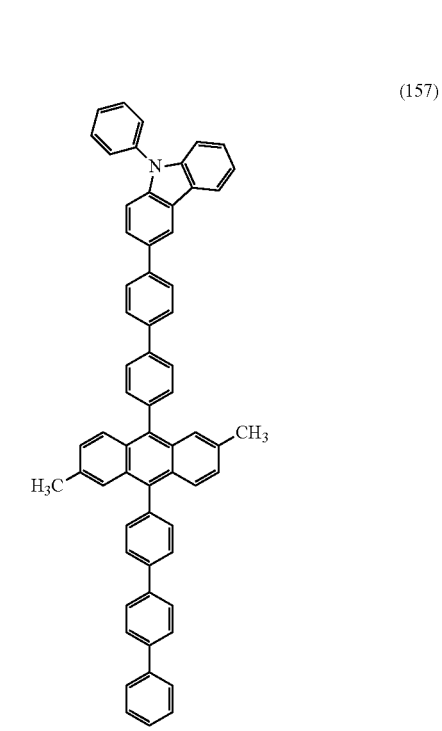

41
-continued
(158)
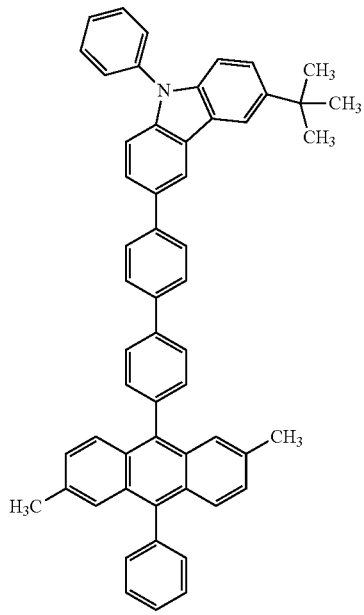
(159)
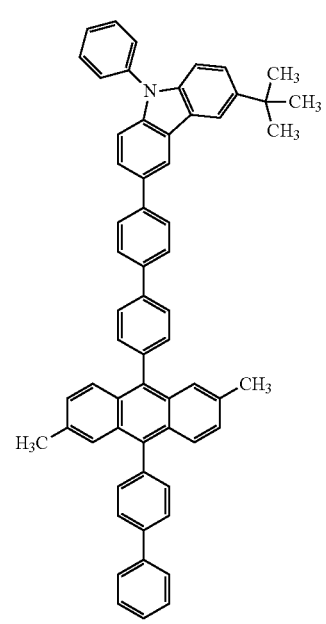
42
-continued
(160)
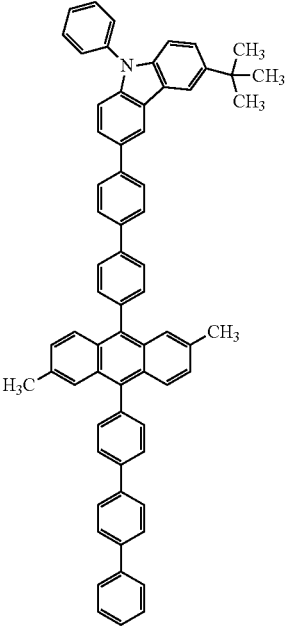
(161)
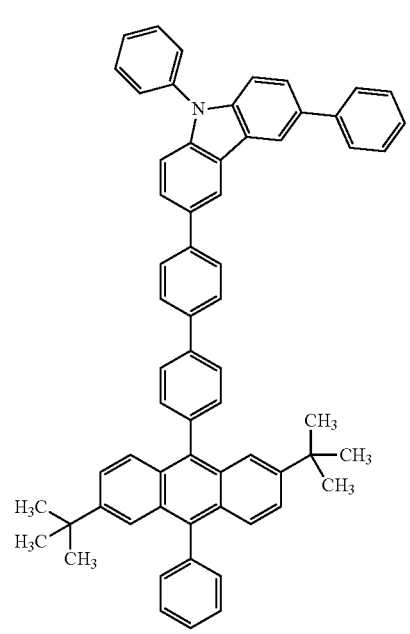

(162) 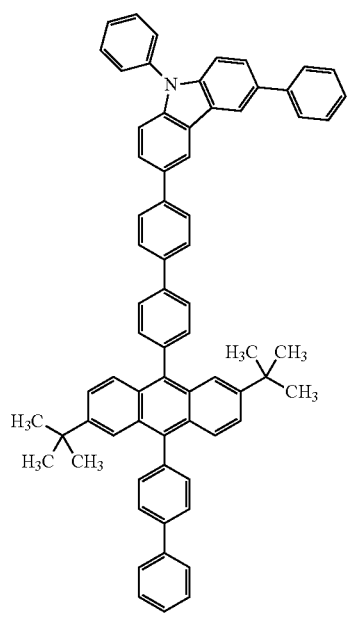
(164) 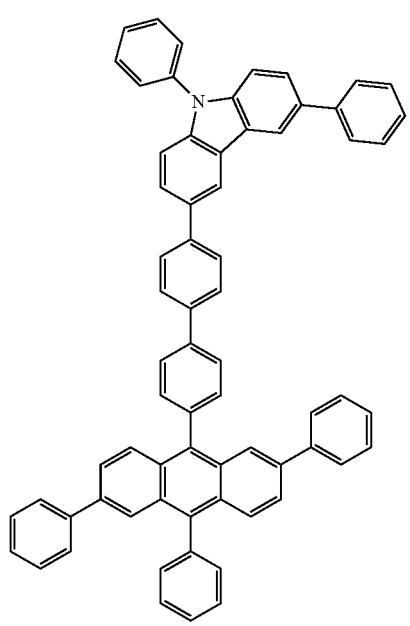
(163) 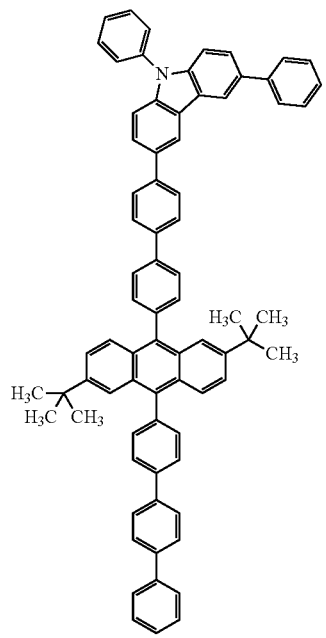
(165) 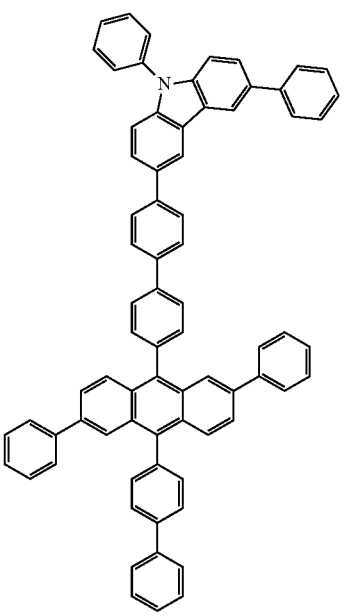

(166)
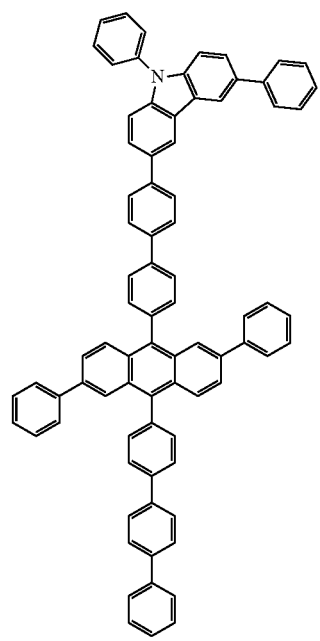
(168)
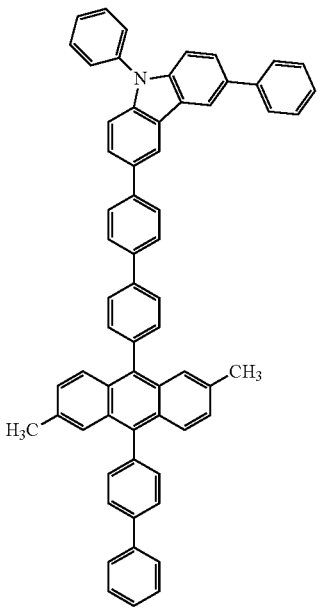
(167)
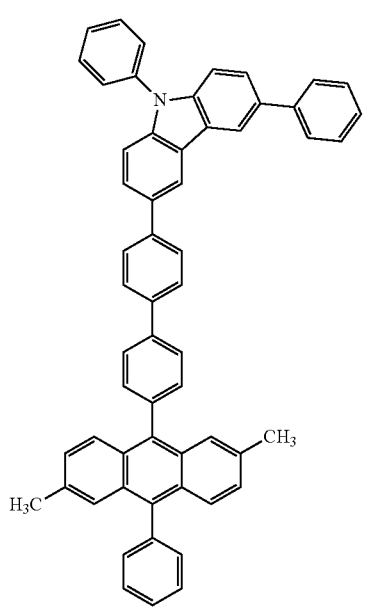
(169)
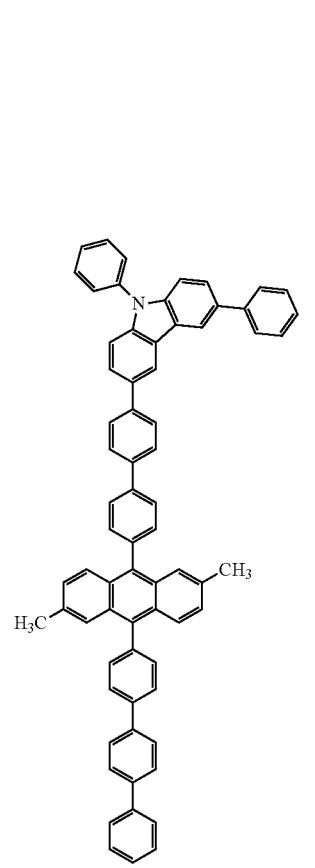

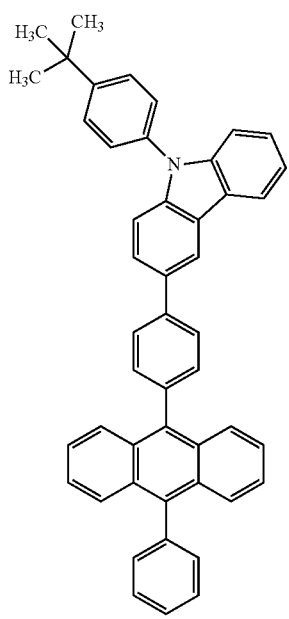
(170)
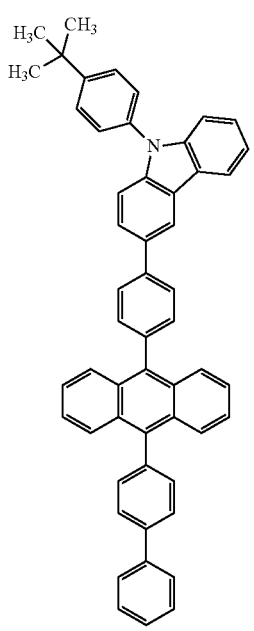
(171)
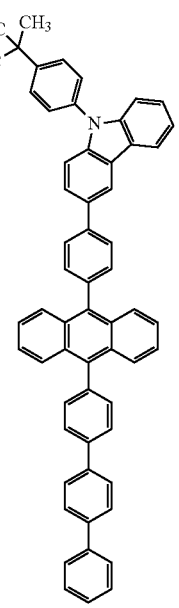
(172)
(173)

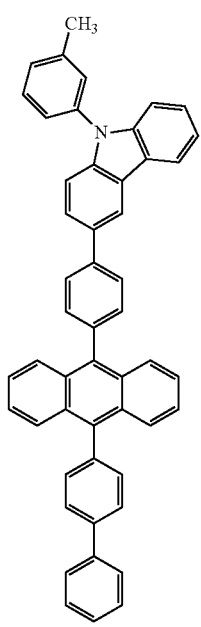
(174)
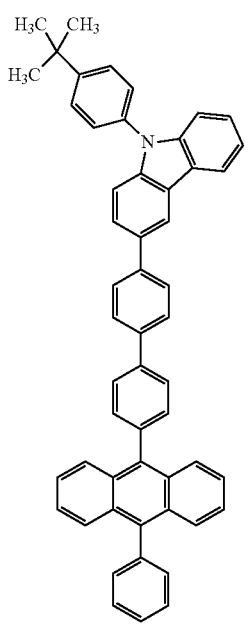
(176)
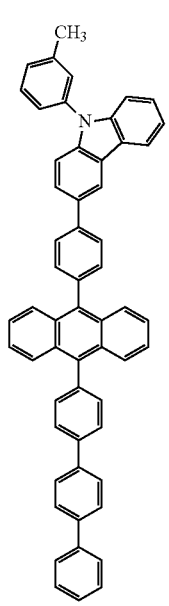
(175)
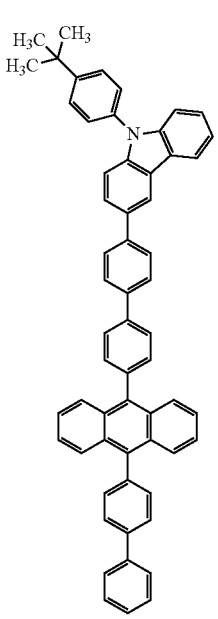
(177)

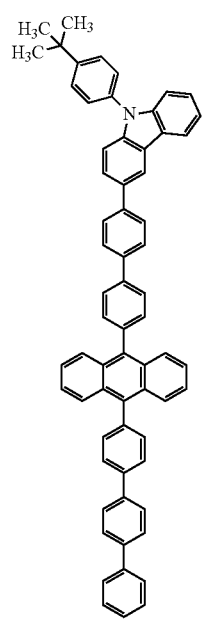 (178)
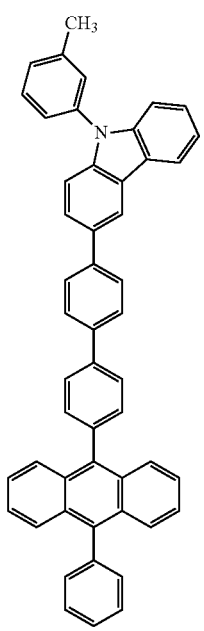 (179)
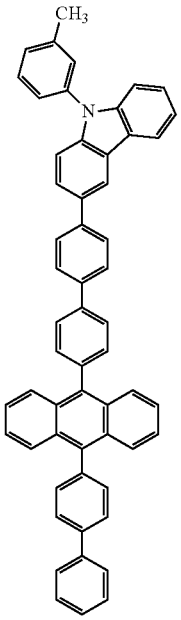 (180)
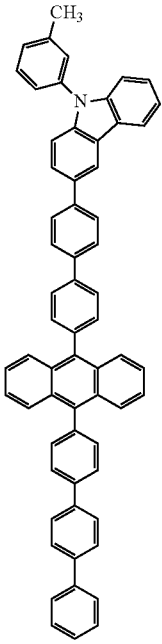 (181)

(182)
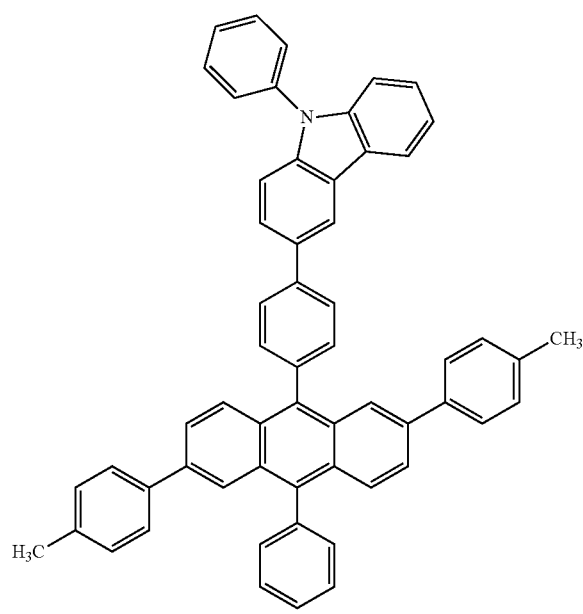
(184)
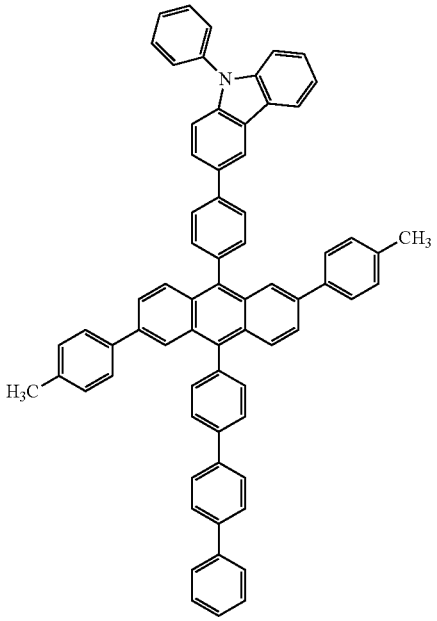
(183)
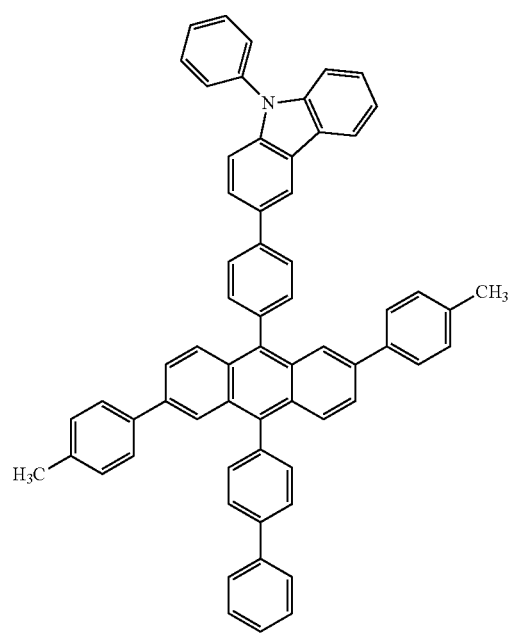
(185)
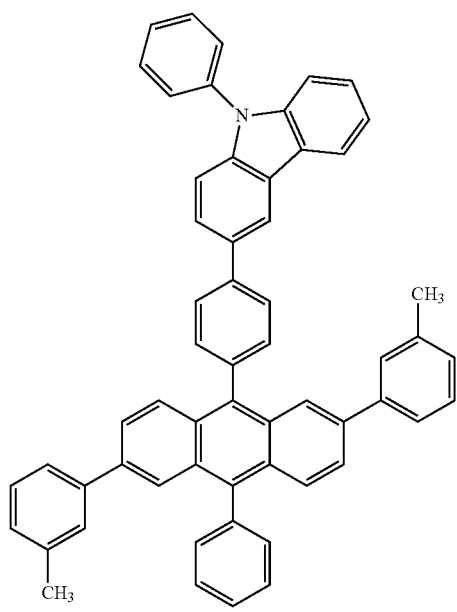

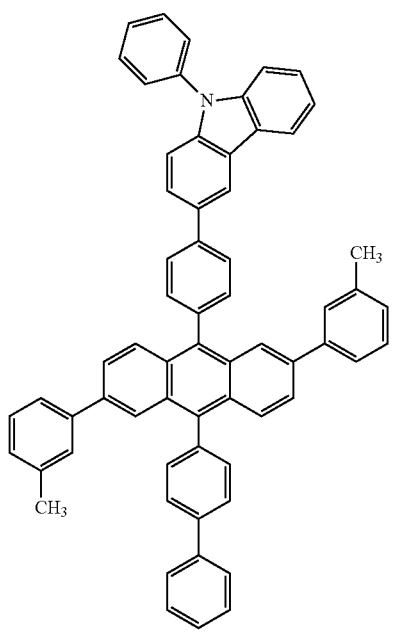
(186)
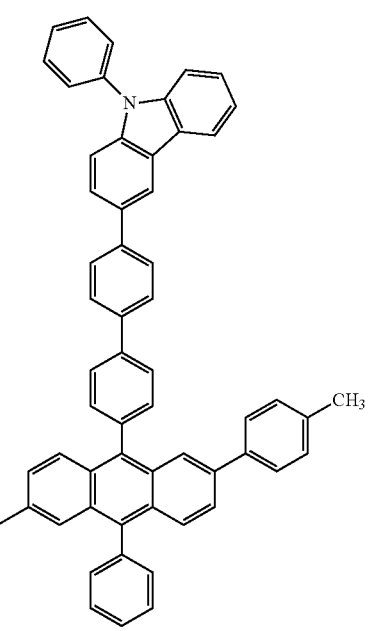
(188)
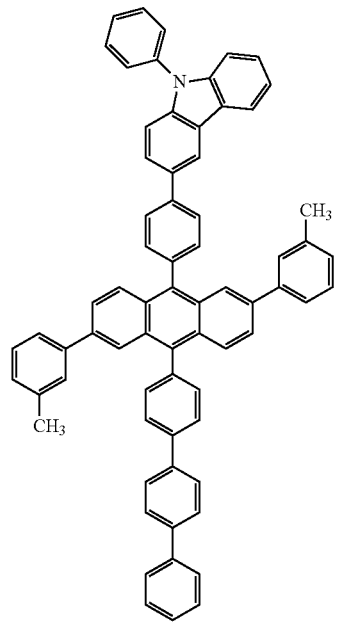
(187)
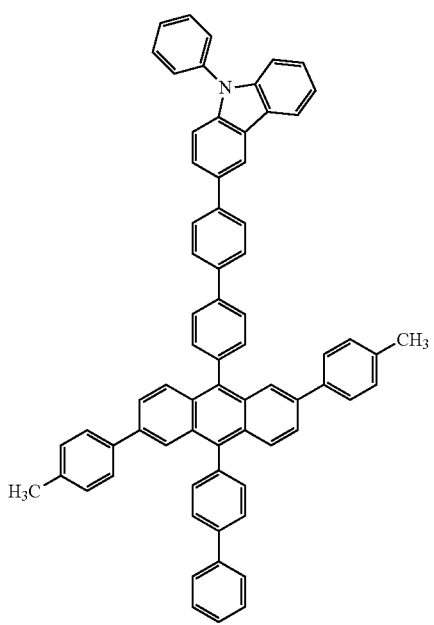
(189)

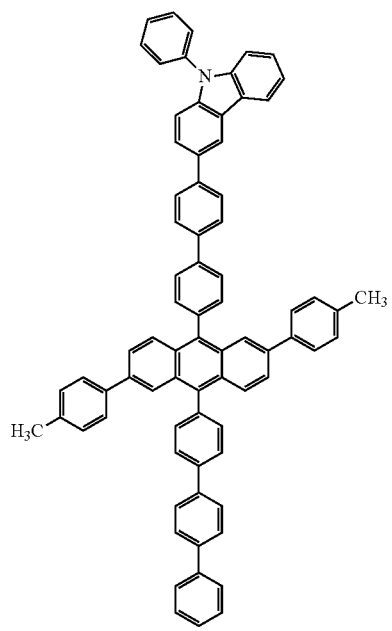 (190)
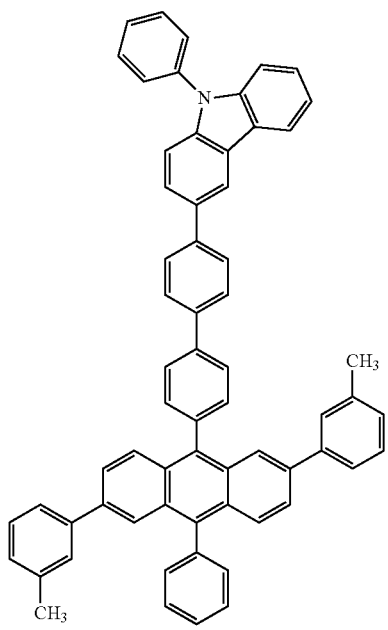 (191)
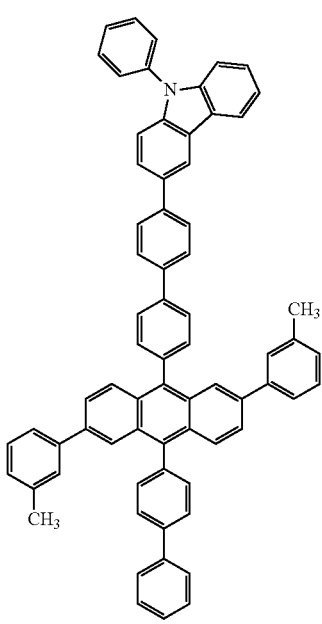 (192)
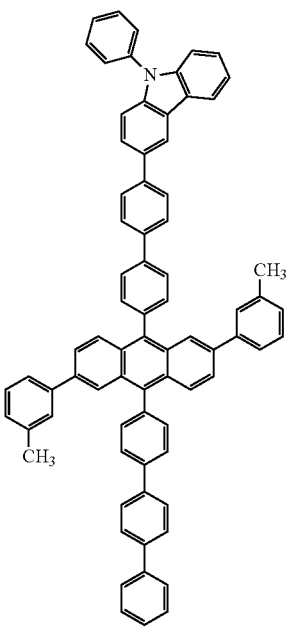 (193)

(194)
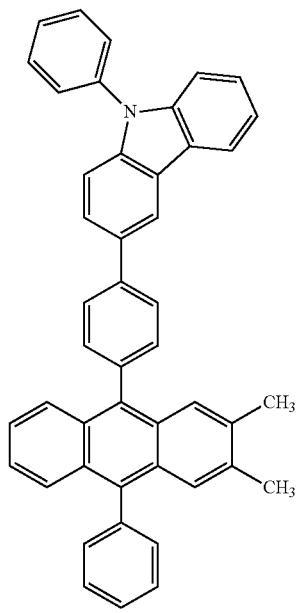
(195)
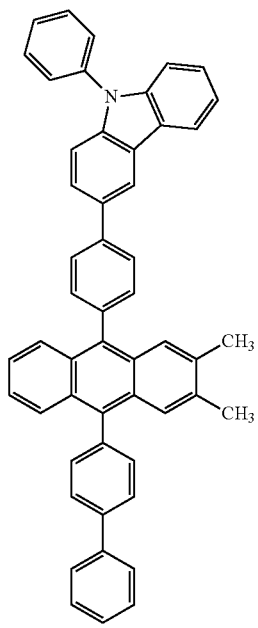
(196)
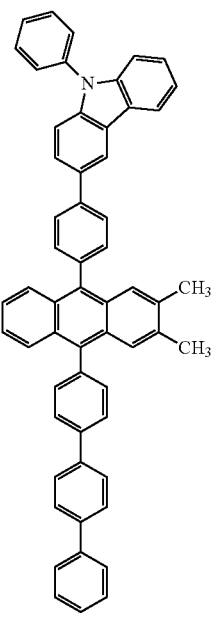
(197)
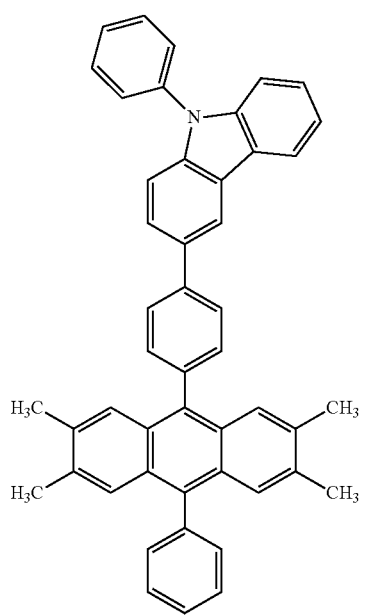

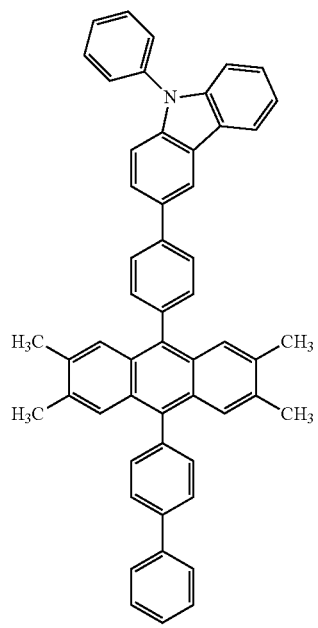
(198)
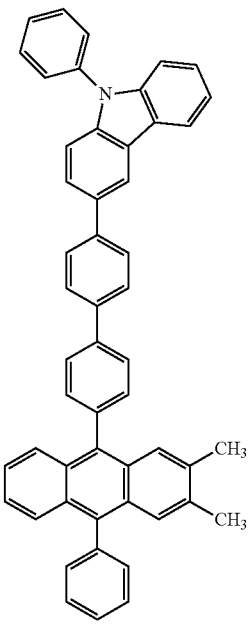
(200)
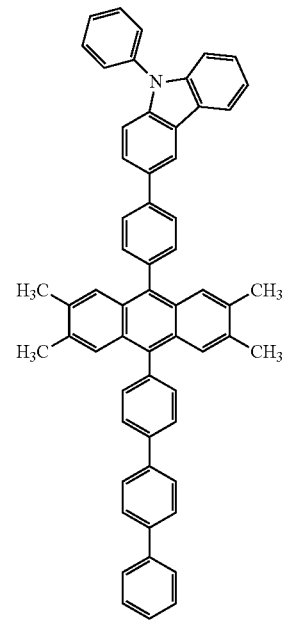
(199)
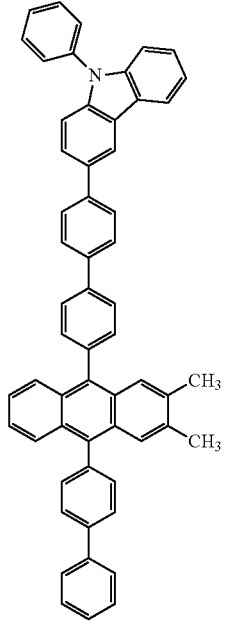
(201)

(202)
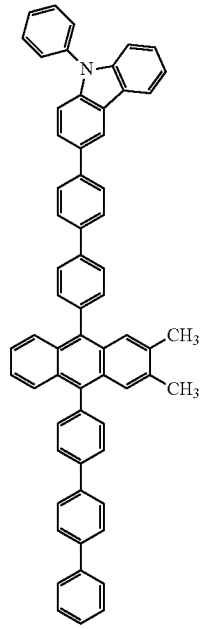
(204)
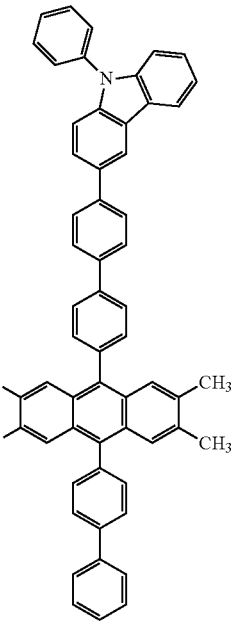
(203)
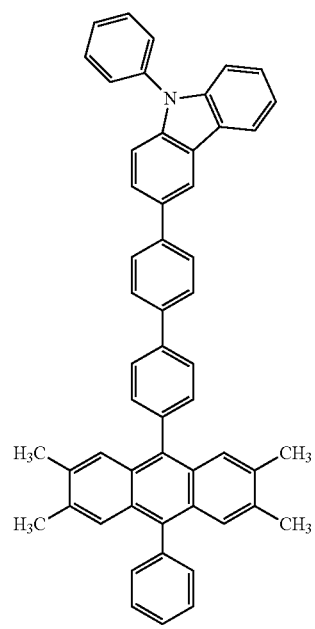
(205)
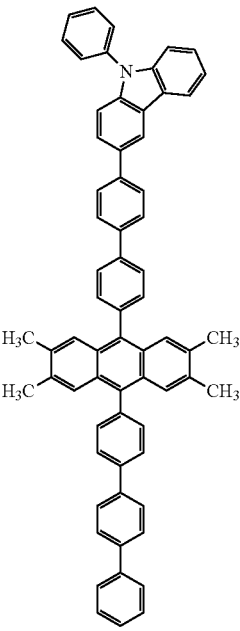

(206)
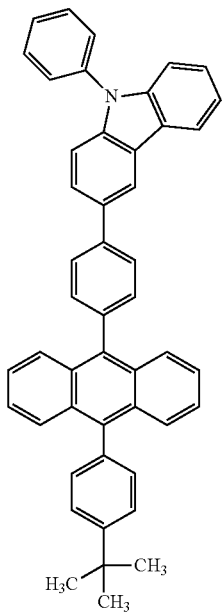
(207)
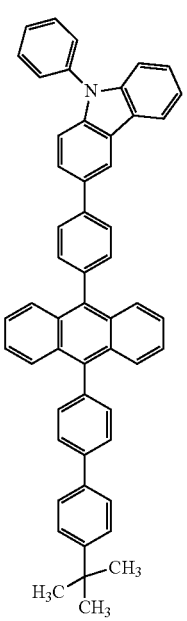
(208)
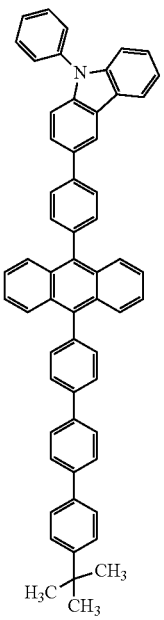
(209)
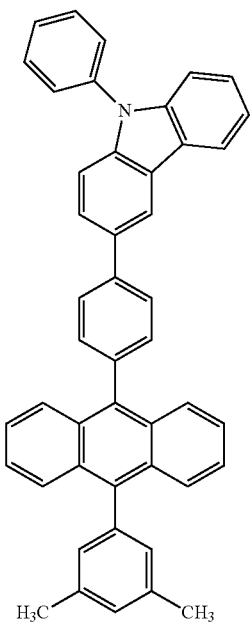

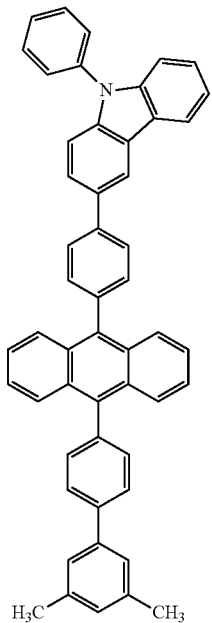 (210)
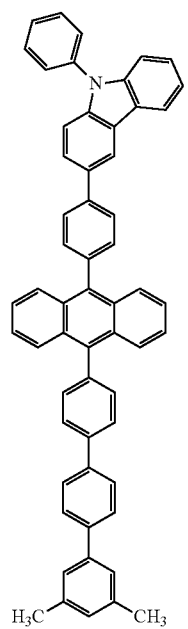 (211)
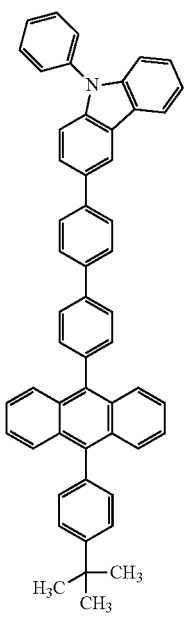 (212)
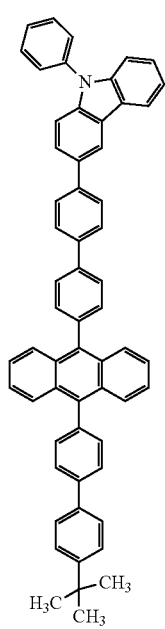 (213)

(214)
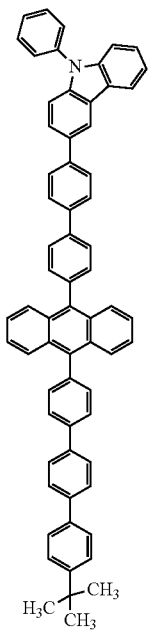
(215)
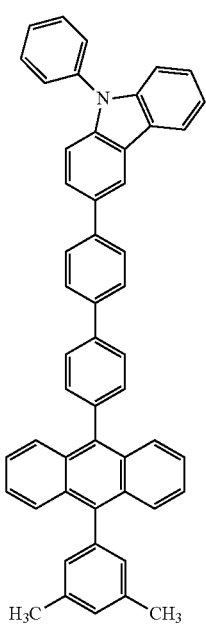
(216)
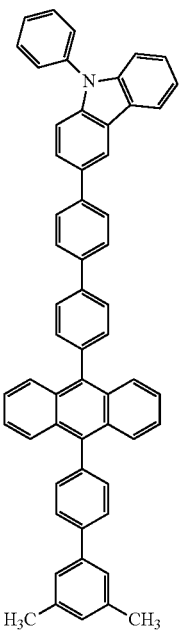
(217)
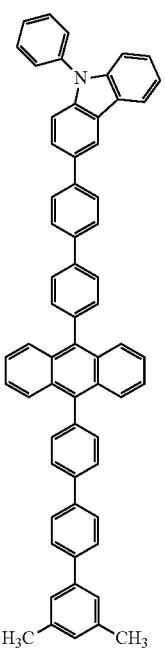

71
(218)
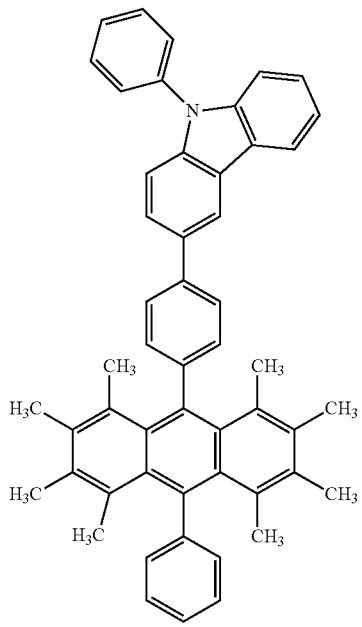
72
(220)
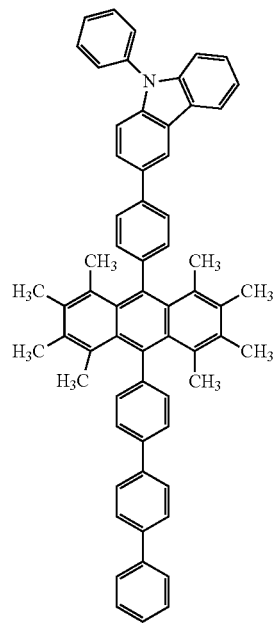
(219)
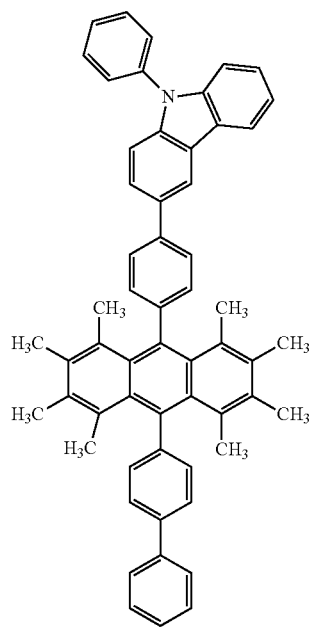
(221)
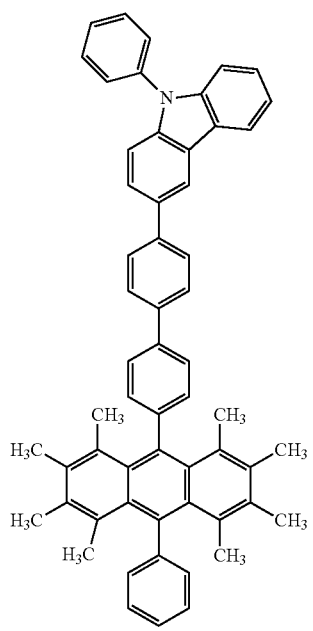

73
-continued
(222)
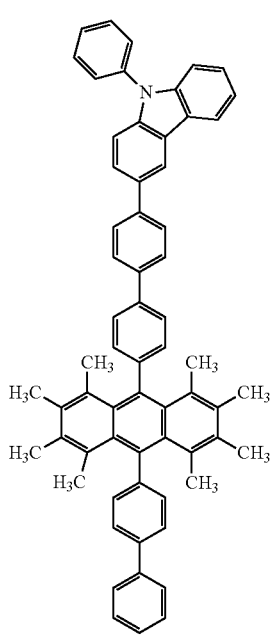
74
-continued
(224)
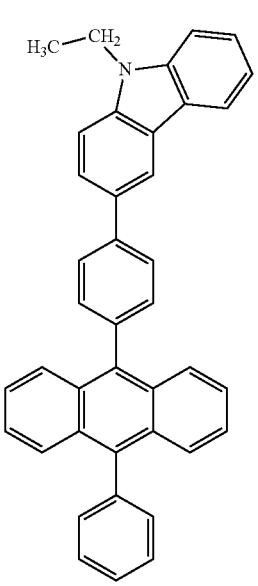
(223)
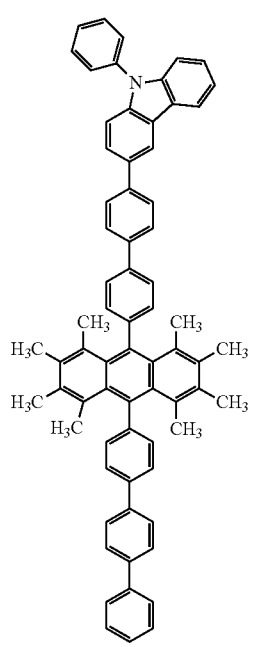
(225)
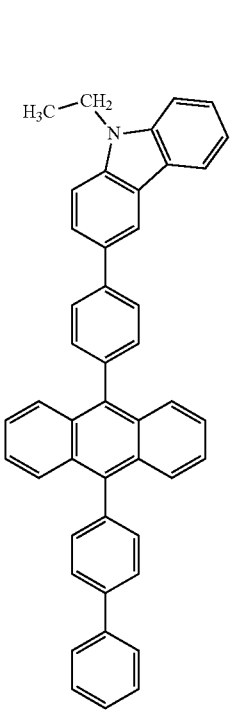

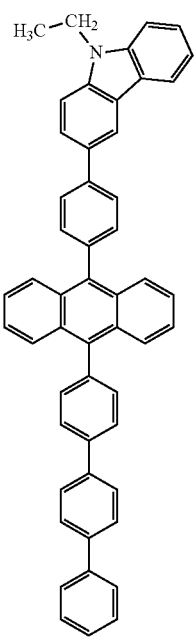
(226)
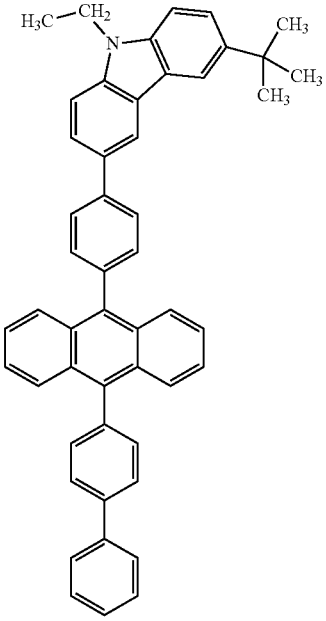
(228)
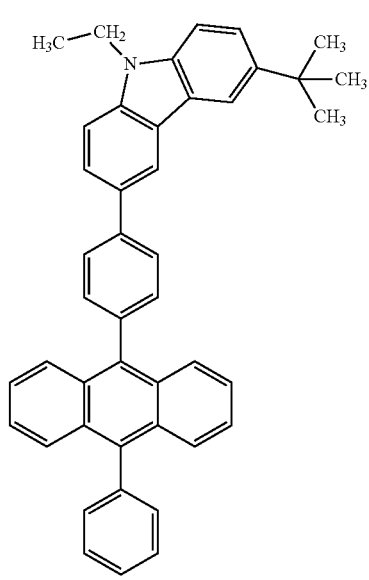
(227)
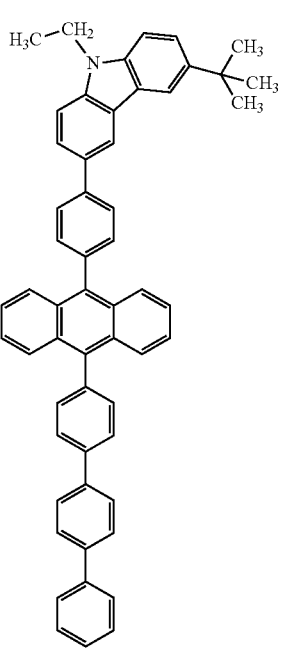
(229)

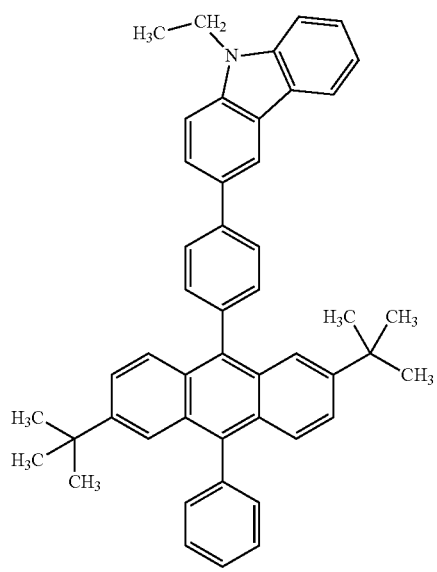
(230)
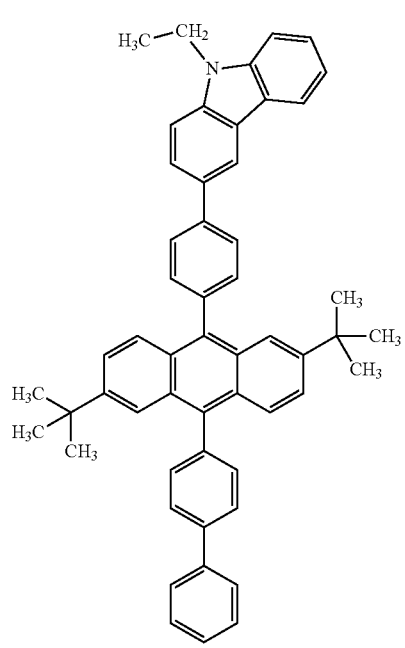
(231)
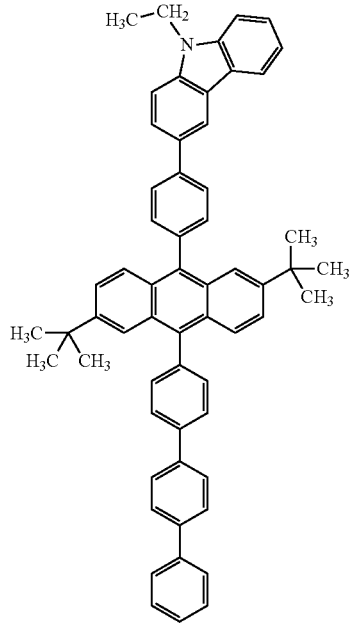
(232)
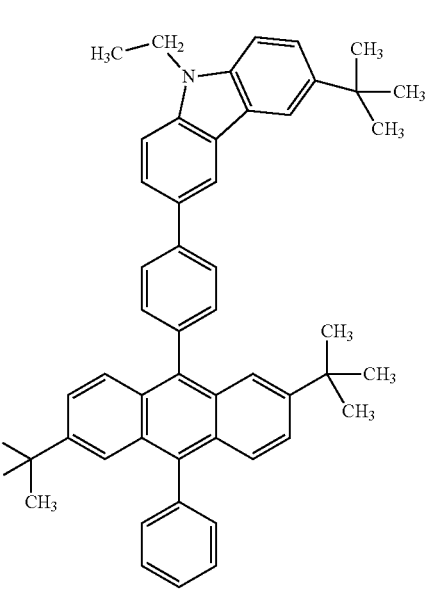
(233)

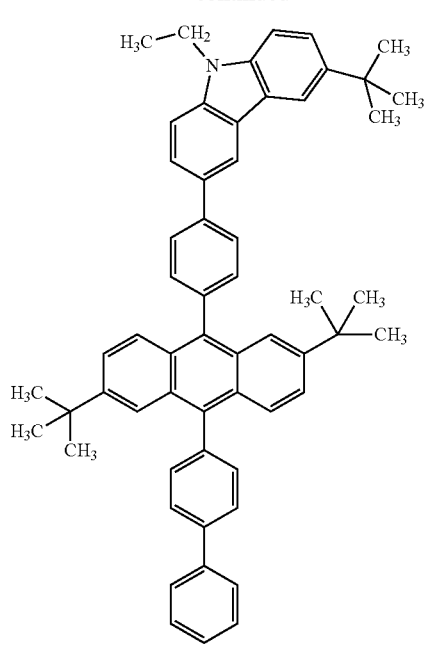 (234)
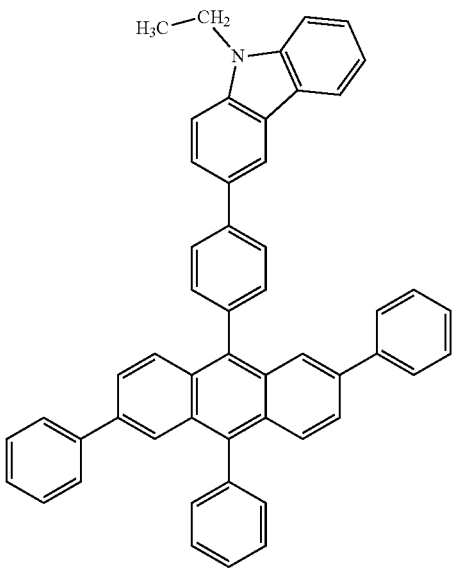 (236)
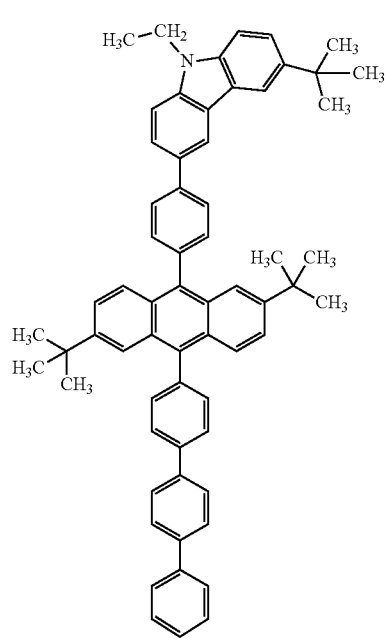 (235)
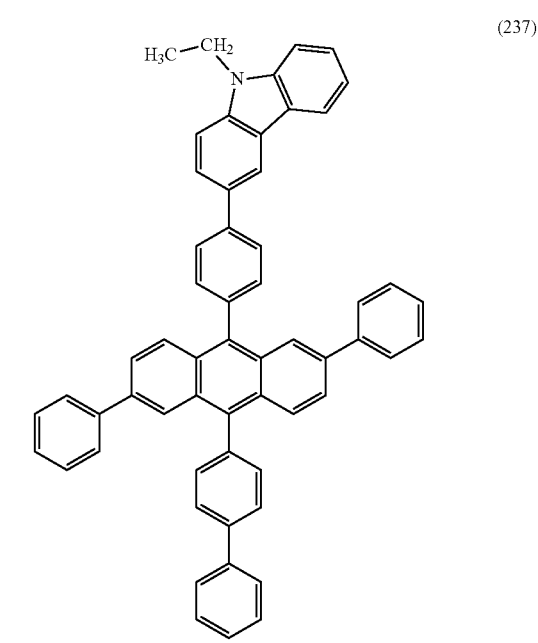 (237)

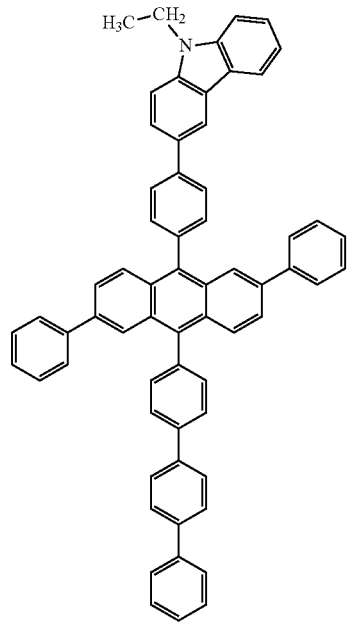
(238)
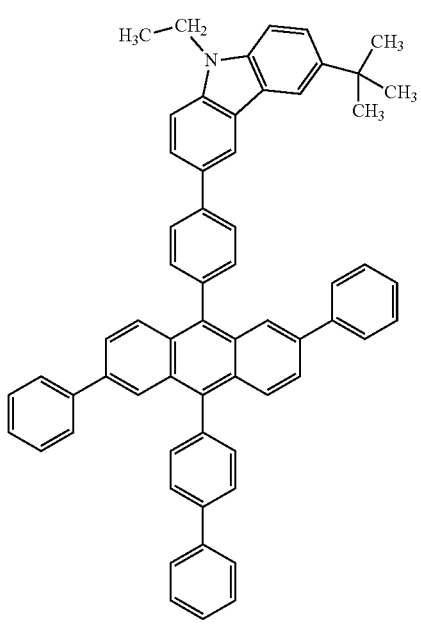
(240)
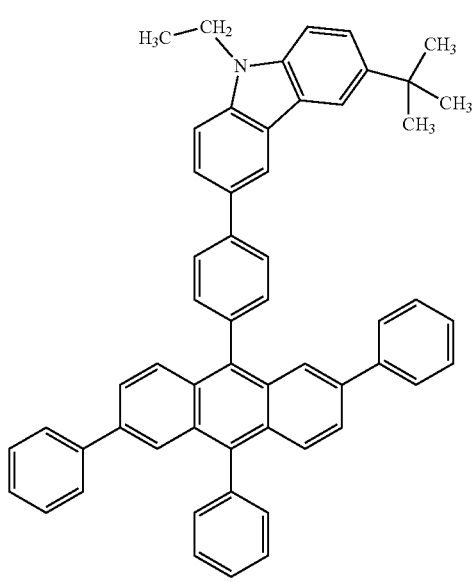
(239)
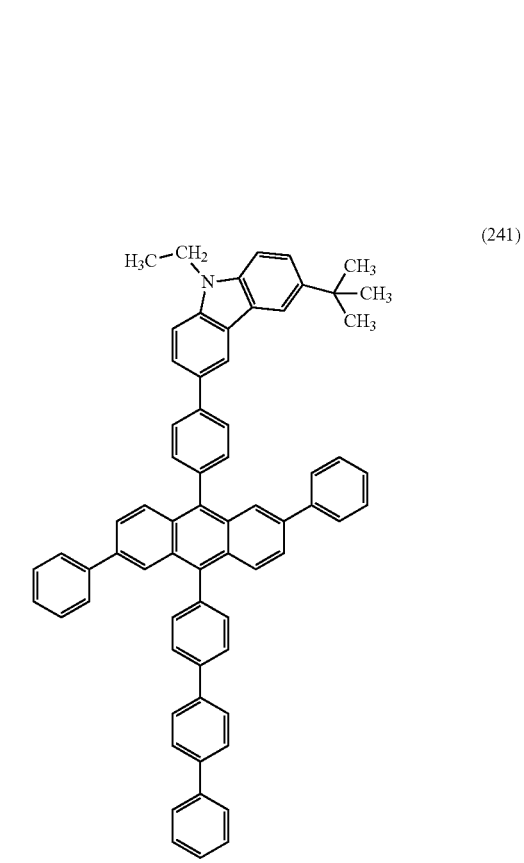
(241)

(242)

(243)

(245)

(246)

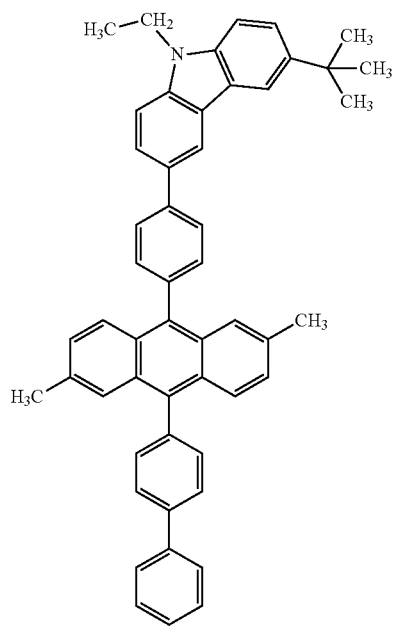
(247)
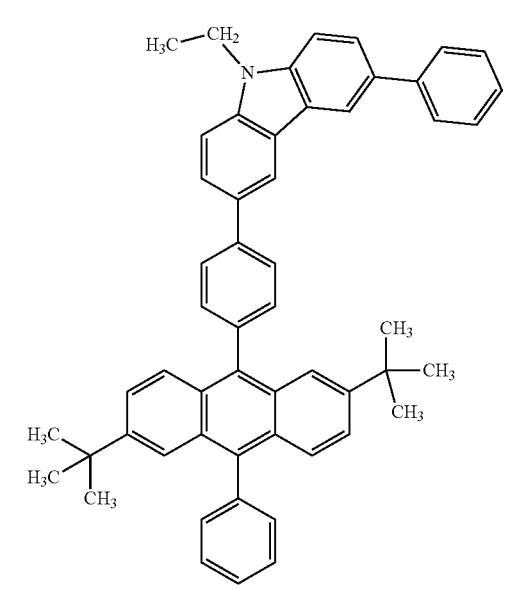
(249)
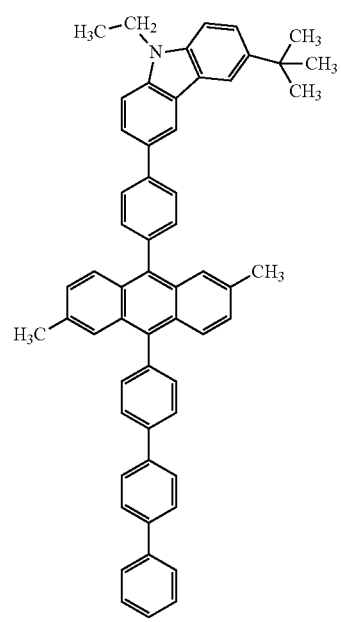
(248)
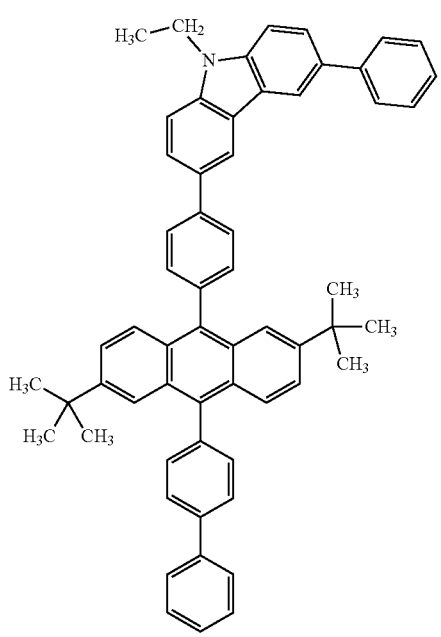
(250)

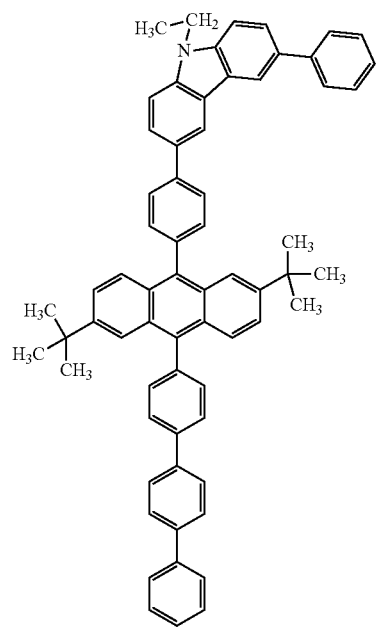
(251)
(252)
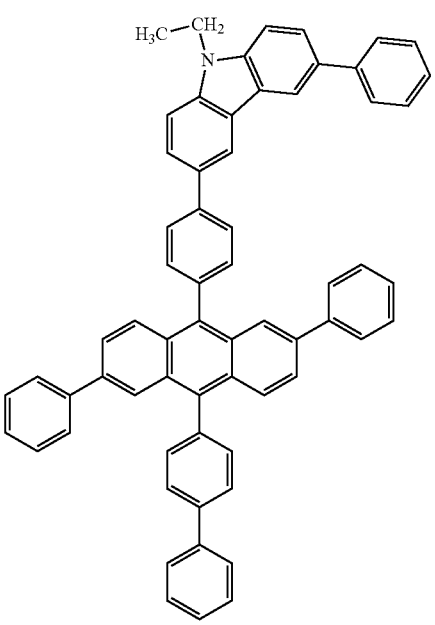
(253)
(254)

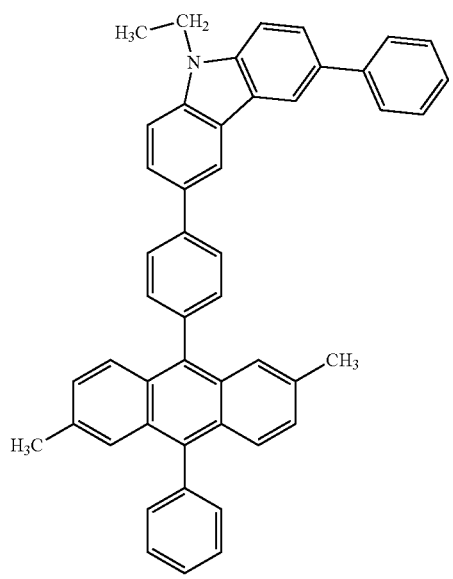 (255)
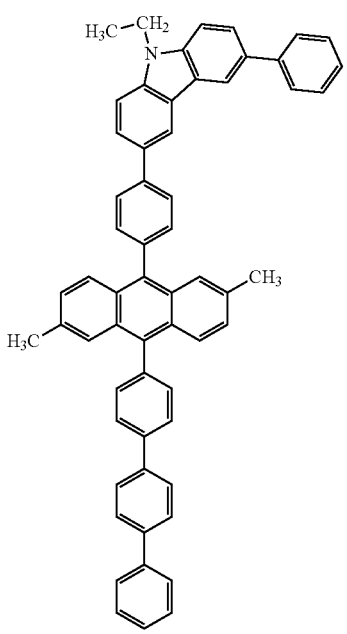 (257)
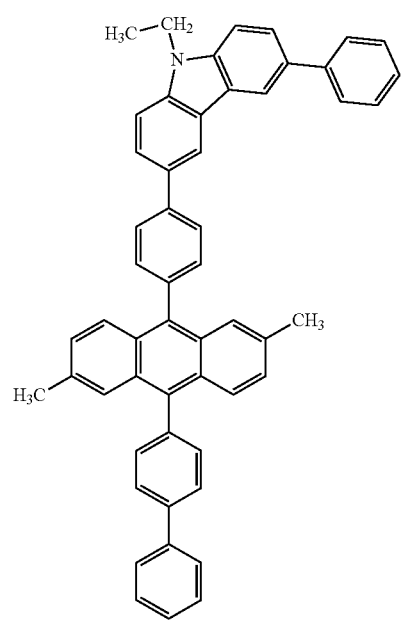 (256)
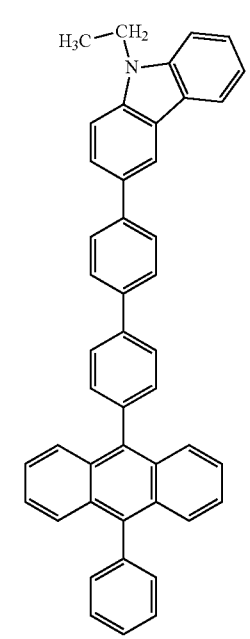 (258)

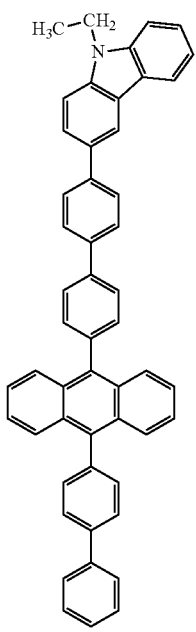
(259)
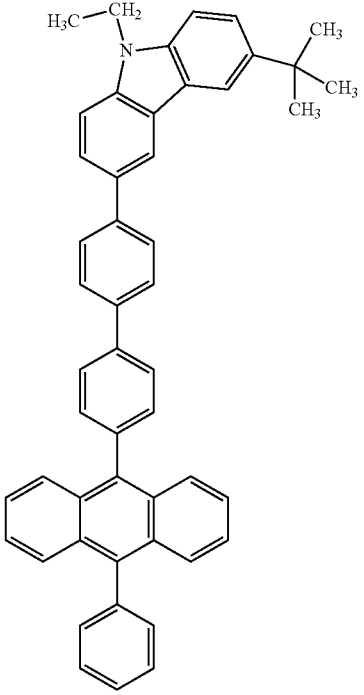
(261)
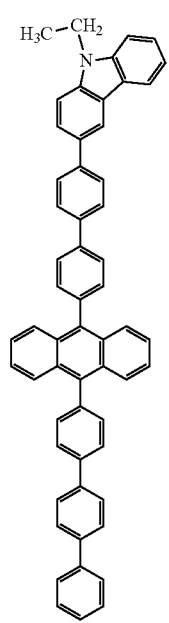
(260)
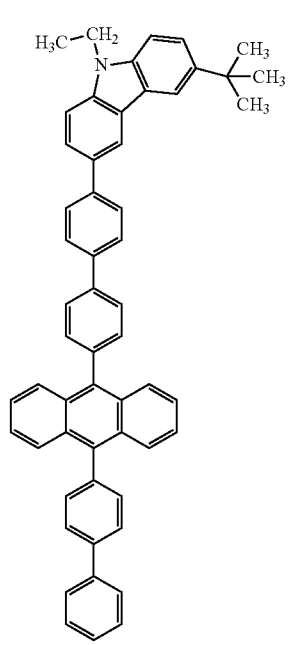
(262)

(263)
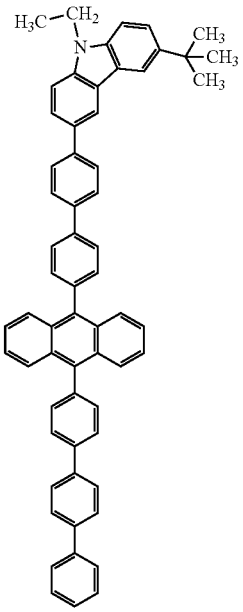
(264)
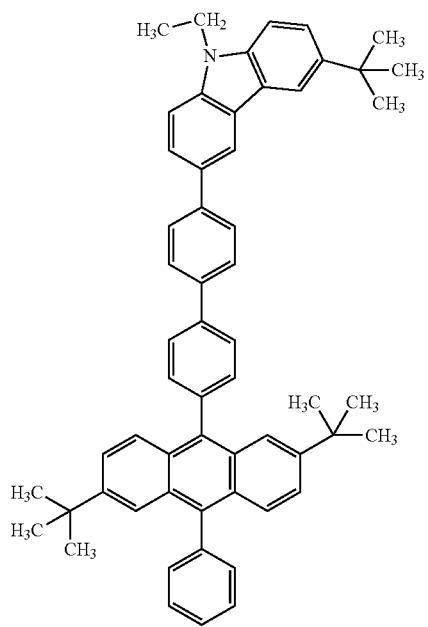
(265)
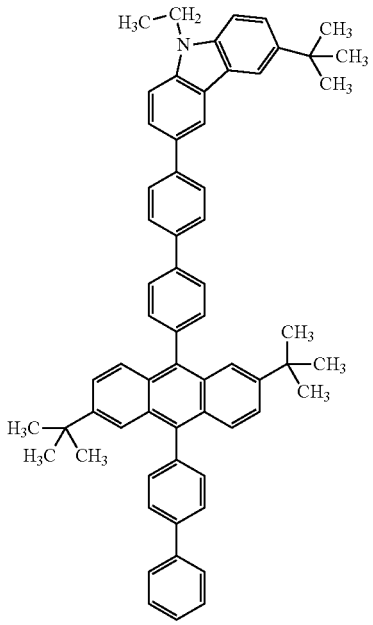
(266)
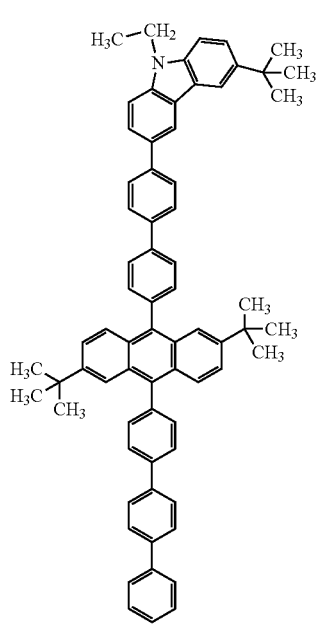

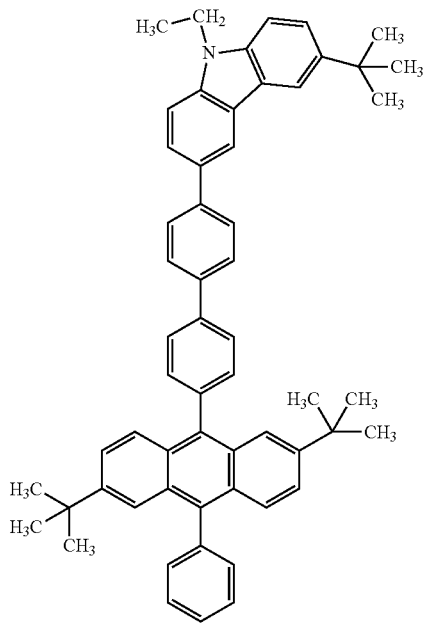
(267)
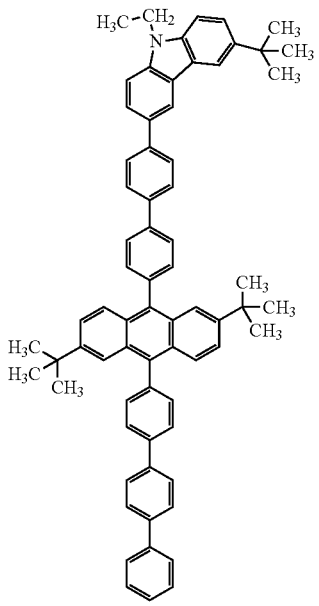
(269)
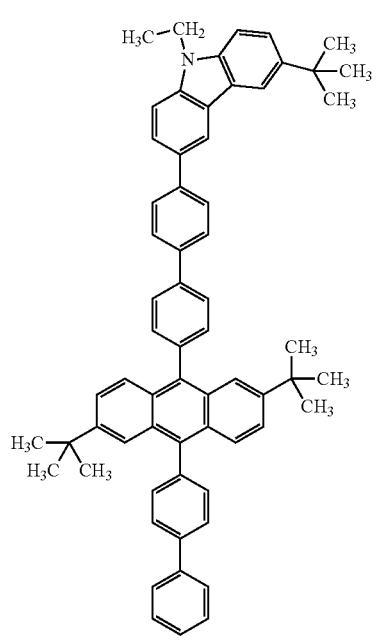
(268)
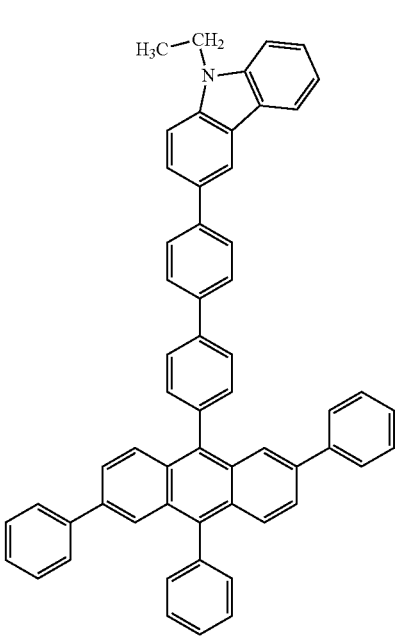
(270)

(271)
(273)
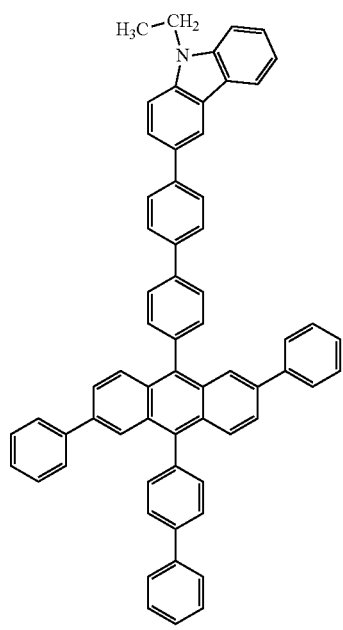
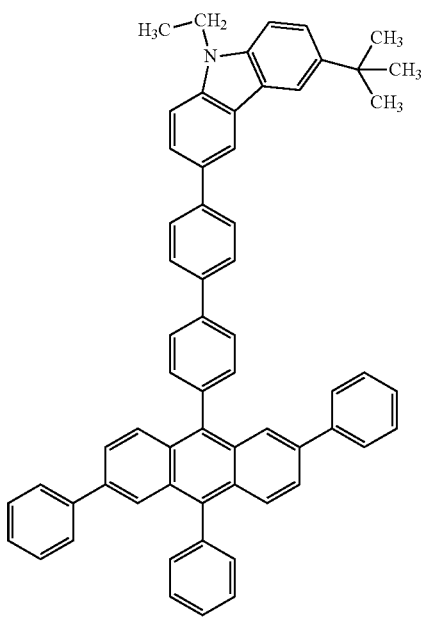
(272)
(274)

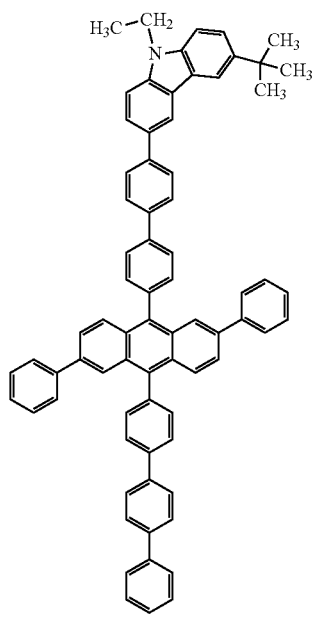 (275)
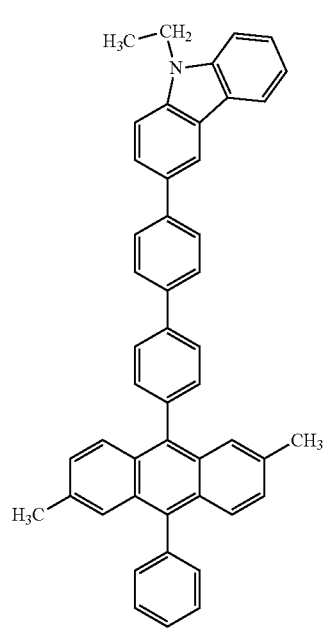 (276)
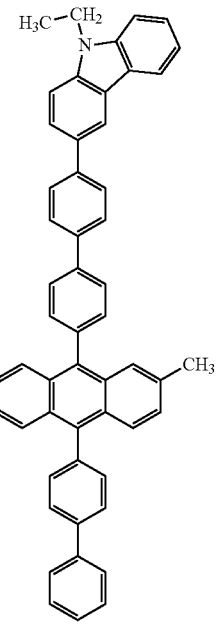 (277)
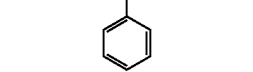 (278)

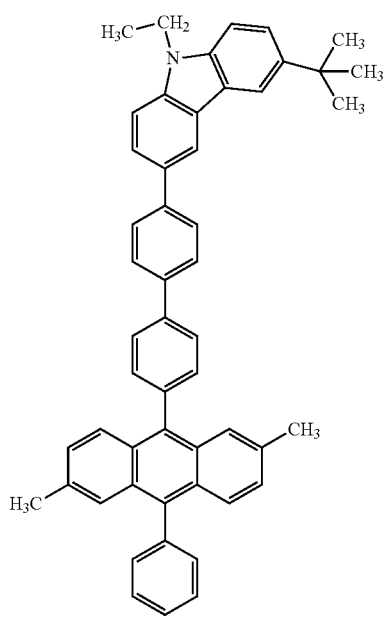
(279)
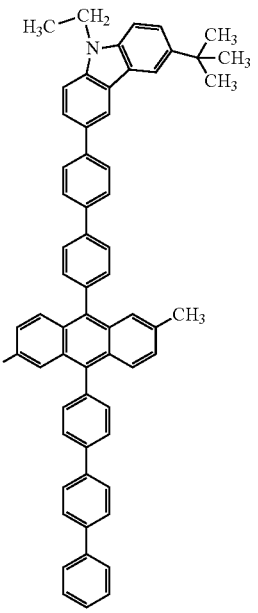
(281)
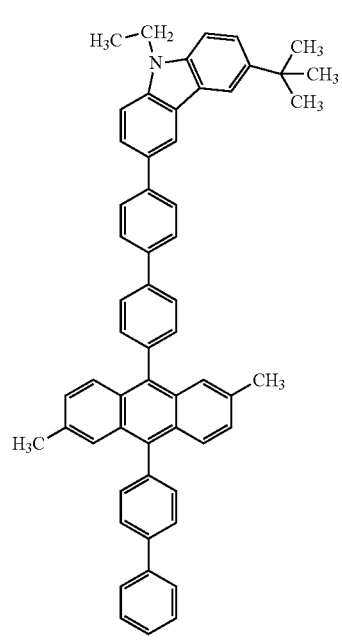
(280)
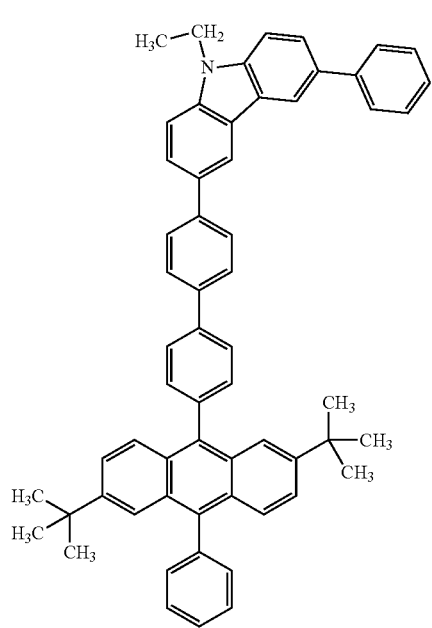
(282)

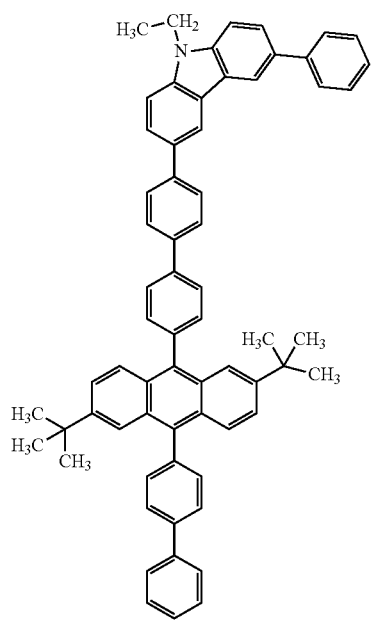
(283)
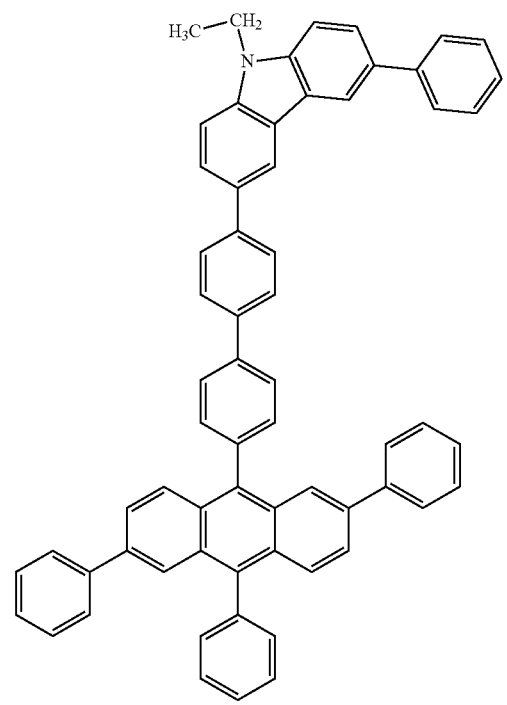
(285)
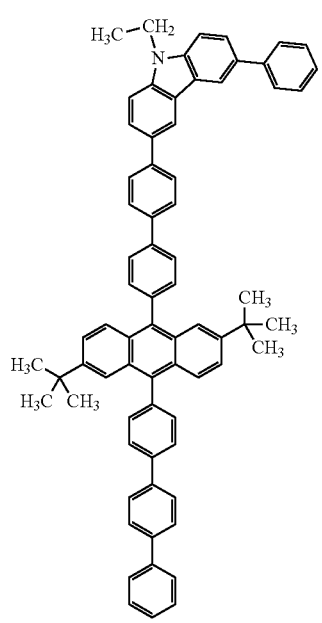
(284)
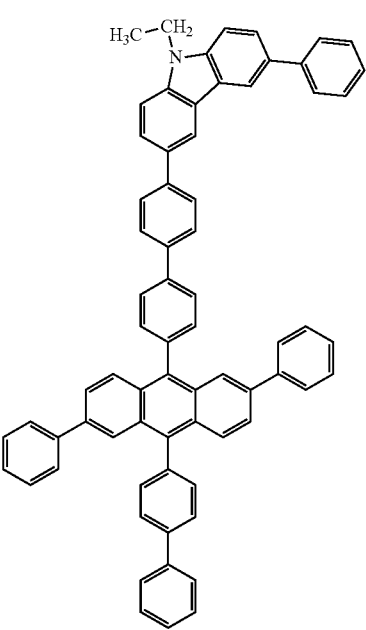
(286)

-continued (287)

(288)

(289)

(290)

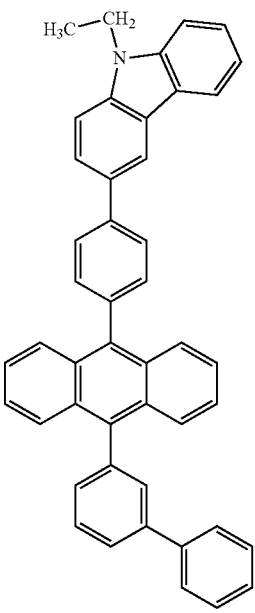 (291)
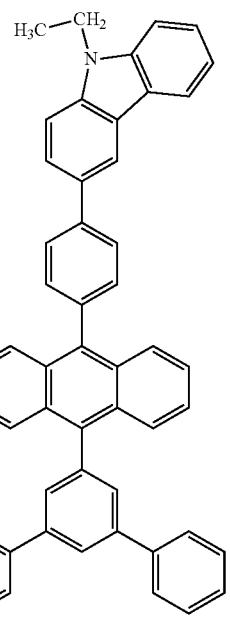 (293)
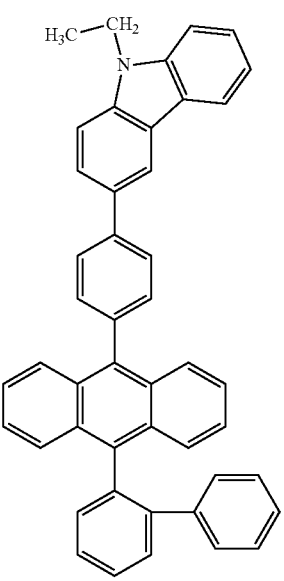 (292)
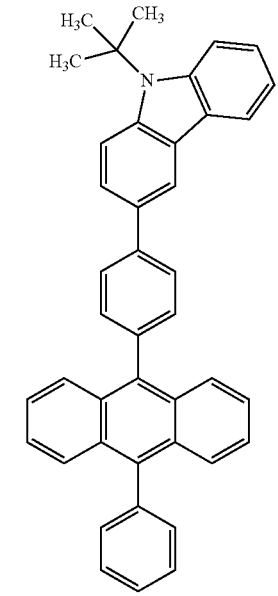 (294)

109 110
-continued -continued
(295)
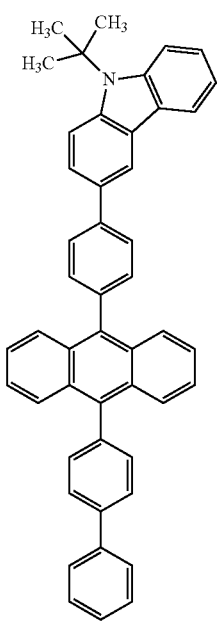
(297)
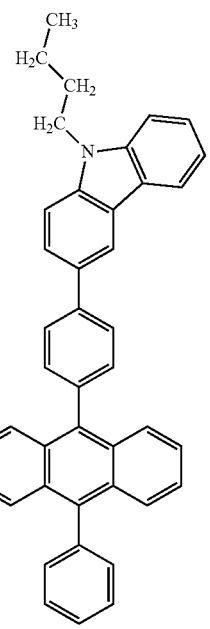
(296)
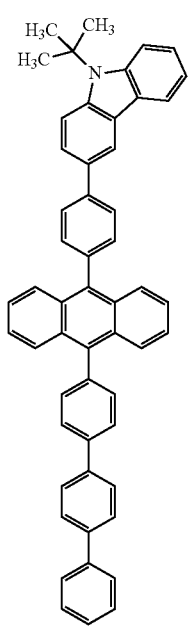
(298)
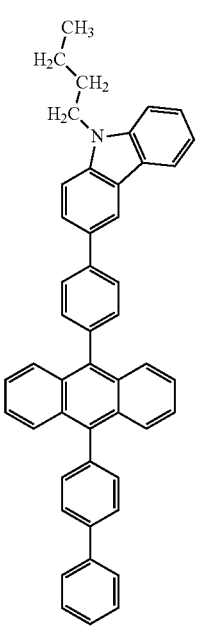

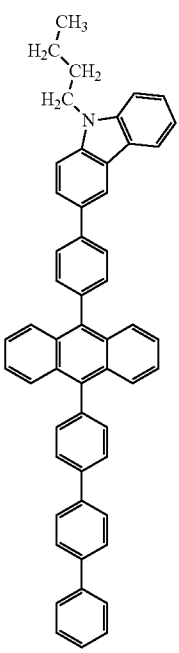
(299)
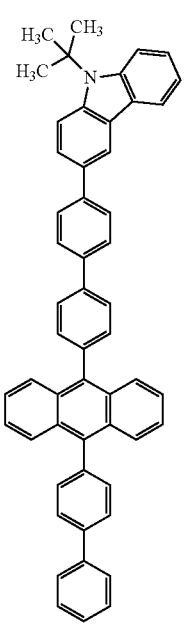
(301)
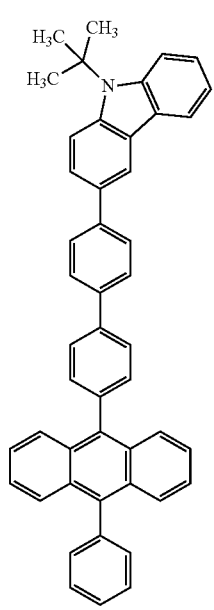
(300)
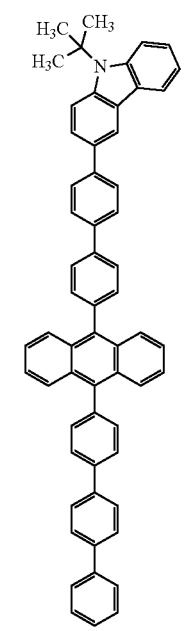
(302)

113
-continued
(303)
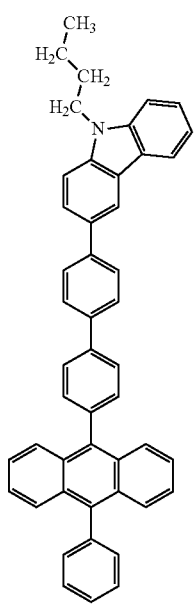
114
-continued
(305)
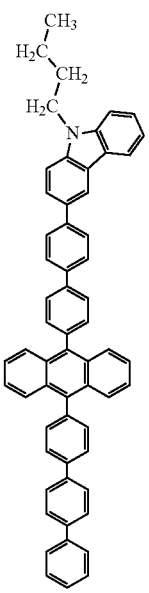
(304)
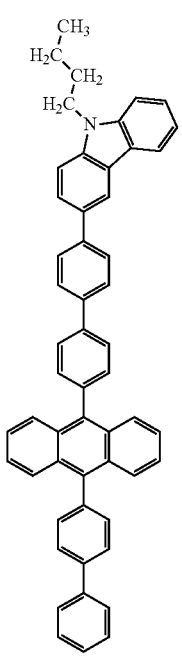
(306)
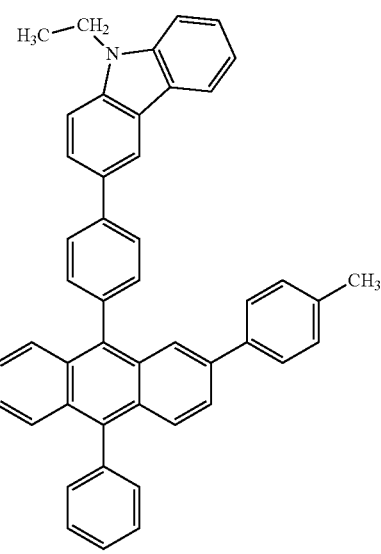

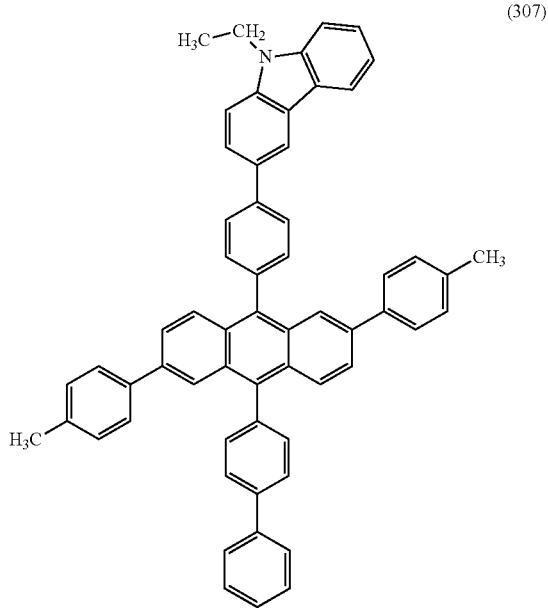
(307)
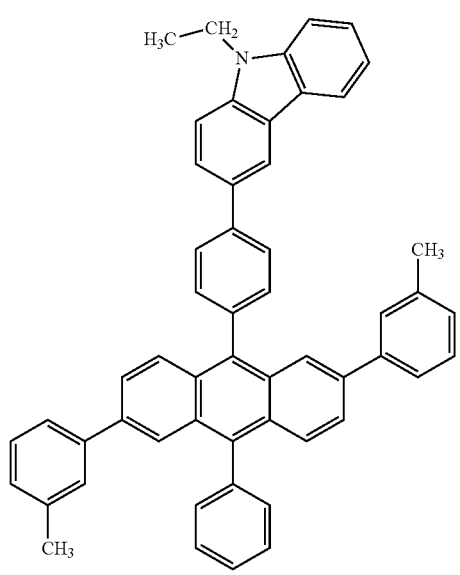
(309)
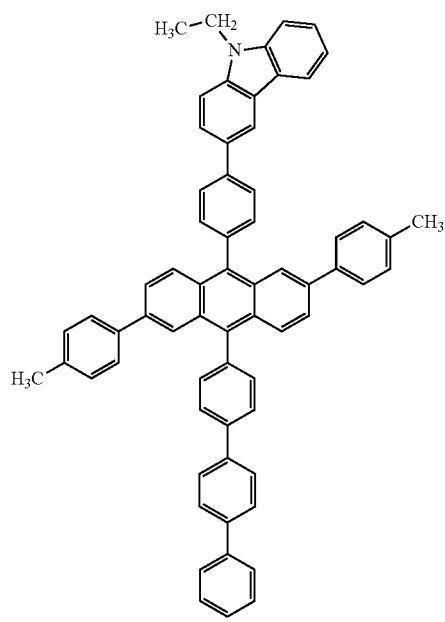
(308)
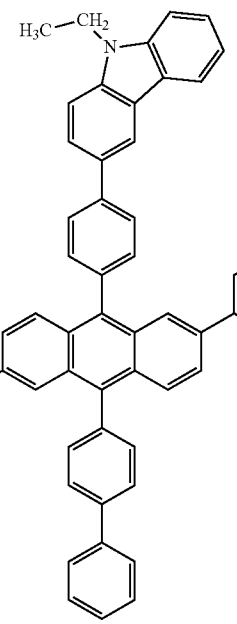
(310)

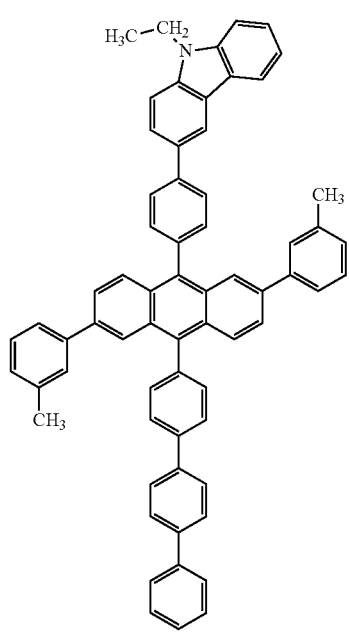
(311)
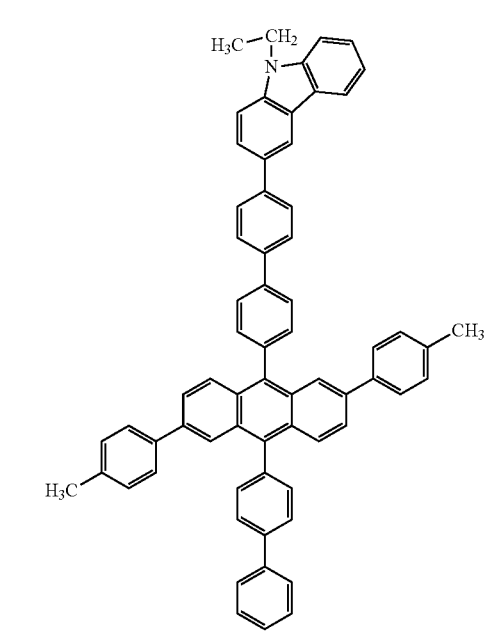
(313)
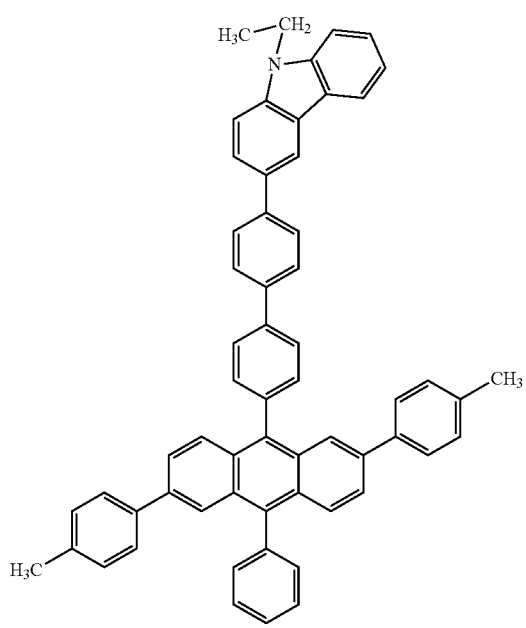
(312)
(314)

119
-continued
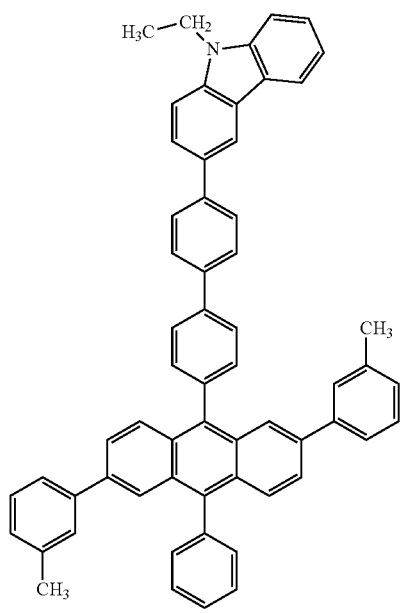
(315)
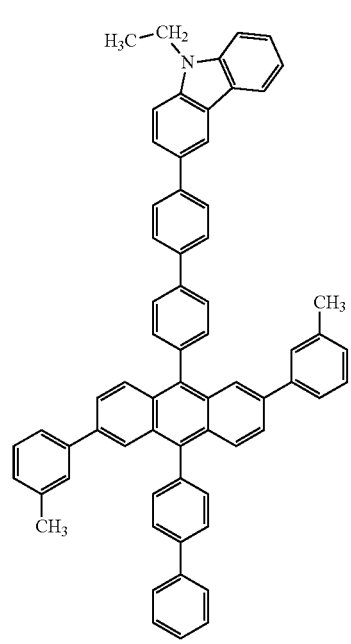
(316)
120
-continued
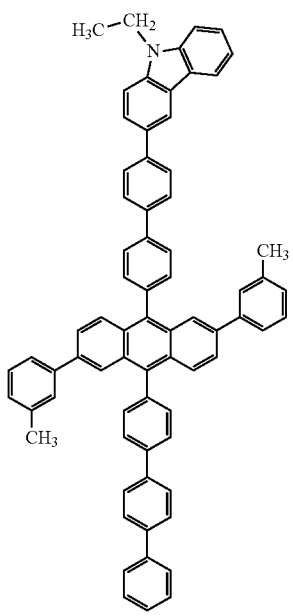
(317)
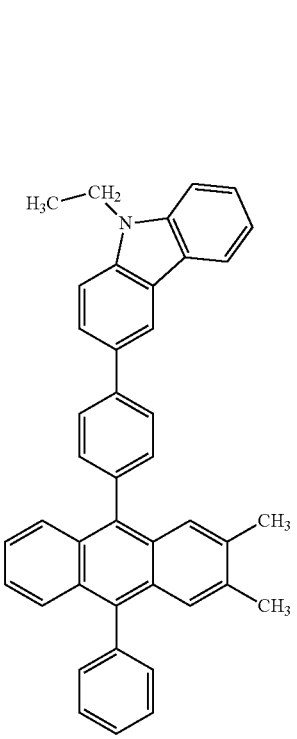
(318)

-continued
(319)
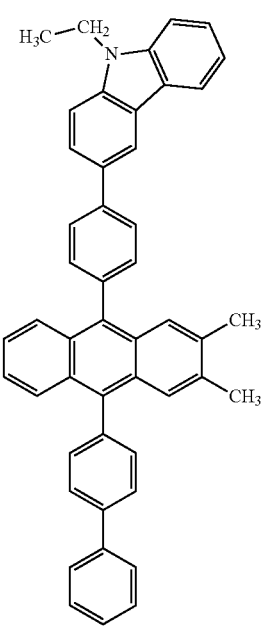
(320)
(321)
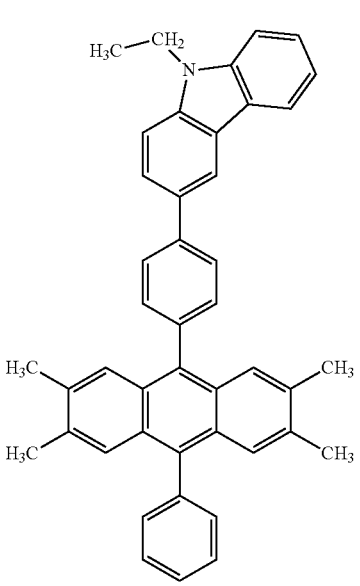
(322)
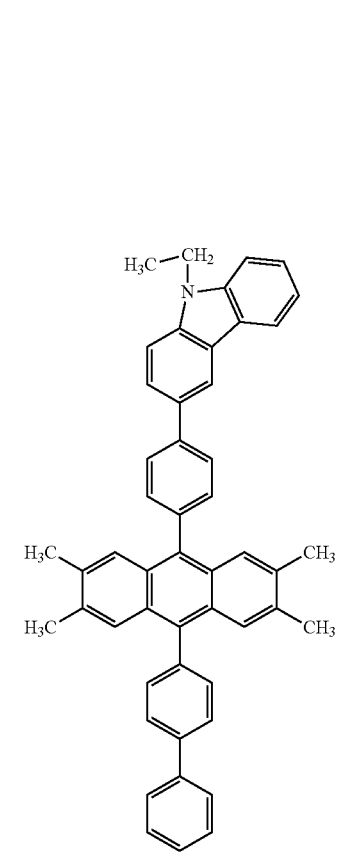

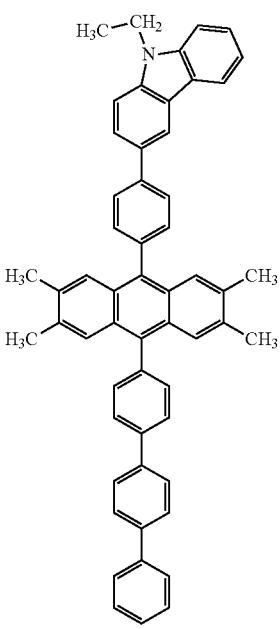
(323)
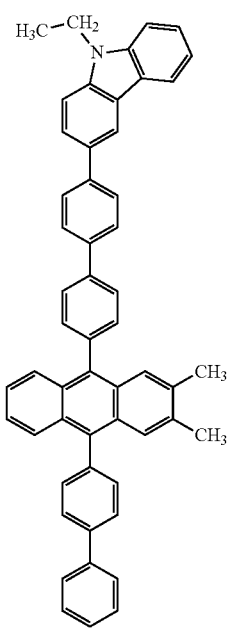
(325)
(324)
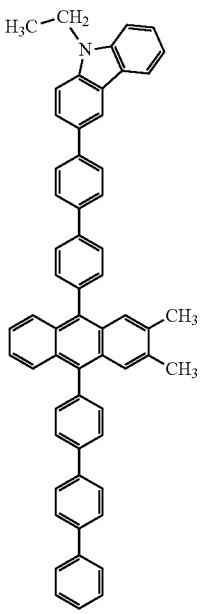
(326)

125
-continued
(327)
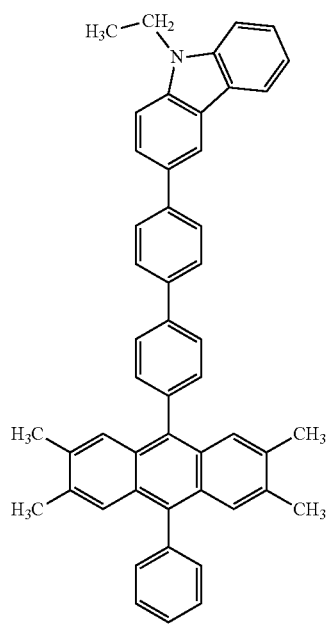
(328)
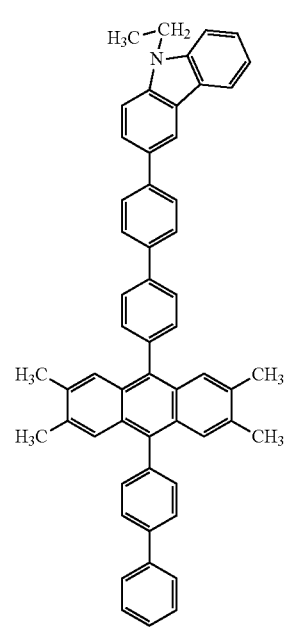
126
-continued
(329)
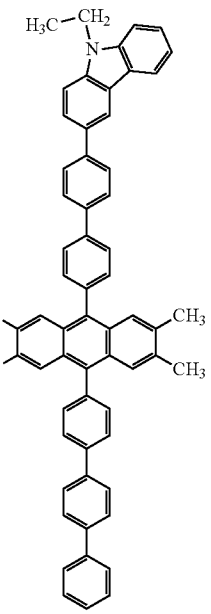
(330)
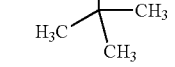

127
-continued (331)

128
-continued (333)

(332)

(334)

129
-continued
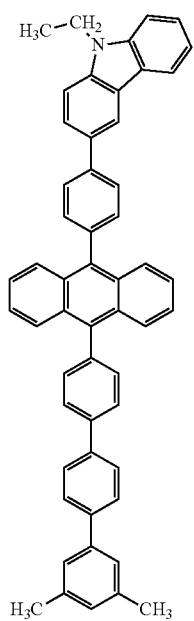
(335)
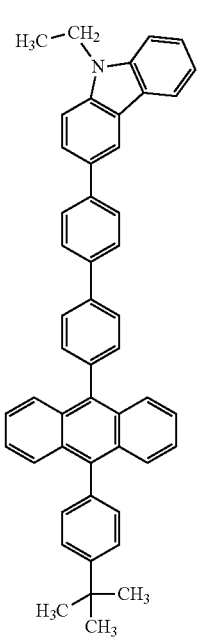
(336)
130
-continued
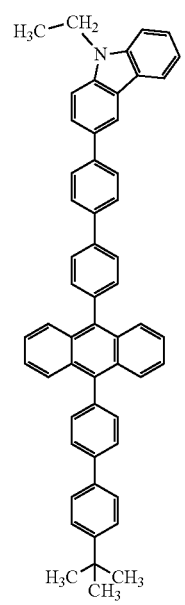
(337)
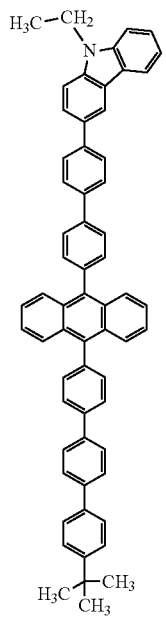
(338)

131
-continued
(339)
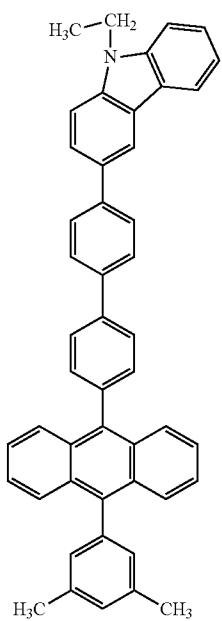
(340)
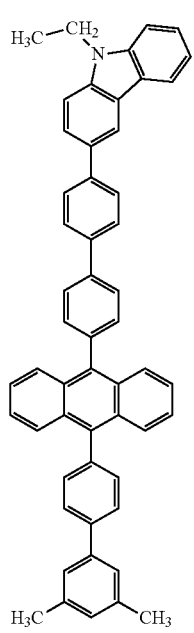
132
-continued
(341)
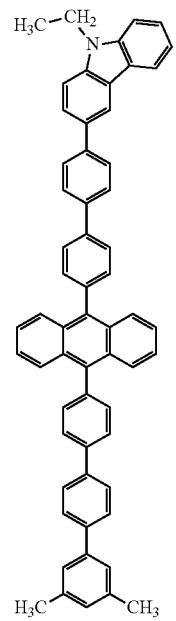
(342)
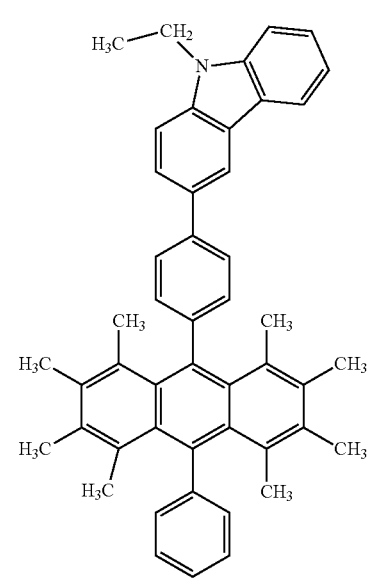

133
-continued
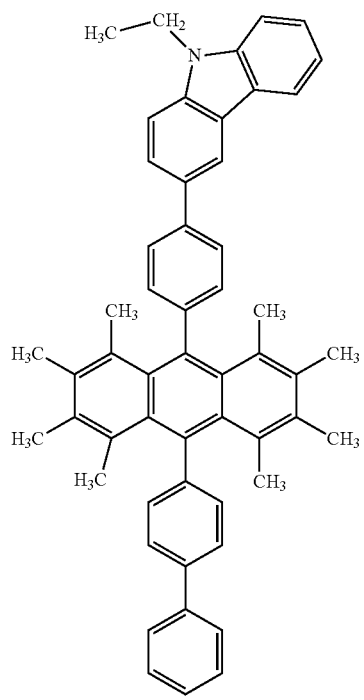
(343)
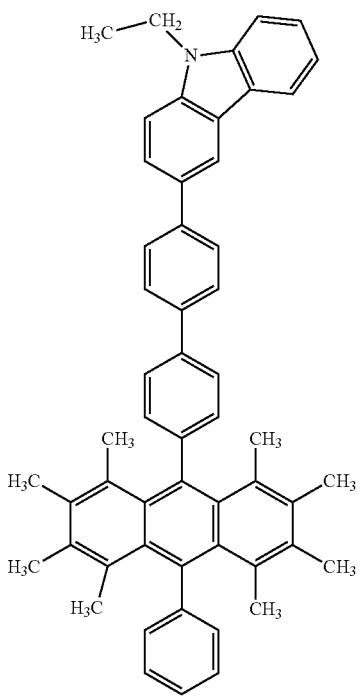
(345)
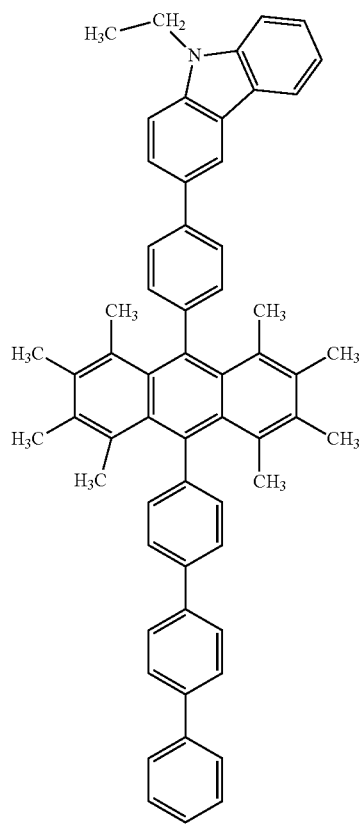
(344)
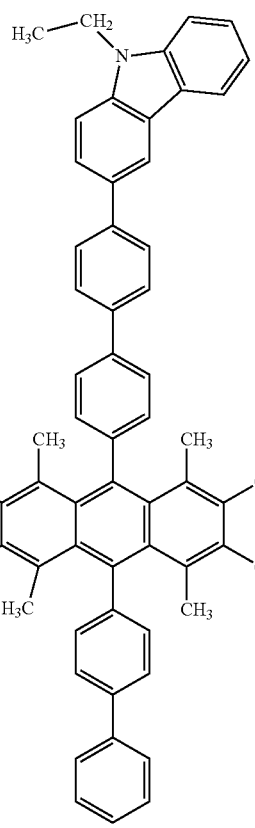
(346)

(347)
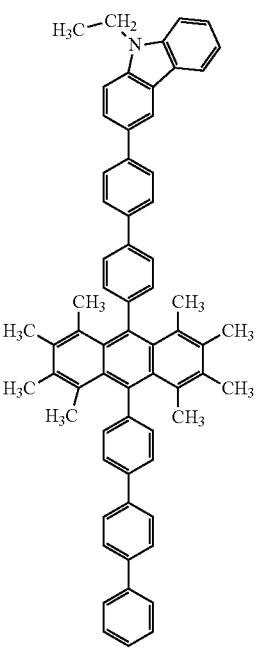
(348)
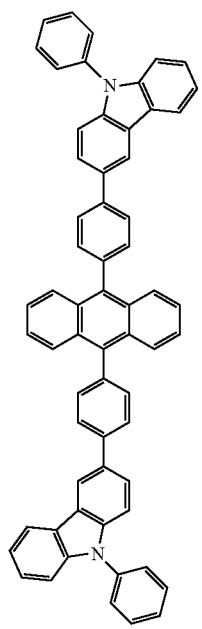
(349)
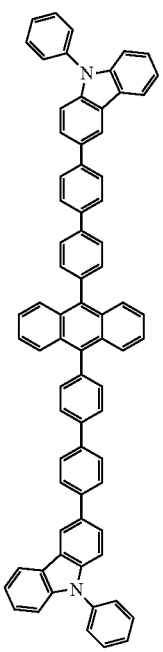
(350)
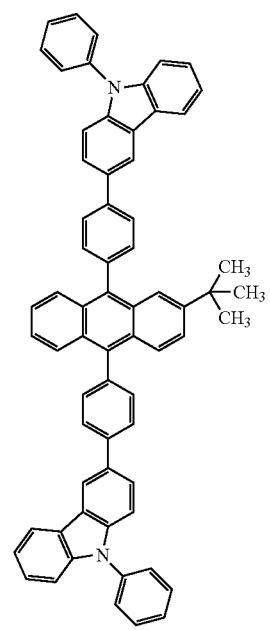

(351)
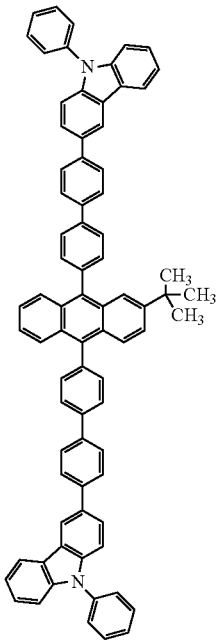
(352)
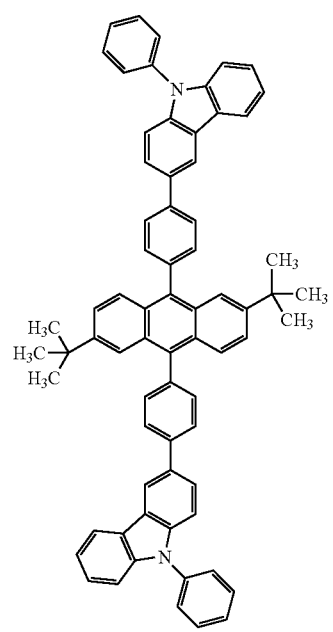
(353)
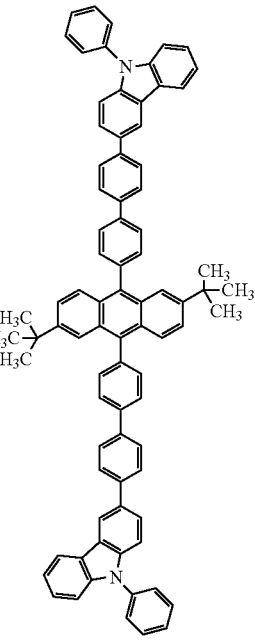
(354)
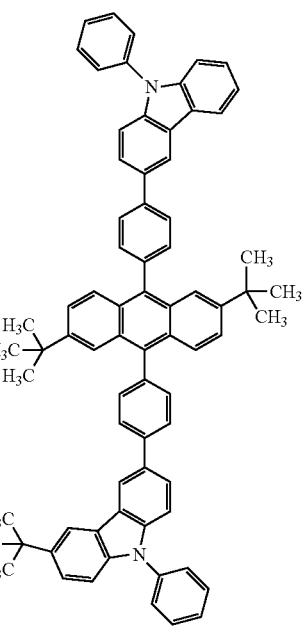

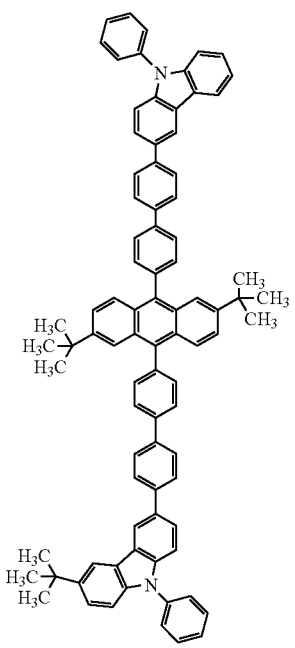
(355)
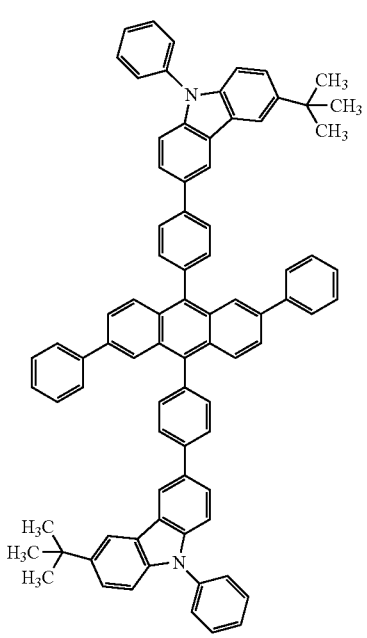
(356)
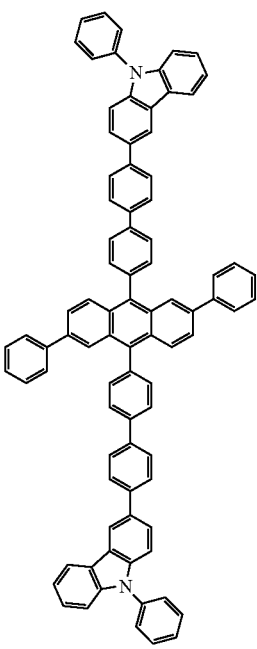
(357)
(358)

(359)
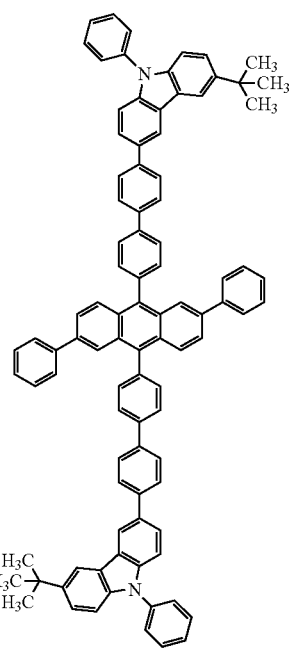
(361)
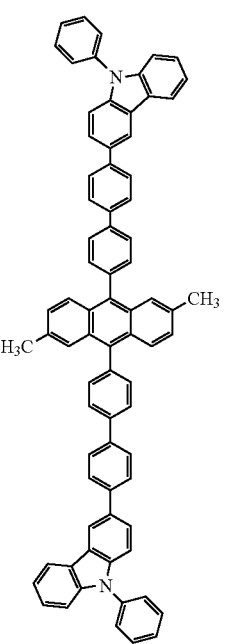
(360)
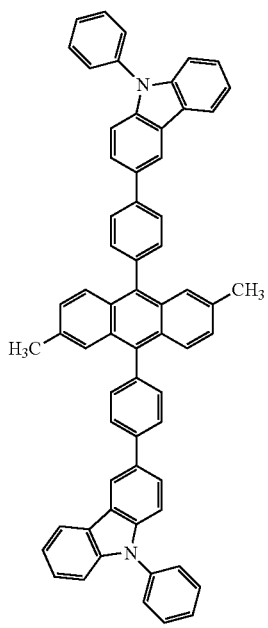
(362)
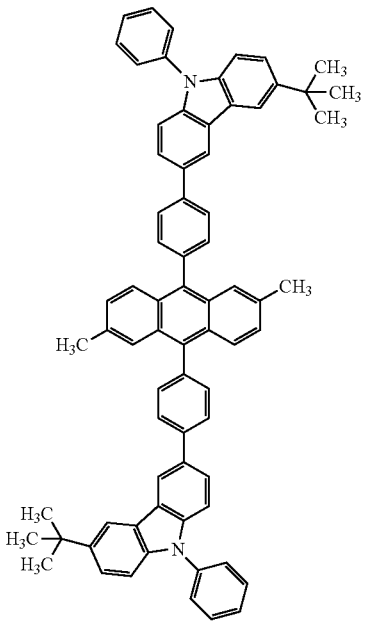

(363)
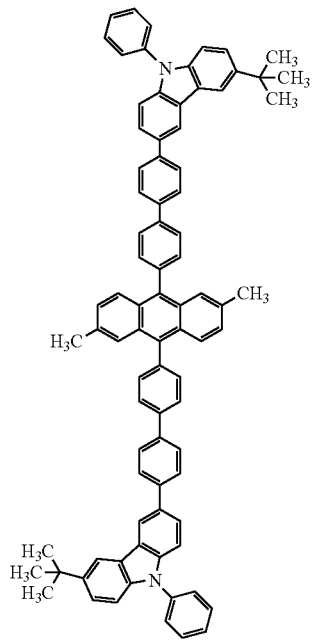
(365)
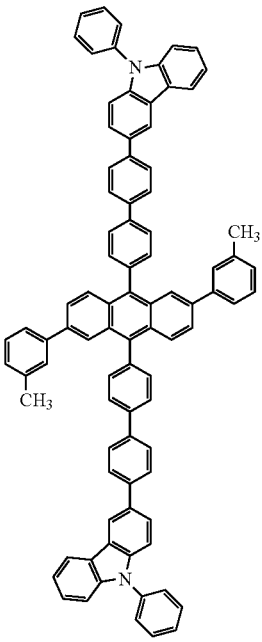
(364)
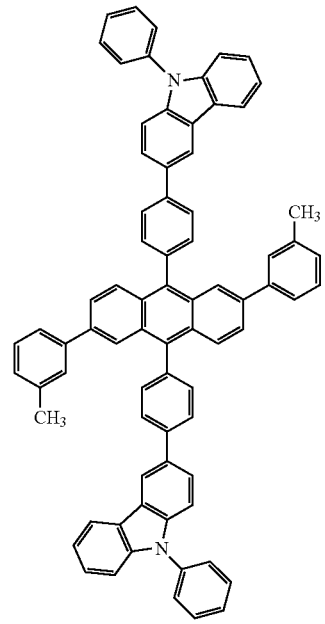
(366)
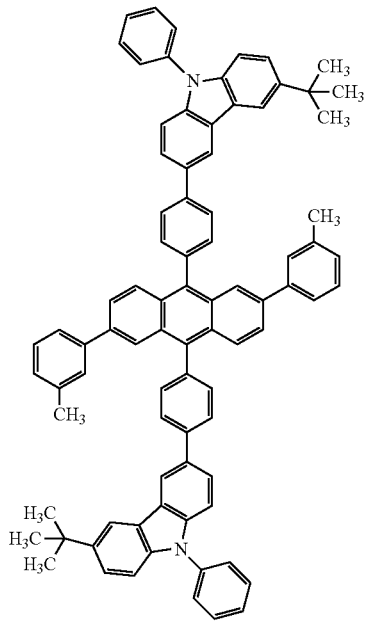

(367)
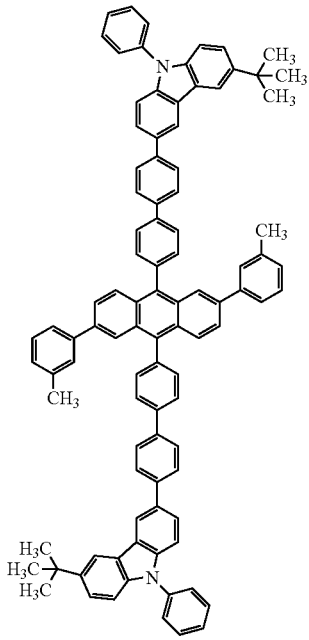
(368)
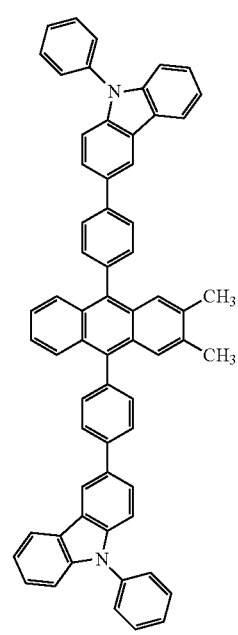
(369)
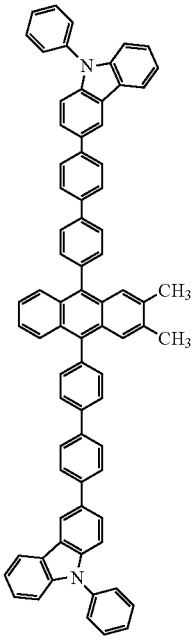
(370)
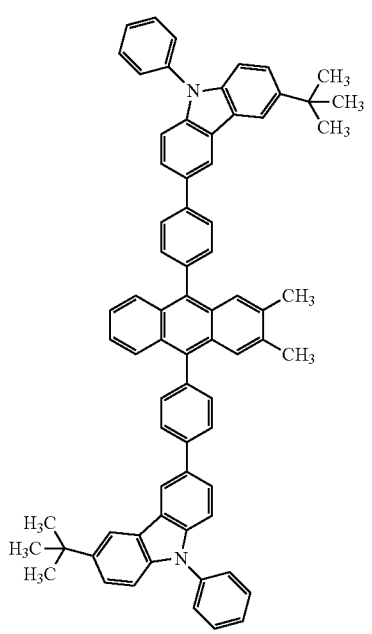

(371) 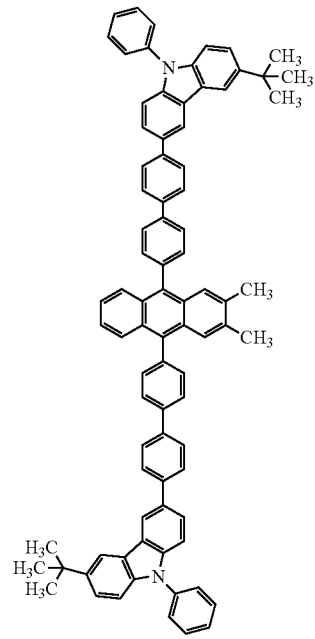
(373) 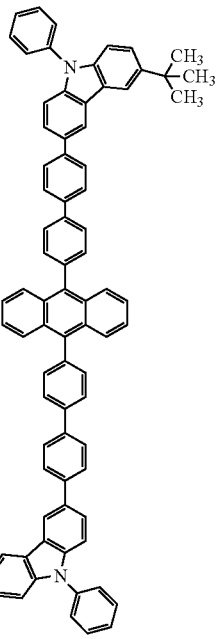
(372) 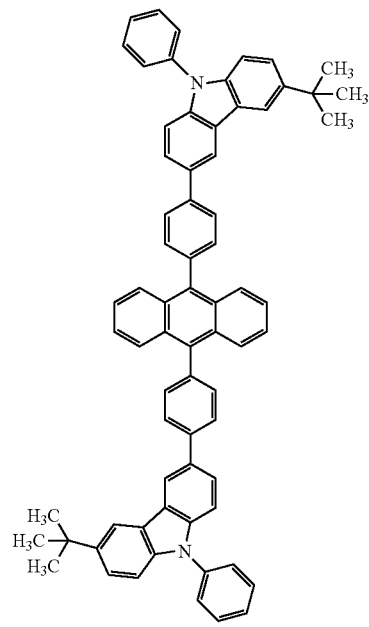
(374) 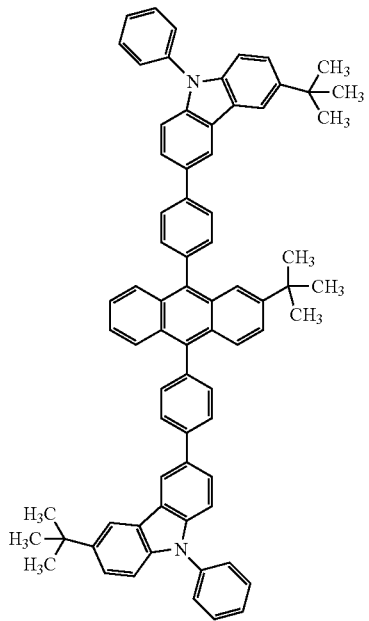

(375)
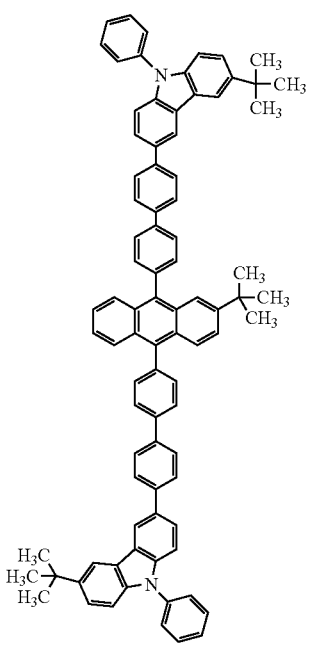
(376)
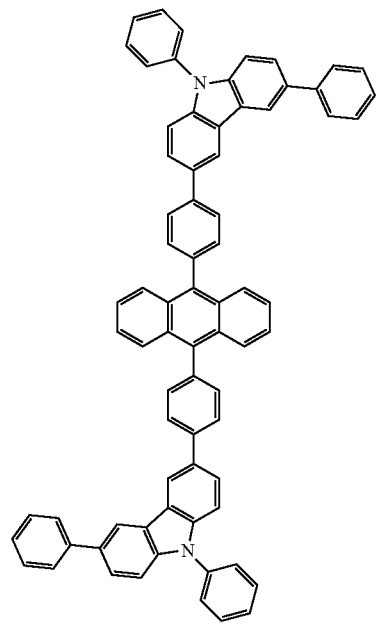
(377)
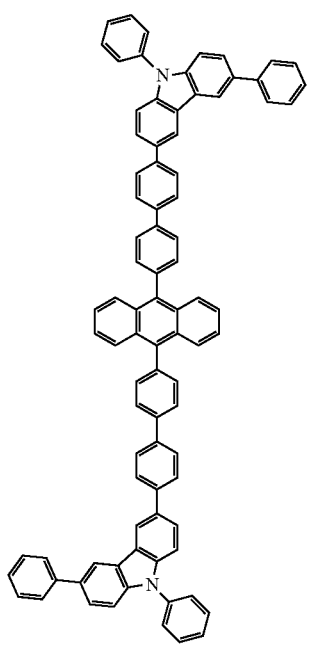
(378)
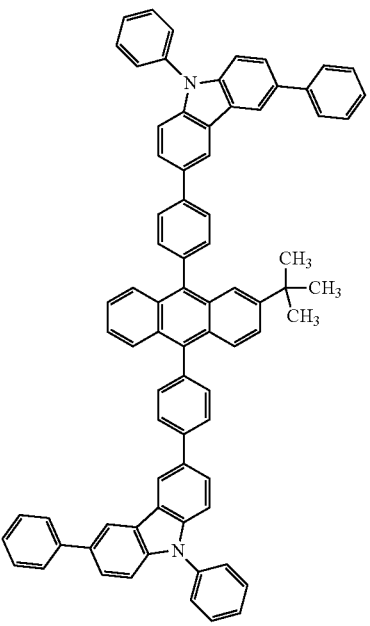

(379)
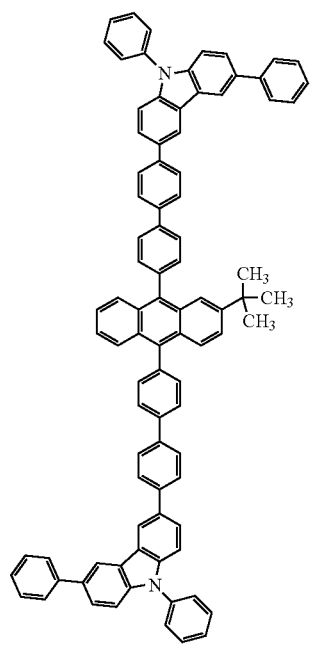
(380)
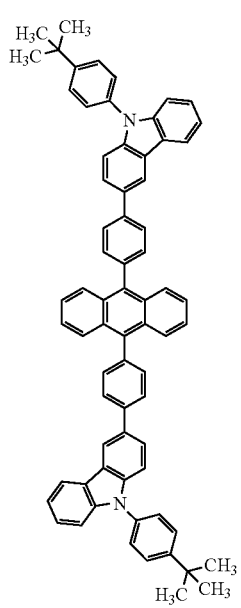
(381)
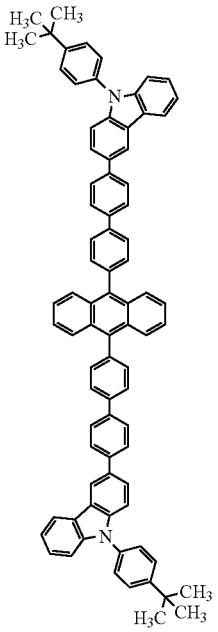
(382)
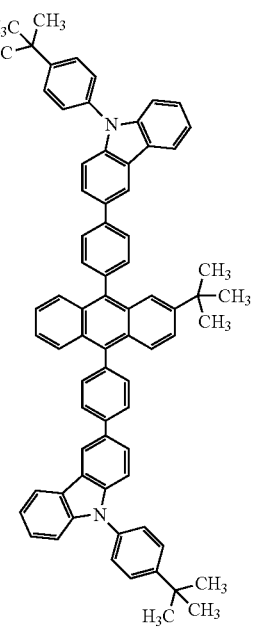

(383) 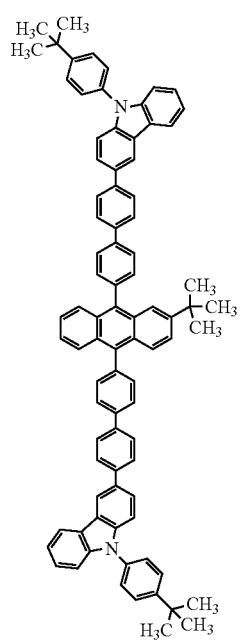
(385) 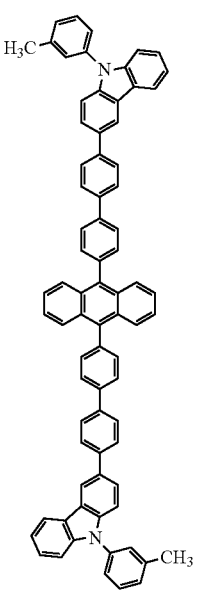
(384) 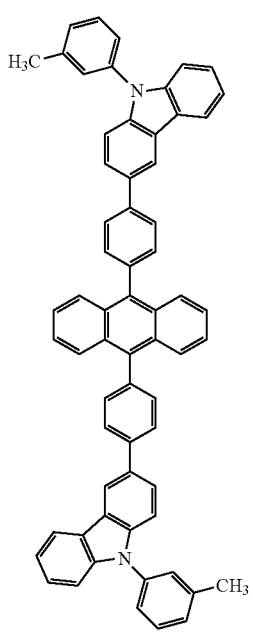
(386)

(387)
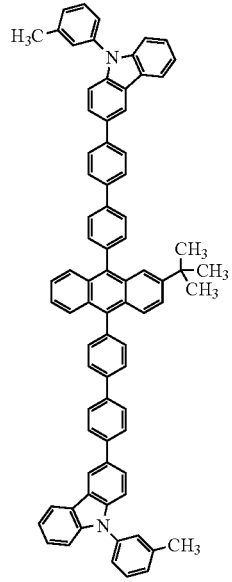
(388)
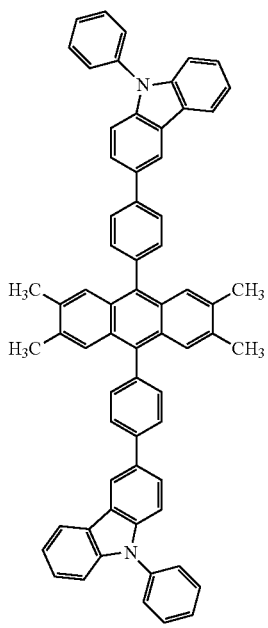
(389)
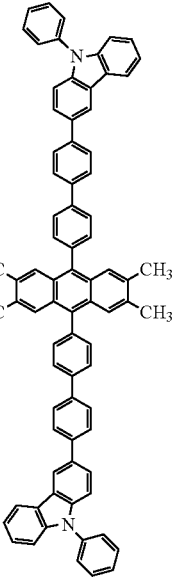
(390)
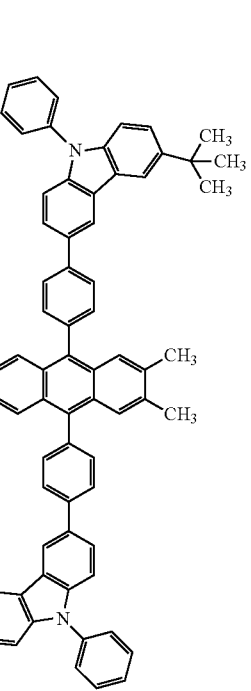

157
-continued
(391)
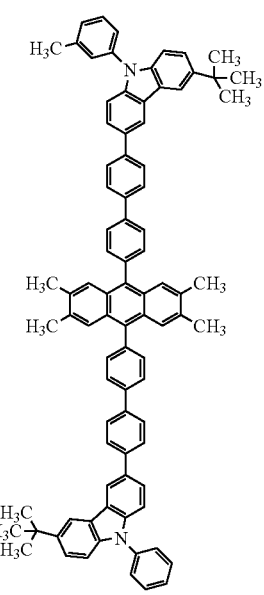
(392)
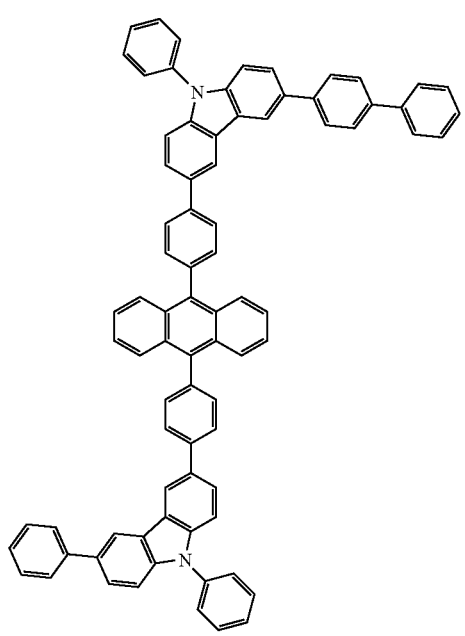
158
-continued
(393)
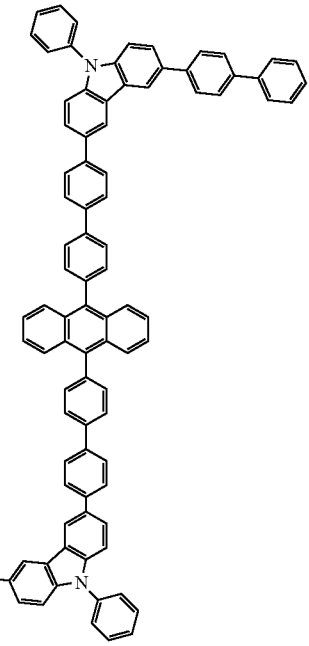
(394)
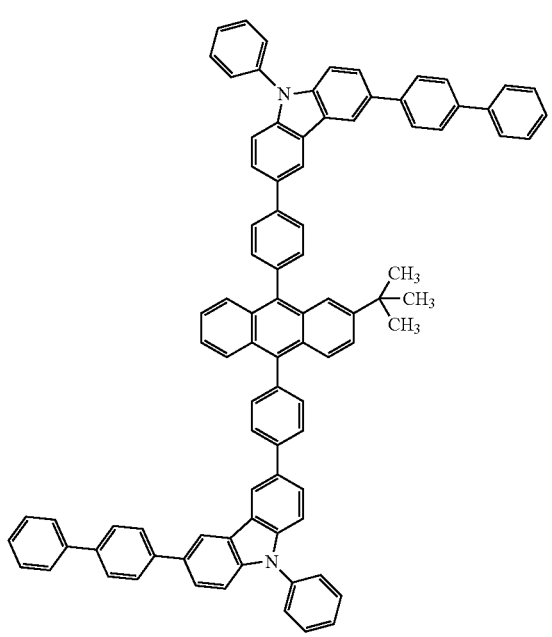

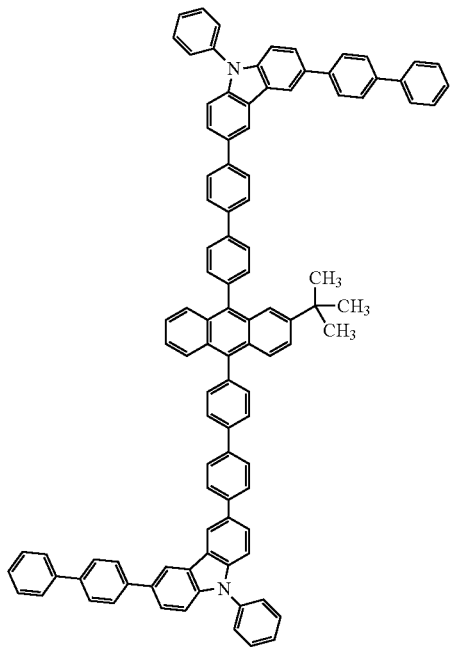
(395)
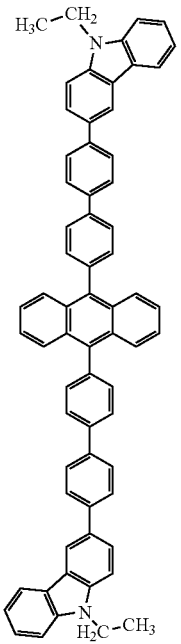
(397)
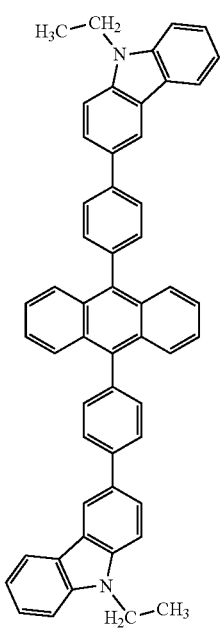
(396)
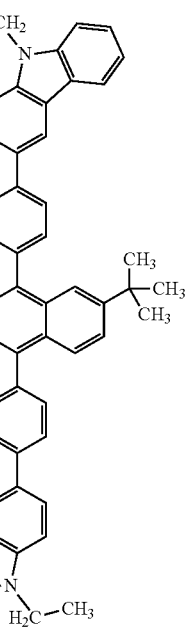
(398)

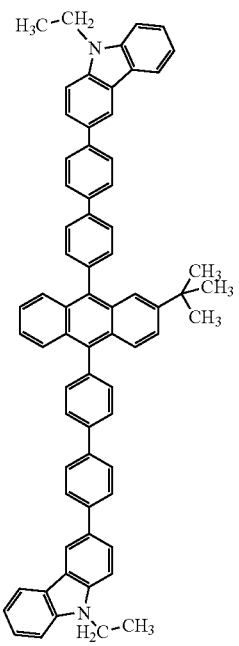
(399)
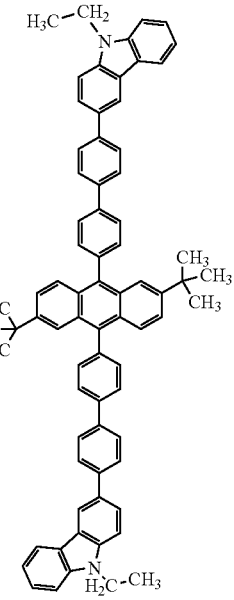
(401)
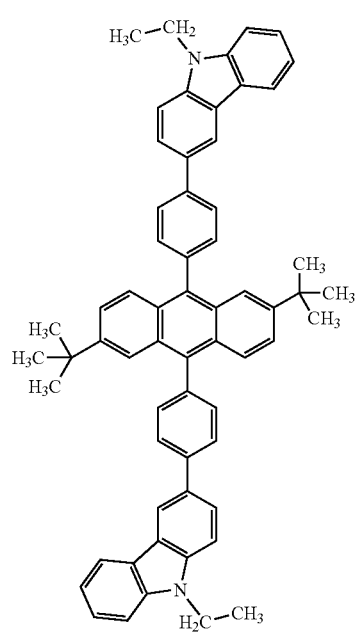
(400)
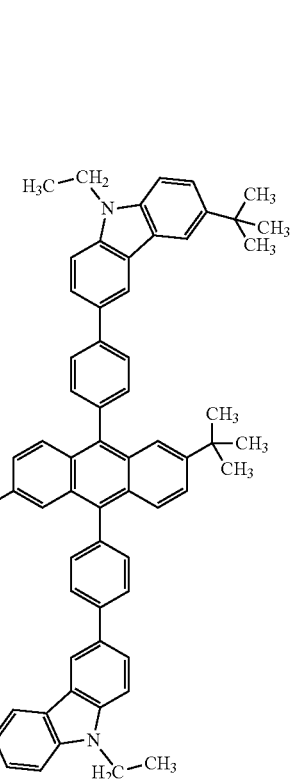
(402)

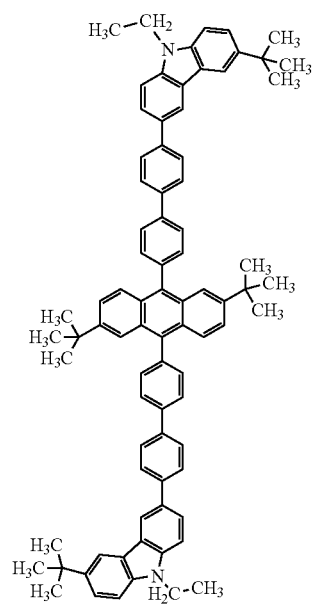
(403)
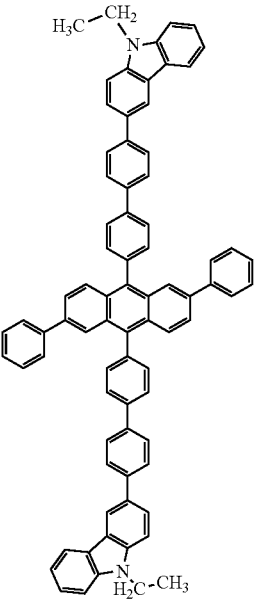
(405)
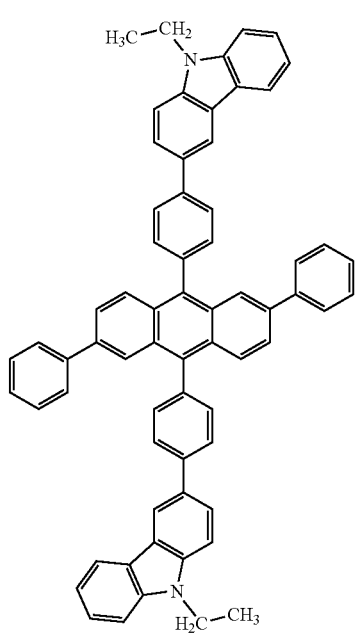
(404)
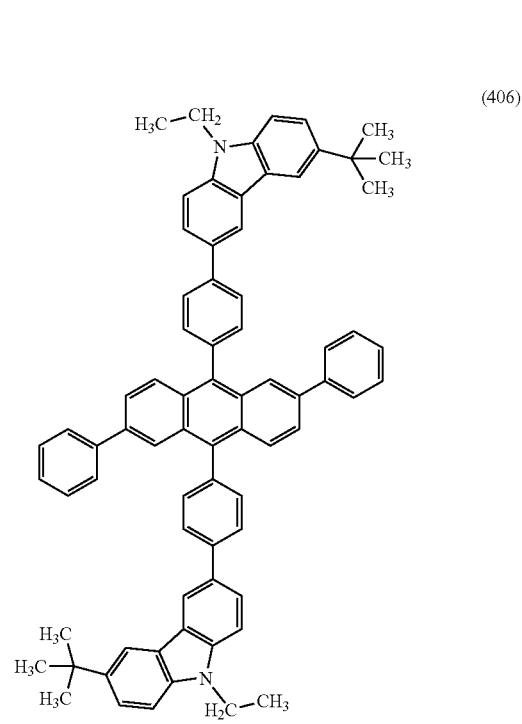
(406)

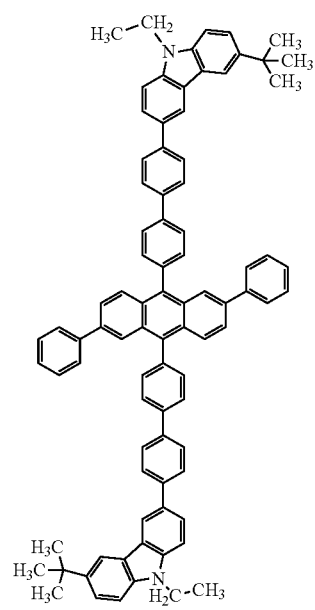
(407)
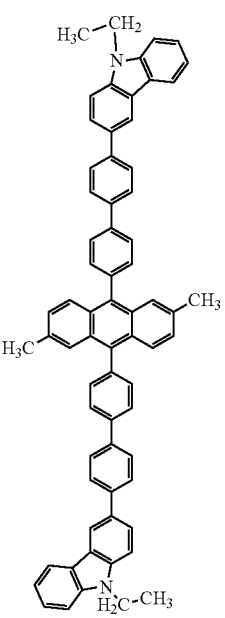
(409)
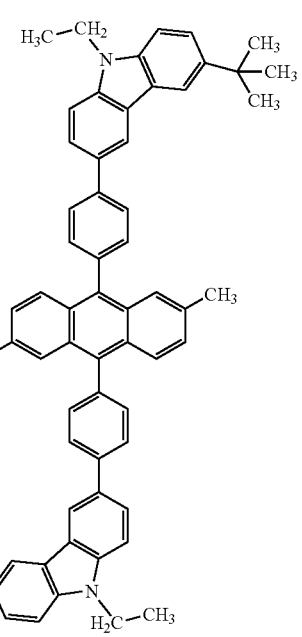
(408)
(410)

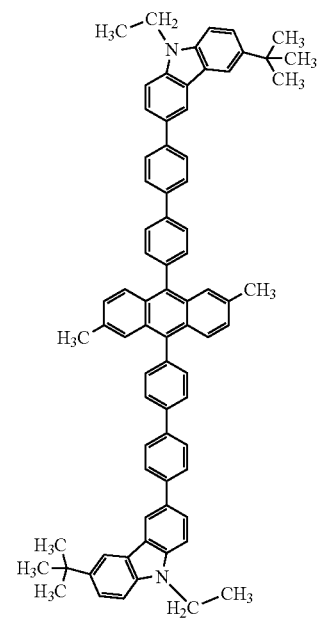 (411)
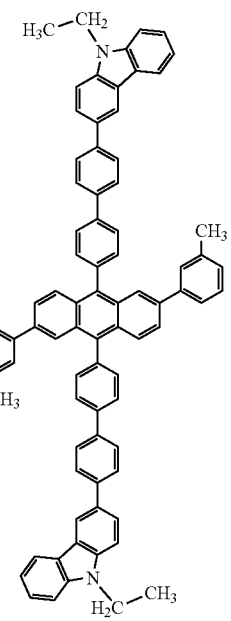 (413)
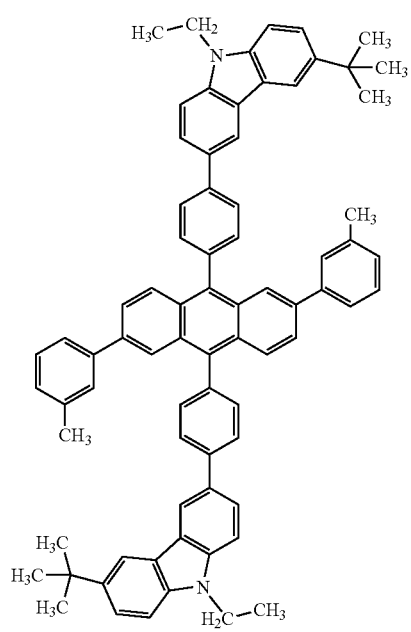 (412)
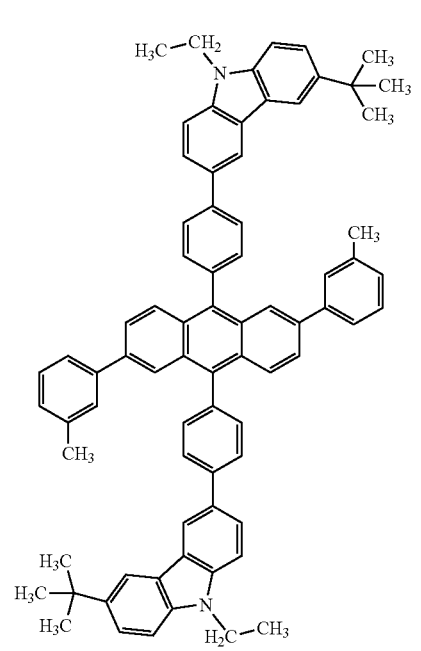 (414)

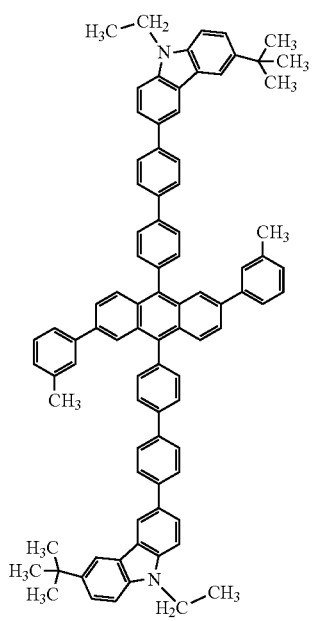 (415)
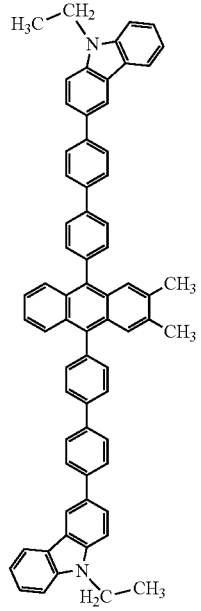 (417)
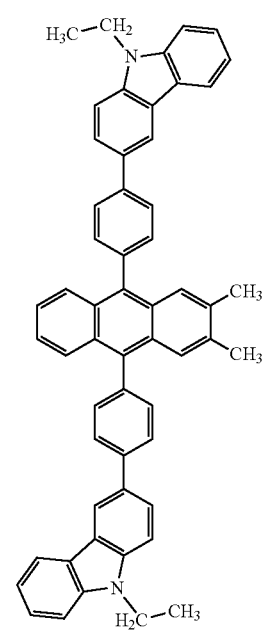 (416)
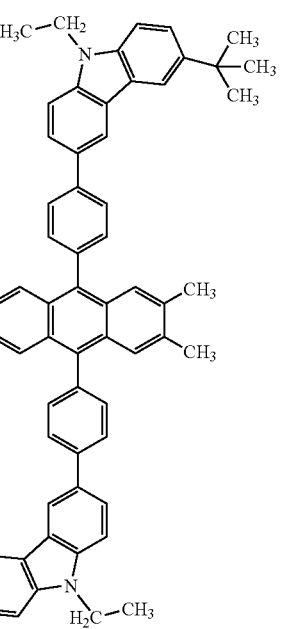 (418)

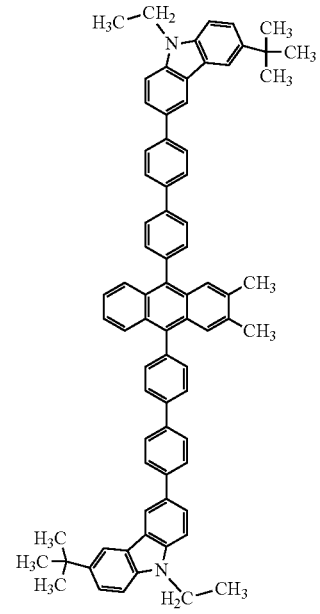
(419)
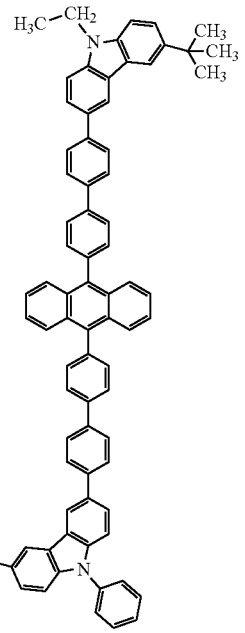
(421)
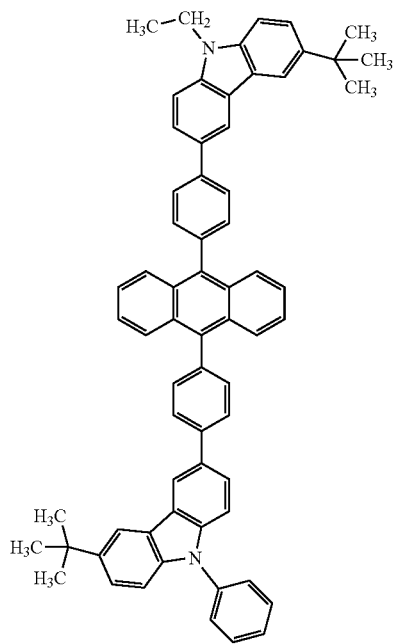
(420)
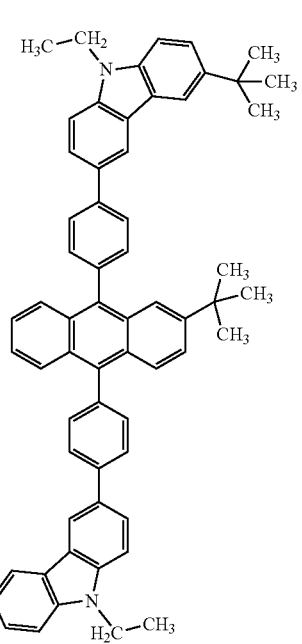
(422)

173
-continued
(423)
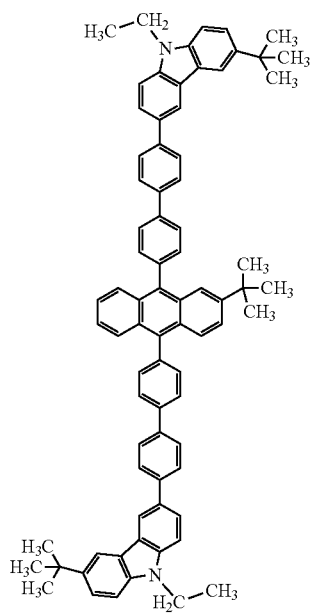
174
-continued
(425)
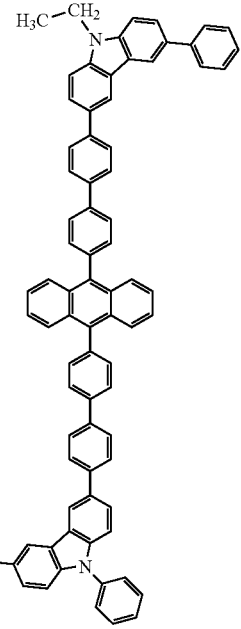
(424)
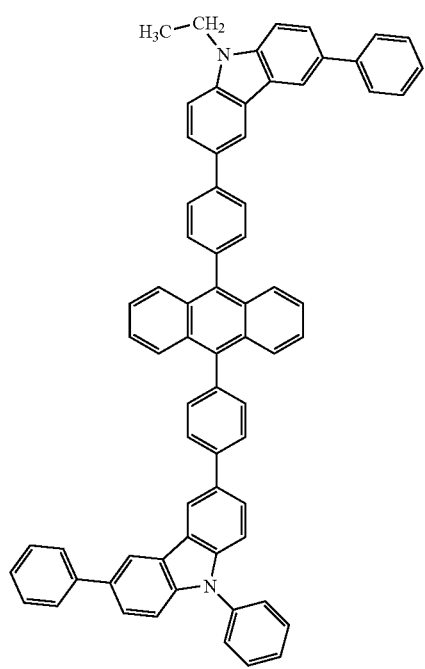
(426)
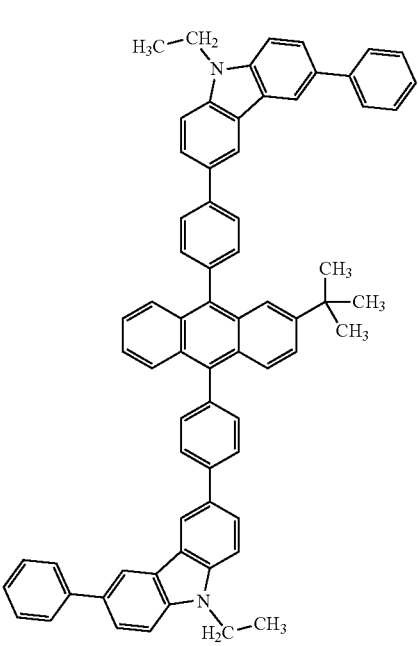

175
-continued
(427)
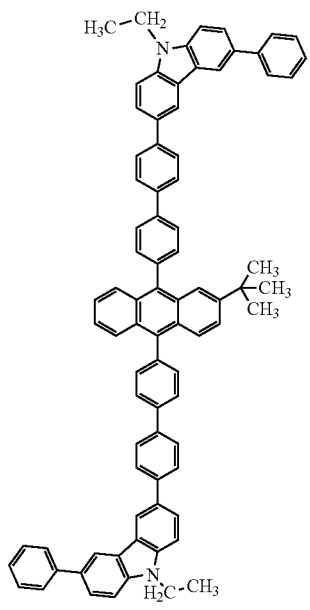
176
-continued
(429)
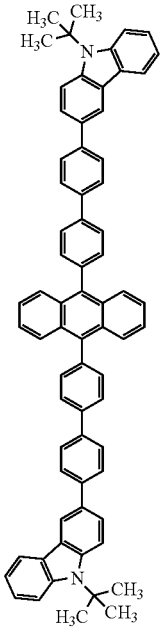
(428)
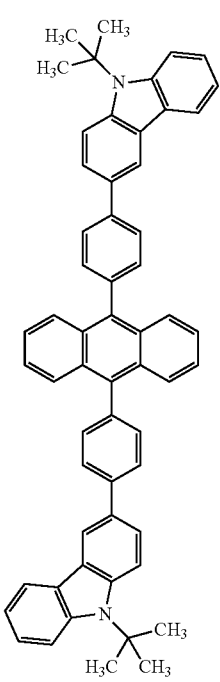
(430)
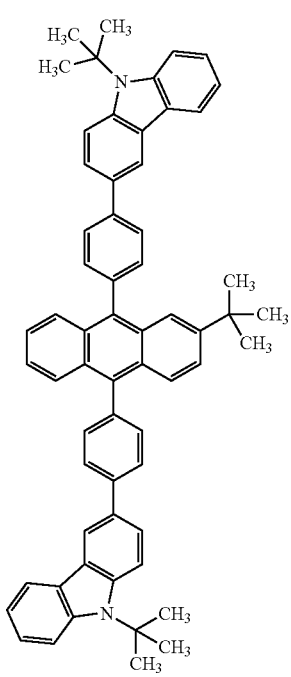

177
-continued
178
-continued
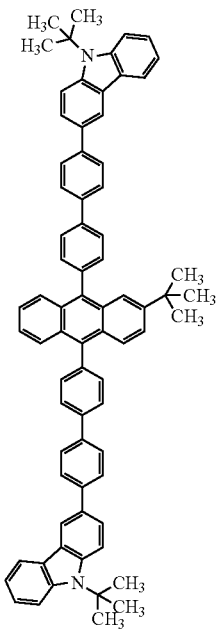
(431)
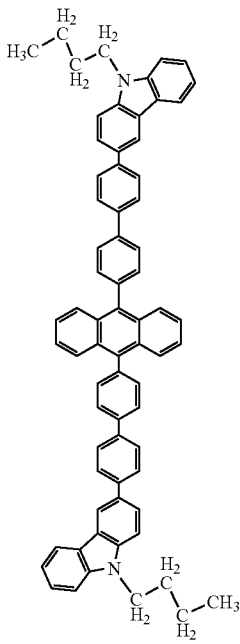
(433)
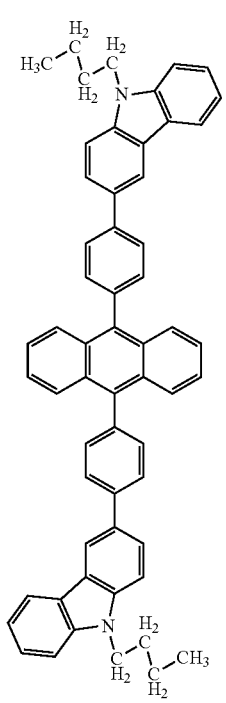
(432)
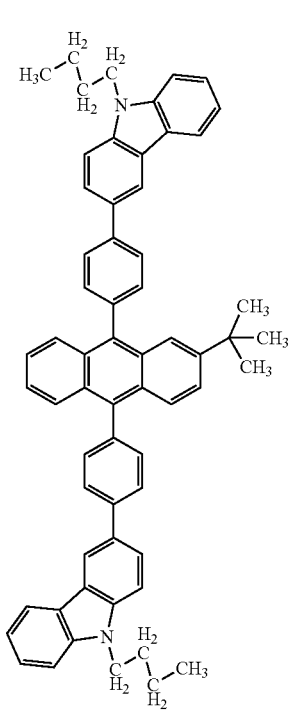
(434)

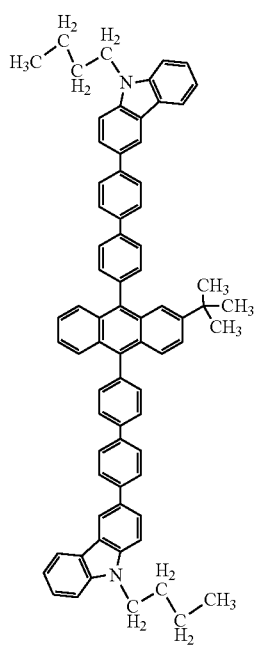 (435)
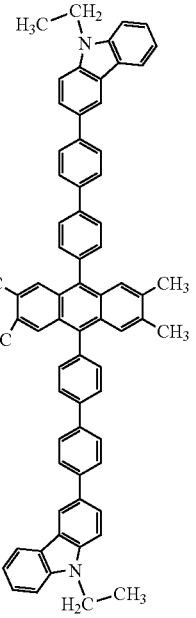 (437)
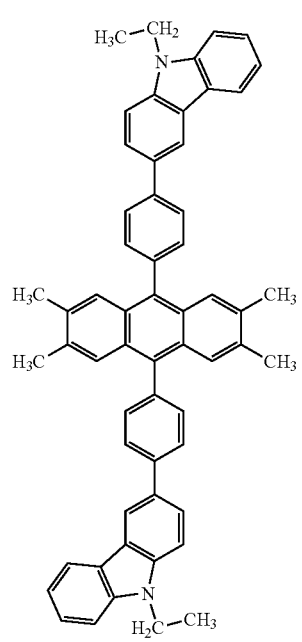 (436)
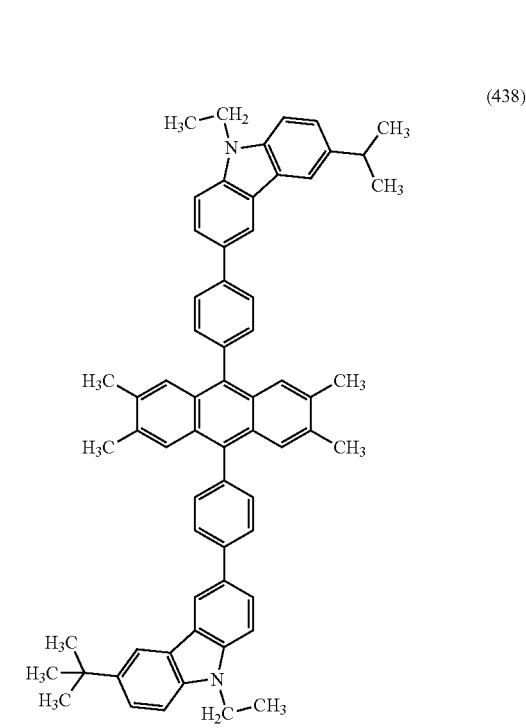 (438)

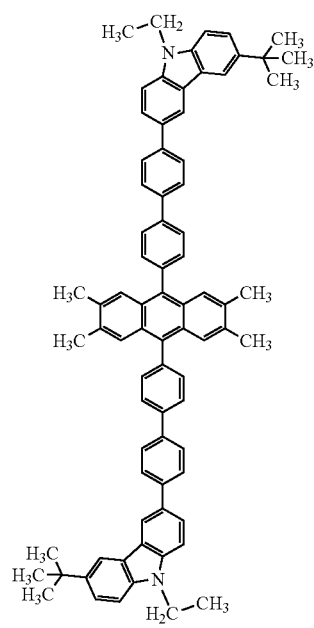
(439)
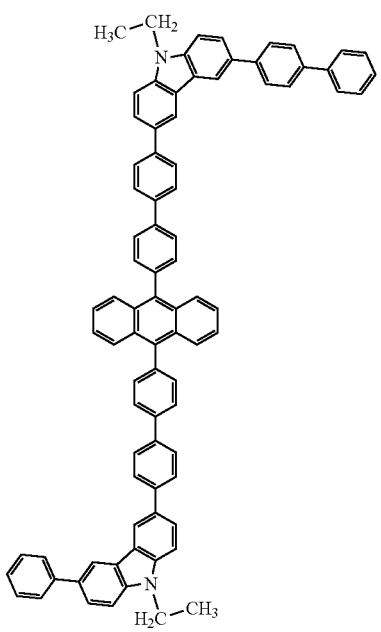
(441)
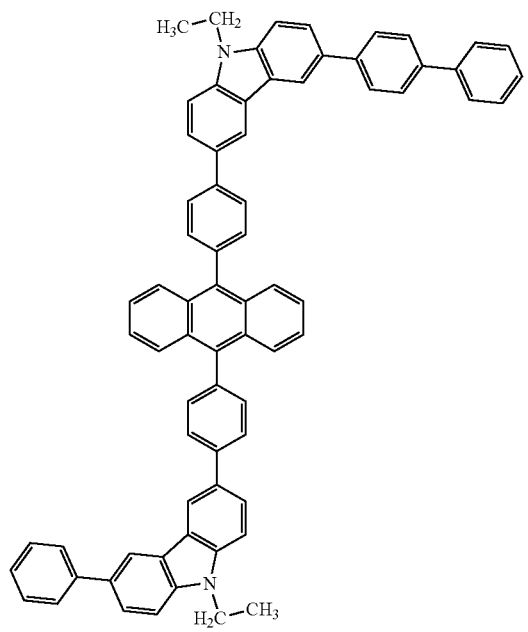
(440)
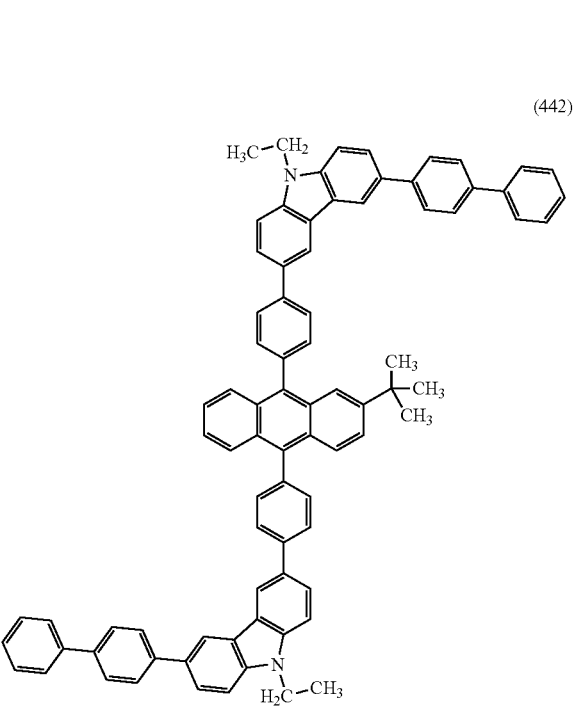
(442)

-continued (443)

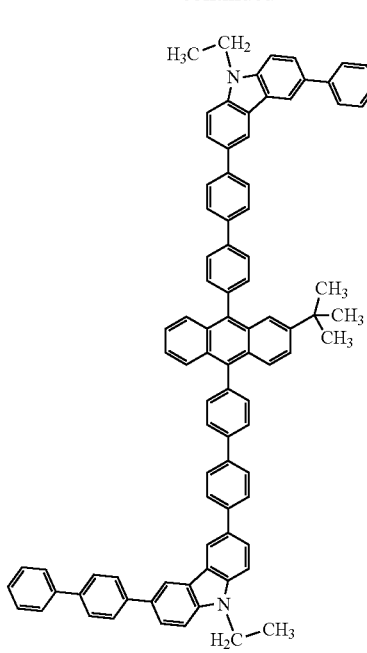

The anthracene derivatives of the present invention can be roughly divided into two modes as described above: the mode where α each having a substituent are bonded at both positions of the 9-position and the 10-position of the anthracene derivative and the mode where the α having a substituent is bonded at only one position of the positions. As a synthesis method thereof, various synthesis reactions can be applied. For example, the anthracene derivatives of the present invention each can be synthesized through a synthesis reaction shown in any of synthesis schemes (A-1) to (A-8) described below. Specifically, the anthracene derivative described in the general formula (1) can be synthesized through a synthesis reaction shown in the synthesis schemes (A-1) to (A-6), and the anthracene derivative described in the general formula (5) can be synthesized through a synthesis reaction shown in the synthesis schemes (A-7) and (A-8). The synthesis method of anthracene derivative of the present invention is not limited to these; synthesis may be performed by another synthesis method. Hereinafter, the synthesis schemes will be detailed.

<Synthesis of Compound Represented by General Formula (1)>

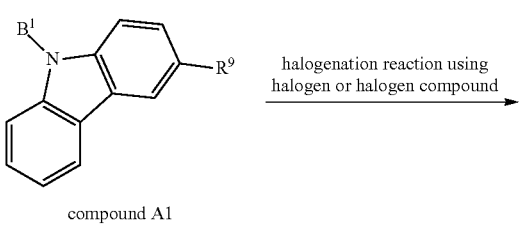

-continued

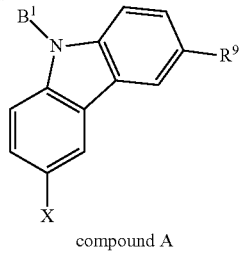

compound A

In the synthesis scheme (A-1), $R^1$ represents any of an alkyl group having 1 to 4 carbon atoms or a substituted or unsubstituted phenyl group, and $R^9$ represents any of hydrogen, an alkyl group having 1 to 4 carbon atoms, or a substituted or unsubstituted phenyl group. In addition, X of compound A which is a carbazole derivative represents halogen, preferably, bromine or iodine. With a bromine compound or an iodine compound (particularly, iodine) used as X, this part X can be reacted more rapidly by coupling reaction or substitution reaction using this compound A as a reactant. The compound A1 which is a carbazole derivative is reacted with halogen or a halogen compound, whereby compound A which is a 3-halide carbazole derivative is obtained. Although there is no limitation on the above-described halogen or halogen compound, iodine ($I_2$), potassium iodide (KI), or N-Iodosuccinimide (NIS) is preferably used for iodination and bromine ($Br_2$) or N-Bromosuccinimide (NBS) is preferably used for bromination. With NBS, the above-described reaction for synthesis can be easily performed at room temperature in a polar solvent of ethyl acetate or the like, which is preferable. With iodine, bromine, or potassium iodide, synthesis can be performed at low cost, which is preferable.

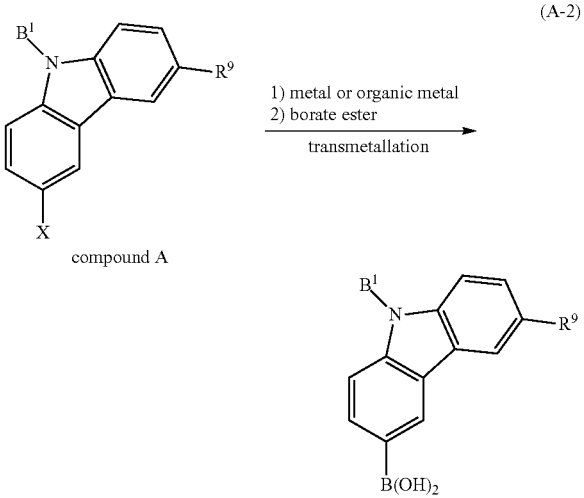

Then, in the synthesis scheme (A-2), the compound A obtained according to the synthesis scheme (A-1) is reacted with metal or organic metal, and borate ester is added to be reacted with, so that compound B which is the carbazole derivative having boronic acid at the 3-position is obtained through transmetallation. Although there is no limitation on the above-described transmetallation using metal or organic metal, Grignard reaction using magnesium, or lithiation reaction using alkyllithium such as butyllithium is preferably used. Further, although there is no limitation on the above-described borate ester, trimethyl borate, triethyl borate, or triisopropyl borate is preferably used.

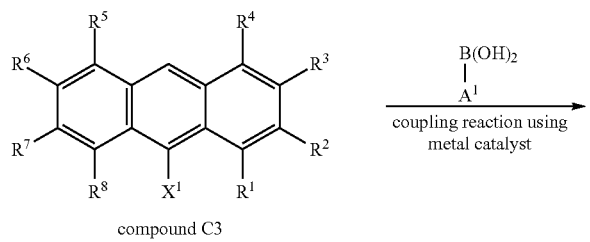

compound C3

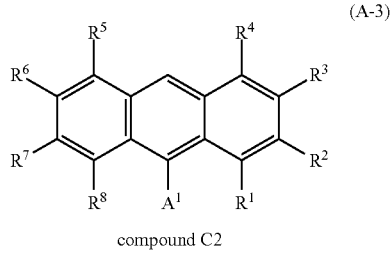

(A-3)

compound C2 halogenation

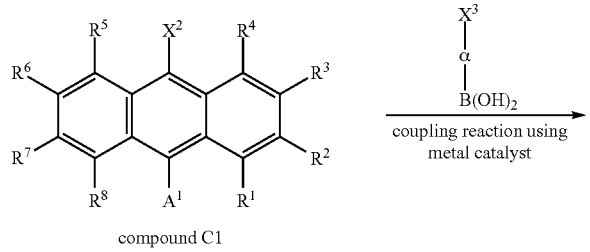

compound C1

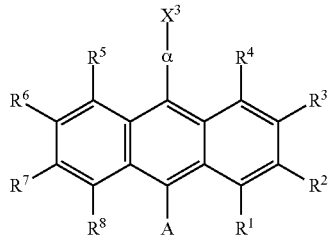

compound C $X^1, X^2, X^3$; Cl or Br or I

In the synthesis scheme (A-3), $A^1$ represents a substituted or unsubstituted phenyl group, $R^1$ to $R^8$ individually represent any of hydrogen, an alkyl group having 1 to 4 carbon atoms, or a substituted or unsubstituted phenyl group, α represents any of a substituted or unsubstituted phenylene group or a substituted or unsubstituted biphenyl-4,4'-diyl group, and $X^1$ to $X^3$ individually represent halogen. Although there is no limitation on the above-described halogen, chlorine, bromine, or iodine is preferably used. The synthesis method of compound C will be described below. First, coupling reaction of compound C3 which is a 9-anthracene halide derivative and arylboronic acid is conducted to synthesize compound C2. Although there is no limitation on the above-described coupling reaction, a metal catalyst is preferably used as a catalyst. In addition, although there is no limitation on the above-described metal catalyst, a palladium catalyst such as palladium acetate (Pd(OAc)$_2$)) or tetrakis(triphenylphosphine)palladium is preferably used. Further, although there is no limitation on a ligand of the above-described palladium catalyst, a phosphor compound such as tris(2-methylphenyl)phosphine is preferably used. Further, in the above-described coupling reaction, a base is preferably added in order to promote the reaction. Although there is no limitation on the above-described base, potassium carbonate ($K_2CO_3$) or sodium carbonate (NaCO$_3$) is preferably used.

Next, the compound C2 which is an anthracene derivative is halogenated to synthesize compound C1 which is a 10-anthracene halide derivative. Although there is no limitation on halogen or a halogen compound used in the above-described halogenation reaction, iodine ($I_2$), potassium iodide (KI), or N-Iodosuccinimide (NIS) is preferably used far iodination and bromine (Br$_2$) or N-Bromosuccinimide (NBS) is preferably used for bromination. With NBS, the above-described reaction for synthesis can be easily performed at room temperature in a polar solvent of ethyl acetate or the like, which is preferable. With iodine, bromine, or potassium iodide, synthesis can be performed at low cost, which is preferable.

Next, coupling reaction of the compound C1 which is a 10-anthracene halide derivative and halogenated aryl boronic acid is conducted to synthesize the compound C.

At that time, it is more preferable that $X^2$ in the compound C1 be iodine and X in the halogenated aryl boronic acid be bromine. With iodine and bromine used as $X^2$ and X respectively, coupling reaction can be selectively performed between an iodine compound and a boronic acid compound. That is, side reaction such as homocoupling of the halogenated aryl boronic acid can be suppressed, so that generation of a byproduct can be suppressed. As a result, the purity of the compound C is increased, which can make purification of the compound C easy. The same can be true for the case where $X^2$ in the compound C1 is iodine and $X^3$ in the halogenated aryl boronic acid is chlorine and the case where $X^2$ in the compound C1 is bromine and $X^3$ in the halogenated aryl boronic acid is chlorine, which are preferable since selective reaction can be performed. Although there is no limitation on the above-described coupling reaction, a metal catalyst is preferably used as a catalyst. In addition, although there is no limitation on the above-described metal catalyst, a palladium catalyst such as palladium acetate ($Pd(OAc_2)$) or tetrakis(triphenylphosphine)palladium is preferably used. Further, although there is no limitation on a ligand of the above-described palladium catalyst, a phosphor compound such as tris(2-methylphenyl)phosphine is preferably used. Further, in the above-described coupling reaction, a base is preferably aided in order to promote the reaction. Although there is no limitation on the above-described base, potassium carbonate ($K_2CO_3$) or sodium carbonate ($NaCO_3$) is preferably used.

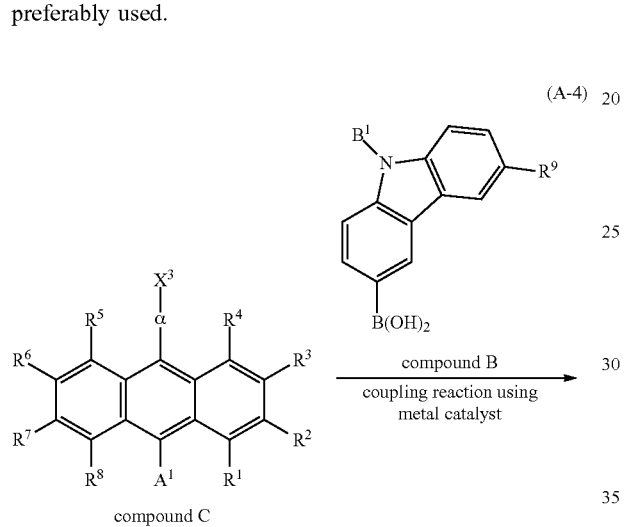

(A-4)

compound P1

$X^1$; Cl or Br or I

Then, in the synthesis scheme (A-4), coupling reaction of the compound C obtained according to the synthesis scheme (A-3) and the compound B obtained according to the synthesis scheme (A-2) is conducted, so that compound P1 which is represented by the same general formula as the general formula (1) is obtained. Although there is no limitation on the above-described coupling reaction, a metal catalyst is preferably used as a catalyst. In addition, although there is no limitation on the above-described metal catalyst, a palladium catalyst such as palladium acetate ($Pd(OAc_2)$) or tetrakis(triphenylphosphine)palladium is preferably used. Further, although there is no limitation on a ligand of the above-described palladium catalyst, a phosphor compound such as tris(2-methylphenyl)phosphine is preferably used. Further, in the above-described coupling reaction, a base is preferably added in order to promote the reaction. Although there is no limitation on the above-described base, potassium carbonate ($K_2CO_3$) or sodium carbonate ($NaCO_3$) is preferably used.

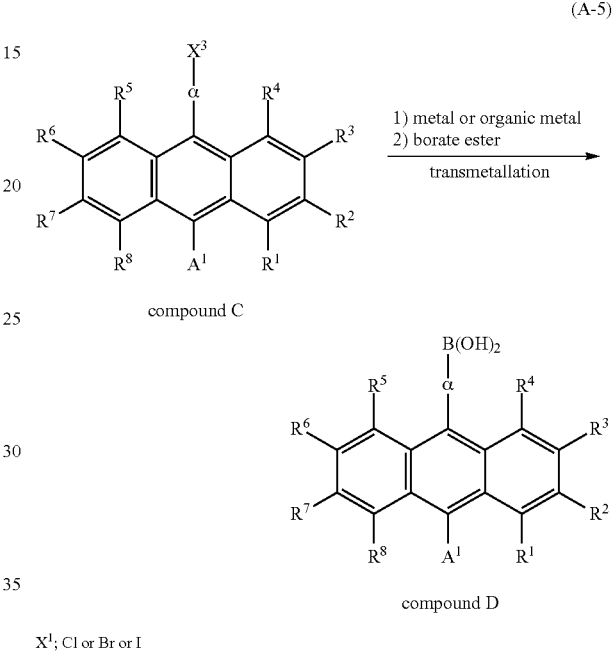

(A-5)

$X^1$; Cl or Br or I

On the other hand, in the synthesis scheme (A-5), the compound C obtained according to the synthesis scheme (A-3) is reacted with metal or organic metal, and borate ester is added to be reacted with, so that compound D which is boronic acid of anthracene derivative is obtained through transmetallation. Although there is no limitation on the above-described transmetallation using metal or organic metal, Grignard reaction using magnesium, or lithiation reaction using alkyllithium such as butyllithium is preferably used. Further, although there is no limitation on the above-described borate ester, trimethyl borate, triethyl borate, or triisopropyl borate is preferably used.

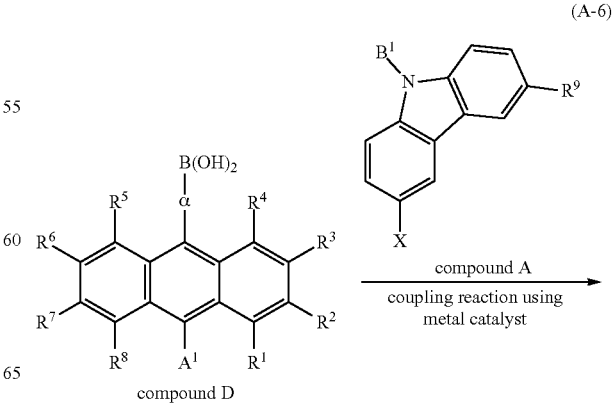

(A-6)

-continued

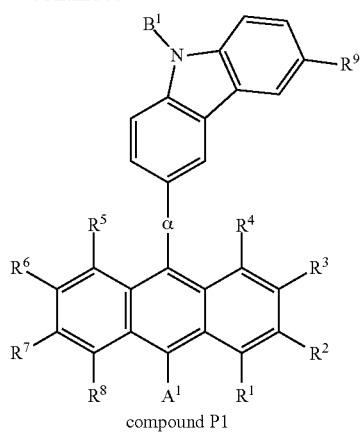
compound P1

X; Cl or Br or I

Then, in the synthesis scheme (A-6), coupling reaction of the compound D obtained according to the synthesis scheme (A-5) and the compound A obtained according to the synthesis scheme (A-1) is conducted, so that the compound P1 which is represented by the same general formula as the general formula (1) is obtained. Although there is no limitation on the above-described coupling reaction, a metal catalyst is preferably used as a catalyst. In addition, although there is no limitation on the above-described metal catalyst, a palladium catalyst such as palladium acetate ($Pd(OAc_2)$) or tetrakis(triphenylphosphine)palladium is preferably used. Further, although there is no limitation on a ligand of the above-described palladium catalyst, a phosphor compound such as tris(2-methylphenyl)phosphine is preferably used. Further, in the above-described coupling reaction, a base is preferably added in order to promote the reaction. Although there is no limitation on the above-described base, potassium carbonate ($K_2CO_3$) or sodium carbonate ($NaCO_3$) is preferably used.

<Synthesis of Compound Represented by General Formula (5)).

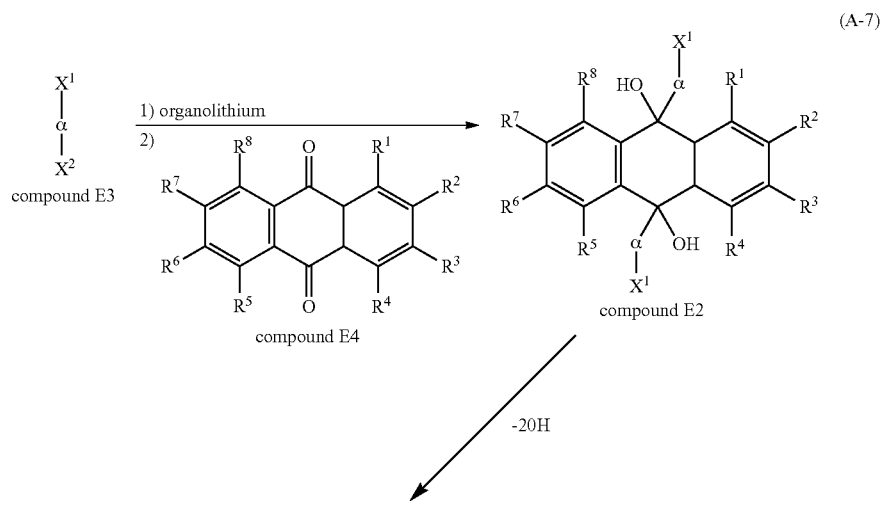

(A-7)

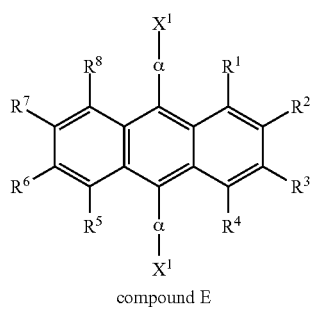
compound E $X^1, X^2$; Cl or Br or I

In the synthesis scheme (A-7), $R^1$ to $R^8$ individually represents any of hydrogen, an alkyl group having 1 to 4 carbon atoms, or a substituted or unsubstituted phenyl group, a represents any of a substituted or unsubstituted phenylene group or a substituted or unsubstituted biphenyl-4,4'-diyl group, and $X^1$ and $X^2$ individually represent halogen. Although there is no limitation on the above-described halogen, chlorine, bromine, or iodine is preferably used. In particular, $X^2$ is preferably bromine or iodine. First, lithiation of compound F3 which is a dehalogenated arene derivative is performed using an organolithium compound and compound E4 which is an anthraquinone derivative is added thereto to be reacted, so that compound E2 which is a 9,10-dihydroanthracene derivative is obtained. Although there is no limitation on the above-described organolithium compound, butyllithium is preferably used. Then, the compound E2 is dehydrated so that compound E which is an anthracene halide derivative is obtained. Although there is no limitation on this reaction, potassium iodide (KI) and Sodium hypophosphite monohydrate (NaPH$_2$O$_2$.H$_2$O) are preferably used.

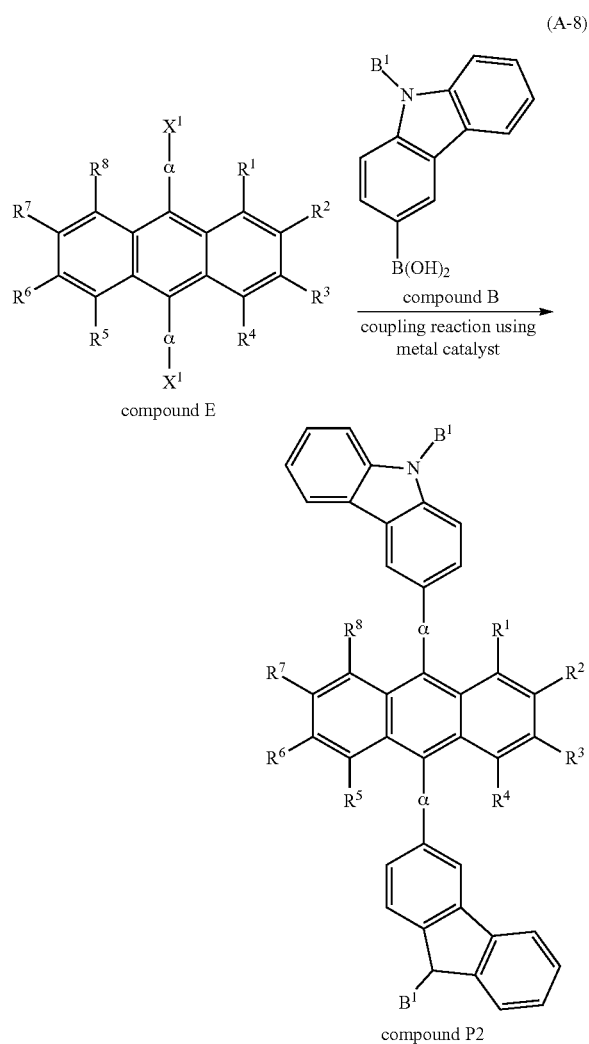

(A-7) and the compound B obtained according to the synthesis scheme (A-2) is conducted, so that compound P2 which is represented by the general formula (5) is obtained. Although there is no limitation on the above-described coupling reaction, a metal catalyst is preferably used as a catalyst. In addition, although there is no limitation on the above-described metal catalyst, a palladium catalyst such as palladium acetate (Pd(OAc)$_2$)) or tetrakis(triphenylphosphine)palladium is preferably used. Further, although there is no limitation on a ligand of the above-described palladium catalyst, a phosphor compound such as tris(2-methylphenyl) phosphine is preferably used. Further, in the above-described coupling reaction, a base is preferably added in cider to promote the reaction. Although there is no limitation on the above-described base, potassium carbonate (K$_2$CO$_3$) or sodium carbonate (NaCO$_3$) is preferably used.

The anthracene derivative of the present invention has an extremely large band gap and can emit light with extremely short wavelength. Therefore, blue light emission with high color purity can be provided.

Further, the anthracene derivative of the present invention has an electron-transporting property and a hole-transporting property. Therefore, it can be preferably used in a light-emitting element.

The anthracene derivative of the present invention is preferable as a host material of a light-emitting layer of a light-emitting element. That is, a light-emitting material having a smaller hand gap than the anthracene derivative of the present invention (hereinafter the light-emitting material is referred to as a dopant) is added into a layer made of the anthracene derivative of the present invention so that light emission from the dopant can be obtained. In this case, since the anthracene derivative of the present invention has an extremely large hand gap, light emission from the dopant can be obtained efficiently instead of light emission from the anthracene derivative of the present invention even in the case of using a dopant emitting light of a relatively short wavelength. Specifically, a light-emitting material having light emission maximum in around 430 nm of the wavelength, which provides high blue color purity, is used as a dopant so that a light-emitting element capable of blue light emission with high color purity can be obtained. In the case where the anthracene derivative of the present invention is used as a host material for blue light emission, $A^1$ is preferably an uncondensed aryl group in order for the increase of band gap. In addition, α is preferably an uncondensed allylene group.

On the other hand, the anthracene derivative of the present invention is added into a layer made of a material having a larger band gap than the anthracene derivative of the present invention (hereinafter the material is referred to as a host) to manufacture a light-emitting element so that light emission from the anthracene derivative of the present invention can be obtained. That is, the anthracene derivative of the present invention can also function as a dopant. In this case, since the anthracene derivative of the present invention has an extremely large band gap and provides light emission of a short wavelength, a light-emitting element capable of blue light emission with high color purity can be manufactured.

The anthracene derivative of the present invention emits light efficiently. With the anthracene derivative of the present invention, a light-emitting element with high emission efficiency can be provided.

Embodiment Mode 2

In Embodiment Mode 2, one made of a light-emitting element using the anthracene derivative of the present invention will be described using FIG. 1.

Then, in the synthesis scheme (A-8), coupling reaction of the compound E obtained according to the synthesis scheme The light-emitting element of the present invention includes a plurality of layers between a pair of electrodes. The plurality of layers is a stack of layers each including a highly carrier injecting substance or a highly carrier transporting substance, combined such that a light emission region should be formed away from the electrodes, i.e., such that carriers should be recombined in a region away from the electrodes.

In this embodiment mode, the light-emitting element includes a first electrode 101, a second electrode 103, and a layer 102 including an organic compound provided between the first electrode 101 and the second electrode 103. Note that, for description of this embodiment mode, hereinafter, the first electrode 101 functions as an anode and the second electrode 103 functions as a cathode. That is, for the description below, light emission is obtained when a voltage is applied to the first electrode 101 and the second electrode 103 such that the potential of the first electrode 101 become higher than that of the second electrode 103.

A substrate 100 is used as a support of the light-emitting element. For the substrate 100, a substrate of glass, plastic, or the like may be used; any other material may be used as long as the substrate 100 functions as a support in a manufacturing process.

It is preferable that the first electrode 101 be formed using a metal, an alloy, or a conductive compound, a mixture thereof, or the like having a high work function (specifically greater than or equal to 4.0 eV). Specifically, for example, there are indium tin oxide (ITO), indium tin oxide containing silicon or silicon oxide, indium zinc oxide (FLU), and indium oxide containing tungsten oxide and zinc oxide (IWZO). Such conductive metal oxide films are normally deposited by sputtering, but may also be formed by application of a sol-gel method or the like. For example, iridium zinc oxide (IZO) can be deposited by a sputtering method using a target in which zinc oxide is added to indium oxide at 1 to 20 wt %. In addition, indium oxide containing tungsten oxide and zinc oxide (IWZO) can be deposited by a sputtering method using a target in which tungsten oxide and zinc oxide are added to indium oxide at 0.5 to 5 wt % and 0.1 to 1 wt % respectively. Ax a target, the following can alternatively be used: gold (Au), platinum (Pt), nickel (Ni), tungsten (W), chromium (Cr), molybdenum (Mo), iron (Fe), cobalt (Co), copper (Cu), palladium (Pd), nitride of a metal material (e.g., titanium nitride), and the like.

There is no particular limitation on the stack structure of the layer 102 including an organic compound. The layer 102 including an organic compound may have a structure in which one or more of layers including a substance having a high electron-transporting property, a substance having a high hole-transporting property, substance having a high electron-injecting property, a substance having a high hole-injecting property, a bipolar substance (a substance having a high electron-transporting property and a high hole-transporting property), and/or the like is combined with the light-emitting layer described in this embodiment mode, as appropriate. For example, a hole-injecting layer, a hole-transporting layer, a hole-blocking layer, a light-emitting layer, an electron-transporting layer, and an electron-injecting layer can be combined as appropriate. In this embodiment mode, the structure in which the layer 102 including an organic compound includes a hole-injecting layer 111, a hole-transporting layer 112, a light-emitting layer 113, an electron-transporting layer 114, and an electron-injecting layer 115 stacked on the first electrode 101 in order will be described. Materials for forming the layers are detailed be low.

The hole-injecting layer 111 is a layer including a substance having a high hole-injecting property. Molybdenum oxide, vanadium oxide, ruthenium oxide, tungsten oxide, manganese oxide, or the like can be used. Alternatively, the hole-injecting layer 111 can be formed of a phthalocyanine compound such as phthalocyanine ($H_2Pc$) or copper phthalocyanine (CuPc), an aromatic amine compound such as 4,4'-bis[N-(4-diphenylaminophenyl)-N-phenylamino]biphenyl (DPAB) or N,N'-bis[4-[bis(3-methylphenyl)amino]phenyl]-N,N'-diphenyl-[1,1'-biphenyl]-4,4'-diamine (DNTPD), a high molecular substance such as poly(3,4-ethylenedioxythiophene)/poly(styrenesulfonic acid) (PEDOT/PSS), or the like.

Alternatively, the hole-injecting layer 111 can be formed of a composite material in which an acceptor substance is mixed into a substance having a high hole-transporting property. Note that when the composite material in which an acceptor substance is mixed into a substance having a high hole-transporting property is used, a material for forming the electrode can be selected regardless of the work function of the electrode. That is, not only a high work-function material, but also a low work-function material can be used for the first electrode 101. As the acceptor substance, 7,7,8,8-tetracyano-2,3,5,6-tetrafluoroquinodimethane (abbreviation: $F_4$-TCNQ), chloranil, and the like. Further, there are transition metal oxides. Furthermore, there are oxides of metals that belong to Group 4 to Group 8 of the periodic table. Specifically, any of vanadium oxide, niobium oxide, tantalum oxide, chromium oxide, molybdenum oxide, tungsten oxide, manganese oxide, or rhenium oxide is preferably used because of their high electron accepting property. Among these, molybdenum oxide is, in particular, preferable because of its stability in the atmosphere, low hygroscopic property, and easiness of handling.

As an organic compound used for the composite material, various compounds such as an aromatic amine compound, a carbazole derivative, aromatic hydrocarbon, and a high molecular compound (e.g., oligomer, dendrimer, or polymer) can be used. Note that the organic compound used for the composite material is preferably an organic compound having a high hole-transporting property. Specifically, a substance having a hole mobility of $10^{-6}$ $cm^2/Vs$ or more is preferably used; however, any other substance can alternatively be used as long as the hole-transporting property thereof is higher than the electron-transporting property thereof. The organic compound that can be used for the composite material is specifically shown below.

For example, as the aromatic amine compound that can be used for the composite material, the following can be given: N,N'-bis(4-methylphenyl)(p-tolyl)-N,N'-diphenyl-p-phenylenediamine (DTDPPA), 4,4'-bis[N-(4-diphenylaminophenyl)-N-phenylamino]biphenyl (DPAB), 4,4'-bis(N-{4-[N'-(3-methylphenyl)-N'-phenylamino]phenyl}-N-phenylamino)biphenyl (DNTPD), 1,3,5-tris[N-(4-diphenylaminophenyl)-N-phenylamino]benzene (DPA3B), and the like.

As the carbazole derivative which can be used for the composite material, specifically, the following can be given: 3-[N-(9-phenylcarbazol-3-yl)-N-phenylamino]-9-phenylcarbazole (PCzPCA1), 3,6-bis(N-(9-phenylcarbazol-3-yl)-N-phenylamino-9-phenylcarbazole (PCzPCA2), 3-[N-(1-naphtyl)-N-(9-phenylcarbazol-3-yl)amino]-9-phenylcarbazole (PCzPCN1), and the like. Further, the following can alternatively be used: 4,4'-di(N-carbazolyl)biphenyl (CBP), 1,3,5-tris[4-(N-carbazoyl)phenyl]benzene (TCPB), 9-[4-(10-phenyl-9-anthryl)phenyl]-9H-carbazole (CzPA), 1,4-bis-[4-(N-carbazolyl)phenyl]-2,3,5,6-tetraphenylbenzene, or the like.

As the aromatic hydrocarbon which can be used for the composite material, the following can be given: 2-tert-butyl-9,10-di(2-naphthyl)anthracene (t-BuDNA), 2-tert-butyl-9,10-di(1-naphthyl)anthracene, 9,10-bis(3,5-diphenylphenyl)anthracene (DPPA), 2-tert-butyl-9,10-bis(4-phenylphenyl)anthracene (t-BuDBA), 9,10-di(2-naphthyl)anthracene (DNA), 9,10-diphenylanthracene (DPAnth), 2-tert-butylanthracene (t-BuAnth), 9,10-bis(4-methyl-1-naphthyl)anthracene (DMNA), 9,10-bis[2-(1-naphthyl)phenyl]-2-tert-butylanthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, and the like. Alternatively, pentacene, coronene, or the like can be used. As described above, aromatic hydrocarbon that has a hole mobility of $1 \times 10^6$ cm$^2$/Vs or more and 14 to 42 carbon atoms is inure preferably used.

Note that the aromatic hydrocarbon which can be used for the composite material may have a vinyl skeleton. As the aromatic hydrocarbon having a vinyl skeleton, for example, there are 4,4'-bis(2,2-diphenylvinyl)biphenyl (DPVBi) 9,10-bis[4-(2,2-diphenylvinyl)phenyl]anthracene (DPVPA), and the like.

Alternatively, the following high molecular compound can be used: poly(N-vinylcarbazole) (PVK), poly(4-vinyltriphenylamine) (PVPA), poly[N-(4-{N'-[4-(4-diphenylamino)phenyl]phenyl-N'-phenylamino}phenyl)methacrylamide](PTPDMA), poly[N,N'-bis(4-butylphenyl)-N,N'-bis(phenyl)benzidine](Poly-TPD), or the like.

The hole-transporting layer 112 is a layer including a high hole-transporting substance. As the high hole-transporting substance, for example, the following aromatic amine compound can be used: 4,4'-bis[N-(1-naphthyl)-N-phenylamino]biphenyl (NPB), N,N'-bis(3-methylphenyl)-N,N'-diphenyl-[1,1'-biphenyl]-4,4'-diamine (TPD), 4,4',4"-tris(N,N-diphenylamino)triphenylamine (TDATA), 4,4',4"-tris[N-(3-methylphenyl)-N-phenylamino]triphenylamine (MTDATA), 4,4'-bis[N-(spiro-9,9'-bifluoren-2-yl)-N-phenylamino]biphenyl (BSPB), or the like. Such substances as described above are mainly substances each having a hole mobility of $10^6$ cm$^2$/Vs or more. Any other substance may alternatively be used as long as the hole-transporting property thereof is higher than the electron-transporting property thereof. Note that the layer including a substance having a high hole-transporting property is not limited to a single layer; a stack of two or more layers each including any of the above-described materials may be employed for the layer including a substance having a high hole-transporting property.

Alternatively, for the hole-transporting layer 112, a high molecular compound such as poly(N-vinylcarbazole) (PVK) or poly(4-vinyltriphenylamine) (PVTPA) can be used.

The light-emitting layer 113 is a layer including a substance having a high light-emitting property. The light-emitting layer 113 of the light-emitting element described in this embodiment mode can be formed using the anthracene derivative of the present invention described in Embodiment Mode 1. Emitting blue light, the anthracene derivative of the present invention can be preferably used for a light-emitting element, as a substance having a high light-emitting property.

The electron-transporting layer 114 is a layer including a substance having a high electron-transporting property. For example, the following metal complex or the like having a quinoline or benzoquinoline skeleton can be used: tris(8-quinolinolato)aluminum (Alq), tris(4-methyl-8-quinolinolato)aluminum (Almq$_3$), bis(10-hydroxybenzo[h]quinolinato)beryllium (BeBq$_2$), bis(2-methyl-8-quinolinolato)(4-phenylphenolato)aluminum (BAlq), or the like. Alternatively, the following metal complex or the like having an oxazole-based or thiazole-based ligand can be used: bis[2-(2'-hydroxyphenyl)benzoxazolato]zinc (Zn(BOX)$_2$), bis[2-(2'-hydroxyphenyl)benzothiazolato]zinc (Zn(BTZ)$_2$), or the like. As an alternative to the metal complex, the following can be used: 2-(4-biphenylyl)-5-(4-tert-butylphenyl)-1,3,4-oxadiazole (PBD), 1,3-bis[5-(p-tert-butylphenyl)-1,3,4-oxadiazol-2-yl]benzene (OXD-7), 3-(4-biphenylyl)-4-phenyl-5-(4-tert-butylphenyl)-1,2,4-triazole (TAZ), bathophenanthroline (BPhen), bathocuproine (BCP), or the like. Such substances as described above are mainly substances each having an electron mobility of $10^{-6}$ cm$^2$/Vs or more. Any other substance may alternatively be used for the electron-transporting layer 114 is long as the electron-transporting property thereof is higher than the hole-transporting property thereof. Note that the electron-transporting layer is not limited to a single layer; a stack of two or more layers each including any of the above-described materials may be employed for the electron-transporting layer.

Alternatively, for the electron-transporting layer 114, a high molecular compound can be used. For example, poly [(9,9-dihexylfluorene-2,7-diyl)-co-(pyridine-3,5-diyl)] (PF-Py), poly[(9,9-dioctylfluorene-2,7-diyl)-co-(2,2'-bipyridine-6,6'-diyl)] (PF-BPy), or the like can be used.

The electron-injecting layer 115 is a layer including a substance having a high electron-injecting property. As the substance having a high electron-injecting property, an alkali metal compound or an alkaline earth metal compound such as lithium (Li), cesium (Cs), barium (Ba), magnesium (Mg), or calcium (Ca), or lithium fluoride (LiF), cesium fluoride (CsF), or calcium fluoride (CaF$_2$), co a compound thereof can be used. Furthermore, a layer made of a substance having a high electron-injecting property, in which an alkali metal, an alkaline earth metal, or a compound thereof is contained, e.g., a layer formed of Alq in which magnesium (Mg) is contained, can alternatively be used. It is more preferable to use a layer made of a substance having a high electron-injecting property, in which an alkali metal or an alkaline earth metal is contained, as the electron-injecting layer, because electrons can be efficiently injected from the second electrode 103.

The second electrode 103 can be formed using a metal, an alloy, or a conductive compound, a mixture of them, or the like having a low work function (specifically less than or equal to 3.8 eV). As specific examples of such cathode materials, the following can be given: elements belonging to Group 1 and Group 2 of the periodic table, that is, alkali metals such as lithium (Li) and cesium (Cs), alkaline earth metals such as magnesium (Mg), calcium (Ca), and strontium (Sr), or alloys thereof (e.g., MgAg and AlLi), rare earth metals such as europium (Eu) and ytterbium (Yb), or allays thereof, and the like. However, by providing a layer for promoting electron injection between the second electrode 103 and the electron-transporting layer 114, any of various conductive materials such as Al, Ag, ITO, or indium tin oxide containing silicon or silicon oxide can be used for the second electrode 103 regardless of its work function. These conductive materials can be deposited by a sputtering method, an inkjet method, a spin coating method, or the like.

Further, the layers included in the layer 102 including an organic compound can be individually formed by any of various methods regardless of a dry process or a wet process. For example, a vacuum deposition method, an inkjet method, a spin-coating method, or the like may be used. Further, different deposition methods may be used for forming the electrodes or the layers.

Furthermore, the electrodes may also be formed by a dry process such as a sputtering method or a vacuum deposition method. Alternatively, the electrodes may be formed by a wet process using a sol-gel method or by a wet process using a metal paste.

For example, when the light-emitting element of the present invention is applied to a display device and manufactured using a large substrate, the light-emitting layer is preferably formed by a wet process. With an inkjet method, light-emitting layers can be easily formed separately for color even when a large substrate is used.

For example, the structure described in this embodiment mode may be formed as follows: the first electrode is formed by a sputtering method which is a dry process, the hole-injecting layer is formed by an inkjet method or a spin coating method which is a wet process, the hole-transporting layer is formed by a vacuum deposition method which is a dry process, the light-emitting layer is formed by an inkjet method which is a wet process, the electron-infecting layer is formed by a vacuum deposition method which is a dry process, and the second electrode is formed by an inkjet method or a spin coating method which is a wet process. Alternatively, the structure may be formed as follows: the first electrode is formed by an inkjet method which is a wet process, the hole-injecting layer is formed by a vacuum deposition method which is a dry process, the hole-transporting layer is formed by an inkjet method or a spin coating method which is a wet process, the light-emitting layer is formed by an inkjet method which is a wet process, the electron-injecting layer is formed by an inkjet method or a spin coating method which is a wet process, and the second electrode is formed by an inkjet method or a spin coating method which is a wet process. Note that there is no limitation on the above manner and that a wet process and a dry process may be combined as appropriate.

Further alternatively, the light-emitting element can be formed as follows: the first electrode is formed by a sputtering method which is a dry process, the hole-injecting layer and the hole-transporting layer are formed by an inkjet method or a spin coating method which is a wet process, the light-emitting layer is formed by an inkjet method which is a wet process, the electron-injecting layer is formed by a vacuum deposition method which is a dry process, and the second electrode is formed by a vacuum deposition method which is a dry process. That is, over the substrate provided with the first electrode which has already been formed to have a desired shape, the layers from the hole-injecting layer to the light-emitting layer can be formed by a wet process, and the layers from the electron-transporting layer to the second electrode thereover can be formed by a dry process. This allows the layers from the hole-injecting layer to the electron-transporting layer to be formed at atmospheric pressure and makes it easy to form the light-emitting layers separately for color. Further, the layers from the electron-injecting layer to the second electrode can be formed in vacuum consistently. Therefore, the manufacturing process can be simplified, and productivity can be improved.

The light-emitting element of the present invention, which has the above-described structure, emits light when a current flows due to the potential difference generated between the first electrode 101 and the second electrode 103 and then holes and electrons recombine in the light-emitting layer 113 which is the layer including a substance having a high light-emitting property. That is, a light mission region is formed in the light-emitting layer 113.

The stack structure provided between the first electrode 101 and the second electrode 103 is not limited to the above. Any other structure can be employed as long as it is a structure in which a light mission region in which holes and electrons are recombined is provided away from the first electrode 101 and the second electrode 103.

That is, there is no particular limitation on the stacked-layer structure: the anthracene derivative of the present invention can be combined with one or more layers including a substance having a high electron-transporting property, a substance having a high hole-transporting property, a substance having a high electron-injecting substance, a substance having a high hole-injecting substance, a bipolar substance (a high electron-transporting property and a high hole-transporting property), a hole-blocking material, and/or the like, as appropriate.

The anthracene derivative of the present invention which emits blue light can be used for the light-emitting layer without the addition of another light-emitting material, as described in this embodiment mode.

With the anthracene derivative of the present invention which has an extremely large band gap and provides light emission of a short wavelength, a light-emitting element capable of blue light emission with high color purity can be manufactured.

The anthracene derivative of the present invention emits light efficiently. Therefore, with the anthracene derivative of the present invention, a light-emitting element with high emission efficiency can be provided.

Embodiment Mode 3

In this embodiment mode, a light-emitting element having a structure different from that described in Embodiment Mode 2 will be described.

The structure in which the anthracene derivative of the present invention is dispersed into another substance in the light-emitting layer 113 described in Embodiment Mode 2 can provide light emission the anthracene derivative of the present invention. With the anthracene derivative of the present invention which emits blue light, a light-emitting element which emits blue light can be provided.

Here, as the substance in which the anthracene derivative of the present invention is dispersed, various materials can be used other than the substance having a high hole-transporting property or the substance having a high electron-transporting property described in Embodiment Mode 2, and the following can be given as examples thereof: 4,4'-di(N-carbazolyl)biphenyl (CBP), 2,2(,2((-(1,3,5-benzenetriyl)tris(1-phenyl-1H-benzimidazole) (TPBI), 9,10-di(2-naphthyl)anthracene (DNA), 2-tert-butyl-9,10-di(2-naphthyl)anthracene (t-BuDNA), and 9-[4-(N-carbazolyl)phenyl]-10-phenylanthracene (CzPA). Alternatively, as the substance in which the anthracene derivative of the present invention is dispersed, a high molecular compound can be used. For example, poly(N-vinylcarbazole) (PVK), poly(4-vinyltriphenylamine) (PVTPA), poly[N-(4-{N'-[4-(4-diphenylamino)phenyl]phenyl-N'-phenylamino}phenyl)methacrylamide](PTPDMA), poly[N,N'-bis(4-butylphenyl)-N,N'-bis(phenyl)benzidine](Poly-TPD), poly[(9,9-dihexylfluorene-2,7-diyl)-co-(pyridine-3,5-diyl)] (PF-Py), poly[(9,9-dioctylfluorene-2,7-diyl)-co-(2,2'-bipyridine-6,6'-diyl)](PF-BPy), or the like can be used.

Since the anthracene derivative of the present invention has an extremely large band gap and provides light emission of a short wavelength, a light-emitting element capable of blue light emission with blue color purity can be manufactured.

Note that, as for the other layers than the light-emitting layer 113, the structure described in Embodiment Mode 2 can be used as appropriate.

Embodiment Mode 4

In this embodiment mode, a light-emitting element having a structure different from those of described in Embodiment Modes 2 and 3 will be described.

The structure in which a light-emitting substance is dispersed into the anthracene derivative of the present invention, of the light-emitting layer 113 described in Embodiment Mode 2 can provide the light-emitting element of this embodiment mode and light emission from the light-emitting substance of the element can be provided.

In the case where the anthracene derivative of the present invention is used as a material in which another light-emitting substance is dispersed, a light emission color derived from the light-emitting substance can be obtained. Further, a mixed color resulted from the anthracene derivative of the present invention and the light-emitting substance dispersed in the anthracene derivative can also be obtained.

Various materials can be used as the light-emitting substance which is dispersed in the anthracene derivative of the present invention. In specific, a fluorescent substance which emits fluorescence can be used: N,N'-diphenylquinacridone (DPQd), coumarin 6, coumarin 545T, 2-(2-{2-[4-(dimethylamino)phenyl]ethenyl}-6-methyl-4H-pyran-4-ylidene)propanedinitrile (DCM1), 2-{2-methyl-6-[2-(2,3,6,7-tetrahydro-1H,5H-benzo[ij]quinolizin-9-yl)ethenyl]-4H-pyran-4-ylidene}propanedinitrile (DCM2), N,N'-dimethylquinacridone (DMQd), 2-tert-butyl-4-dicyanomethylene-6-[2-(1,1,7,7-tetramethyl-2,3,6,7-tetrahydro-1H,5H-benzo[ij]quinolizin-9-yl)ethenyl]-4H-pyran (DCJTB), 5,12-diphenyltetracene (DPT), 4-(9H-carbazol-9-yl)-4'-(10-phenyl-9-anthryl)triphenylamine (YGAPA), 9,10-bis(4-{N-(9-carbazolyl)phenyl]-N-phenylamino}phenyl)-2-tert-butylanthracene (YGABPA), 9-phenyl-10-(4-[N-phenyl-N-{3-(N-phenyl)carbazolyl}]amino)phenylanthracene (PCAPA), 9,10-bis{4-[N-(4-diphenylaminophenyl)-N-phenylamino]phenyl}-2-tert-butylanthracene (DPABPA), 4,4'-bis{N-[4-(carbazol-9-yl)phenyl]-N-phenylamino}stilbene (YGA2S), 4-{N-[4-(carbazol-9-yl)phenyl]-N-phenylamino}stilbene (YGAS), 4,4'-bis[N-(9-phenyl-9H-carbazol-3-yl)-N-phenylamino]stilbene (PCA2S), 4,4'-bis(2,2-diphenylvinyl)biphenyl (DPVBi), 2,5,8,11-tetra(tert-butyl)perylene (TBP), perylene, 1,3,6,8-tetraphenylpyrene, or the like. Alternatively, phosphorescent substance which emits phosphorescence can be used: bis[2,3-bis(4-fluorophenyl)quinoxalinato]iridium(III) acetylacetonate (Ir(Fdpq)$_2$(acac)), (2,3,7,8,12,13,17,18-octaethyl-21H,23H-porphyrinato)platinum(II), or the like.

Since the anthracene derivative of the present invention has an extremely large band gap, light emission from the dopant can be obtained efficiently instead of light emission from the anthracene derivative of the present invention even in the case of using a dopant emitting light of a relatively short wavelength. Specifically, a light-emitting material having light emission maximum in around 450 nm of the wavelength, which provides high blue color purity, is used as a dopant so that a light-emitting element capable of blue light emission with high color purity can be obtained. The anthracene derivative of the present invention can also be used as the host material not only in the case of using a dopant emitting blue light but also in the case of using a dopant emitting light having wavelengths from blue- to red-light emission.

Note that, as for the other layers than the light-emitting layer 113, the structure described in Embodiment Mode 2 can be used as appropriate.

Embodiment Mode 5

In this embodiment mode, a light-emitting element having a structure different from those of described in Embodiment Modes 2 to 4 will be described using FIG. 2.

In the light-emitting element described in this embodiment mode, a first layer 121 and a second layer 122 are provided in the light-emitting layer 113 of the light-emitting element described in Embodiment Mode 2.

The light-emitting layer 113 includes a layer having a high light-emitting property. In the light-emitting element of the present invention, the light-emitting layer 113 includes the first layer 121 and the second layer 122. The first layer 121 includes a first organic compound and an organic compound having a hole-transporting property, and the second layer 122 includes a second organic compound and an electron-transporting organic compound. The first layer 121 is provided on and in contact with the first electrode side, that is, on and in contact with the anode side of the light-emitting element.

The first organic compound and the second organic compound are substances having a high light-emitting property. Various materials can be used for each of them. In specific, a fluorescent substance which emits fluorescence can be used: N,N'-diphenylquinacridone (DPQd), coumarin 6, coumarin 545T, 2-(2-{2-[4-(dimethylamino)phenyl]ethenyl}-6-methyl-4H-pyran-4-ylidene)propanedinitrile (DCM1), 2-{2-methyl-6-[2-(2,3,6,7-tetrahydro-1H,5H-benzo[ij]quinolizin-9-yl)ethenyl]-4H-pyran-4-ylidene}propanedinitrile (DCM2), N,N'-dimethylquinacridone (DMQd), 2-tert-butyl-4-dicyanomethylene-6-[2-(1,1,7,7-tetramethyl-2,3,6,7-tetrahydro-1H,5H-benzo[ij]quinolizin-9-yl)ethenyl]-4H-pyran (DCJTB), 5,12-diphenyltetracene (DPT), 4-(9H-carhazol-9-yl)-4'-(10-phenyl-9-anthryl)triphenylamine (YGAPA), 9,10-bis(4-{N-(9-carbazolyl)phenyl]-N-phenylamino}phenyl)-2-tert-butylanthracene (YGABPA), 9-phenyl-10-(4-[N-phenyl-N-{3-(N-phenyl)carbazolyl}]amino)phenylanthracene (PCAPA), 9,10-bis{4[N-(4-diphenylaminophenyl)-N-phenylamino]phenyl}-2-tert-butylanthracene (DPABPA), 4,4'-bis{N-[4-(carbazol-9-yl)phenyl]-N-phenylamino}stilbene (YGA2S), 4-{N-[4-(carbazol-9-yl)phenyl]-N-phenylamino}stilbene (YGAS), 4,4'-bis[N-(9-phenyl-9H-carbazol-3-yl)-N-phenylamino]stilbene (PCA2S), 4,4'-bis(2,2-diphenylvinyl)biphenyl (DPVBi), 2,5,8,11-tetra(tert-butyl)perylene (TBP), perylene, 1,3,6,8-tetraphenylpyrene, or the like. The first organic compound and the second organic compound may be the same or different from each other.

The organic compound having a hole-transporting property included in the first layer 121 is a substance which has the hole-transporting property higher than the electron-transporting property. The organic compound having an electron-transporting property included in the second layer 122 is a substance which has the electron-transporting property higher than the hole-transporting property. The anthracene derivative of the present invention, which has an electron-transporting property, can be preferably used for the second layer 122. The anthracene derivative of the present invention, which also has a hole-transporting property, can also be preferably used for the first layer 121.

Regarding the light-emitting element of the present invention having the above-described structure will be described below using FIG. 2.

Figure 2:
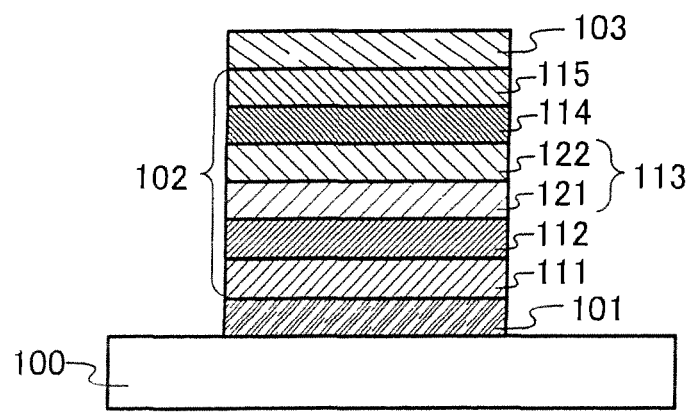
FIG. 2 illustrates a light-emitting element according to an aspect of the present invention.

In FIG. 2, holes injected from the first electrode 101 are injected into the first layer 121 through the hole-injecting layer 111 and the like. The holes injected into the first layer 121 are transported through the first layer 121 into the second layer 122. Here, since the organic compound having an electron-transporting property included in the second layer 122 is a substance which has the electron-transporting property higher than the hole-transporting property, the holes injected into the second layer 122 are difficult to move, which results in the presence of a large number of holes near the interface between the first layer 121 and the second layer 122 and the suppression of the phenomenon in which holes reach the electron-transporting layer 114 without recombining with electrons Meanwhile, electrons injected from the second electrode 103 are injected into the second layer 122 through the electron-injecting layer 115 and the like. The electrons injected into the second layer 122 are transported through the second layer 122 into the first layer 121. Here, since the organic compound having a hole-transporting property included in the first layer 121 is a substance which has the hole-transporting property higher than the electron-transporting property, the electrons injected into the first layer 121 are difficult to move, which results in the suppression of the phenomenon in which electrons reach the hole-transporting layer 112 without recombining with holes.

As a result of this, a large number of holes and electrons are present in a region near the interface between the first layer 121 and the second layer 122, so that recombination probability in the region near the interface is increased. That is, a light-emitting region is formed in the vicinity of the center of the light-emitting layer 113. As a result, occurrence of the phenomenon in which holes reach the electron-transporting layer 114 without recombining with electrons or electrons reach the hole-transporting layer 112 without recombining with holes can be suppressed, whereby a redaction in the probability of recombination can be prevented. Thus, the reduction of carrier balance with time can be prevented, which leads to increase of reliability.

Further, as described above using FIG. 2, in the light-emitting element described in this embodiment mode, it is preferable that the difference in HOMO level between that of the anthracene derivative of the present invention used for the organic compound having a hole-transporting property and that of the organic compound having an electron-transporting property be small in order to structure the light-emitting element such that holes are injected into the second layer 122 from the first layer 121. In addition, it is preferable that the difference in LUMO level between that of the anthracene derivative of the present invention used for the organic compound having a hole-transporting property and that of the organic compound having an electron-transporting property be small in order to structure the light-emitting element such that electrons are injected into the first layer 121 from the second layer 122. If the difference in HOMO level between that of the organic compound having a hole-transporting property and that of the organic compound having an electron-transporting property is large, the light-emitting region is deviated to be on the first layer side or second layer side. Similarly, if the difference in LUMO level between that of the organic compound having a hole-transporting property and that of the organic compound having an electron-transporting property is large, the light-emitting region is deviated to be on the first layer side or second layer side. Accordingly, the difference between the HOMO level of the anthracene derivative used for the organic compound having a hole-transporting property and the HOMO level of the organic compound having an electron-transporting property is preferably 0.3 eV or less, and more preferably 0.1 eV or less. The LUMO level of the anthracene derivative used for the organic compound having a hole-transporting property and the LUMO level of the organic compound having an electron-transporting property is preferably 0.3 eV or less, and more preferably 0.1 eV or less.

Further, since light mission can be obtained front the light-emitting element by recombination of electrons and holes, it is preferable that the organic compound used for the light-emitting layer 113 keep stable with respect to repetitive redox reactions. In other words, the organic compound is preferably reversible to the oxidative reaction and the reductive reaction. In particular, it is preferable that the organic compound having a hole transporting property and the organic compound having an electron transporting property keep stable even when an oxidative reaction and a reductive reaction are repeated. It can be confirmed by employing the cyclic voltammetry (CV) measurement that the anthracene derivative of the present invention keeps stable even when an oxidative reaction and a reductive reaction are repeated. Therefore, the anthracene derivative of the present invention can be preferably used for the light-emitting layer 113. Note that in this embodiment mode, it is necessary that the anthracene derivative of the present invention is used for either layer such as the light-emitting layer 113.

Specifically, changes of an oxidation peak potential (Epa) in the oxidative reaction of the organic compound or a reduction peak potential (Epc) in the reductive reaction, changes of the peak shape, and the like are measured, thereby confirming whether organic compound keep stable even when the oxidative reaction and the reductive reaction are repeated. It is preferable that in the organic compound having a hole-transporting property and the organic compound having an electron-transporting property used for the light-emitting layer 113, the changes in the intensity of the oxidation peak potential and the intensity of the reduction peak potential be less than 50%, more preferably less than 30%. In other words, for example, it is preferable that the peak intensity of 50% or more be kept even when the oxidation peak potential decreases, more preferably the peak intensity of 70% or more be kept. Meanwhile, it is preferable that the changes of the values of the oxidation peak potential and the reduction peak potential be 0.05 V or less, more preferably 0.02 V or less.

The same substance is used as the substance having a high light-emitting property included in the first layer and the substance having a high light-emitting property included in the second layer, thereby making it possible to emit light in the vicinity of the center of the light-emitting layer. On the other hand, if different substances having a high light-emitting property are used for the first layer and the second layer, there is a possibility that light is emitted from only one of the first layer and the second layer. Therefore, the substance having a light-emitting property included in the first layer and the substance having a light-emitting property included in the second layer are preferably the same.

Since the anthracene derivative of the present invention is preferable for excitation of a substance having a high light-emitting property that emits light having wavelengths from blue- to blue green-light, the element structure described in this embodiment mode is particularly effective for a light-emitting element for blue light emission and a light-emitting element for blue green light emission. The anthracene derivative of the present invention may be used for a light-emitting element for green or red light emission. This embodiment mode can be combined with any other embodiment mode as appropriate.

Embodiment Mode 6

In this embodiment mode, a mode of a light-emitting element in which a plurality of light-emitting units according to the present invention are stacked (hereinafter, referred to as a stacked-type element) will be described using FIG. 3. This light-emitting element has a plurality of light-emitting units between a first electrode and a second electrode. Each light-emitting unit can have a structure similar to that of the layer 102 including an organic compound described in any of Embodiment Modes 2 to 5. That is, the light-emitting element described in each of Embodiment Modes 2 to 5 is a light-omitting element having a single light-emitting unit, and in this embodiment mode, a light-emitting element having a plurality of light-emitting units will be described.

Figure 3:
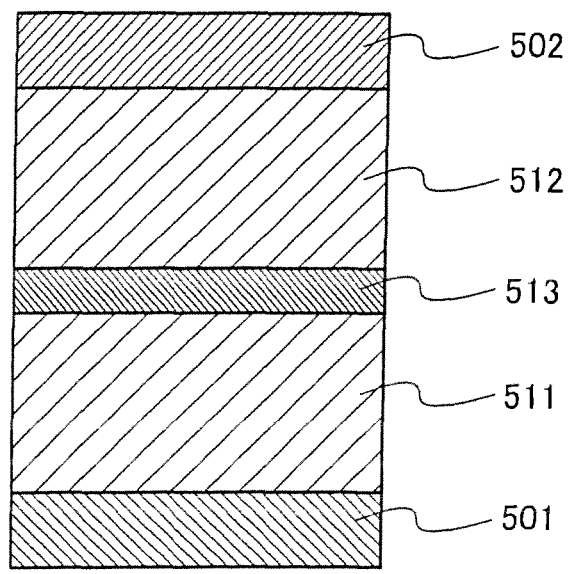
FIG. 3 illustrates a light-emitting element according to an aspect of the present invention.

In FIG. 3, a first light-emitting unit 511 and a second light-emitting unit 512 are stacked between a first electrode 501 and a second electrode 502. Materials similar to those in Embodiment Mode 2 can be applied to the first electrode 501 and the second electrode 502. The first light-emitting unit 511 and the second light-emitting unit 512 individually have a structure similar to the layer including an organic compound described in any of Embodiment Modes 2 to 4.

A charge-generating layer 513 includes a composite material of an organic compound and a metal oxide. This composite material of an organic compound and a metal oxide are described in Embodiment Mode 2 and contains an organic compound and a metal oxide such as vanadium oxide, molybdenum oxide, or tungsten oxide. As the organic compound, various compounds such as an aromatic amine compound, a carbazole derivative, aromatic hydrocarbon, and a high molecular compound (e.g., oligomer, dendrimer, or polymer) can be used. It is preferable that an organic compound having a hole mobility of $10^{-6}$ cm$^2$/Vs or more be used as a hole-transporting organic compound; however, any other substance may be used as the hole-transporting organic compound as long as the substance has the hole-transporting property higher than the electron-transporting property. The composite material of an organic compound and a metal oxide is superior in carrier-injecting property and carrier-transporting property, and accordingly, low-voltage, low-current driving can be realized.

Note that the charge-generating layer 513 may be formed with a combination of a composite material of an organic compound and a metal oxide and another material. For example, the charge-generating layer 513 may be formed with a combination of a layer including the composite material of an organic compound and a metal oxide and a layer including one compound selected from electron-donating substances and a compound having a high electron-transporting property. Further, the charge-generating layer 513 may be formed with a combination of a layer including the composite material of an organic compound and a metal oxide and a transparent conductive film.

In any cases, there is no limitation on the material of the charge-generating layer 513 interposed between the first light-emitting unit 511 and the second light-emitting unit 512 as long as electrons are injected to a light-emitting unit on one side and holes are injected to a light-emitting unit on the other side when a voltage is applied to the first electrode 501 and the second electrode 502.

In this embodiment mode, the light-emitting element having two light-emitting units is explained; similarly, the present invention can also be applied to a light-emitting element in which three or more light-emitting units are stacked. When the charge-generating layer is provided between the pair of electrodes so as to partition the plural light-emitting units like the light-emitting element of this embodiment mode, the element can have long lifetime with high luminance with low current density kept. In the case where the light-emitting element is applied to lighting as an application example, voltage drop due to resistance of an electrode material can be reduced. Accordingly, uniform light emission on a large area can be achieved. Moreover, a light-emitting device with low power consumption, which can be driven at low voltage, can be achieved.

This embodiment can be combined with another embodiment mode as appropriate.

Embodiment Mode 7

In this embodiment mode, a light-emitting device manufactured using the anthracene derivative of the present invention will be described.

In this embodiment mode, the light-emitting device manufactured using the anthracene derivative of the present invention will be described using FIGS. 4A and 4B. FIG. 4A is a top view of the light-emitting device, and FIG. 4B is a cross-sectional view taken along line A-A' in FIG. 4A. This light-emitting device includes a driver circuit portion (a source-side driver circuit) 401, a pixel portion 402, and a driver circuit portion (a gate-side driver circuit) 403, which are shown with dotted lines, so as to control light emission from a light-emitting element. Reference numeral 404 denotes a sealing substrate and 405 denotes a scaling material, and there is a space 407 surrounded by the sealing material 405.

Note that a lead wiring 408 is a wiring for transmitting signals which are input to the source-side driver circuit 401 and the gate-side driver circuit 403, and receives a video signal, a clock signal, a start signal, a reset signal, or the like from a flexible printed circuit (FPC) 409 serving as an external input terminal. The FPC may be provided with a printed wiring hoard (PWB), though not shown. The light-emitting device in this specification includes not only a light-emitting device itself but also a light-emitting device to which the FPC or the PWB is attached.

Next, a cross-sectional structure will be described using FIG. 4B. The driver circuit portions and the pixel portion are formed over an element substrate 410. In FIG. 4B, the source-side driver circuit 401 which is the driver circuit portion and one pixel in the pixel portion 402 are shown.

In the source driver circuit 401, a CMOS circuit, which is a combination of an n-channel TFT 423 and a p-channel TFT 424, is formed. The driver circuit may include various CMOS circuits, PMOS circuits, or NMOS circuits. Further, although a driver-integration type device, in which the driver circuitry is formed over the same substrate as the pixel portion, is described in this embodiment mode, the driver circuitry is not necessarily formed over the same substrate as the pixel portion and may be formed outside the substrate.

The pixel portion 402 is formed of a plurality of pixels each having a switching TFT 411, a current-controlling TFT 412, and a first electrode 413 electrically connected to a drain of the current-controlling TFT 412. An insulator 411 is formed to cover an end portion of the first electrode 413; a positive photosensitive acrylic resin film is used in this embodiment mode.

The insulator 414 is formed so as to have a curved surface having curvature at an upper end portion or lower end portion thereof in order to provide good coverage. For example, when positive type photosensitive acrylic is used as the material of the insulator 414, it is preferable that the insulator 414 have a curved surface with a curvature radius (0.2 to 3 μm) only at its upper end. The insulator 414 can be formed using either a negative type which becomes insoluble in an etchant by light irradiation or a positive type which becomes soluble in an etchant by light irradiation.

A layer 416 including an organic compound and a second electrode 417 are formed over the first electrode 413. It is preferable to use a material having a high work function as the material of the first electrode 413 functioning as the anode. For example, not only a single layer film such as an ITO film, an indium tin oxide film containing silicon, an indium oxide film including zinc oxide at 2 to 20 wt %, a titanium nitride film, a chromium film, a tungsten film, a Zn film, or a Pt film, but also a stacked layer of a titanium nitride film and a film including aluminum as its main component, a three-layer structure of a titanium nitride film, a film including aluminum as its main component, and a titanium nitride film, or the like can be used. It is to be noted that if a stacked-layer structure is employed, the resistance as a wiring can be low, a good ohmic contact can be provided, and besides, function as an anode can be provided.

The layer 416 including an organic compound is formed by various methods such as an deposition method using an evaporation mask, an inkjet method, or a spin coating method. The layer 416 including an organic compound contains the anthracene derivative described in Embodiment Mode 1. In addition, another material included in the layer 416 including an organic compound may be a low molecular compound or a high molecular compound (the category includes an oligomer and a dendrimer).

As a material of the second electrode 417 which is formed over the layer 416 including an organic compound and functions as a cathode, it is preferable to use a material having a low work function (e.g., Al, Mg, Li, Ca, or an alloy or a compound thereof such as MgAg, MgIn, AlLi, LiF, or $CaF_2$). Note that when light generated in the layer 416 including an organic compound is transmitted through the second electrode 417, it is preferable that the second electrode 417 be a stacked layer of a thin metal film and a transparent conductive film (e.g., ITO, indium oxide containing zinc oxide of 2 wt % to 20 wt %, indium tin oxide containing silicon or silicon oxide, or zinc oxide (ZnO)).

The sealing substrate 404 is attached to the element substrate 410 by using the sealing material 405, so that a light-emitting element 418 is provided in the space 407 surrounded by the element substrate 410, the sealing substrate 404, and the sealing material 405. Note that the space 407 is filled with a filler; the space 407 may be filled with an inert gas (e.g., nitrogen or argon) or the sealing material 405.

It is preferable that an epoxy resin be used for the sealing material 405. Further, it is preferable that such a material allow as little moisture and oxygen as possible to penetrate. As a material of the sealing substrate 404, a glass substrate, a quartz substrate, a plastic substrate made of fiberglass-reinforced plastics (FRP), polyvinyl fluoride (PVF), polyester, acrylic, or the like can be used.

In this manner, the light-emitting device manufactured using the anthracene derivative of the present invention can be obtained.

With the anthracene derivative of the present invention, which has high emission efficiency, a light-emitting element with high emission efficiency can be provided.

Since the anthracene derivative of the present invention has an extremely large band gap, a light-emitting element capable of blue light emission with high color purity can be provided.

With the light-emitting element using the anthracene derivative of the present invention, which has high emission efficiency, a light-emitting device with low power consumption can be provided.

Further, with the light-emitting element using the anthracene derivative of the present invention, which is capable of blue light emission with high color purity, a light-emitting device with high color reproducibility can be provided.

Figure 5A:
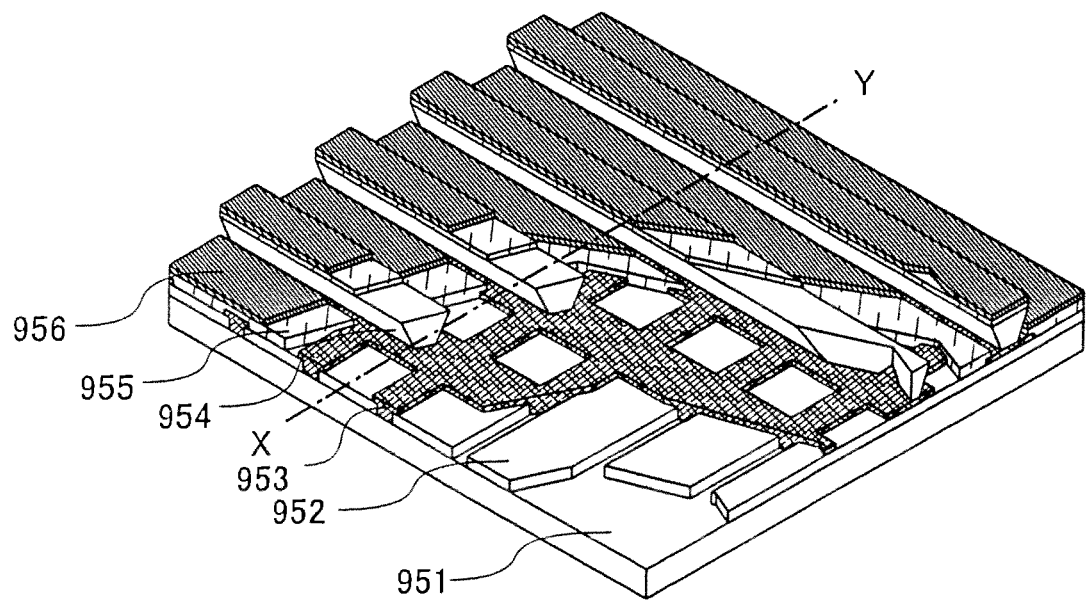
FIGS. 5A and 5B illustrate a light-emitting device according to an aspect of the present invention.
Figure 5B:
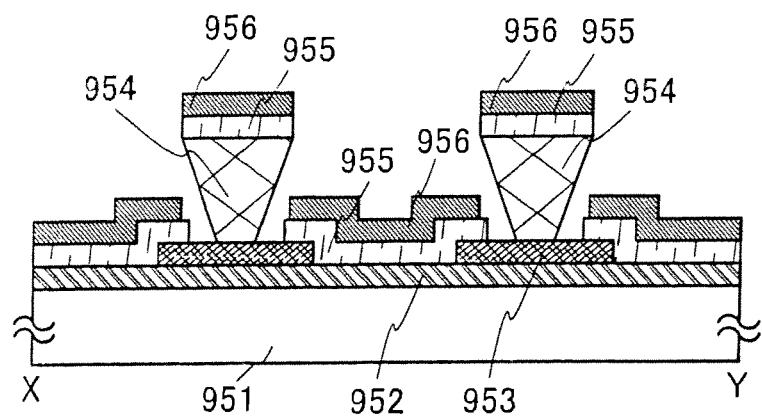

As described above, in this embodiment mode, an active matrix light-emitting device in which operation of a light-emitting element is controlled by a transistor is described. The present invention may also be applied to a passive matrix light-emitting device. FIGS. 5A and 5B show a passive matrix light-emitting device which is manufactured by application of the present invention. FIG. 5A is a perspective view of the light-emitting device, and FIG. 5B is a cross-sectional view of FIG. 5A taken along line X-Y. In FIGS. 5A and 5B, a layer 955 including an organic compound is provided between an electrode 952 and an electrode 956 over a substrate 951. The edge of the electrode 952 is covered with an insulating layer 953. A bank layer 954 is provided over the insulating layer 953. The sidewalls of the bank layer 954 are aslope so that a distance between both sidewalls is gradually narrowed toward the surface of the substrate. That is, a cross section in the direction of a narrow side of the bank layer 954 has a trapezoidal shape, and the bottom side (which faces a surface of the insulating layer 953 and is in contact with the insulating layer 953) is shorter than the top side (which faces the surface of the insulating layer 953 and is not in contact with the insulating layer 953). By providing the bank layer 954 in this manner, defects of the light-emitting element due to static charge and the like can be prevented. The passive matrix light-emitting device can also be driven with low power consumption when it includes the light-emitting element of the present invention.

Embodiment Mode 8

In this embodiment mode, electronic devices of the present invention, each of which includes the light-emitting device described in Embodiment Mode 7, will be described. The electronic devices of the present invention each have a display portion which includes the anthracene derivative described in Embodiment Mode 1 and a display portion with power consumption reduced.

As examples of the electronic devices including the light-emitting element manufactured using the anthracene derivative of the present invention, there are televisions, cameras such as video cameras and digital cameras, goggle type displays its (head-mounted displays), navigation systems, audio replay devices (e.g., car audio systems and audio systems), computers, game machines, portable information terminals (e.g., mobile computers, cellular phones, portable game machines, and electronic book readers), image replay devices in which a recording medium is provided (devices that are capable of replaying recording media such as digital versatile discs (DVDs) and equipped with a display device that can display an image), and the like. Specific examples of these electronic devices are illustrated in FIGS. 6A to 6D.

Figure 6A:
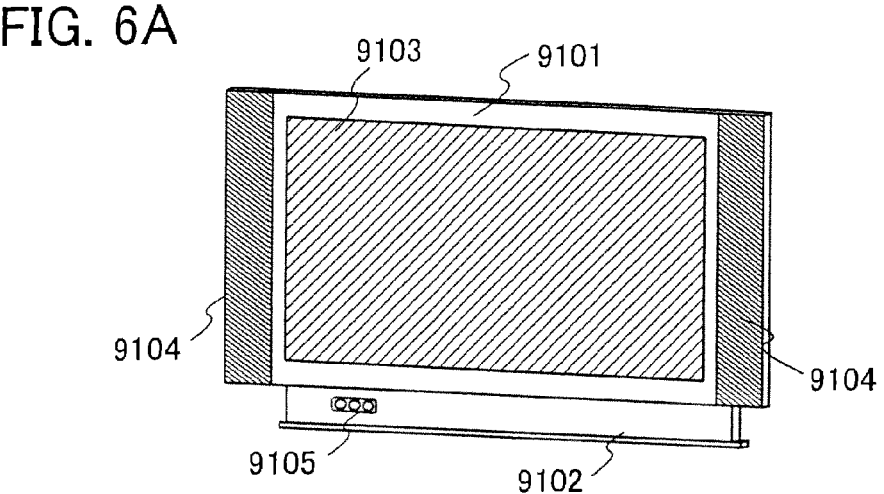
FIGS. 6A to 6D illustrate electronic devices according to an aspect of the present invention.

FIG. 6A illustrates a television set according to the present invention, which includes a chassis 9101, a supporting base 9102, a display portion 9103, a speaker portion 9104, a video input terminal 9105, and the like. In this television set, the display portion 9103 includes light-emitting elements similar to those described in any of Embodiment Modes 2 to 6, which are arranged in matrix. The light-emitting elements feature high emission efficiency. Since the display portion 9103 includes the light-emitting elements having a similar feature, the power consumption of this television set is reduced. Due to such a feature, power supply circuits in the television set can be dramatically reduced or downsized, whereby the chassis 9101 and the supporting base 9102 can be reduced in size and weight. In the television set according to the present invention, low power consumption, high image quality, and reduced size and weight are achieved; therefore, a product suitable for living environments can be provided. Further, since the light-emitting element using the anthracene derivative described in Embodiment Mode 1 can emit light with high color purity, a television set including a display portion with high color reproducibility can be provided.

Figure 6B:
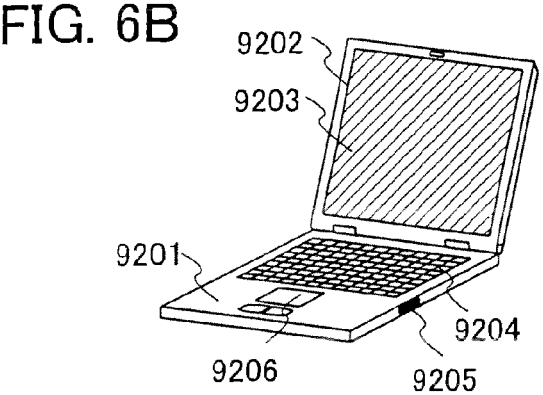

FIG. 6B illustrates a computer according to the present invention, which includes a main body 9201, a chassis 9202, a display portion 9203, a keyboard 9204, an external connection port 9205, a pointing device 9206, and the like. In this computer, the display portion 9203 includes light-emitting elements similar to those described in any of Embodiment Modes 2 to 6, which are arranged in matrix. The light-emitting elements feature high emission efficiency. Since the display portion 9203 includes the light-emitting elements having a similar feature, the power consumption of this computer is reduced. Due to such a feature, power supply circuits in the computer can be dramatically reduced or downsized, whereby the main body 9201 and the chassis 9202 can be reduced in size and weight. In the computer according to the present invention, low power consumption, high image quality, and reduced size and weight are achieved; therefore, a product suitable for the environments can be provided. Further, since the light-emitting element using the anthracene derivative described in Embodiment Mode 1 can emit light with high color purity, a computer including a display portion with high color reproducibility can be provided.

Figure 6C:
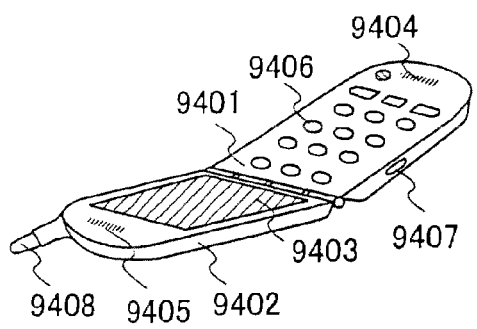

FIG. 6C illustrates a cellular phone according to the present invention, which includes a main body 9401, a chassis 9402, a display portion 9403, an audio input portion 9404, an audio output portion 9405, operation keys 9406, an external connection port 9407, an antenna 9408, and the like. In this cellular phone, the display portion 9403 includes light-emitting elements similar to those described in each of Embodiment Modes 2 to 6, which are arranged in matrix. The light-emitting elements feature high emission efficiency. Since the display portion 9403 includes the light-emitting elements having a similar feature, the power consumption of this cellular phone is reduced. Due to such a feature, power supply circuits in the cellular phone can be dramatically reduced or downsized, whereby the main body 9401 and the chassis 9402 can be reduced in size and weight. In the cellular phone according to the present invention, low power consumption, high image quality, and a small size and light weight are achieved; therefore, a product suitable for carrying can be provided. Further, since the light-emitting element using the anthracene derivative described in Embodiment Mode 1 can emit light with high color purity, a cellular phone including a display portion with high color reproducibility can be provided.

Figure 6D:
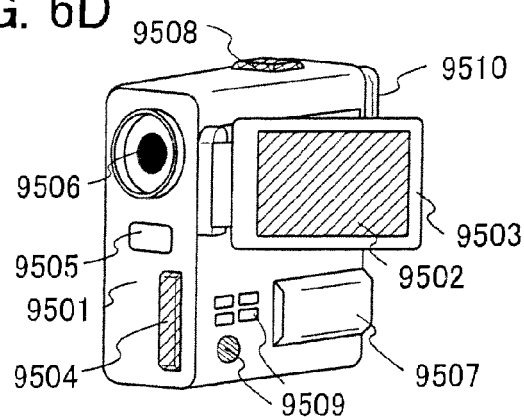

FIG. 6D illustrates a camera according to the present invention, which includes a main body 9501, a display portion 9502, a chassis 9503, an external connection part 9504, a remote control receiving portion 9505, an image receiving portion 9506, a battery 9507, an audio input portion 9508, operation keys 9509, an eye piece portion 9510, and the like. In this camera, the display portion 9502 includes light-emitting elements similar to those described in any of Embodiment Modes 2 to 6, which are arranged in matrix. The light-emitting elements feature high emission efficiency. Since the display portion 9502 includes the light-emitting elements having a similar feature, the power consumption of this camera is reduced. Due to such a feature, power supply circuits in the camera can be dramatically reduced or downsized, whereby the main body 9501 can be reduced in size and weight. In the camera according to the present invention, low power consumption, high image quality, and reduced size and weight are achieved; therefore, a product suitable for carrying can be provided. Further, since the light-emitting element using the anthracene derivative described in Embodiment Mode 1 can emit light with high color purity, a camera including a display portion with high color reproducibility can be provided.

As described above, the applicable range of the light-emitting device of the present invention is quite wide so that the light-emitting device can be applied to electronic devices of a variety of fields. By using the anthracene derivative of the present invention, an electronic device having a display portion with high emission efficiency can be provided. Furthermore, an electronic device including a display with high color reproducibility can be provided.

The light-emitting device of the present invention can also be used as a lighting apparatus. One made in which the light-emitting device of the present invention is used as a lighting apparatus will be described using FIG. 7.

Figure 7:
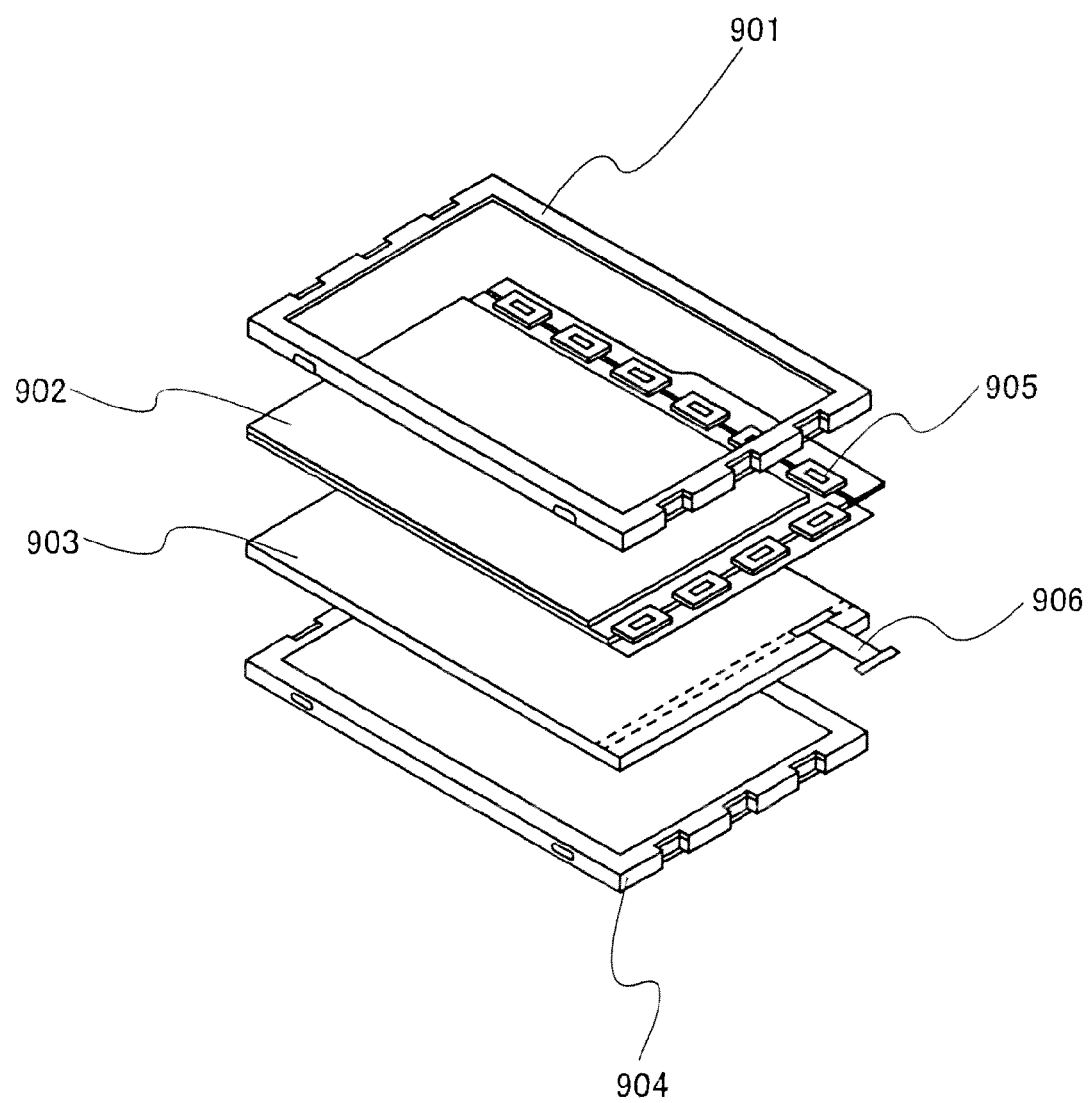
FIG. 7 illustrates a lighting apparatus according to an aspect of the present invention.

FIG. 7 illustrates an example of a liquid crystal display device in which the light-emitting device of the present invention is used as a backlight. The liquid crystal display device illustrated in FIG. 7 includes a chassis 901, a liquid crystal layer 902, a backlight 903, and a chassis 904. The liquid crystal layer 902 is connected to a driver IC 905. Further, as the backlight 903, the light-emitting device of the present invention is used and a current is supplied through a terminal 906.

When the light-emitting device of the present invention is used as the backlight of the liquid crystal display device, a backlight having high emission efficiency with power consumption reduced can be provided. Further, the light-emitting device of the present invention is a plane emission lighting apparatus and can also have a large area; accordingly, it is possible that the backlight have a larger area and the liquid crystal display device have a larger display area. Further, since the light-emitting device of the present invention has a thin shape with low power consumption, a display device can also be reduced in thickness and power consumption.

Figure 8:
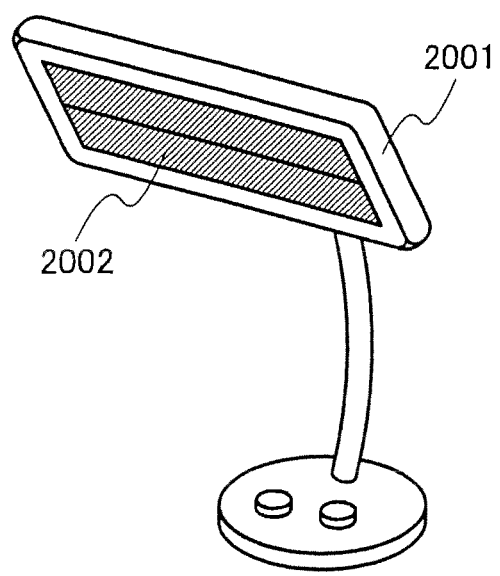
FIG. 8 illustrates a lighting apparatus according to an aspect of the present invention.

FIG. 8 illustrates an example in which the light-emitting device to which the present invention is applied is used as a desk lamp which is a lighting apparatus. A desk lamp illustrated in FIG. 8 includes a chassis 2001 and a light source 2002, and the light-emitting device of the present invention is used as the light source 2002. Since the light-emitting device of the present invention has high emission efficiency, the desk lamp also has high emission efficiency.

Figure 9:
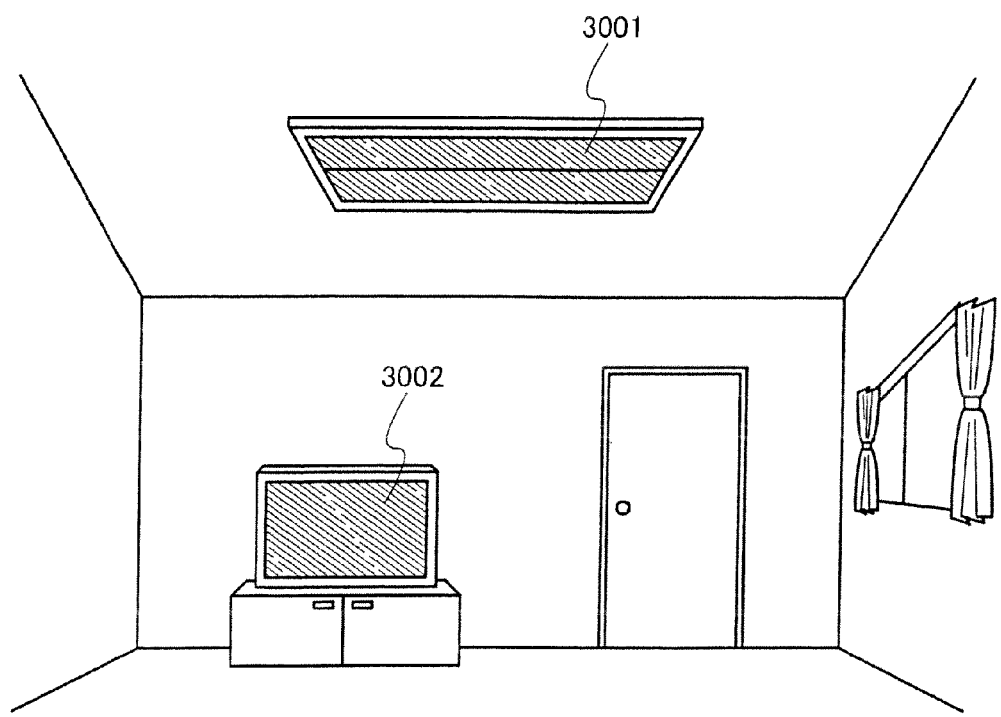
FIG. 9 illustrates a light-emitting device according to an aspect of the present invention.

FIG. 9 illustrates an example in which the light-emitting device to which the present invention is applied is used as an indoor lighting apparatus 3001. Since the area of the light-emitting device of the present invention can be large, the light-emitting device of the present invention can be used as a lighting apparatus having a large area. Further, having a thin shape and reducing power consumption, the light-emitting device of the present invention can be used as a lighting apparatus having a thinner shape with power consumption reduced. In a room where the light-emitting device to which the present invention is thus applied is used as the indoor lighting apparatus 3001, a television set 3002 according to the present invention, as described in FIG. 6A, is placed; then, public broadcasting and movies can be watched. In such a case, since both of the devices consume low power, a dynamic image can be enjoyed in a bright room without concern about electricity charges.

Example 1

Synthesis Example 1

In this synthesis example, a synthesis method of 9-phenyl-3-[4-(10-phenyl-9-anthryl)phenyl]-9H-carbazol (abbreviation: PCzPA) which is the anthracene derivative of the present invention represented by structural formula (88) below will be detailed.

(88)

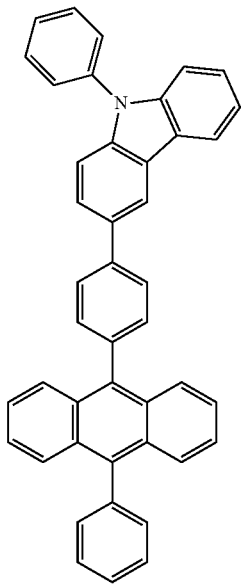

Step 1: Synthesis of
9-(4-Bromophenyl)-10-phenylanthracene
(abbreviation: PA)

(1) Synthesis of 9-phenylanthracene

Into a 200 mL three-neck flask were put 5.4 g (21 mmol) of 9-bromoanthracene, 2.6 g (21 mmol) of phenylboronic acid, 60 mg (0.2 mmol) of palladium(II) acetate (abbreviation: Pd(OAc)$_2$), 10 mL (20 mmol) of potassium carbonate aqueous solution (2.0 mol/L), 260 mg (0.8 mmol) of tris(o-tolyl)phosphine (abbreviation: P(o-tolyl)$_3$), and 20 mL of 1,2-dimethoxyethane (abbreviation: DME), and then the mixture was stirred at 80° C. in a nitrogen atmosphere for 9 hours. After the reaction, a precipitated solid was collected by suction filtration, dissolved in toluene, and filtered through Florisil (produced by Wako Pure Chemical Industries, Ltd., Catalog No. 540-00135), celite (produced by Wako Pure Chemical Industries, Ltd., Catalog No. 531-16855), and alumina. The obtained filtrate was washed with water and saturated aqueous solution and magnesium sulfate was added so that the moisture was removed. This suspending solution was naturally filtered and the obtained filtrate was concentrated, whereby 22 g of a light-brown solid of 9-phenylanthracene, which was the object of the synthesis, was obtained in a yield of 85% (synthesis scheme (a-1)),

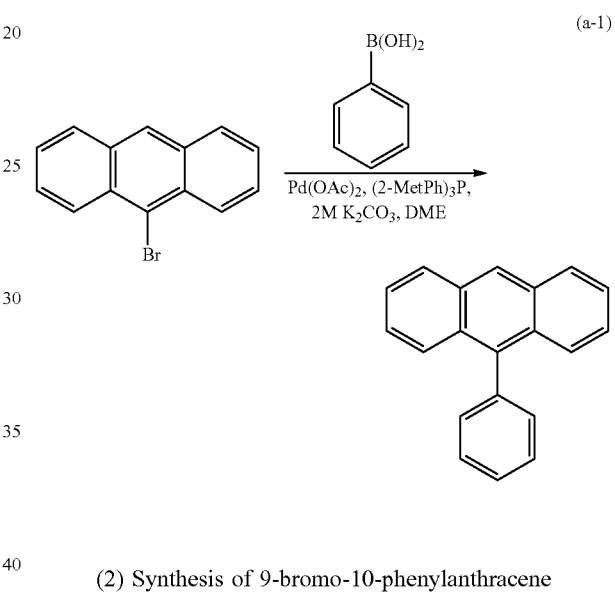

(a-1)

(2) Synthesis of 9-bromo-10-phenylanthracene 6.0 g (24 mmol) of 9-phenylanthracene obtained by the above Step 1(1) was dissolved in 80 mL of carbon tetrachloride. Then, the mixture was stirred while dropping a solution in which 3.8 g (21 mmol) of bromine was dissolved in 10 mL of carbon tetrachloride, using a dropping funnel. After the dropping, this mixture was further stirred at room temperature for 1 hour to be reacted. After the reaction, sodium thiosulfate solution was added into the reaction solution, and the mixture was stirred. After that, an organic layer thereof was washed with aqueous sodium hydroxide and saturated saline in this order. Then, magnesium sulfate was added to the organic layer, so that the moisture was removed. This suspending solution was naturally filtered, so that a filtrate was obtained. The obtained filtrate was concentrated, dissolved in toluene, and filtered through Florisil (produced by Wako Pure Chemical Industries, Ltd., Catalog No. 540-00135), celite (produced by Wako Pure Chemical Industries, Ltd., Catalog No. 531-16855), and alumina. The obtained filtrate was concentrated and recrystallized with a mixed solvent of dichloromethane and hexane, whereby 7.0 g of a light-yellow solid of 9-bromo-10-phenylanthracene, which was the object of the synthesis, was obtained in a yield of 89% (synthesis scheme (a-2)).

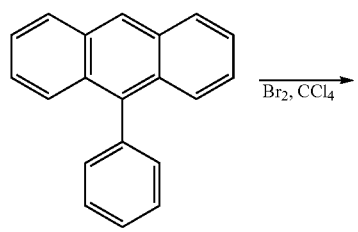

(a-2)

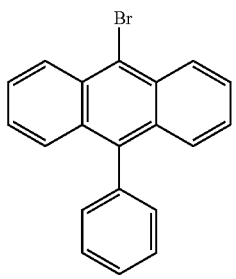

(3) Synthesis of 9-iodine-10-phenylanthracene

In a nitrogen atmosphere, 3.3 g (10 mmol) of 9-bromo-10-phenylanthracene obtained by the above Step 1(2) was dissolved in 80 ml, of tetrahydrofuran (abbreviation: THF) and the temperature of the atmosphere was cooled to −78° C. Then, 7.5 mL (12 mmol) of n-butyllithium (abbreviation: n-BuLi) (1.6 mol/L hexane solution) was dropped using a dropping funnel, and this mixture was stirred for 1 hour. Then, a solution in which 5.0 g (20 mmol) of iodine was dissolved in 20 mL of THF was dropped into the mixture, and this mixture was further stirred at −78° C. for 2 hours to be reacted. After the reaction, sodium thiosulfate solution was added into the reaction solution, and the mixture was stirred. After that, an organic layer thereof was washed with sodium thiosulfate solution and saturated saline in this order. Then, magnesium sulfate was added to the organic layer, so that the moisture was removed. This suspending solution was filtered, so that a filtrate was obtained. The obtained filtrate was concentrated to provide a solid. The obtained solid was recrystallized with ethanol, whereby 3.1 g of a light-yellow solid of 9-iodine-10-phenylanthracene, which was the object of the synthesis, was obtained in a yield of 83% (synthesis scheme (a-3)).

(a-3)

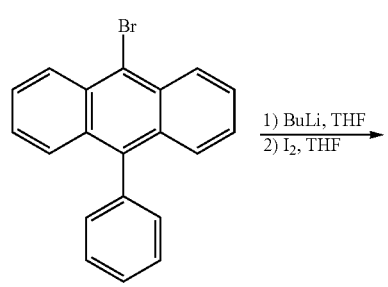

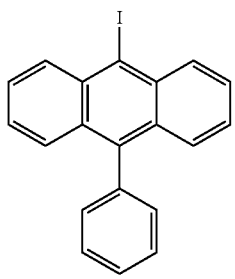

(4) Synthesis of 9-(4-Bromophenyl)-10-phenylanthracene (abbreviation: PA)

Were mixed 1.0 g (2.6 mmol) of 9-iodine-10-phenylanthracene obtained by the above Step 1(3), 540 mg (2.7 mmol)) of p-bromophenylboronic acid, 46 mg (30 μmol) of tetrakis(triphenylphosphine)palladium(0), 3.0 mL (6.0 mmol) of 2.0 mol/L potassium carbonate aqueous solution, and 10 mL of toluene, and the mixture was stirred at 80° C. for 9 hours to be reacted. After the reaction, toluene was added therein, and the mixture was filtered through Florisil (produced by Wako Pure Chemical Industries, Ltd., Catalog No. 540-00135), celite (produced by Wako Pure Chemical Industries, Ltd., Catalog No. 531-15855), and alumina. The obtained filtrate was washed with water and saturated saline, and magnesium sulfate was added so that the moisture was removed. This suspending solution was naturally filtered and the obtained filtrate was concentrated, so that a solid was obtained. The obtained solid was recrystallized with a mixed solution of chloroform and hexane, whereby 560 mg of a light-brown solid of 9-(4-Bromophenyl)-10-anthracene (abbreviation: PA), which was the object of the synthesis, was obtained in a yield of 45% (synthesis scheme (a-4)).

(a-4)

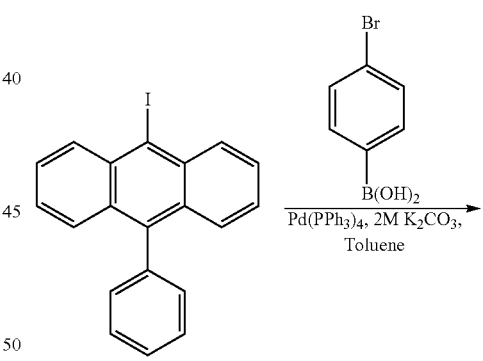

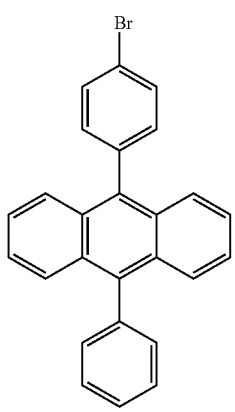

Step 2: Synthesis of 4-(10-phenyl-9-anthryl)phenylboronic acid

In a 500 mL three-neck flask were stirred 20 g (49 mmol) of 9-(4-Bromophenyl)-10-phenylanthracene obtained by the above Steps 1(1) to 1(4) and 300 mL of tetrahydrofuran (abbreviation: THF) in a nitrogen atmosphere at −78° C. Then, 34 mL (54 mmol) of n-butyllithium (1.6 mol/L hexane solution) was dropped, and this mixture was stirred for 2 hours at the same temperature. After that, 13 mL (110 mmol) of trimethyl borate was added therein, and the mixture was stirred for 24 hours at mom temperature. After the reaction, 200 mL of 1.0 mol/L hydrochloric acid was added therein, and the mixture was stirred for 1 hour at room temperature. After that, an organic layer thereof was washed with water and separated into an organic layer and a water layer, and the obtained water layer was further extracted with ethyl acetate. This extracted solution and the organic layer were mixed and washed with saturated aqueous solution, and magnesium sulfate was added therein, so that moisture was removed. Then, suction filtration was performed so that a filtrate was obtained. The obtained filtrate was concentrated to provide a residue. The obtained residue was recrystallized with a mixed solution of chloroform and hexane, whereby 15 g of a powdery white solid of 4-(10-phenyl-9-anthryl)phenylboronic acid, which was the object of the synthesis, was obtained in a yield of 84% (synthesis scheme (a-5)).

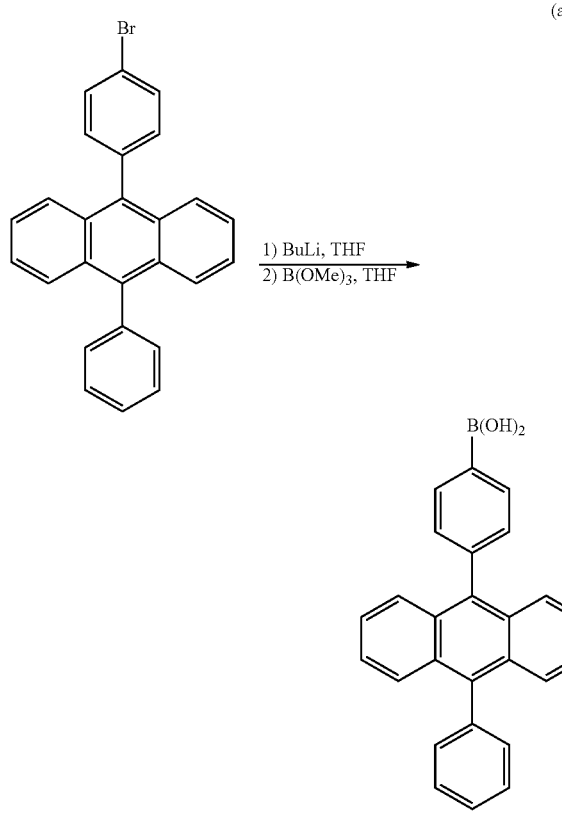

Step 3: Synthesis of 3-bromo-9-phenyl-9H-carbazole

Into a 1000 mL three-neck flask were put 24 g (1.00 mmol) of 9-phenylcarbazole, 18 g (100 mmol) of N-bromosuccinimide, 450 mL of toluene, and 200 mL of ethyl acetate, and the mixture was stirred for 45 hours at room temperature. This suspending solution was washed with water, and magnesium sulfate was added therein, so that moisture was removed. Then, the suspending solution was filtered to provide a filtrate was obtained. The obtained filtrate was concentrated and dried, whereby 32 g of a caramel-like solid of 3-promo-9-phenyl-9H-carbazole, which was the object of the synthesis, was obtained in a yield of 99% (synthesis scheme (a-6)).

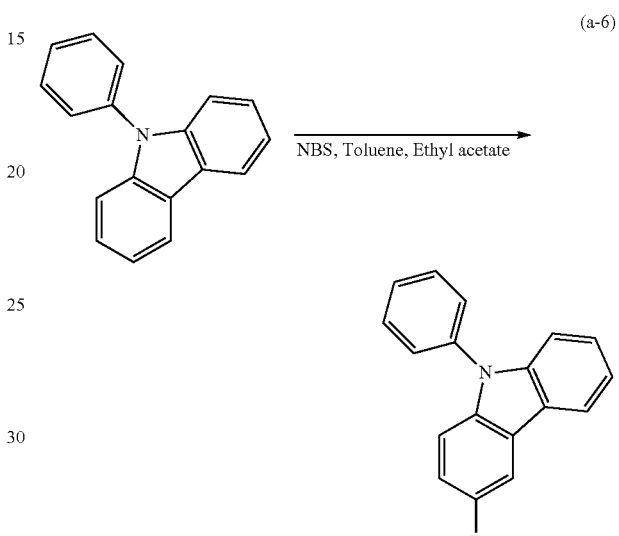

Step 4: Synthesis of 9-phenyl-3-[4-(10-phenyl-9-anthryl)phenyl]-9H-carbazol (abbreviation: PCzPA)

In a 100 mL three-neck flask were stirred 2.6 g (7.0 mmol) of 4-(10-phenyl-9-anthryl)phenylboronic acid obtained by the above Step 2, 2.3 g (7.0 mmol) of 3-bromo-9-phenyl-9H-carbazole obtained by the above Step 3, 2.0 mg (10 μmol) of Palladium(II) acetate (abbreviation: Pd(OAc)$_2$), 6.0 mg (20 μmol) of tris(o-tolyl)phosphine (abbreviation: P(o-tolyl)$_3$), 5 mL (10 mmol) of potassium carbonate aqueous solution (2 mol/L), and 20 mL of 1,2-dimethoxyethane (abbreviation: DME) in a nitrogen atmosphere for 6.5 hours while being heated at 90° C. After that, the temperature of this suspending solution was cooled to room temperature, and the mixture was filtered through Florisil (produced by Wako Pure Chemical Industries, Ltd., Catalog No. 540-00135), alumina, and celite (produced by Wako Pure Chemical Industries, Ltd., Catalog No. 531-16855) while 200 mL of toluene was added. The obtained filtrate was condensed, and acetone and methanol were added therein, ultrasonic waves were applied thereto, and then recrystallization thereof was performed. Accordingly, 3.8 g of a powdery light-yellow solid of 9-phenyl-3-[4-(10-phenyl-9-anthryl)phenyl]-9H-carbazol (abbreviation: PCzPA), which was the object of the synthesis, was obtained in a yield of 95% (synthesis scheme (a-7)).

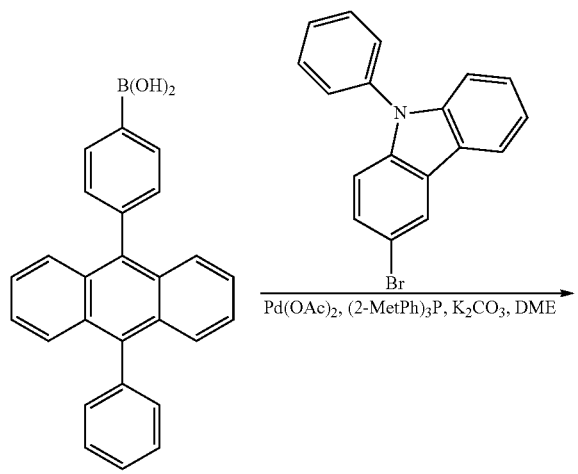

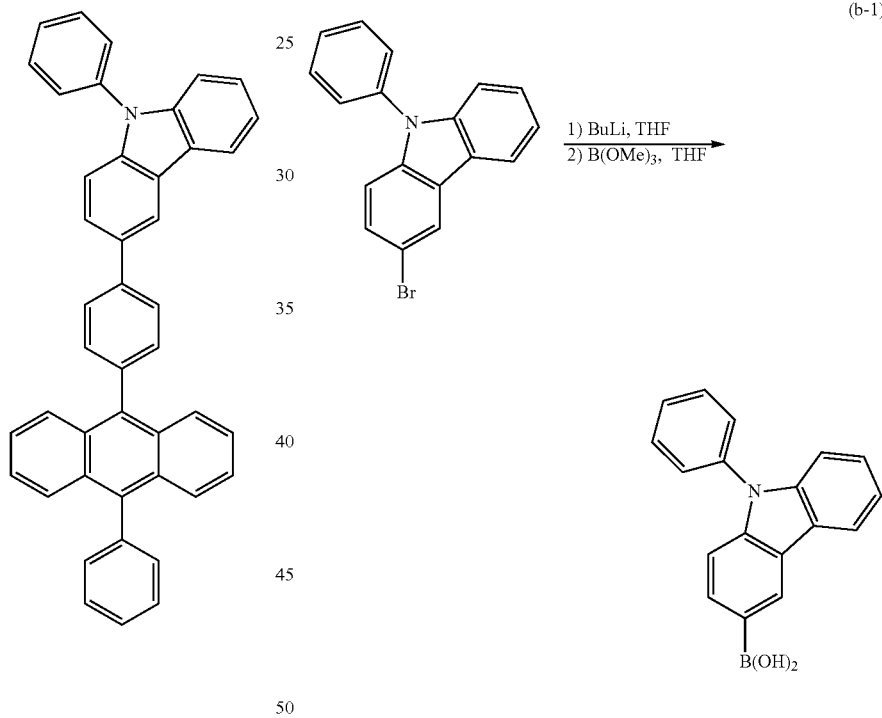

Synthesis Example 2

In this synthesis example, a synthesis method of 9-phenyl-3-[4-(10-phenyl-9-anthryl)phenyl]-9H-carbazol (abbreviation: PCzPA), which is different from Synthesis Example 1 will be detailed.

Step 1: Synthesis of 9-phenyl-9H-carbazol-3-boronic acid

In a 0.500 mL three-neck flask were stirred 29 g (90 mmol) of 3-bromo-9-phenylcarbazole obtained by the above Step 3 described in Synthesis Example 1 and 200 mL of tetrahydrofuran (abbreviation: THF) at −78° C. to provide a solution. Then, 110 mL (69 mmol) of n-butyllithium (1.6 mol/L hexane solution) was dropped therein, and the mixture was stirred for 2 hours at the same temperature. Furthermore, 13 mL (140 mmol) trimethyl borate was added therein, and the mixture was stirred for 24 hours at roam temperature. After the reaction, 200 mL of 1.0 mol/L hydrochloric acid was added therein, and the mixture was stirred for 1 hour at room temperature. This mixture was washed with water, aqueous sodium hydroxide, and water in this order, and magnesium sulfate was added so that the moisture was removed. This suspending solution was filtered and the obtained filtrate was concentrated. Then, chloroform and hexane were added therein, ultrasonic waves were applied thereto, and then recrystallization thereof was performed. Accordingly, 21 g of a powdery white solid of 9-phenyl-9H-carbazol-3-boronic acid, which was the object of the synthesis, was obtained in a yield of 80% (synthesis scheme (b-1)).

Step 2: Synthesis of 9-phenyl-3-[4-(10-phenyl-9-anthryl)phenyl]-9H-carbazol (abbreviation: PCzPA)

In a 200 mL three-neck flask were stirred 1.9 g (4.7 mmol) of 9-(4-Bromophenyl)-10-phenylanthracene (abbreviation: PA) obtained by the above Steps 1(1) to 1(4) described in Synthesis Example 1, 1.4 g (4.7 mmol) of 9-phenyl-9H-carbazol-3-boronic acid obtained by the above Step 1 described in Synthesis Example 2, 5.6 mg (25 μmol) of Palladium(II) acetate (abbreviation: Pd(OAc)$_2$), 52 mg (170 μmol) of tris(o-tolyl)phosphine (abbreviation: P(o-tolyl)$_3$), 7 mL (15 mmol) of potassium carbonate aqueous solution (2.0 mol/L), and 40 mL of 1,2-dimethoxyethane (abbreviation: DME) in a nitrogen atmosphere for 7 hours while being heated at 90° C. After that, the temperature of this suspending solution was cooled to room temperature, and the mixture was filtered to provide a residue. The obtained residue was dissolved into 50 mL of hot toluene, and the mixture was filtered through Florisil (produced by Wako Pure Chemical Industries, Ltd., Catalog No. 540-00135), alumina, and celite (produced by Wako Pure Chemical Industries, Ltd., Catalog No. 531-16855) while 400 mL of toluene was added. The obtained filtrate was condensed, hexane was added therein, ultrasonic waves were applied thereto, and then recrystallization thereof was performed. Accordingly, 2.0 g of a powdery light-yellow solid of 9-phenyl-3-[4-(10-phenyl-9-anthryl)phenyl]-9H-carbazol (abbreviation: PCzPA), which was the object of the synthesis, was obtained in a yield of 75% (synthesis scheme (b-2)).

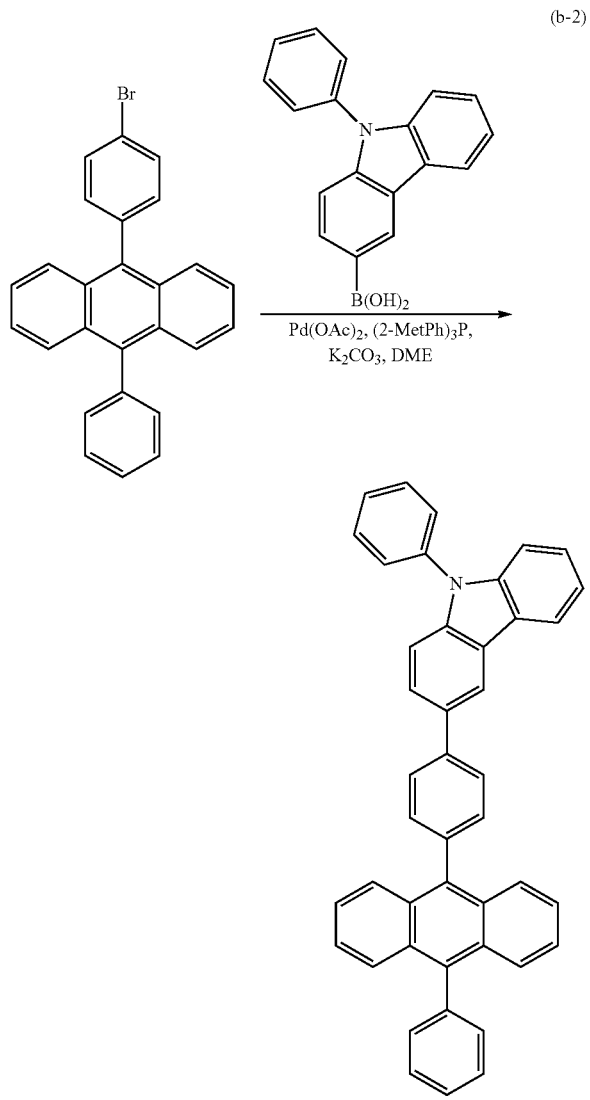

(b-2)

Figure 10A:
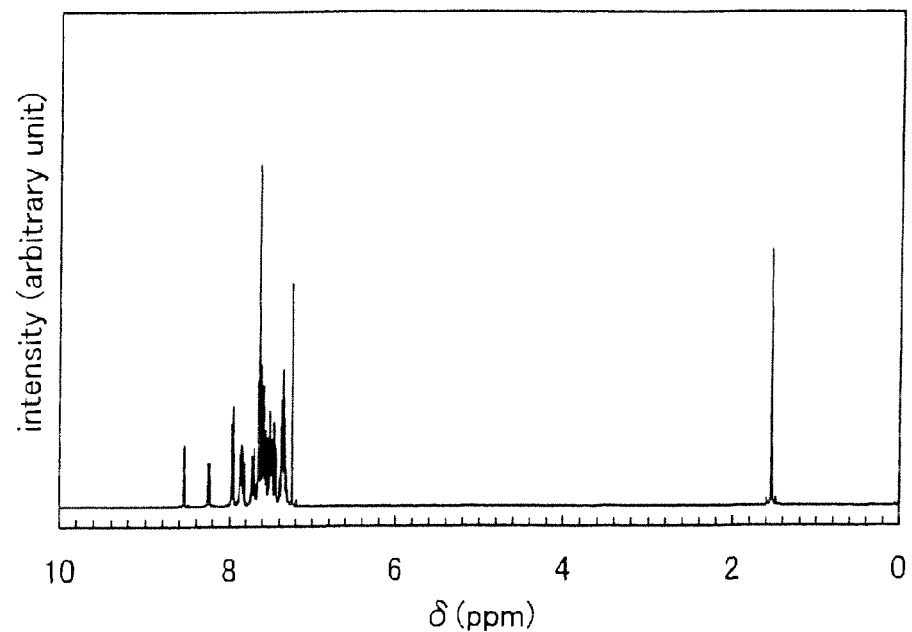
FIGS. 10A and 10B are charts of $^1$H NMR of PCzPA.
Figure 10B:
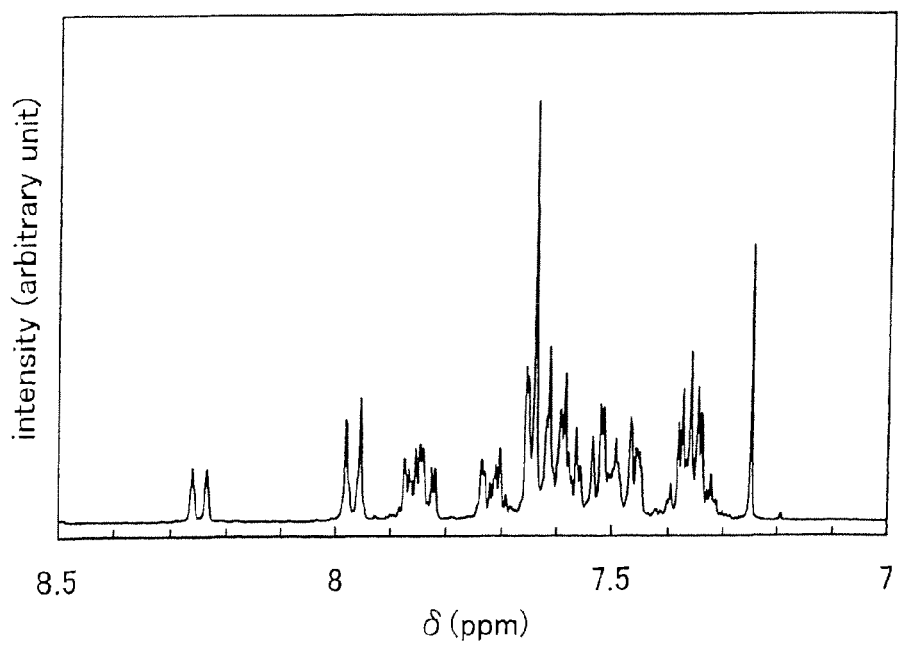

The solid obtained by any of the above Step 4 described in Synthesis Example 1 and the above Step 2 described in Synthesis Example 2 was measured by $^1$H NMR. The measurement data are given below. FIGS. 10A and 10B are $^1$H NMR charts. Note that FIG. 10B is a chart magnifying the range of 7.0 to 8.5 ppm in FIG. 10A.

$^1$H NMR (300 MHz, CDCl$_3$): δ (ppm)=7.32-7.98 (m, 27H), 8.25 (d, 7.8 Hz, 1H), 8.55 (d, =1.5 Hz, 1H).

Figure 11:
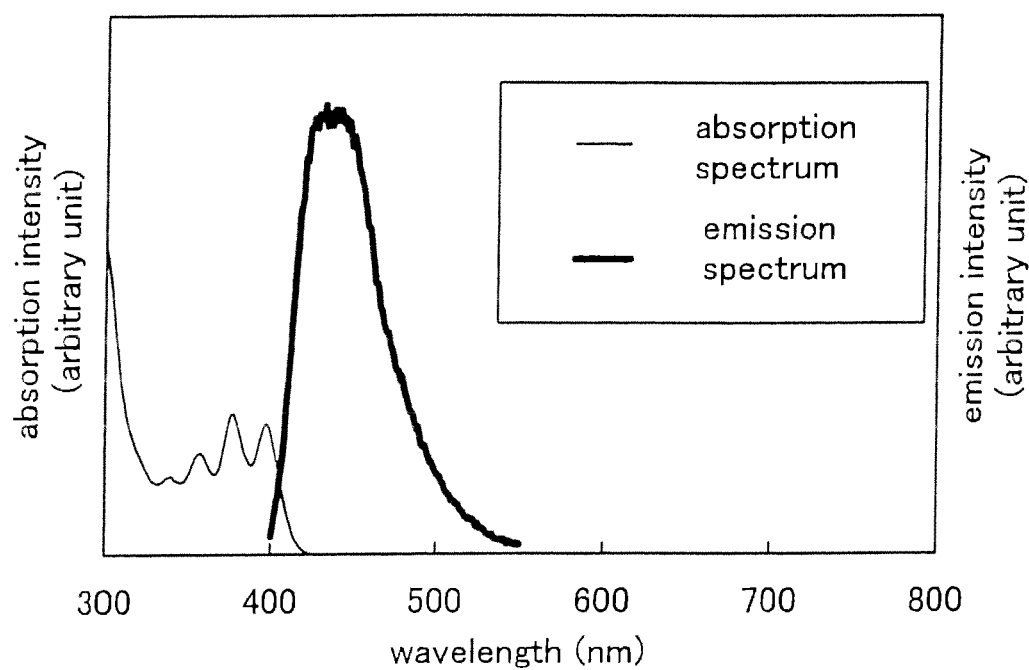
FIG. 11 is a graph showing the absorption spectrum and the emission spectrum of PCzPA in a toluene solution.
Figure 12:
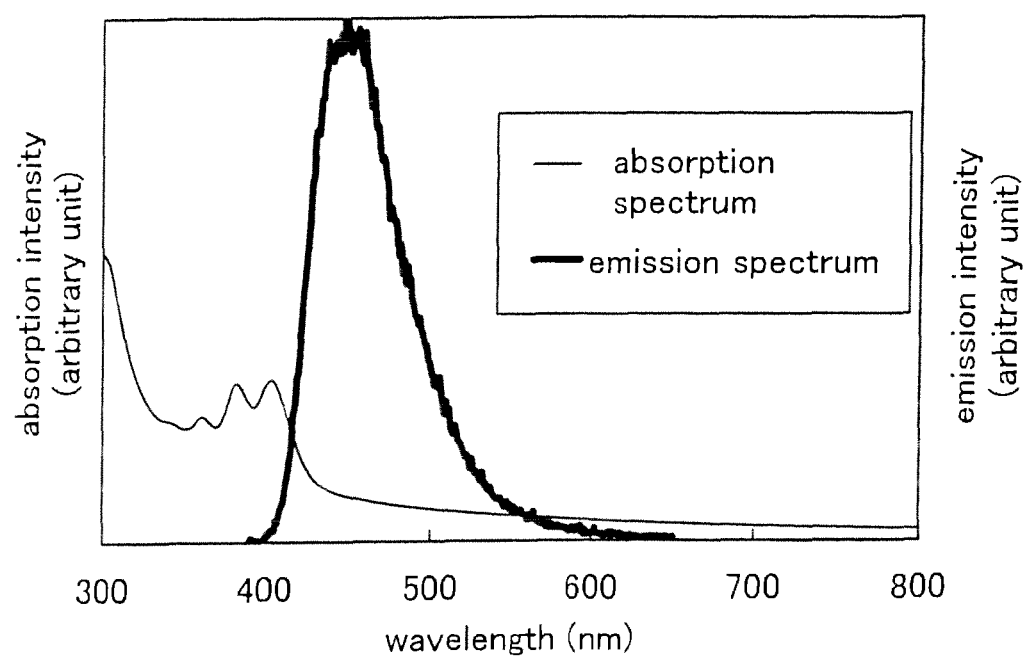
FIG. 12 is a graph showing the absorption spectrum and the emission spectrum of PCzPA in a thin film.

Further, the absorption spectrum of PCzPA was measured. The measurement was performed with an ultraviolet-visible light spectrophotometer (V-550DS, manufactured by JASCO Corporation), using a toluene solution, at room temperature. The emission spectrum of PCzPA was also measured. The measurement was performed with a fluorescence spectrophotometer (FS920, manufactured by Hamamatsu Photonics Corporation), using a toluene solution, at room temperature. The measurement results are shown in FIG. 11. Further, a thin film of PCzPA, which was deposited by a vapor deposition method, was similarly measured. The measurement results are shown in FIG. 12. In FIGS. 11 and 12, the horizontal axis indicates the wavelength (nm) and the vertical axis indicates the absorption intensity or emission intensity (arbitrary unit).

It is seen from FIGS. 11 and 12 that light emission from PCzPA has a peak at 448 nm in the thin film state and has a peak at 440 nm in the toluene solution. Thus, it is found that PCzPA is also suitable for, in particular, a light-emitting substance that emits blue light.

Figure 13:
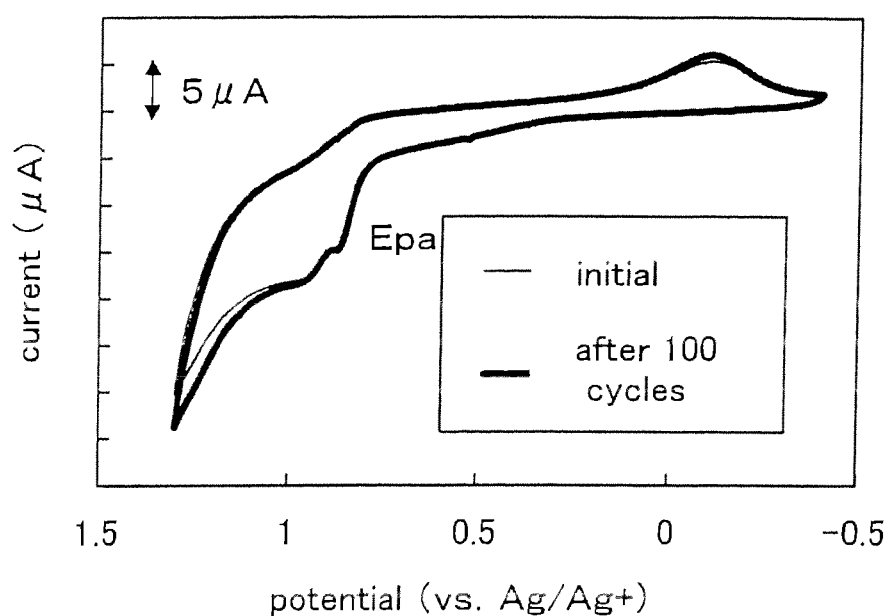
FIG. 13 is a graph of cyclic voltammetry (CV) measurement (oxidation reaction) of PCzPA.
Figure 14:
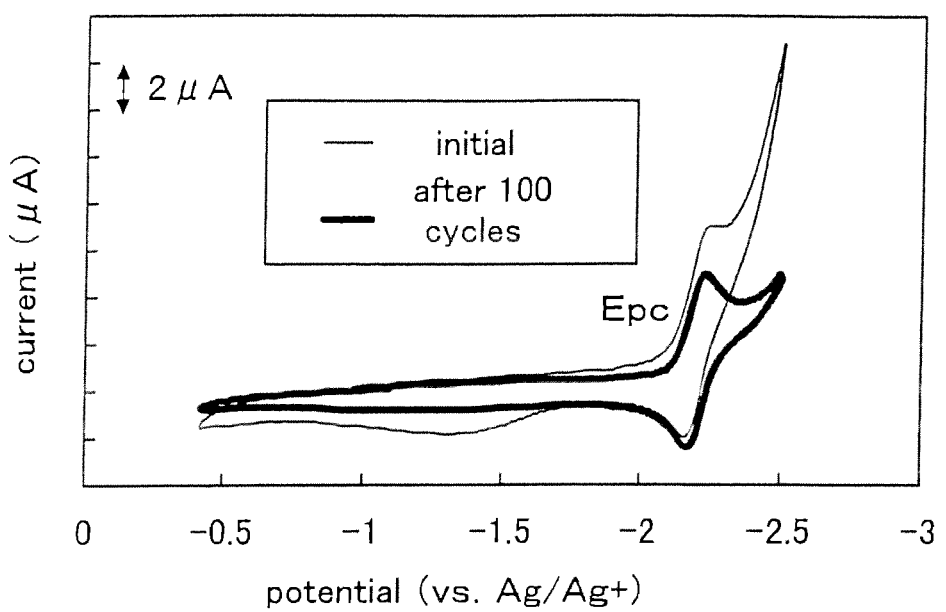
FIG. 14 is a graph of cyclic voltammetry (CV) measurement (reduction reaction) of PCzPA.

The oxidation-reduction characteristics of PCzPA were measured by cyclic voltammetry (CV). An electrochemical analyzer (ALS model 600a, manufactured by BAS Inc.) was used for the measurement. Further, dimethylformamide (DMF) and tetra-n-butylammonium perchlorate (n-Bu$_4$NClO$_4$) were used as a solvent and a supporting electrolyte, respectively, and the amount thereof adjusted to yield a concentration of 10 mmol/L of DMF. Furthermore, the amount of PCzPA was adjusted to yield a concentration of 1 mmol/L of the electrolysis solution. A platinum electrode (PTE platinum electrode, produced by BAS Inc.), a platinum electrode (Pt counter electrode for VC-3, produced by BAS Inc.), and an Ag/Ag$^+$ electrode (RE5 non-aqueous solvent reference electrode, produced by BAS Inc.) were used as a working electrode, an auxiliary electrode, and a reference electrode, respectively. The measurement was performed at a scan rate of 0.1 V/s for 100 cycles. The measurement results on oxidation reaction are shown in FIG. 13. The measurement results on reduction reaction are shown in FIG. 14. In FIGS. 13 and 14, the horizontal axis indicates a potential (V) of the working electrode with respect to the reference electrode, and the vertical axis indicates a current value (A) between the working electrode and the auxiliary electrode.

Seeing FIG. 13, the oxidation potential of PCzPA was 0.88 V (with respect to the Ag/Ag$^+$ electrode). Seeing FIG. 14, the reduction potential of PCzPA was −2.24 V (with respect to the Ag/Ag$^+$ electrode). Through the measurement for 100 cycles of scanning, distinct oxidation peaks and reduction peaks were observed in the CV curves. Therefore, it is found that the anthracene derivative of the present invention is a substance in which the reversibility of oxidation-reduction reactions is excellent.

Synthesis Example 3

In this synthesis example, a synthesis method of 3,3'-(2-tert-buthylanthracene-9,10'-diyldi-4,1-phenylene)bis(9-phenyl-9H-carbazole) (abbreviation: PCzBPA) which is the anthracene derivative of the present invention represented by structural formula (98) below will be detailed.

(98)

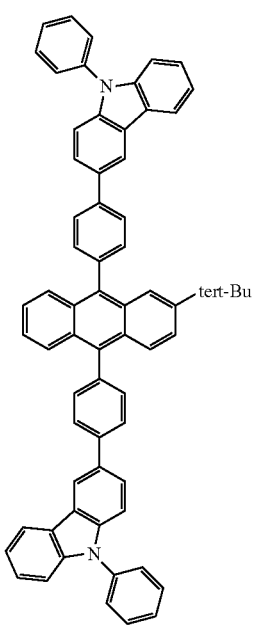

Step 1: Synthesis of 9,10-bis(4-bromophenyl)-2-tert-buthylanthracene (abbreviation: BPA)

(1) Synthesis of 9,10-bis(4-bromophenyl)-2-tert-buthyl-9,10-dihydroxy-9,10-dihydroanthracene Under nitrogen gas stream, 1.6 mol/L of butyl lithium hexane solution (13 mL) was dropped into dehydrated ether solution (200 mL) of 1,4-dibromobenzene (5.0 g) at −78° C. After the dropping, the mixture was stirred for 1 hour at the same temperature. Then, dehydrated ether solution (40 mL) of 2.8 g of 2-tert-butylanthraquinone (11 mmol) was dropped into the mixture at −78° C. Thereafter, the temperature of the reaction solution was slowly increased to room temperature. Then, the solution was stirred at room temperature for 24 hours, water was added therein, and extracted with ethyl acetate. Then, an organic layer thereof was washed with saturated saline, dried with magnesium sulfate, filtered, and concentrated. The obtained residue was purified with silica-gel chromatography (developing solvent, hexane-ethyl acetate), whereby 5.5 g of 9,10-bis(4-bromophenyl)-2-tert-buthyl-9,10-dihydroxy-9,10-dihydroanthracene was obtained in a yield of 90% (synthesis scheme (c-1)).

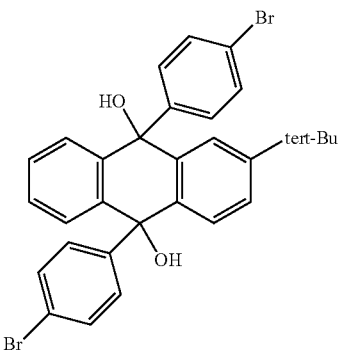

The solid obtained by the above Step 1(1) described in Synthesis Example 3 was measured by $^1$H NMR. The measurement data are given below.

$^1$H NMR (300 MHz, CDCl$_3$): δ (ppm)=1.31 (s, 9H), 2.81 (s, 1H), 2.86 (s, 1H), 6.82-6.86 (m, 4H), 7.13-7.16 (m, 4H), 7.36-7.43 (m, 3H), 7.53-7.70 (m, 4H).

(2) Synthesis of 9,10-bis(4-bromophenyl)-2-tert-buthylanthracene (abbreviation: BPA)

Suspension with 12 ml of glacial acetic acid was performed on 987 mg (1.6 mmol) of 9,10-bis(4-bromophenyl)-2-tert-buthyl-9,10-dihydroxy-9,10-dihydroanthracene obtained by the above Step 1(1) described in Synthesis Example 3, 664 mg (4.0 mmol) of potassium iodide, and 1.48 g (14 mmol) of sodium phosphinate monohydrate. Then, the mixture was refluxed and stirred while being heated for 2 hours. The reaction mixture was cooled down to room temperature and a generated precipitate was filtered, and then the obtained solid was washed with about 50 mL of methanol. The obtained solid was dried, whereby 700 mg of a cream-colored powder of 9,10-bis(4-bromophenyl)-2-tert-buthylanthracene (abbreviation: BPA) was obtained in a yield of 82% (synthesis scheme (c-2)).

(c-1)

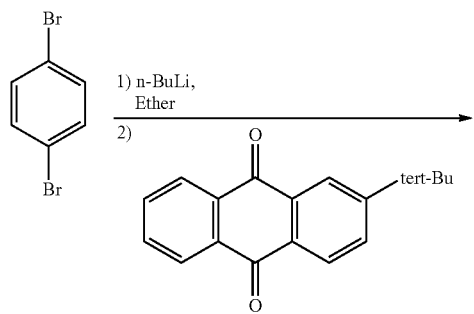

(c-2)

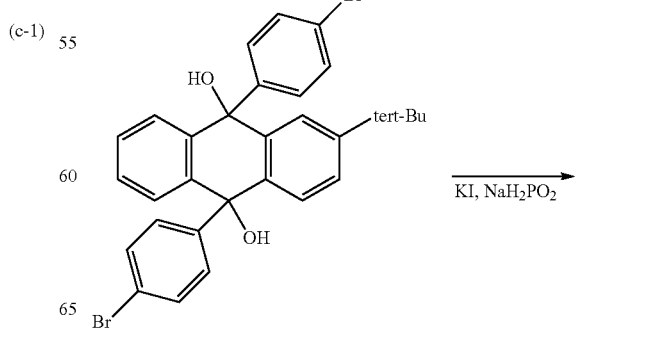

-continued

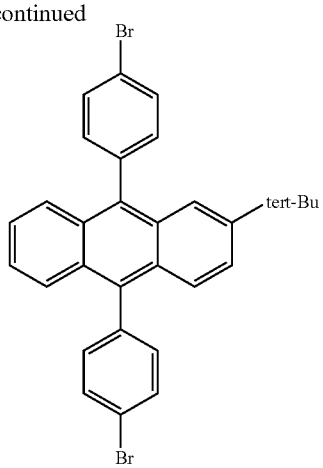

The solid obtained by the above Step 1(2) described in Synthesis Example 3 was measured by $^1$H NMR and $^{13}$C NMR. The measurement data are given below.

$^1$H NMR (300 MHz, CDCl$_3$): δ (ppm)=1.28 (s, 9H), 7.25-7.37 (m, 6H), 7.44-7.48 (m, 1H), 7.56-7.65 (m, 4H), 7.71-7.76 (m, 4H). NMR (74 MHz, CDCl$_3$): δ (ppm)=30.8, 35.0, 120.8, 121.7, 121.7, 124.9, 125.0, 125.2, 126.4, 126.6, 126.6, 128.3, 129.4, 129.7, 129.9, 131.6, 131.6, 133.0, 133.0, 135.5, 135.7, 138.0, 138.1, 147.8.

Step 2: Synthesis of 3,3'-(2-tert-buthylanthracene-9,10'-diyldi-4,1-phenylene)bis(9-phenyl-9H-carbazole) (abbreviation: PCzBPA)

In a 200 mL three-neck flask were stirred 1.6 g (3.0 mmol) of 9,10-bis(4-bromophenyl)-2-tert-buthylanthracene (abbreviation: BPA) obtained by the above Steps 1(1) to 1(2) described in Synthesis Example 3, 1.7 g (6.0 mmol) of 9-phenyl-9H-carbazol-3-boronic acid obtained by the above Step 1(1) described in Synthesis Example 2, 13 mg (60 μmol) of Palladium(II) acetate (abbreviation: Pd(OAc)$_2$), 36 mg (120 μmol) of tris(o-tolyl)phosphine (abbreviation: P(o-tolyl)$_3$), 5 mL (10 mmol) of potassium carbonate aqueous solution (2.0 mol/L), 20 mL of toluene, and 5 ml of ethanol in a nitrogen atmosphere for 5.5 hours while being heated at 90° C. After that, the temperature of this suspending solution was cooled to room temperature, and the mixture was filtered through Florisil (produced by Wako Pure Chemical Industries, Ltd., Catalog No. 540-00135), silica gel, and celite (produced by Wako Pure Chemical Industries, Ltd., Catalog No. 531-16855) while 200 mL of toluene was added. The obtained filtrate was washed with water, and magnesium sulfate was added therein so that moisture was removed. This suspending solution was filtered through Florisil (produced by Wake Pure Chemical Industries, Ltd., Catalog No. 540-00135), silica gel, alumina, and celite (produced by Wako Pure Chemical Industries, Ltd., Catalog No. 531-16855), and the obtained filtrate was condensed. Then, using silica gel column chromatography (toluene:hexane=1:1), the object of the synthesis was batched off. Then, ethyl acetate and methanol were added into the batched object, ultrasonic waves were applied thereto, and recrystallization thereof was performed. Accordingly, 1.8 g of a light-yellow powder of 3,3'-(2-tert-buthylanthracene-9,10'-diyldi-4,1-phenylene)bis(9-phenyl-9H-carbazole) (abbreviation: PCzBPA), which was the object of the synthesis, was obtained in a yield of 67% (synthesis scheme (c-3)).

(c-3)

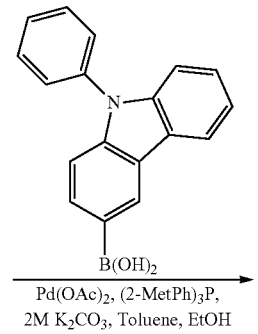

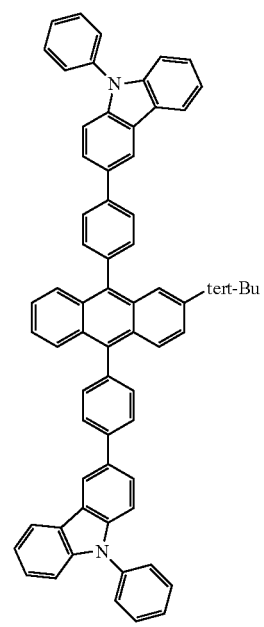

Figure 15A:
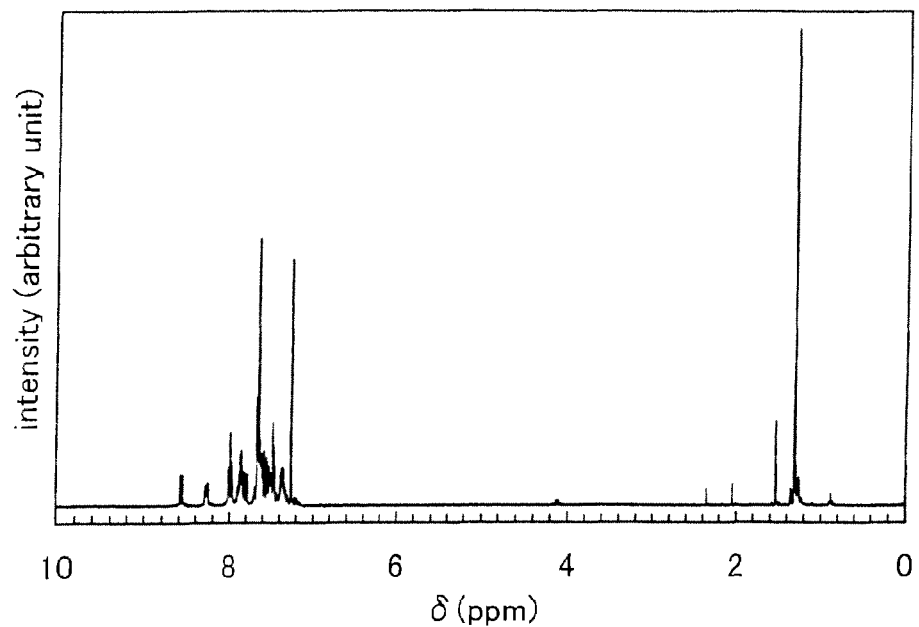
FIGS. 15A and 15B are charts of $^1$H NMR of PCzBPA.
Figure 15B:
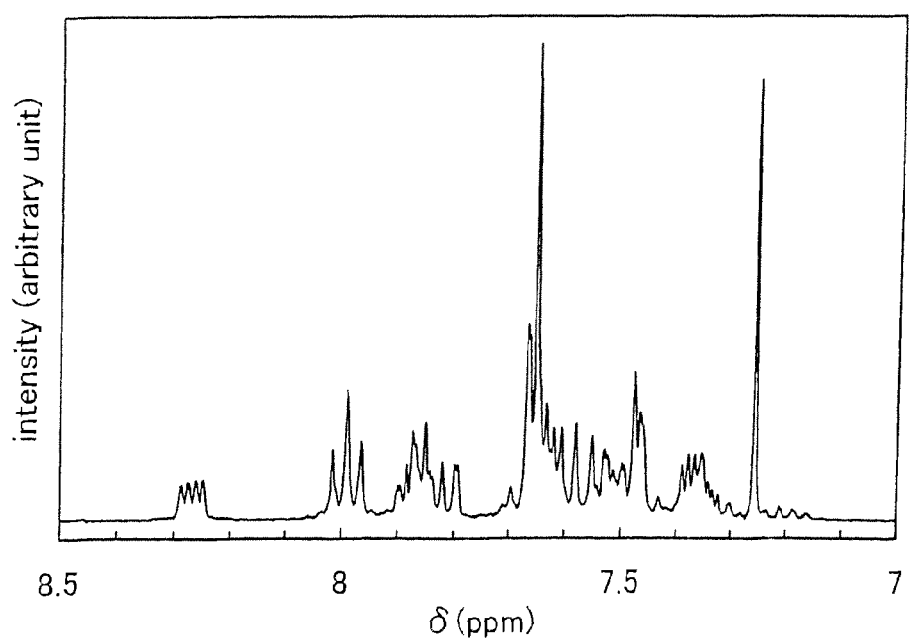

The solid obtained by the above Step 3 described in Synthesis Example 3 was measured by $^1$H NMR. The measurement data are given below. FIGS. 15A and 15B are $^1$H NMR charts. Note that FIG. 15B is a chart magnifying the range of 7.0 to 8.5 ppm in FIG. 15A.

$^1$H NMR (300 MHz, CDCl$_3$): δ (ppm)=1.31 (s, 9H), 7.32-7.90 (m, 31H), 7.99 (t, 1=7.8, 4H), 8.25-8.29 (m, 2H), 8.57 (d, J=8.1, 2H).

Figure 16:
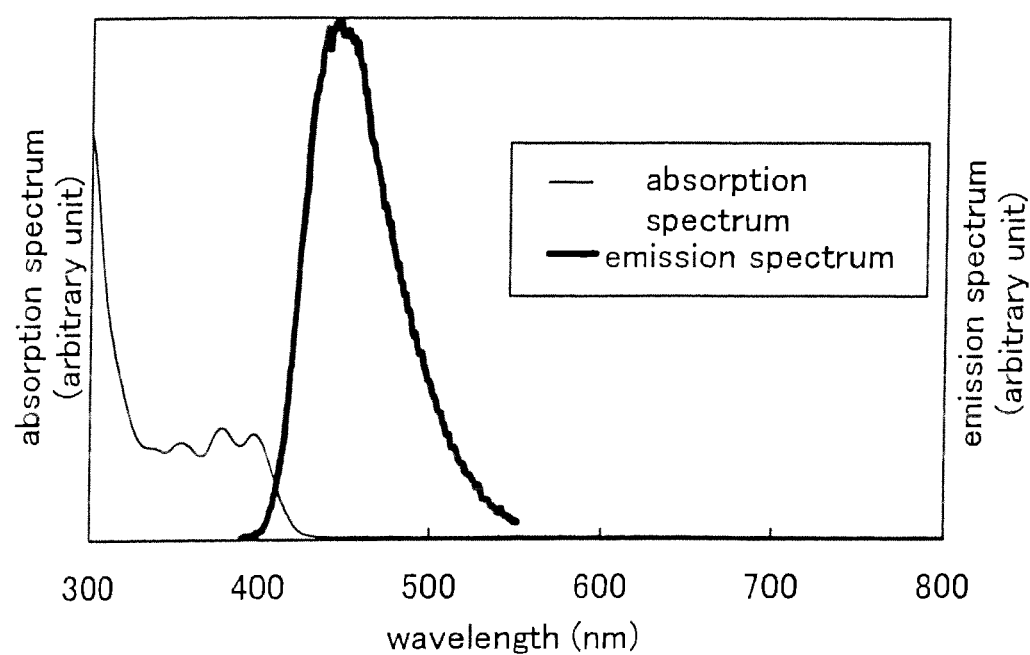
FIG. 16 is a graph showing the absorption spectrum and the emission spectrum of PCzBPA in a toluene solution.
Figure 17:
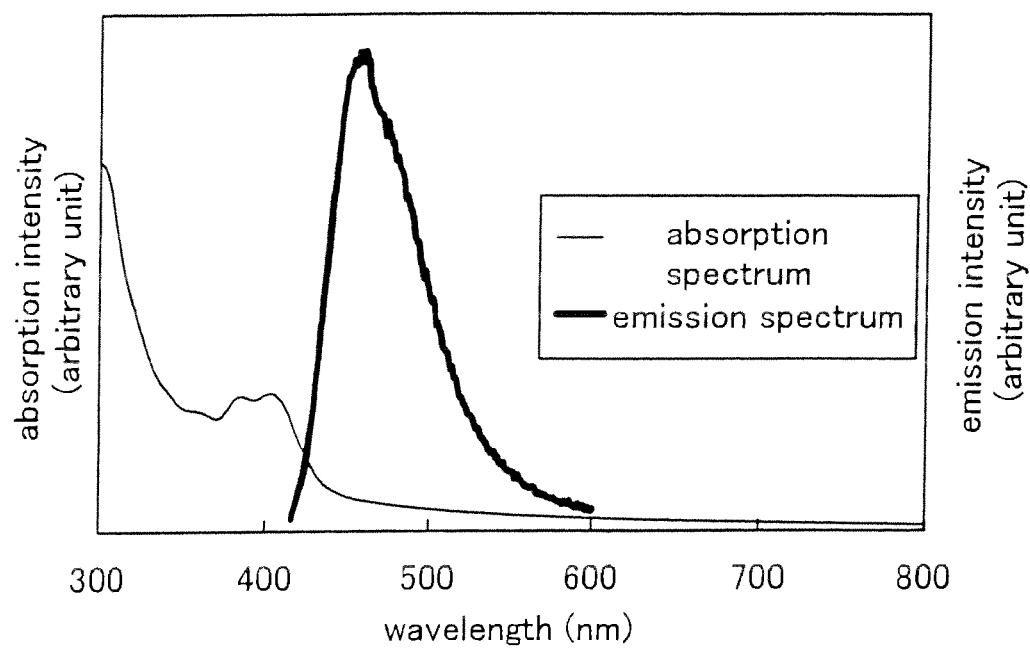
FIG. 17 is a graph showing the absorption spectrum and the emission spectrum of PCzBPA in a thin film.

Further, the absorption spectrum of PCzBPA was measured. The measurement was performed with an ultraviolet-visible light spectrophotometer (V-550DS, manufactured by JASCO Corporation), using a toluene solution, at morn temperature. The emission spectrum of PCzBPA was also measured. The measurement was performed with a fluorescence spectrophotometer (FS920, manufactured by Hamamatsu Photonics Corporation), using a toluene solution, at room temperature. The measurement results are shown in FIG. 16. Further, a thin film of PCzBPA, which was deposited by an deposition method, was similarly measured. The measurement results are shown in FIG. 17. In FIGS. 16 and 17, the horizontal axis indicates the wavelength (nm) and the vertical axis indicates the absorption intensity or emission intensity (arbitrary unit).

It is seen from FIGS. 16 and 17 that light emission from PCzBPA has a peak at 457 nm in the thin film state and has a peak at 445 nm in the toluene solution. Thus, it is found that PCzBPA is also suitable for, in particular, a light-emitting substance that emits blue light.

Example 2

Figure 18:
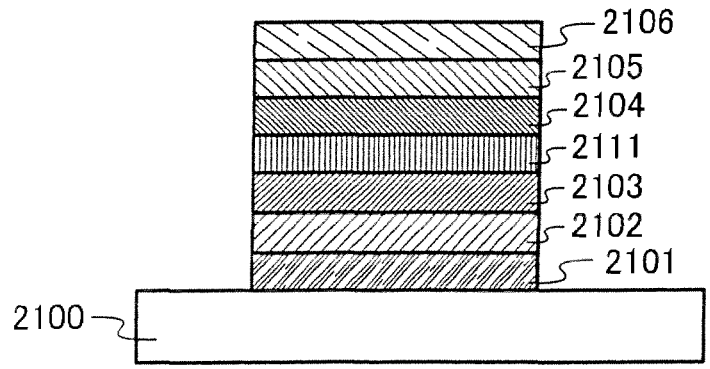
FIG. 18 illustrates a light-emitting element of Example 2.

In this example, a method for manufacturing a light-emitting element using PCzPA as a light-emitting material of a light-emitting layer, and characteristics thereof will be described using FIG. 18. Chemical formulae of organic compounds used in this example are described below.

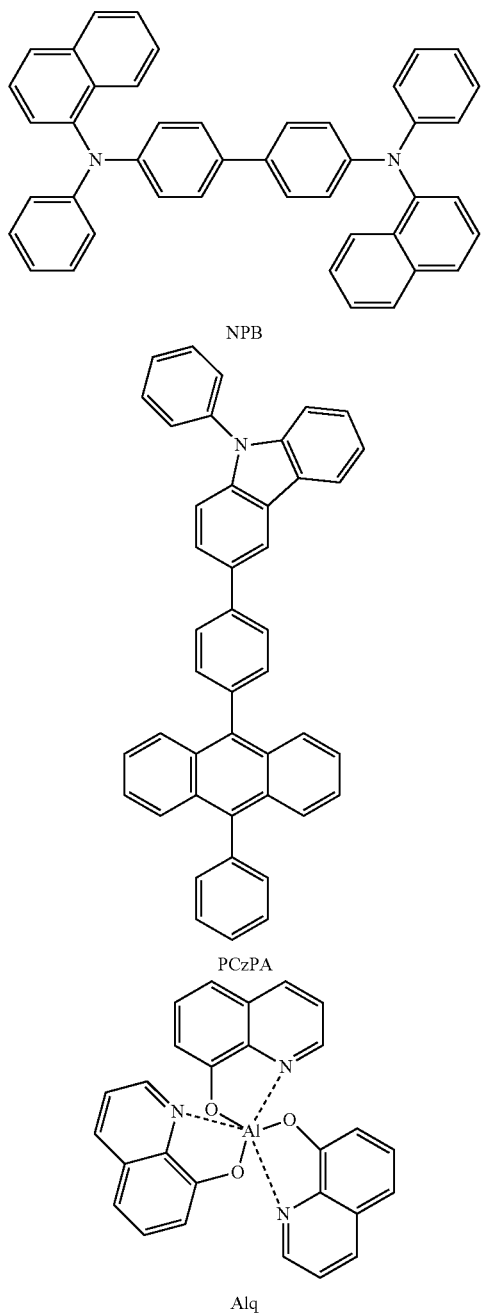

NPB

PCzPA

Alq (Light-Emitting Element 1)

First, indium tin oxide containing silicon oxide was deposited on a glass substrate 2100 by a sputtering method to form a first electrode 2101. Note that the thickness of the first electrode 2101 was set to 110 nm and the area of the electrode was set to an area of 2 mm×2 mm.

Next, the substrate provided with the first electrode was fixed to a substrate holder provided in a vacuum evaporation apparatus such that a surface of the substrate, where the first electrode was formed, faced downward, and then the pressure was reduced to about $10^{-4}$ Pa. Then, 4,4'-bis[N-(1-naphthyl)-N-phenylamino]biphenyl (abbreviation: NPB) and molybdenum(VI) oxide were co-deposited on the first electrode 2101 by a vapor deposition method using resistance heating, whereby a layer 2102 including a composite material of an organic compound and an inorganic compound was formed. The thickness of the layer 2102 was set to 50 nm and the weight ratio of NPB to molybdenum(VI) oxide was adjusted so to be 4:1 (=NTB:molybdenum oxide). Note that the co-deposition method is a vapor deposition method in which vapor deposition is performed from a plurality of vapor-deposition sources at the same time in one treatment chamber.

Next, NPB was deposited to a thickness of 10 nm on the layer 2102 including a composite material by a vapor deposition method using resistance heating, thereby forming a hole-transporting layer 2103.

Furthermore, PCzPA which is the anthracene derivative of the present invention, synthesized in Synthesis Example 1 of Example 1, was vapor-deposited, thereby forming a light-emitting layer 2111 with a thickness of 40 nm on the hole-transporting layer 2103.

After that, tris(8-quinolinolato)aluminum (abbreviation: Alq) was deposited nil the light-emitting layer 2111 to a thickness of 10 nm by a vapor deposition method using resistance heating, thereby forming an electron-transporting layer 2104.

Furthermore, Alq and lithium were co-deposited to a thickness of 10 nm on the electron-transporting layer 2104, thereby forming an electron-injecting layer 2105. The weight ratio between Alq and lithium was adjusted so as to be 1:0.01 (=Alq:lithium).

Lastly, aluminum was deposited to a thickness of 200 nm on the electron-injecting layer 2105 by a vapor deposition method using resistance heating, thereby forming a second electrode 2106. Accordingly, light-emitting element 1 was formed.

Figure 19:
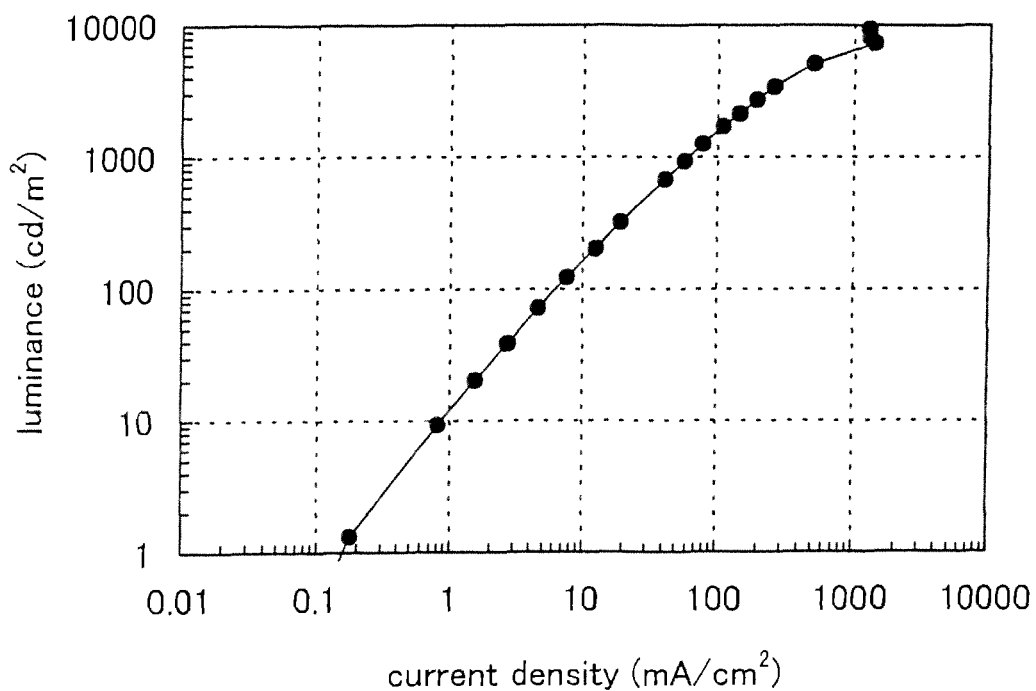
FIG. 19 is a graph showing the current density-luminance characteristic of the light-emitting element according to Example 2.
Figure 20:
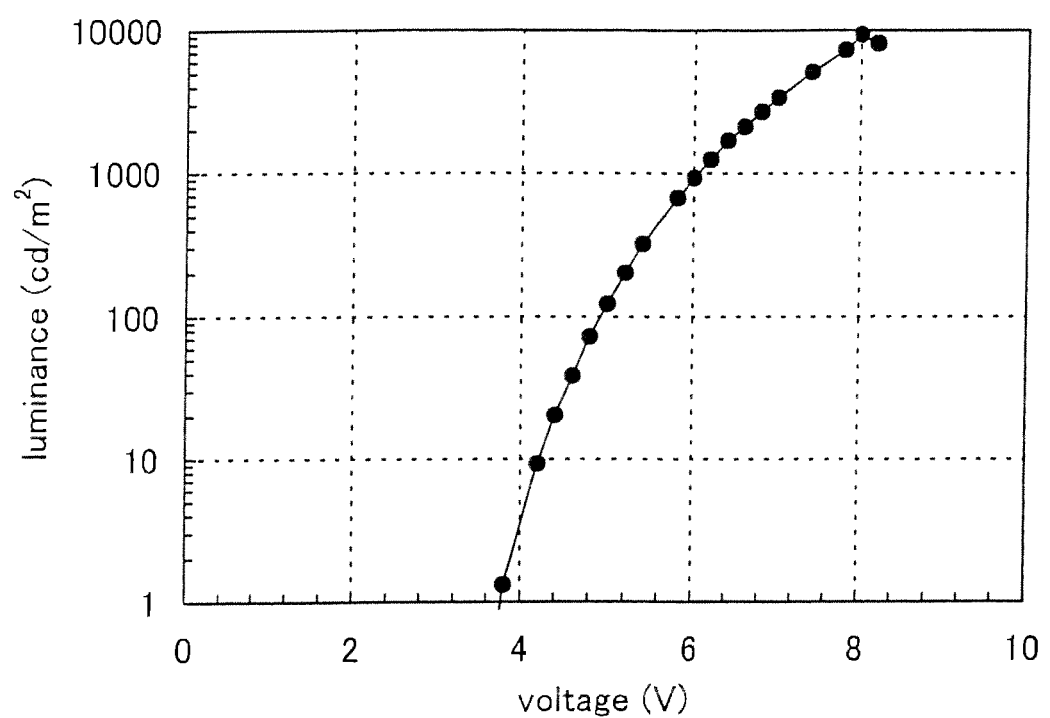
FIG. 20 is a graph showing the voltage-luminance characteristic of the light-emitting element according to Example 2.
Figure 21:
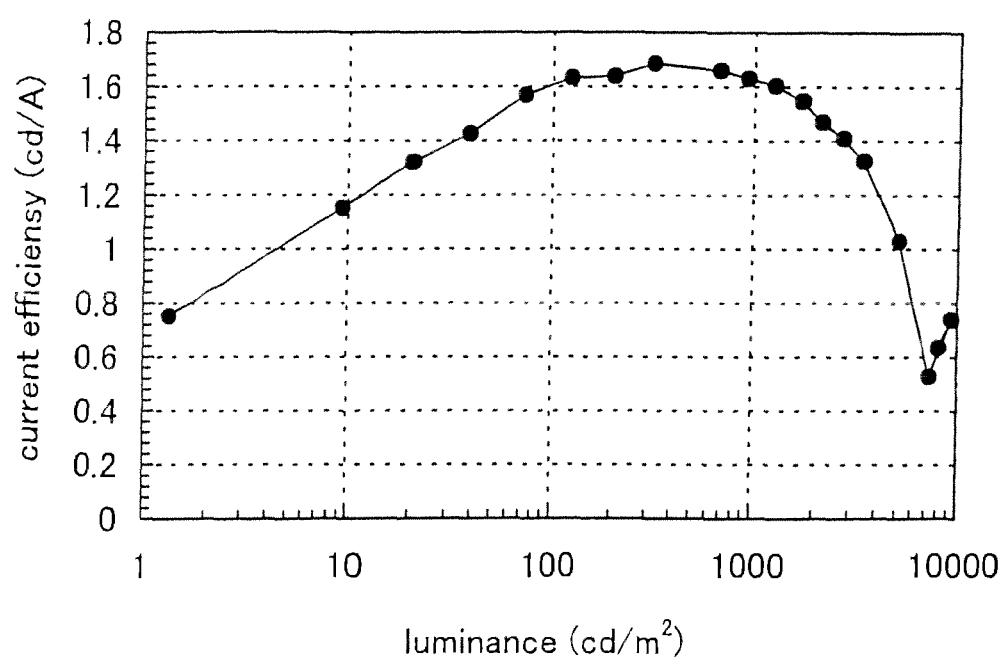
FIG. 21 is a graph showing the luminance-current efficiency characteristic of the light-emitting element according to Example 2.
Figure 22:
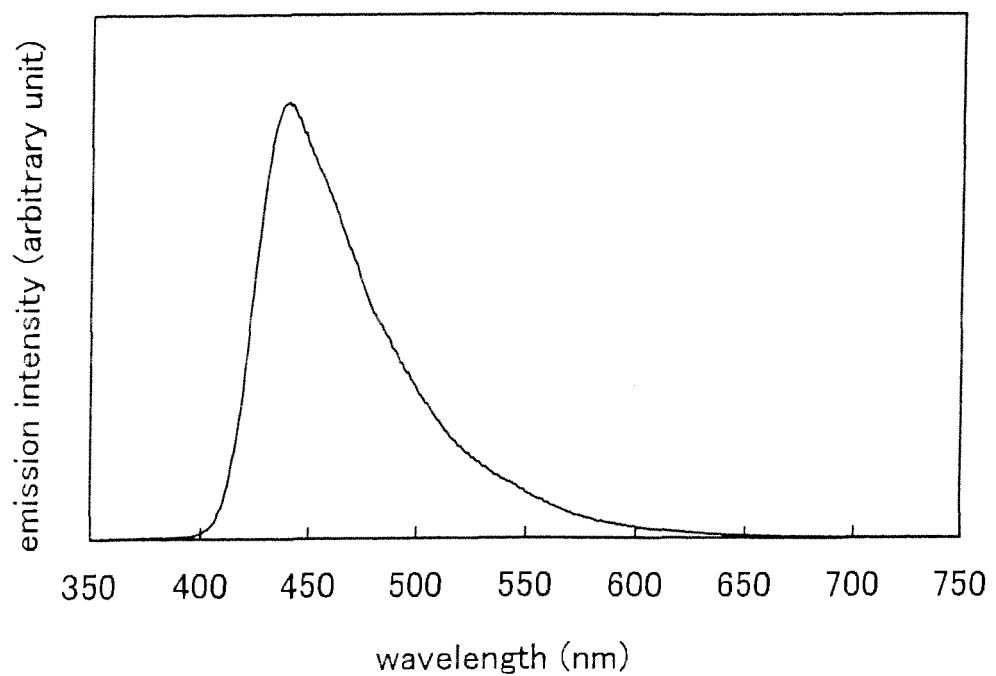
FIG. 22 is a graph showing an emission spectrum of the light-emitting element according to Example 2.

FIG. 19 shows the current density vs. luminance characteristic of the light-emitting element 1. FIG. 20 shows the voltage vs. luminance characteristic of the light-emitting element 1. FIG. 21 shows the luminance vs. current efficiency characteristic of the light-emitting element 1. FIG. 22 shows an emission spectrum when a current of 1 mA flows. From FIG. 22, it was found that light emission derived from PCzPA which is the anthracene derivative of the present invention was obtained. Further, it was also found that the CIE chromaticity coordinates of the light-emitting element 1 at a luminance of 1000 cd/m² were (x, y)=(0.15, 0.12) and blue light emission with very high color purity was able to be obtained. From FIG. 21, it was found that the current efficiency at the luminance of 1000 cd/m² was 1.6 cd/A and the light-emitting element 1 emitted light efficiently. Further, from FIG. 20, it was found that the voltage at which light emission starts was less than 4 V and the driving, voltage was low. Note that the values of the CIF chromaticity coordinates were measured using a luminance meter (a color luminance meter BM-5A manufactured by Topcon Corporation); the same is true for the other values of the CIE chromaticity coordinates described below.

In this manner, it is found that the anthracene derivative of the present invention can be preferably used for a light-emitting element.

Example 3

In this example, a method for manufacturing a light-emitting element using PCzPA as a host material of a light-emitting layer, and characteristics thereof will be described using FIG. 18. Chemical formulae of organic compounds used in this example are described below.

(Light-Emitting Element 2)

Light-emitting element 2 was formed in a similar manner to the light-emitting element 2 described in Example 2, except the following: PCzPA and 4-(9H-carbazol-9-yl)-4'-(10-phenyl-9-anthryl)triphenylamine (YGAPA) were co-deposited instead of PCzPA in the light-emitting layer 2111 of the light-emitting element 2 described in Example 2, and the light-emitting layer 2111 was formed to have a thickness of 40 nm over the hole-transporting layer 2103. The weight ratio of PCzPA to YGAPA was adjusted so to be 1:0.04 PCzPA:YGAPA).

Figure 23:
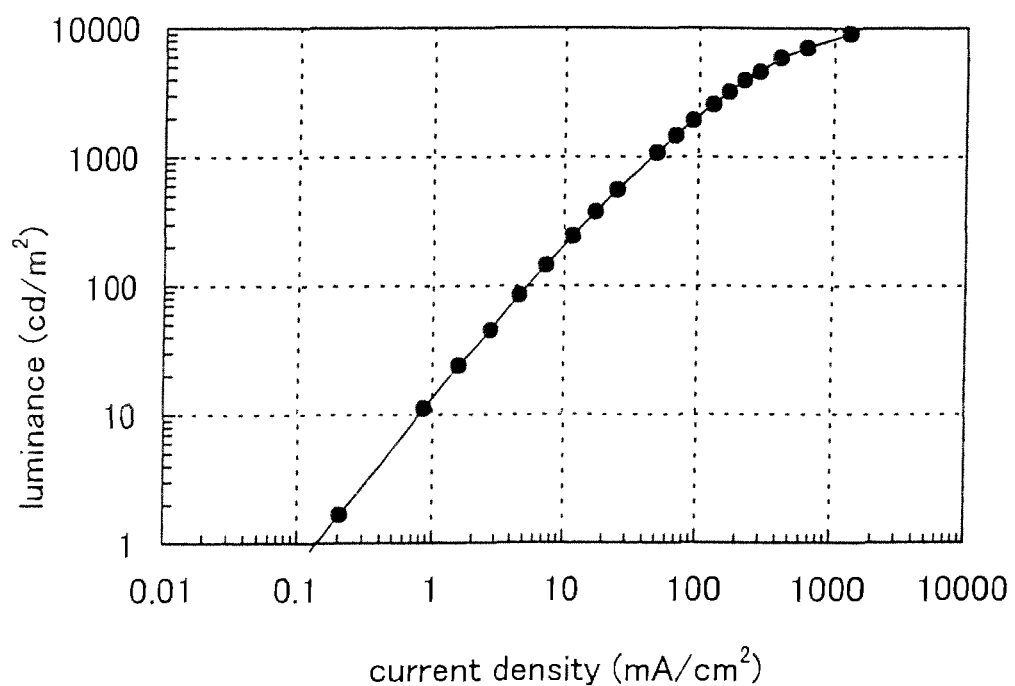
FIG. 23 is a graph showing the current density-luminance characteristic of a light-emitting element according to Example 3.
Figure 24:
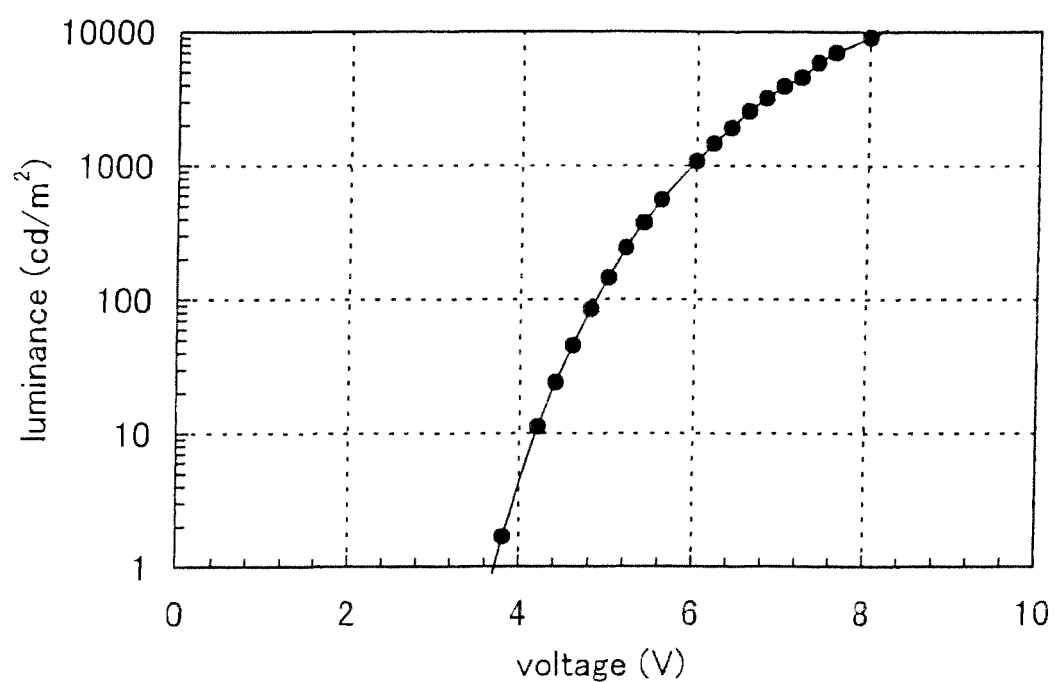
FIG. 24 is a graph showing the voltage-luminance characteristic of the light-emitting element according to Example 3.

FIG. 23 shows the current density vs. luminance characteristic of the light-emitting element 2. FIG. 24 shows the voltage vs. luminance characteristic of the light-emitting

Figure 25:
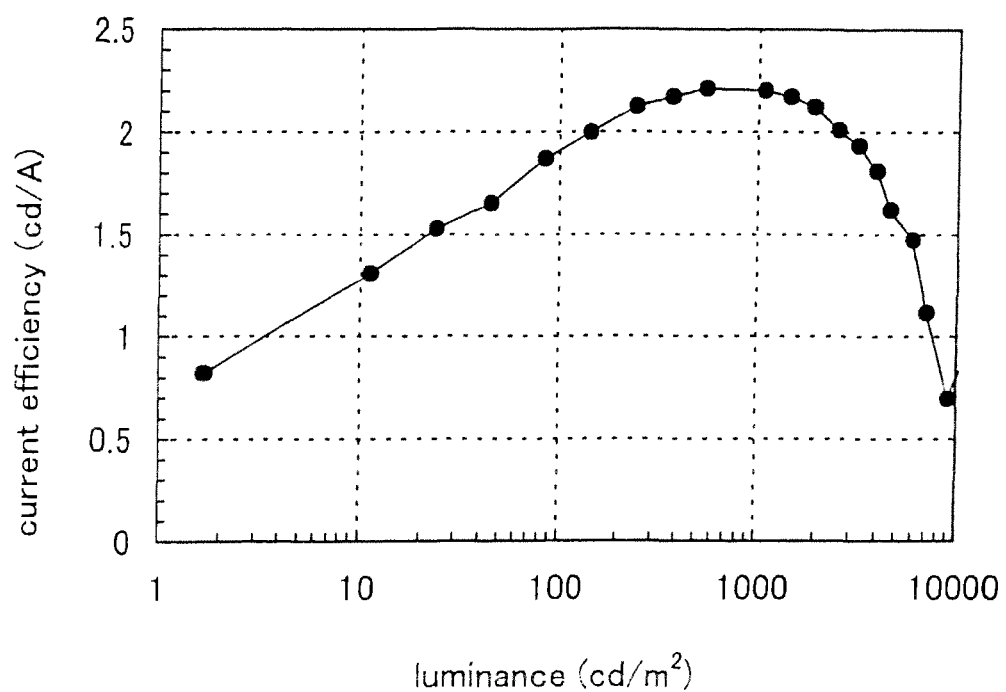
FIG. 25 is a graph showing the luminance-current efficiency characteristic of the light-emitting element according to Example 3.
Figure 26:
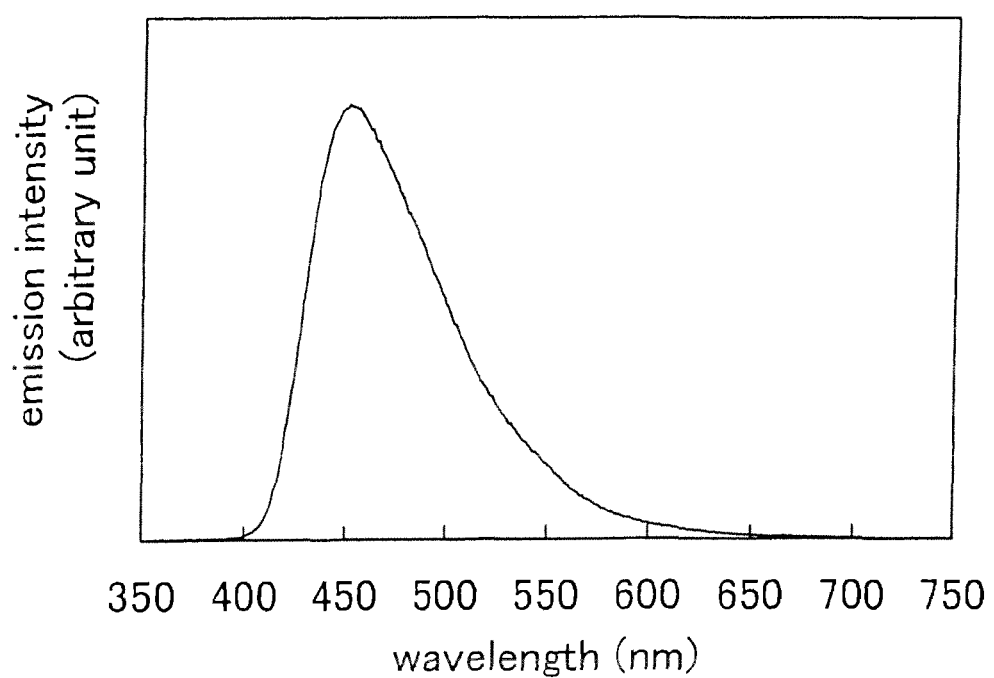
FIG. 26 is a graph showing an emission spectrum of the light-emitting element according to Example 3.

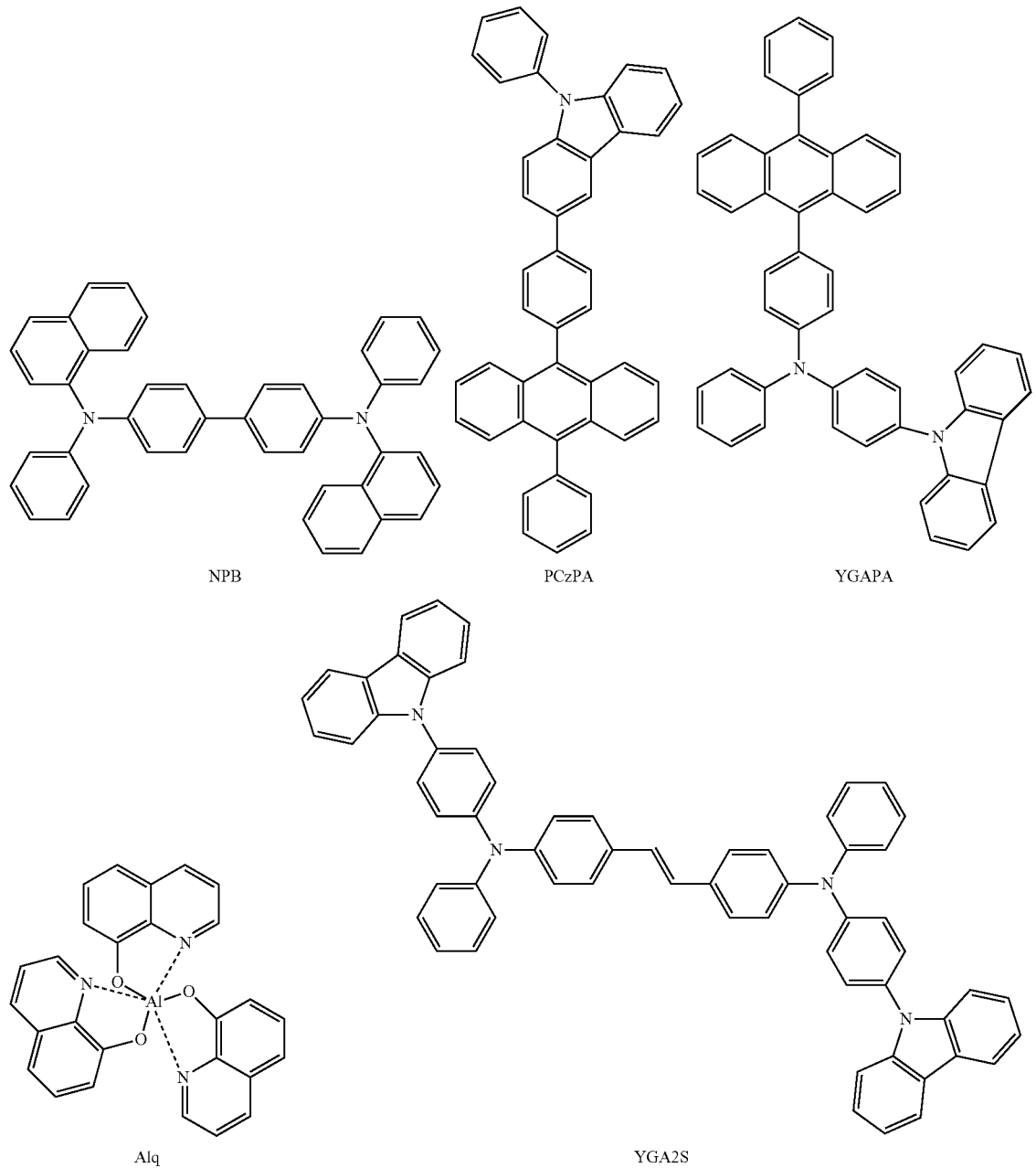

element 2. FIG. 25 shows the luminance vs. current efficiency characteristic of the light-emitting element 2. FIG. 26 shows an emission spectrum when a current of 1 mA flows. From FIG. 26, it was found that light emission derived from YGAPA was obtained. Further, it was also found that the CIE chromaticity coordinates of the light-emitting element 2 at a luminance of 1000 cd/m$^2$ were (x, y)=(0.16, 0.16) and blue light emission with very high color purity was able to be obtained. From FIG. 25, it was found that the current efficiency at the luminance of 1000 cd/m$^2$ was 2.2 cd/A and the light-emitting element 2 emitted light efficiently. Further, from FIG. 24, it was found that the voltage at which light emission starts was less than 4 V and the driving voltage was low.

In this manner, it is found that the anthracene derivative of the present invention can be preferably used as a host material of a light-emitting layer, in particular, as a host material for a dopant emitting blue light.

(Light-Emitting Element 3)

Light-emitting element 3 was formed in a similar manner to the light-emitting element 1 described in Example 2, except the following: PCzPA and 4,4'-bis{N-[4-(carbazol-9-yl)phenyl]-N-phenylamino}stilbene (YGA2S) were co-deposited instead of PCzPA in the light-emitting layer 2111 of the light-emitting element 1 described in Example 2; the light-emitting layer 2111 was formed to have a thickness of 30 nm over the hole-transporting layer 2103; and Alq and lithium were co-deposited so that the electron-injecting layer 2105 had a thickness of 20 nm. The weight ratio of PCzPA to YGA2S was adjusted so to be 1:0.05 (=PCzPA:YGA2S).

Figure 27:
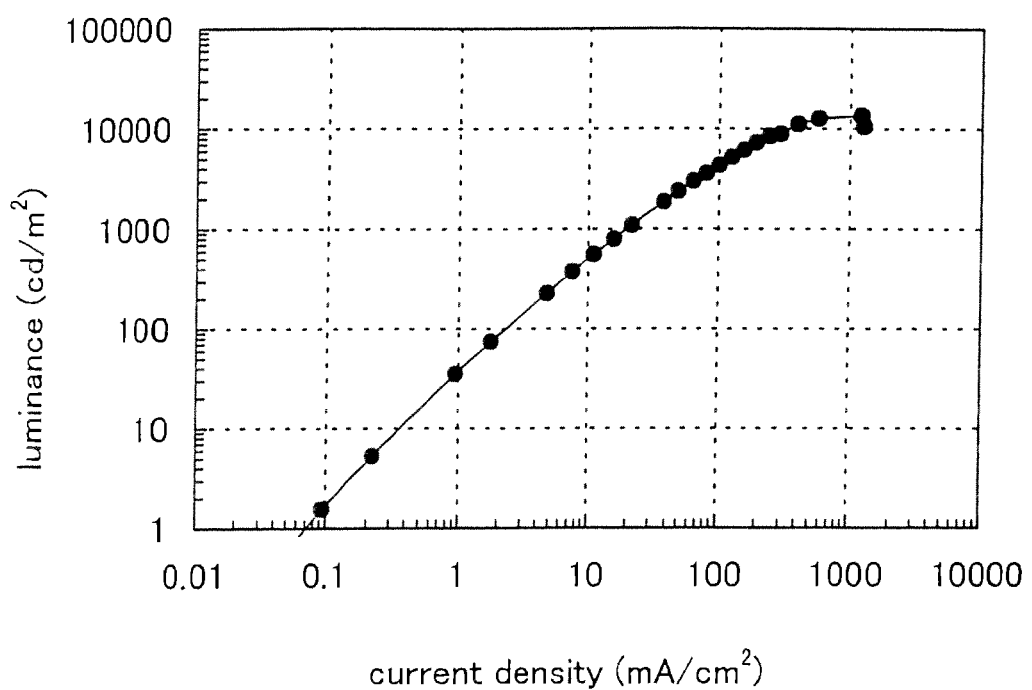
FIG. 27 is a graph showing the current density-luminance characteristic of a light-emitting element according to Example 3.
Figure 28:
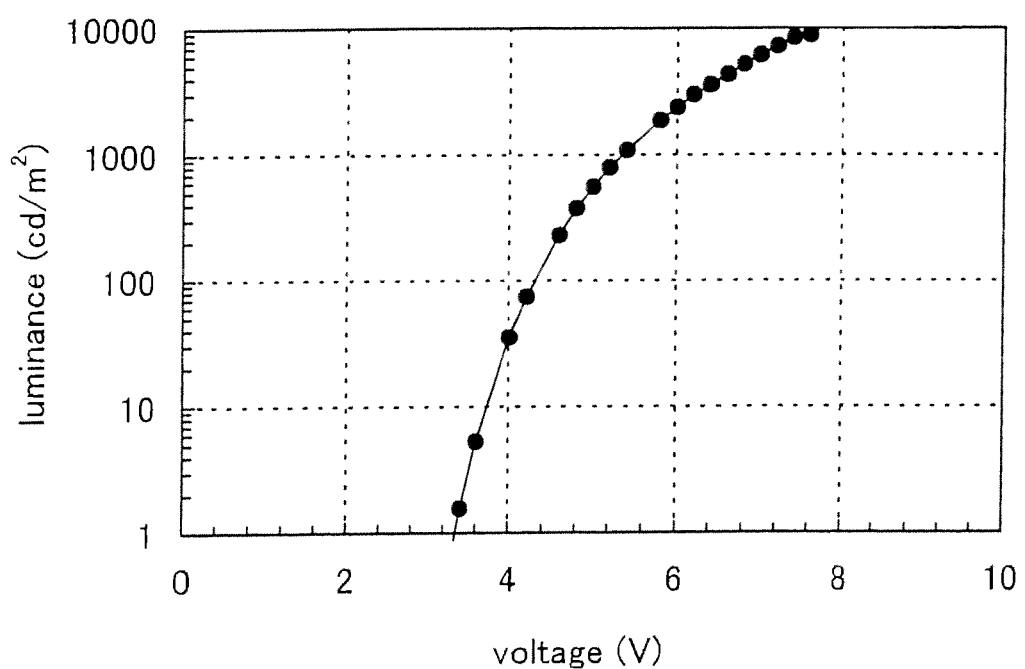
FIG. 28 is a graph showing the voltage-luminance characteristic of the light-emitting element according to Example 3.
Figure 29:
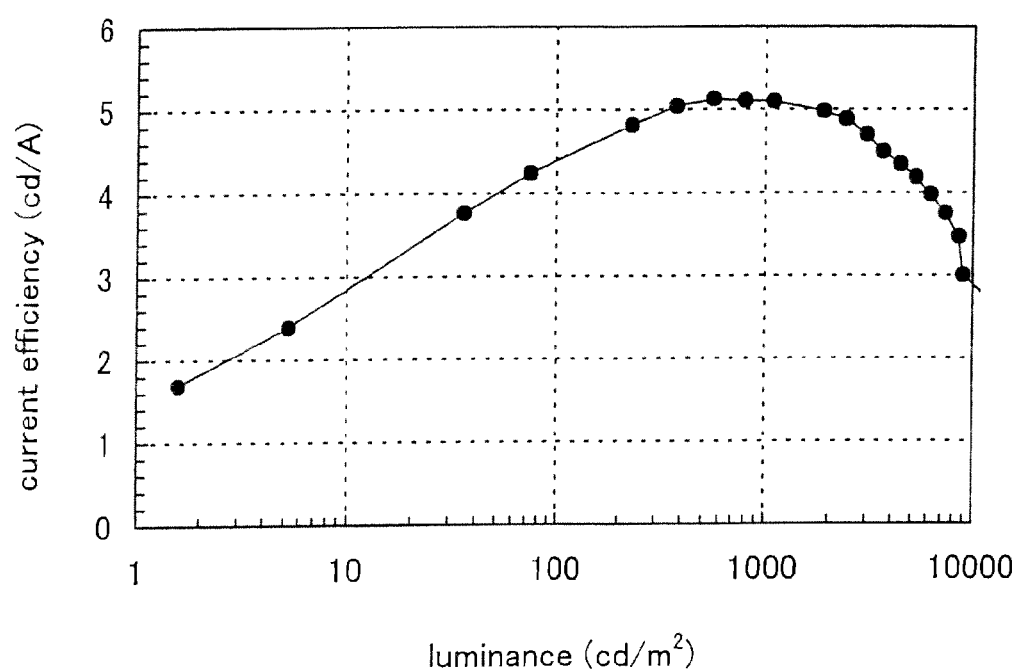
FIG. 29 is a graph showing the luminance-current efficiency characteristic of the light-emitting element according to Example 3.
Figure 30:
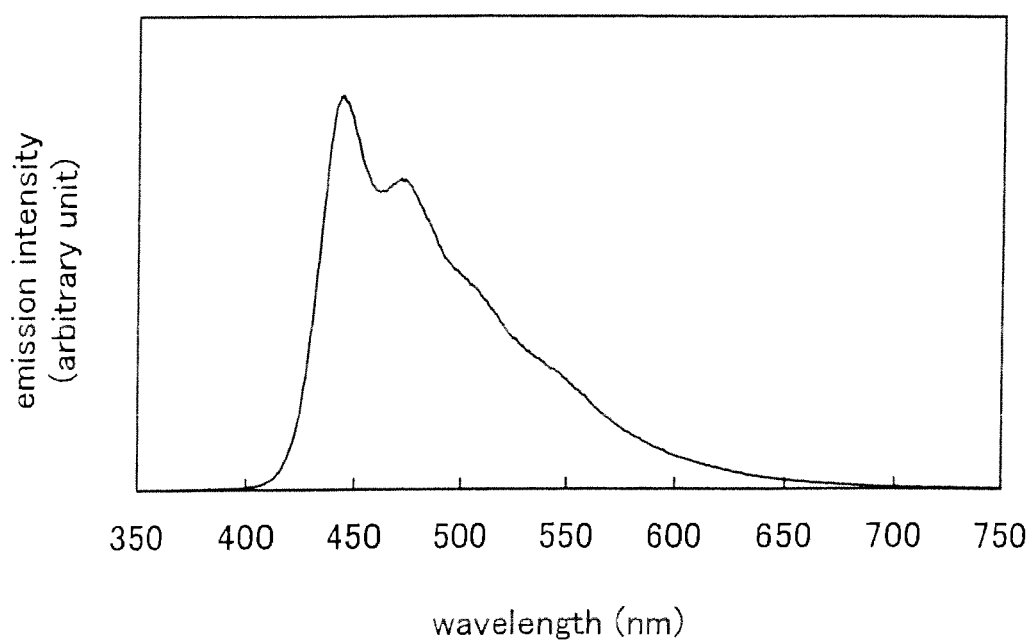
FIG. 30 is a graph showing an emission spectrum of the light-emitting element according to Example 3.

FIG. 27 shows the current density vs. luminance characteristic of the light-emitting element 3. FIG. 28 shows the voltage vs. luminance characteristic of the light-emitting element 3. FIG. 29 shows the luminance vs. current efficiency characteristic of the light-emitting element 3. FIG. 30 shows an emission spectrum in when a current of 1 mA flows. From FIG. 30, it was found that light emission derived from YGA2S was obtained. Further, it was also found that the CIE chromaticity coordinates of the light-emitting element 3 at a luminance of 1000 cd/m$^2$ were (x, y)=(0.18, 0.20) and blue light emission with very high color purity was able to be obtained. From FIG. 29, it was found that the current efficiency at the luminance of 1000 cd/m$^2$ was 5.1 cd/A and the light-emitting element 3 emitted light efficiently. Further, from FIG. 28, it was found that the voltage at which light emission starts was less than 4 V and the driving voltage was low.

In this manner, it is found that the anthracene derivative of the present invention can be preferably used as a host material of a light-emitting layer, in particular, as a host material for a dopant emitting blue light.

Example 4

Figure 31:
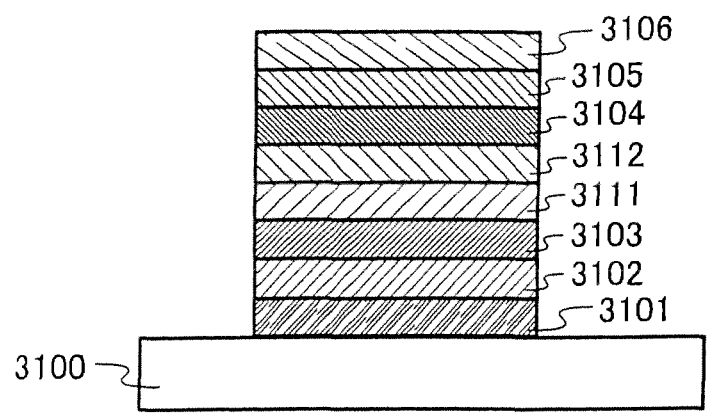
FIG. 31 illustrates a light-emitting element of Example 4.

In this example, a method for manufacturing a light-emitting element with two-layer structure using PCzPA as a host material of a light-emitting layer, and characteristics thereof will be described using FIG. 31. Chemical formulae of organic compounds used in this example are described below.

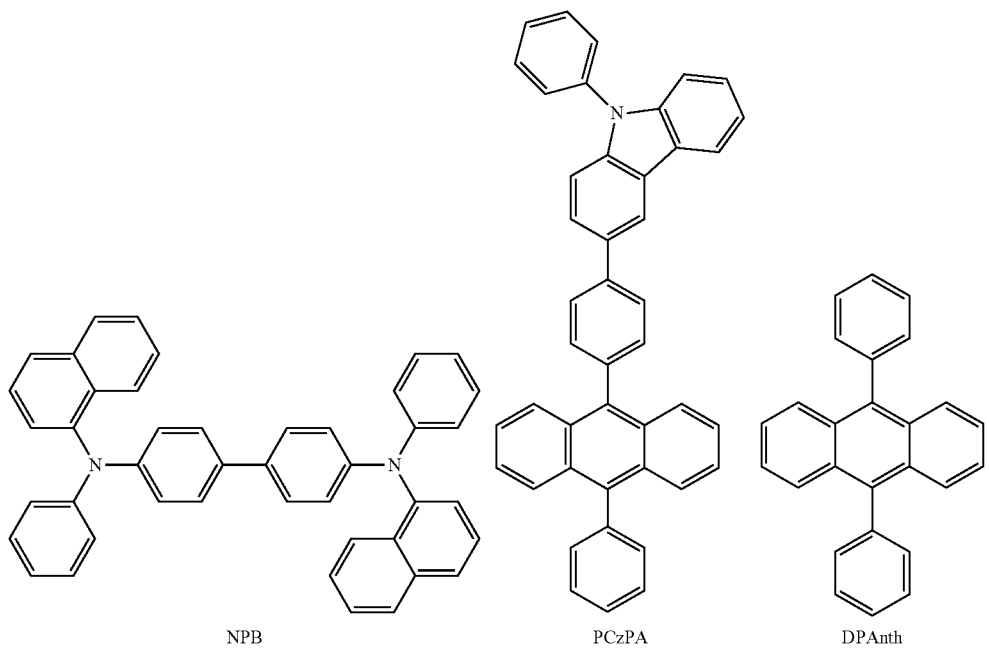

NPB          PCzPA          DPAnth

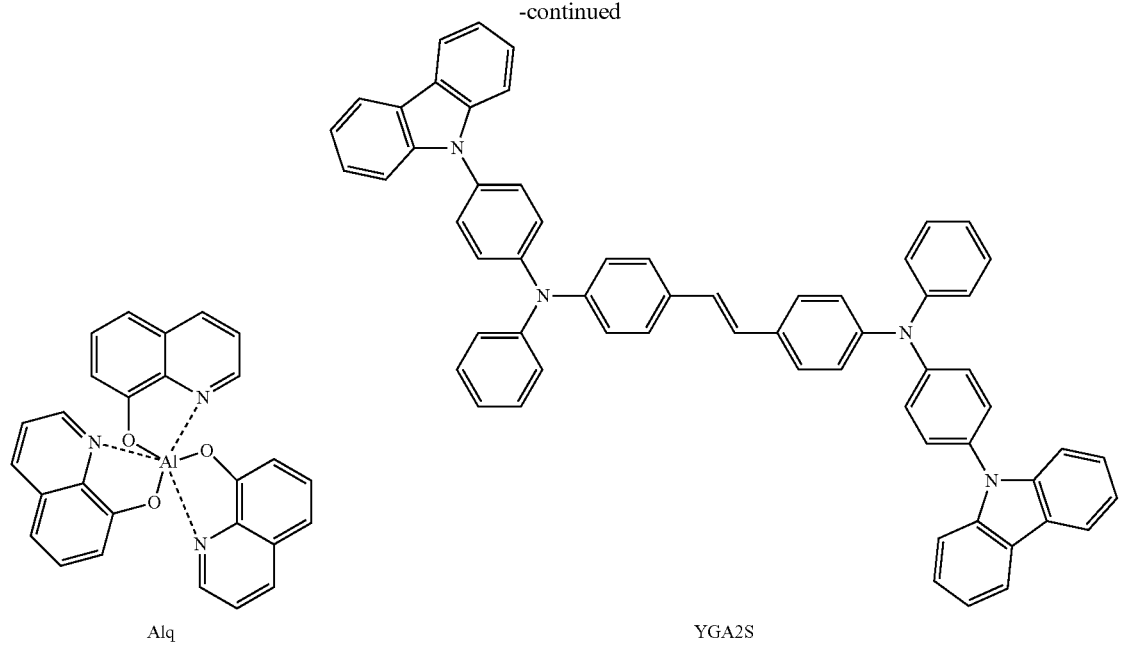

Alq   YGA2S (Light-Emitting Element 4)

First, indium tin oxide containing silicon oxide was deposited on a glass substrate 3100 by a sputtering method to form a first electrode 3101. Note that the thickness of the first electrode 3101 was set to 110 nm and the area of the electrode was set to an area of 2 mm×2 mm.

Next, the substrate provided with the first electrode was fixed to a substrate holder provided in a vacuum evaporation apparatus such that a surface of the substrate, where the first electrode was formed, faced downward, and then the pressure was reduced to shout $10^{-4}$ Pa. Then, 4,4'-bis[N-(1-naphthyl)-N-phenylamino]biphenyl (abbreviation: NPB) and molybdenum(VI) oxide were co-deposited on the first electrode 3101 by a vapor deposition method using resistance heating, whereby a layer 3102 including a composite material of an organic compound and an inorganic compound was formed. The thickness of the layer 3102 was set to 50 nm and the weight ratio of NPB to molybdenum(VI) oxide was adjusted so to be 4:1 (=NPB:molybdenum oxide).

Next, NPB was deposited to a thickness of 10 nm on the layer 3102 including a composite material by a vapor deposition method using resistance heating, thereby forming a hole-transporting layer 3103.

Furthermore, 9,10-diphenylanthracene (DPAnth) and 4,4'-bis{N-[4-(carbazol-9-yl)phenyl]-N-phenylamino}stilbene (YGA2S) were co-deposited, thereby forming a first layer 3111 with a thickness of 30 nm on the hole-transporting layer 3103. The weight ratio of DPAnth to YGA2S was adjusted so to be 1:0.1(=DPAnth:YGA2S).

Furthermore, PCzPA and 4,4'-bis{N-[4-(carbazol-9-yl)phenyl]-N-phenylamino}stilbene (YGA2S) were co-deposited, thereby forming a second layer 3112 with a thickness of 30 nm on the first layer 3111. The weight ratio of PCzPA to YGA2S was adjusted so to be 1:0.05 (=PCzPA:YGA2S).

After that, Alq was deposited to a thickness of 10 nm on the second layer 3112 by a vapor deposition method using resistance heating, thereby forming an electron-transporting layer 3104.

Furthermore, Alq and lithium were co-deposited to a thickness of 20 nm on the electron-transporting layer 3104, thereby forming an electron-injecting layer 3105. The weight ratio between Alq and lithium was adjusted so as to be 1:0.01 (=Alq:lithium).

Lastly, aluminum was deposited to a thickness of 200 nm on the electron-injecting layer 3105 by a vapor deposition method using resistance heating, thereby forming a second electrode 3106. Accordingly, light-emitting element 4 was formed.

Figure 32:
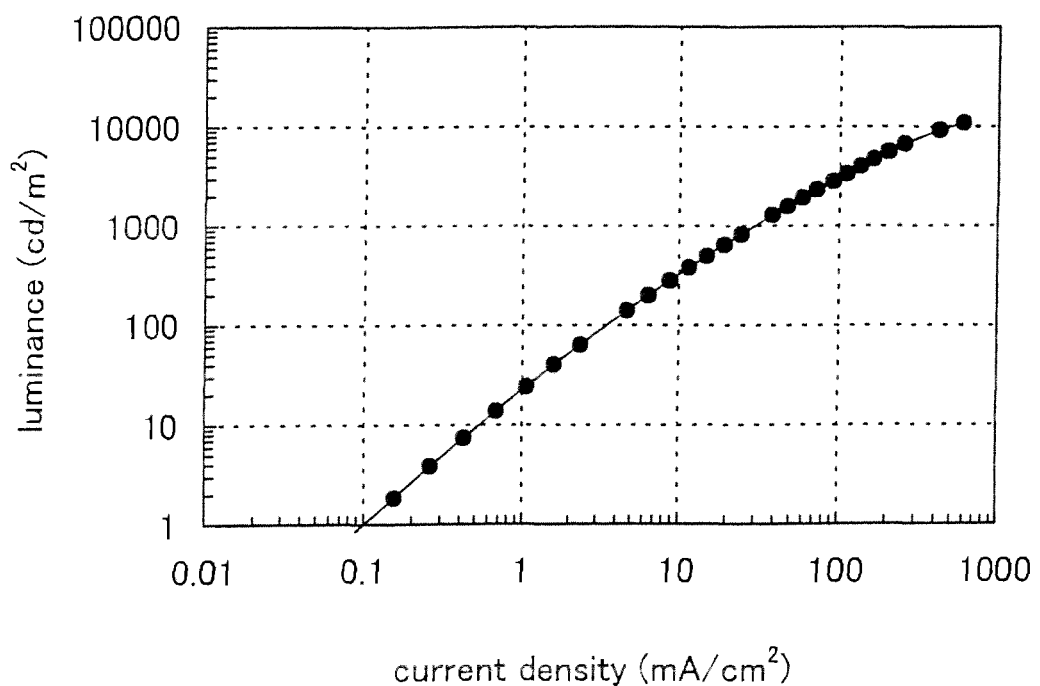
FIG. 32 is a graph showing the current density-luminance characteristic of the light-emitting element according to Example 4.
Figure 33:
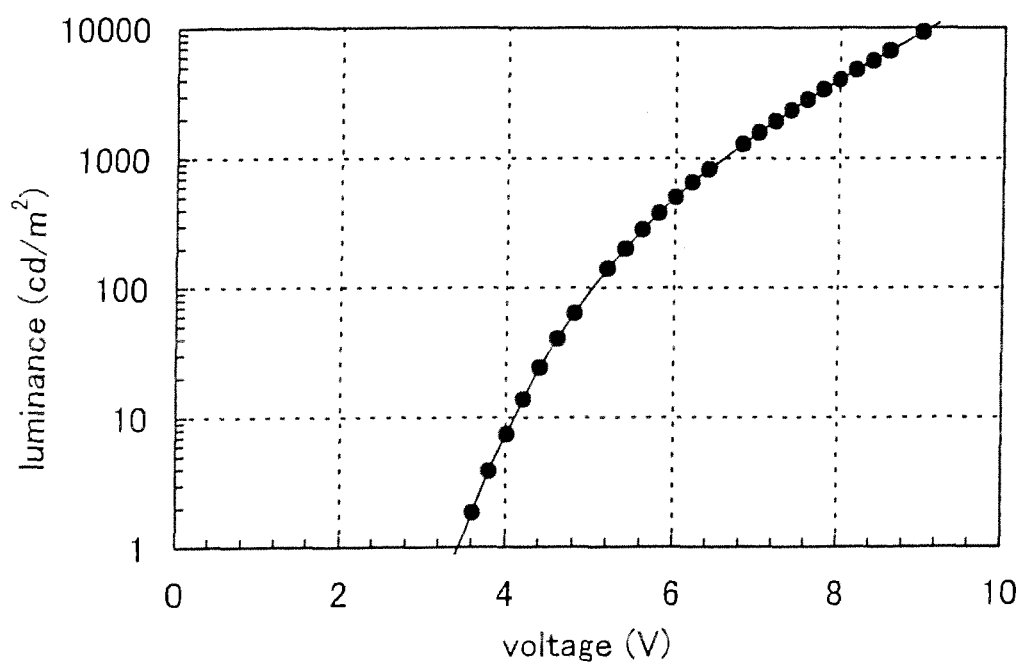
FIG. 33 is a graph showing the voltage-luminance characteristic of the light-emitting element according to Example 4.
Figure 34:
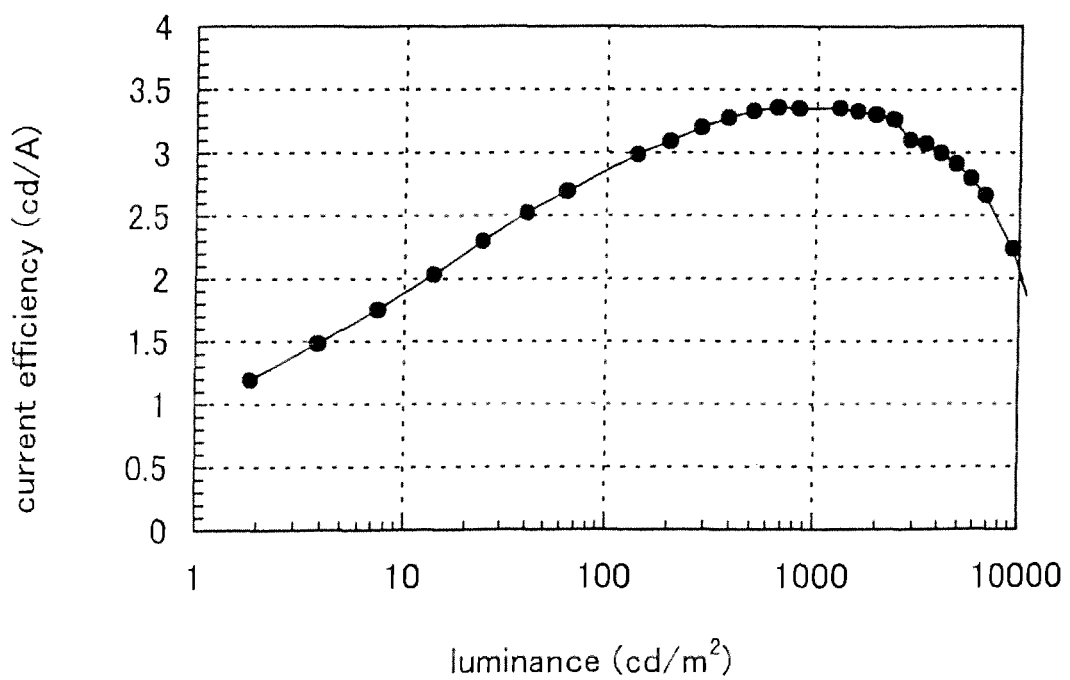
FIG. 34 is a graph showing the luminance-current efficiency characteristic of the light-emitting element according to Example 4.
Figure 35:
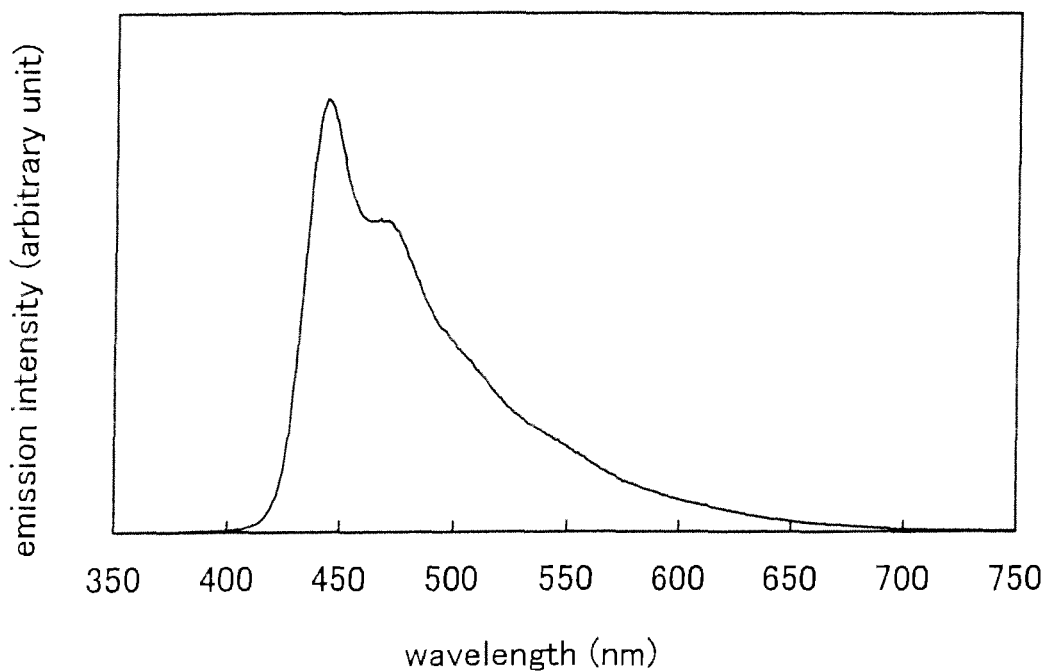
FIG. 35 is a graph showing an emission spectrum of the light-emitting element according to Example 4.

FIG. 32 shows the current density vs. luminance characteristic of the light-emitting element 4. FIG. 33 shows the voltage vs. luminance characteristic of the light-emitting element 4. FIG. 34 shows the luminance vs. current efficiency characteristic of the light-emitting element 4. FIG. 35 shows an emission spectrum when a current of 1 mA flows. From FIG. 35, it was found that light emission derived from YGA2S was obtained. Further, it was also found that the CIE chromaticity coordinates of the light-emitting element 4 at a luminance of 1000 cd/m² were (x, y)=(0.18, 0.17) and blue light emission with very high color purity was able to be obtained. From FIG. 34, it was found that the current efficiency at the luminance of 1000 cd/m² was 3.3 cd/A and the light-emitting element 4 emitted light efficiently. Further, from FIG. 33, it was found that the voltage at which light emission starts was less than 4 V and the driving voltage was low.

In this manner, it is found that the anthracene derivative of the present invention can be preferably used as a host material of a light-emitting layer, in particular, as a host material for a dopant emitting blue light.

From the above, it was found that with a light-emitting element manufactured using the anthracene derivative of the present invention, a light-emitting element, a light-emitting device, and an electronic device with high light emission efficiency, capable of blue light emission with high color purity can be provided.

The present application is based on Japanese Patent Application serial No. 2007-330688 filed with Japan Patent Office en Dec. 21, 2007, the entire contents of which are hereby incorporated by reference.

What is claimed is:

1. A method for synthesizing a compound represented by the following formula:

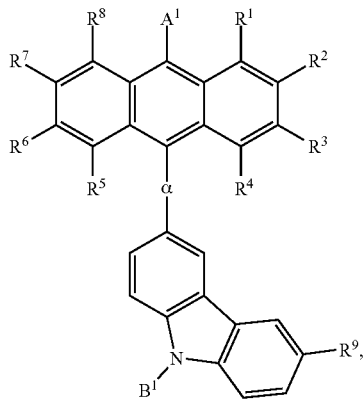

the method comprising:
performing a reaction of an organic halide with an organic boronic acid,
wherein:
the organic halide is represented by the following formula:

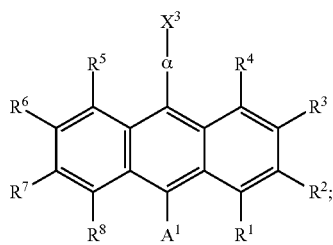

the organic boronic acid is represented by the following formula:

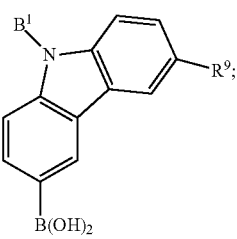

A¹ is selected from the following substituents:

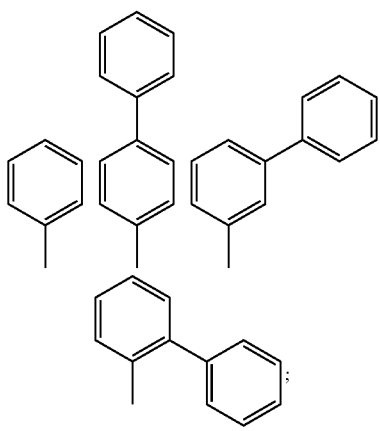

B¹ is selected from an alkyl group having 1 to 4 carbon atoms and a substituted or unsubstituted phenyl group;
α is a substituted or unsubstituted 1,4-phenylene group;
R¹ to R⁹ are individually selected from hydrogen, an alkyl group having 1 to 4 carbon atoms, and a substituted or unsubstituted phenyl group; and
X³ is halogen.

2. The method according to claim 1, wherein:
B¹ is a substituted phenyl group; and
a substituent of the substituted phenyl group for B¹ is selected from hydrogen, an alkyl group having 1 to 4 carbon atoms, and a substituted or unsubstituted phenyl group.

3. The method according to claim 1, wherein R⁹ is hydrogen.

4. The method according to claim 1, wherein B¹ is an unsubstituted phenyl group.

5. The method according to claim 1, wherein the reaction is performed in the presence of a palladium catalyst.

6. A method for manufacturing a light-emitting device, the method comprising;
performing a reaction of an organic halide with an organic boronic acid to prepare an organic compound represented by the following formula:

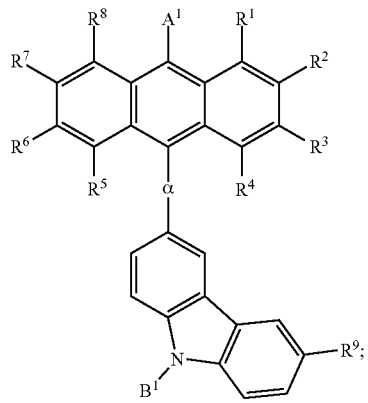

forming a layer over a first electrode so that the layer includes the organic compound; and
forming a second electrode over the layer,
wherein:
the organic halide is represented by the following formula:

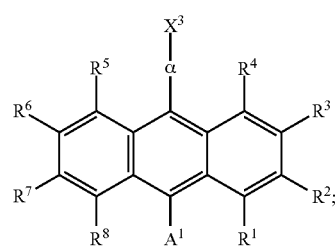

the organic boronic acid is represented by the following formula:

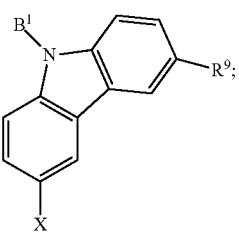

$A^1$ is selected from the following substituents:

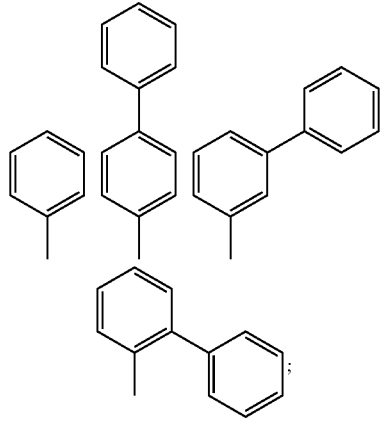

$B^1$ is selected from an alkyl group having 1 to 4 carbon atoms and a substituted or unsubstituted phenyl group;

α is a substituted or unsubstituted 1,4-phenylene group;

$R^1$ to $R^9$ are individually selected from hydrogen, an alkyl group having 1 to 4 carbon atoms, and a substituted or unsubstituted phenyl group; and $X^3$ is halogen.

7. The method according to claim 6, wherein:

$B^1$ is a substituted phenyl group; and a substituent of the substituted phenyl group for $B^1$ is selected from hydrogen, an alkyl group having 1 to 4 carbon atoms, and a substituted or unsubstituted phenyl group.

8. The method according to claim 6, wherein $R^9$ is hydrogen.

9. The method according to claim 6, wherein $B^1$ is an unsubstituted phenyl group.

10. The method according to claim 6, wherein the reaction is performed in the presence of a palladium catalyst.

* * * * *